United States Patent
To et al.

(10) Patent No.: US 9,168,047 B2
(45) Date of Patent: Oct. 27, 2015

(54) MINIMALLY INVASIVE DISCECTOMY

(76) Inventors: John T. To, Newark, CA (US); Dan Zaretzka, Castro Valley, CA (US); Myra I. L. Fabro, San Jose, CA (US); Stewart M. Kume, Emerald Hills, CA (US)

(*) Notice: Subject to any disclaimer, the term of this patent is extended or adjusted under 35 U.S.C. 154(b) by 33 days.

(21) Appl. No.: 12/753,788

(22) Filed: Apr. 2, 2010

(65) Prior Publication Data
US 2011/0087257 A1    Apr. 14, 2011

Related U.S. Application Data

(63) Continuation-in-part of application No. 12/509,356, filed on Jul. 24, 2009, now abandoned.

(60) Provisional application No. 61/165,968, filed on Apr. 2, 2009, provisional application No. 61/223,343, filed on Jul. 6, 2009.

(51) Int. Cl.
*A61B 17/32* (2006.01)
*A61B 17/16* (2006.01)
(Continued)

(52) U.S. Cl.
CPC ......... *A61B 17/1617* (2013.01); *A61B 17/1671* (2013.01); *A61B 17/32002* (2013.01);
(Continued)

(58) Field of Classification Search
CPC ........... A61B 17/1617; A61B 17/1671; A61B 17/22012; A61B 17/32
USPC ........... 606/159, 168, 170; 600/104, 114, 564
See application file for complete search history.

(56) References Cited

U.S. PATENT DOCUMENTS 177,490 A     5/1876  Fones et al.
4,061,146 A  12/1977  Baehr et al.
(Continued)

FOREIGN PATENT DOCUMENTS

WO    WO-93/20742 A1   10/1993
WO    WO-02/055146 A1   7/2002
(Continued)

OTHER PUBLICATIONS

Adulkasem, W. et al. (Dec. 2002). "Early Experience of Endoscopy-assisted Anterior Spinal Surgery," *Journal of Orthopaedic Surgery* 10(2):152-159.
(Continued)

*Primary Examiner* — Victor Nguyen
(74) *Attorney, Agent, or Firm* — Morrison & Foerster LLP; Ross M. Carothers

(57) ABSTRACT

Systems and methods for minimally invasive discectomy procedures are described herein. The systems include a bendable flexible cannula may have a straight configuration suitable for insertion and withdrawal into spinal tissue, and a curved configuration suitable for accessing certain areas of a vertebral disc that may be difficult to reach in the straight configuration. A cannula is straightened by inserting a straight stylet therethrough. The straight stylet may have a deflectable region that facilitates its insertion into the cannula. Removal of a straight stylet from a cannula may allow the cannula to assume its curved configuration. The systems may be used with tissue removal devices, and certain variations of tissue removal devices may include a collector for aspiration, as well as a travel limiter to restrict inadvertent motions of the tissue removal devices within a vertebral structure.

12 Claims, 73 Drawing Sheets

(51) Int. Cl.
  *A61B 17/3207* (2006.01)
  *A61B 17/88* (2006.01)
  *A61B 17/00* (2006.01)
  *A61B 19/00* (2006.01)

(52) U.S. Cl.
  CPC . *A61B17/320758* (2013.01); *A61B 17/320725* (2013.01); *A61B 17/8811* (2013.01); *A61B 2017/003* (2013.01); *A61B 2017/00261* (2013.01); *A61B 2017/00331* (2013.01); *A61B 2017/00398* (2013.01); *A61B 2017/00685* (2013.01); *A61B 2017/00734* (2013.01); *A61B 2017/00867* (2013.01); *A61B 2017/320064* (2013.01); *A61B 2017/320733* (2013.01); *A61B 2017/320775* (2013.01); *A61B 2019/464* (2013.01)

(56) References Cited

U.S. PATENT DOCUMENTS

| | | | |
|---|---|---|---|
| 4,466,429 A | 8/1984 | Loscher et al. | |
| 4,545,374 A | 10/1985 | Jacobson | |
| 4,573,448 A | 3/1986 | Kambin | |
| 4,603,694 A | 8/1986 | Wheeler | |
| 4,646,738 A | 3/1987 | Trott | |
| 4,711,607 A | 12/1987 | Wynosky et al. | |
| 4,796,642 A | 1/1989 | Harris | |
| 4,857,046 A | 8/1989 | Stevens et al. | |
| 5,078,723 A | 1/1992 | Dance et al. | |
| 5,100,423 A | 3/1992 | Fearnot | |
| 5,108,404 A | 4/1992 | Scholten et al. | |
| 5,158,552 A * | 10/1992 | Borgia et al. | 604/164.12 |
| 5,215,105 A | 6/1993 | Kizelshteyn et al. | |
| 5,217,474 A | 6/1993 | Zacca et al. | |
| 5,286,253 A | 2/1994 | Fucci | |
| 5,304,141 A | 4/1994 | Johnson et al. | |
| 5,313,962 A | 5/1994 | Obenchain | |
| 5,354,266 A | 10/1994 | Snoke | |
| 5,370,647 A | 12/1994 | Graber et al. | |
| 5,383,884 A | 1/1995 | Summers | |
| 5,395,317 A | 3/1995 | Kambin | |
| 5,396,880 A | 3/1995 | Kagan et al. | |
| 5,399,164 A | 3/1995 | Snoke et al. | |
| 5,411,514 A | 5/1995 | Fucci et al. | |
| 5,423,311 A | 6/1995 | Snoke et al. | |
| 5,437,630 A | 8/1995 | Daniel et al. | |
| 5,439,464 A | 8/1995 | Shapiro | |
| 5,460,170 A | 10/1995 | Hammerslag | |
| 5,496,269 A | 3/1996 | Snoke | |
| 5,512,034 A | 4/1996 | Finn et al. | |
| 5,529,580 A | 6/1996 | Kusunoki et al. | |
| 5,556,376 A | 9/1996 | Yoon | |
| 5,569,178 A | 10/1996 | Henley | |
| 5,591,187 A | 1/1997 | Dekel | |
| 5,667,520 A | 9/1997 | Bonutti | |
| 5,685,826 A | 11/1997 | Bonutti | |
| 5,695,513 A | 12/1997 | Johnson et al. | |
| 5,707,359 A | 1/1998 | Bufalini | |
| 5,707,362 A * | 1/1998 | Yoon | 604/164.03 |
| 5,707,390 A | 1/1998 | Bonutti | |
| 5,735,792 A | 4/1998 | Vanden Hoek et al. | |
| 5,762,629 A | 6/1998 | Kambin | |
| 5,792,044 A | 8/1998 | Foley et al. | |
| 5,830,188 A | 11/1998 | Abouleish | |
| 5,836,947 A | 11/1998 | Fleischman et al. | |
| 5,846,221 A | 12/1998 | Snoke et al. | |
| 5,857,996 A | 1/1999 | Snoke | |
| 5,882,329 A | 3/1999 | Patterson et al. | |
| 5,885,258 A | 3/1999 | Sachdeva et al. | |
| 5,885,292 A | 3/1999 | Moskovitz et al. | |
| 5,891,153 A | 4/1999 | Peterson | |
| 5,902,263 A | 5/1999 | Patterson et al. | |
| 5,941,869 A | 8/1999 | Patterson et al. | |
| 5,964,716 A | 10/1999 | Gregoire et al. | |
| 5,968,062 A | 10/1999 | Thomas et al. | |
| 5,976,146 A | 11/1999 | Ogawa et al. | |
| 6,007,487 A | 12/1999 | Foley et al. | |
| 6,010,493 A | 1/2000 | Snoke | |
| 6,042,596 A | 3/2000 | Bonutti | |
| 6,068,642 A | 5/2000 | Johnson et al. | |
| 6,162,170 A | 12/2000 | Foley et al. | |
| 6,187,000 B1 | 2/2001 | Davison et al. | |
| 6,206,822 B1 | 3/2001 | Foley et al. | |
| 6,217,509 B1 | 4/2001 | Foley et al. | |
| 6,319,242 B1 | 11/2001 | Patterson et al. | |
| 6,361,488 B1 | 3/2002 | Davison et al. | |
| 6,371,968 B1 | 4/2002 | Kogasaka et al. | |
| 6,375,634 B1 | 4/2002 | Carroll | |
| 6,379,346 B1 | 4/2002 | McIvor et al. | |
| 6,464,682 B1 | 10/2002 | Snoke | |
| 6,470,209 B2 | 10/2002 | Snoke | |
| 6,471,697 B1 * | 10/2002 | Lesh | 606/41 |
| 6,520,907 B1 | 2/2003 | Foley et al. | |
| 6,524,320 B2 | 2/2003 | DiPoto | |
| RE38,018 E | 3/2003 | Anctil et al. | |
| 6,530,926 B1 | 3/2003 | Davison | |
| 6,530,933 B1 | 3/2003 | Yeung et al. | |
| 6,540,747 B1 | 4/2003 | Marino | |
| 6,554,799 B1 | 4/2003 | Hatamura et al. | |
| 6,575,899 B1 | 6/2003 | Foley et al. | |
| 6,592,559 B1 | 7/2003 | Pakter et al. | |
| 6,595,958 B1 | 7/2003 | Mickley | |
| 6,652,553 B2 | 11/2003 | Davison et al. | |
| 6,673,023 B2 | 1/2004 | Pflueger | |
| 6,679,833 B2 | 1/2004 | Smith et al. | |
| 6,780,175 B1 | 8/2004 | Sachdeva et al. | |
| 6,793,656 B1 | 9/2004 | Mathews | |
| 6,800,084 B2 | 10/2004 | Davison et al. | |
| 6,811,558 B2 | 11/2004 | Davison et al. | |
| 6,821,276 B2 | 11/2004 | Lambrecht et al. | |
| 6,827,716 B2 | 12/2004 | Ryan et al. | |
| 6,837,891 B2 | 1/2005 | Davison et al. | |
| 6,857,943 B2 | 2/2005 | Kapgan | |
| 6,875,219 B2 | 4/2005 | Arramon et al. | |
| 6,916,330 B2 | 7/2005 | Simonson | |
| 6,925,323 B2 | 8/2005 | Snoke | |
| 7,001,397 B2 | 2/2006 | Davison et al. | |
| 7,033,369 B2 | 4/2006 | Davison et al. | |
| 7,037,321 B2 | 5/2006 | Sachdeva et al. | |
| 7,048,694 B2 * | 5/2006 | Mark et al. | 600/564 |
| 7,108,705 B2 | 9/2006 | Davison et al. | |
| 7,144,393 B2 | 12/2006 | DiPoto et al. | |
| 7,179,225 B2 | 2/2007 | Shluzas et al. | |
| 7,223,278 B2 | 5/2007 | Davison et al. | |
| 7,241,297 B2 | 7/2007 | Shaolian et al. | |
| 7,338,495 B2 | 3/2008 | Adams | |
| 7,416,533 B2 * | 8/2008 | Gellman et al. | 600/562 |
| 7,591,790 B2 | 9/2009 | Pflueger | |
| 2002/0016624 A1 | 2/2002 | Patterson et al. | |
| 2002/0138091 A1 | 9/2002 | Pflueger | |
| 2003/0130673 A1 | 7/2003 | Trerotola | |
| 2003/0195551 A1 | 10/2003 | Davison et al. | |
| 2004/0078051 A1 | 4/2004 | Davison et al. | |
| 2004/0098012 A1 | 5/2004 | Davison et al. | |
| 2004/0116954 A1 | 6/2004 | Pagliuca et al. | |
| 2004/0236328 A1 | 11/2004 | Paul et al. | |
| 2005/0043754 A1 | 2/2005 | Davison et al. | |
| 2005/0267502 A1 | 12/2005 | Hochman | |
| 2006/0036273 A1 | 2/2006 | Siegal | |
| 2006/0089662 A1 | 4/2006 | Davison et al. | |
| 2006/0206118 A1 | 9/2006 | Kim et al. | |
| 2006/0258951 A1 | 11/2006 | Bleich et al. | |
| 2006/0276821 A1 | 12/2006 | Davison et al. | |
| 2007/0021767 A1 * | 1/2007 | Breznock | 606/185 |
| 2007/0055259 A1 | 3/2007 | Norton et al. | |
| 2007/0060935 A1 | 3/2007 | Schwardt et al. | |
| 2007/0066977 A1 | 3/2007 | Assell et al. | |
| 2007/0106246 A1 | 5/2007 | Modesitt | |
| 2007/0149990 A1 | 6/2007 | Palmer et al. | |
| 2007/0162062 A1 | 7/2007 | Norton et al. | |
| 2007/0173939 A1 | 7/2007 | Kim et al. | |
| 2007/0213735 A1 | 9/2007 | Saadat et al. | |
| 2008/0033465 A1 | 2/2008 | Schmitz et al. | |

(56) References Cited

U.S. PATENT DOCUMENTS

| | | |
|---|---|---|
| 2008/0051812 A1 | 2/2008 | Schmitz et al. |
| 2008/0058588 A1 | 3/2008 | Emanuel |
| 2008/0119846 A1 | 5/2008 | Rioux |
| 2008/0228192 A1 | 9/2008 | Beyar et al. |
| 2009/0018507 A1 | 1/2009 | Schmitz et al. |
| 2009/0062872 A1 | 3/2009 | Chin et al. |
| 2009/0177161 A1 | 7/2009 | McGuckin, Jr. et al. |
| 2009/0259126 A1 | 10/2009 | Saal et al. |

FOREIGN PATENT DOCUMENTS

| | | |
|---|---|---|
| WO | WO-02/098300 A2 | 12/2002 |
| WO | WO-2004/073500 A2 | 9/2004 |
| WO | WO-2004/073500 A3 | 9/2004 |
| WO | WO-2006/072941 A2 | 7/2006 |
| WO | WO-2007/008710 A2 | 1/2007 |
| WO | WO-2007/100591 A2 | 9/2007 |
| WO | WO-2007/100591 A3 | 9/2007 |
| WO | WO-2007/124130 A2 | 11/2007 |

OTHER PUBLICATIONS

Baron, E.M. et al. (2005). "Neuroendoscopy for Spinal Disorders: A Brief Review," located at <http://www.medscape.com/viewarticle/520947_print>, last visited on Apr. 10, 2008, 8 pages.

Cardinal Health (2007). "AVAflex™ Curved Injection Needle," 2 pages.

Heavner, J.E. et al. (Aug. 2007). "Lumbosacral Epiduroscopy Complicated by Intravascular Injection," *Anesthesiology* 107(2):347-350.

Igarashi, T. et al. (2004, e-pub. Jun. 11, 2004). "Lysis of Adhesions and Epidural Injection of Steroid/local Anaesthetic During Epiduroscopy Potentially Alleviate Low Back and Leg Pain in Elderly Patients with lumbar Spinal Stenosis," *British Journal of Anaesthesia* 93(2):181-187.

International Search Report mailed Jun. 1, 2010, for PCT Application No. PCT/US2010/029826, filed Apr. 2, 2010, 4 pages.

Le Huec, J.C. et al. (Jan. 1999). "Endoscopic Surgery of the Spine, A Review of 4 Years' Practice," located at <http://www.maitrise-orthop.com/corpusmaitri/orthopaedic/mo81_huec_husson_/texte_us.shtml>, last visited on Apr. 10, 2008, *Maitrise Orthopédique*, 20 pages.

Nash, T.P. (Feb. 2005). "Epiduroscopy for Lumbar Spinal Stenosis," *British Journal of Anaesthesia* 94(2);250, author reply 250-251.

Saringer, W.F. et al. (Mar. 2003). "Endoscopic Anterior Cervical Foraminotomy for Unilateral Radiculopathy: Anatomical Morphometric Analysis and Preliminary Clinical Experience," *J. Neurosurg (Spine 2)*98:171-180.

Yeung, A.T. (Sep. 2000). "The Evolution of Percutaneous Spinal Endoscopy and Discectomy: State of the Art," *The Mount Sinai Journal of Medicine* 67(4):327-332.

Written Opinion mailed Jun. 1, 2010, for PCT Application No. PCT/US2010/029826, filed Apr. 2, 2010, 6 pages.

\* cited by examiner

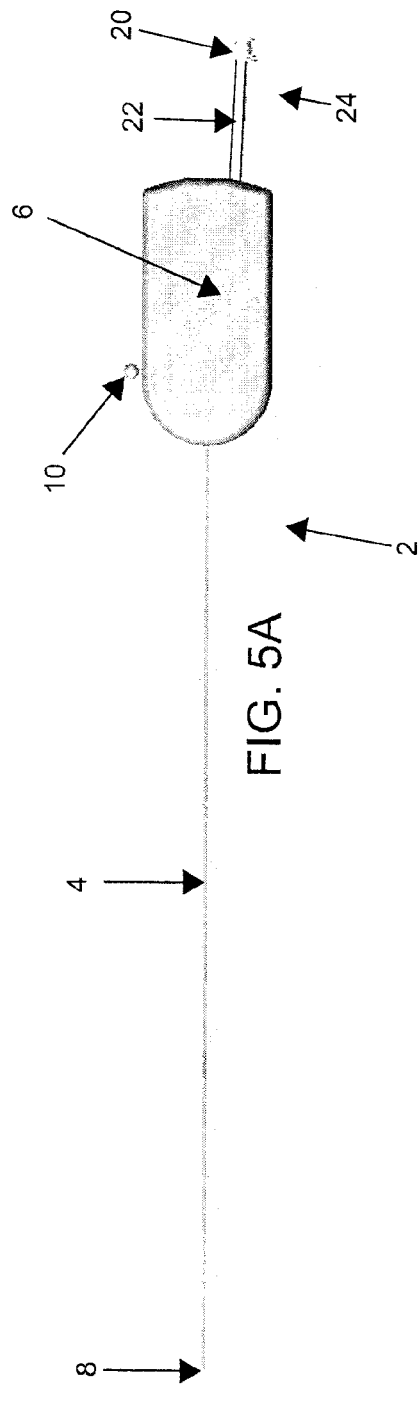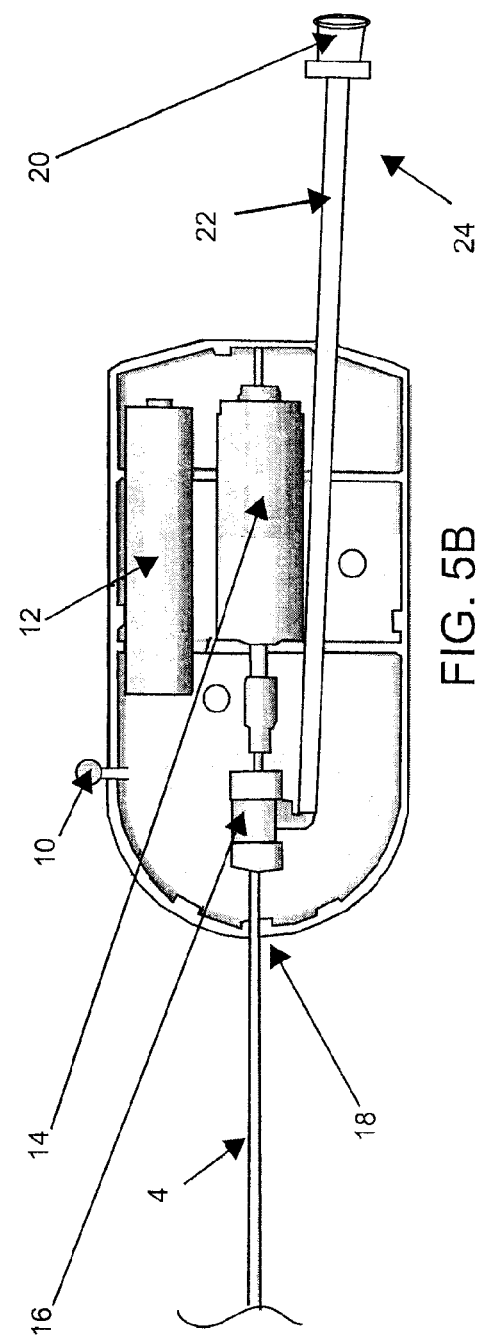

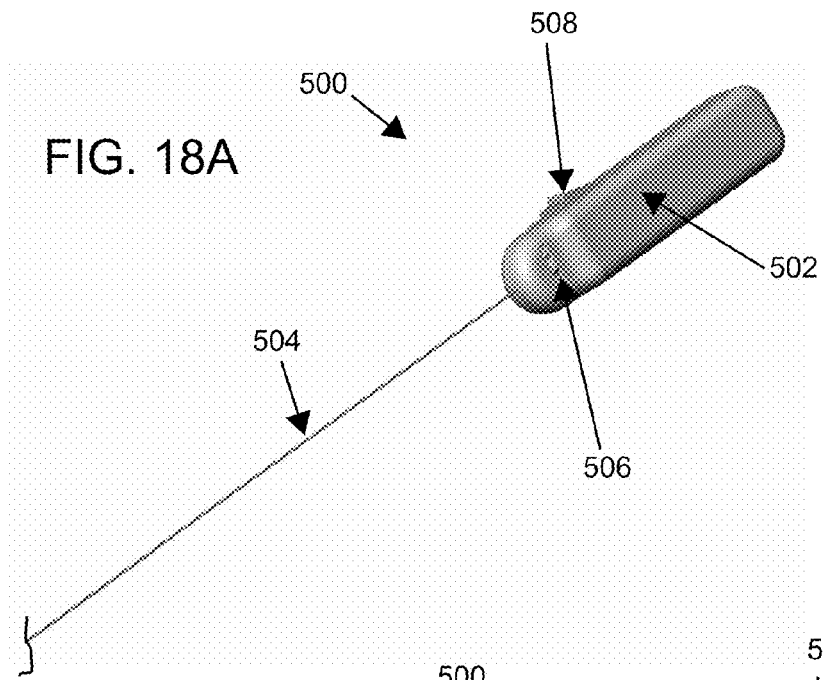
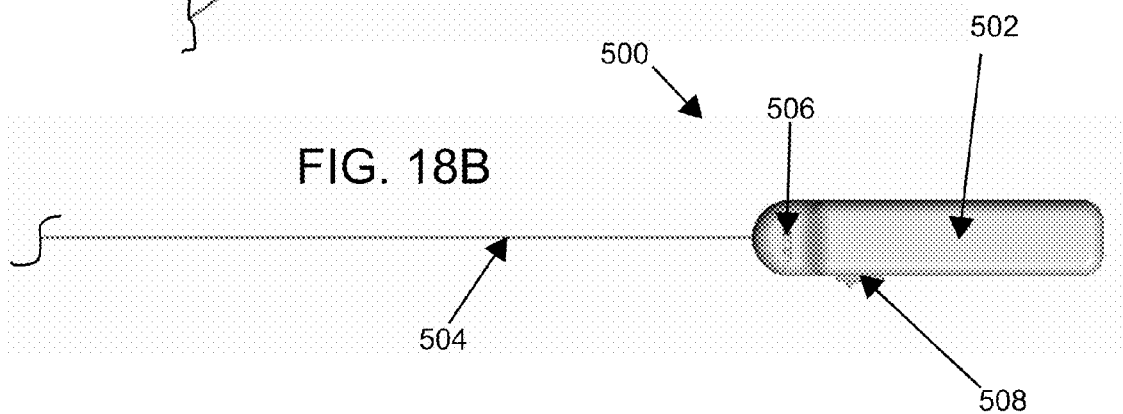

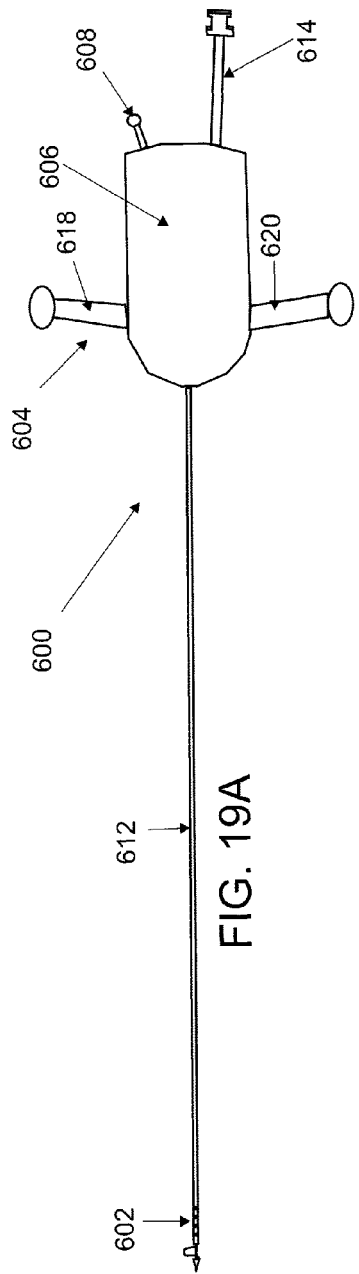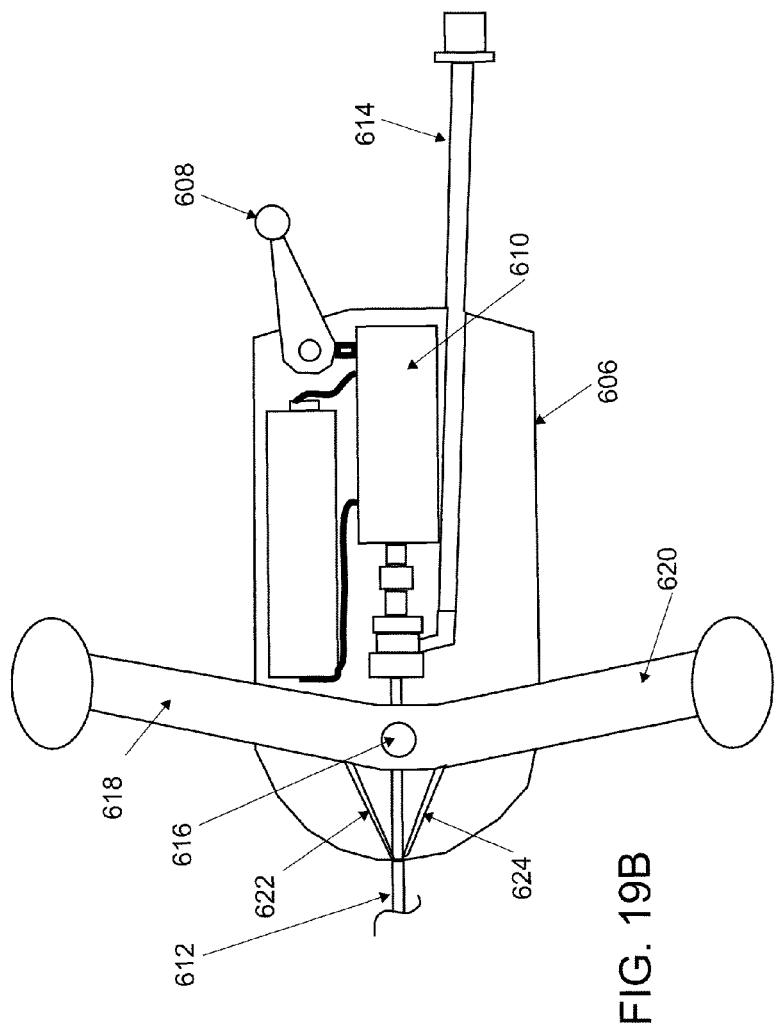
FIG. 19A
FIG. 19B

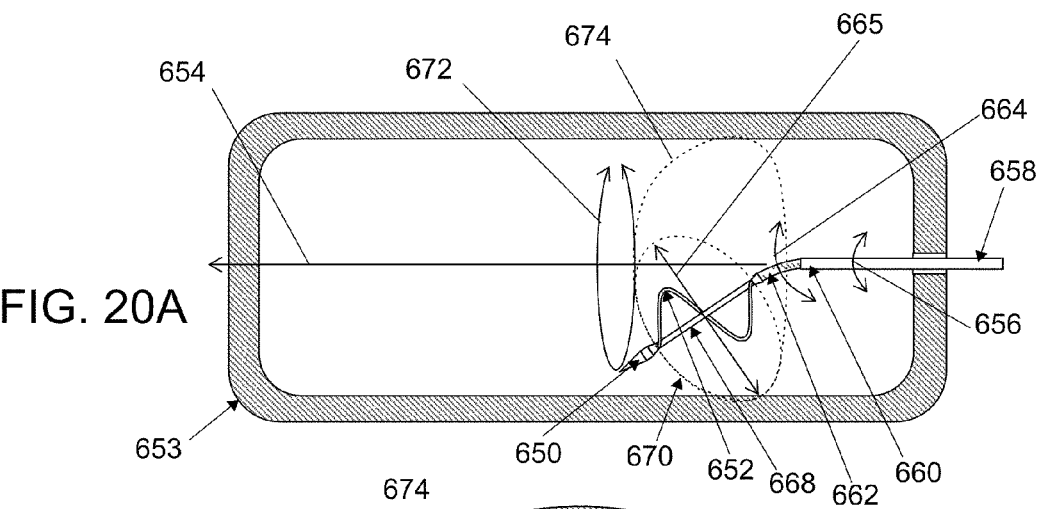
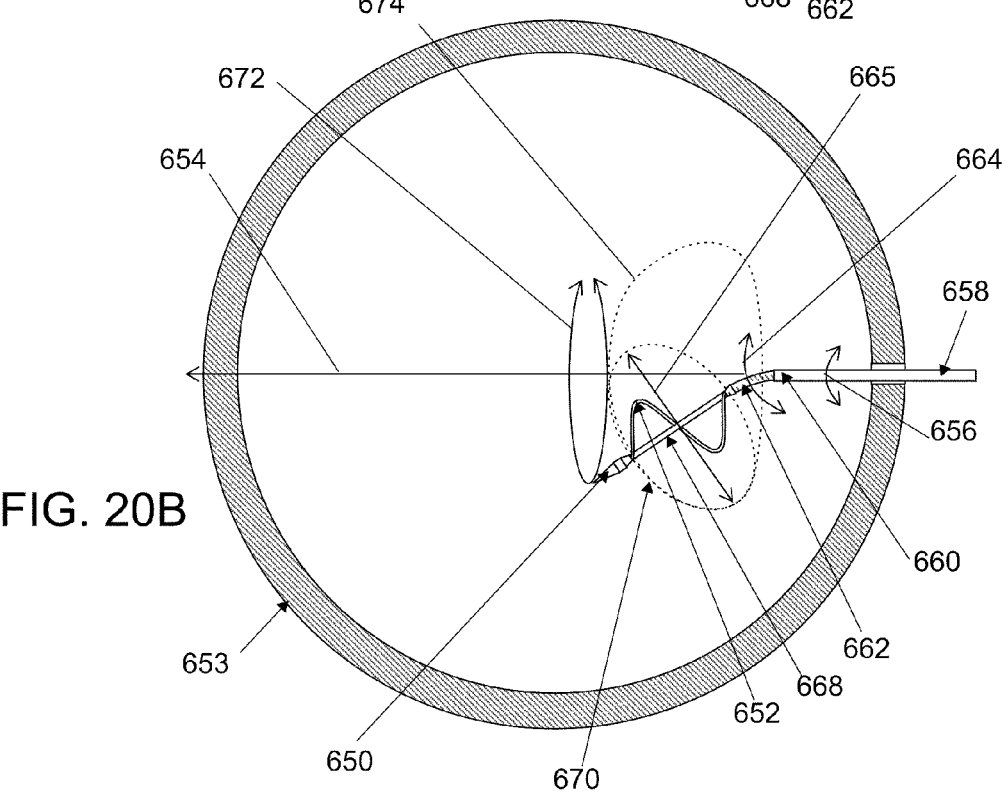

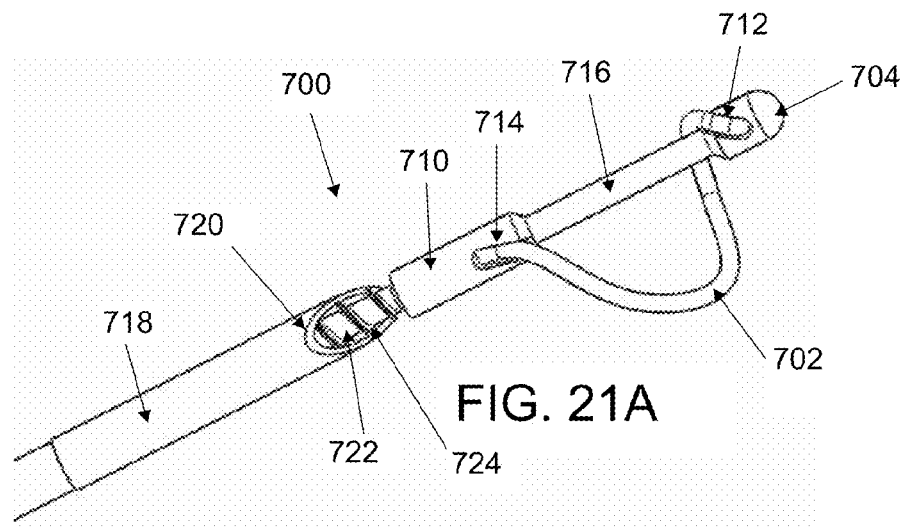
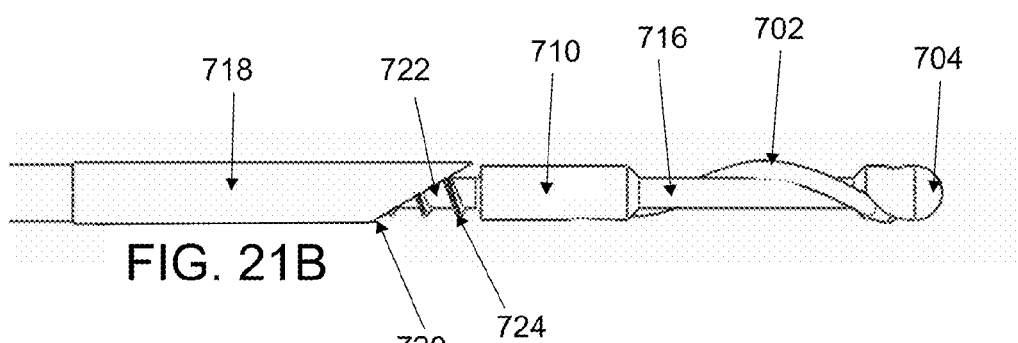
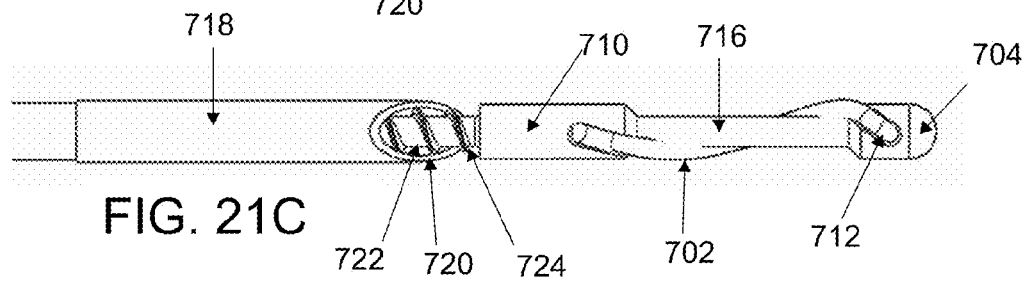
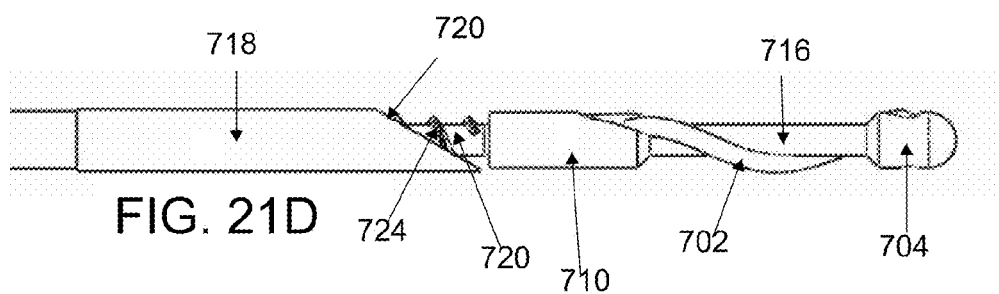

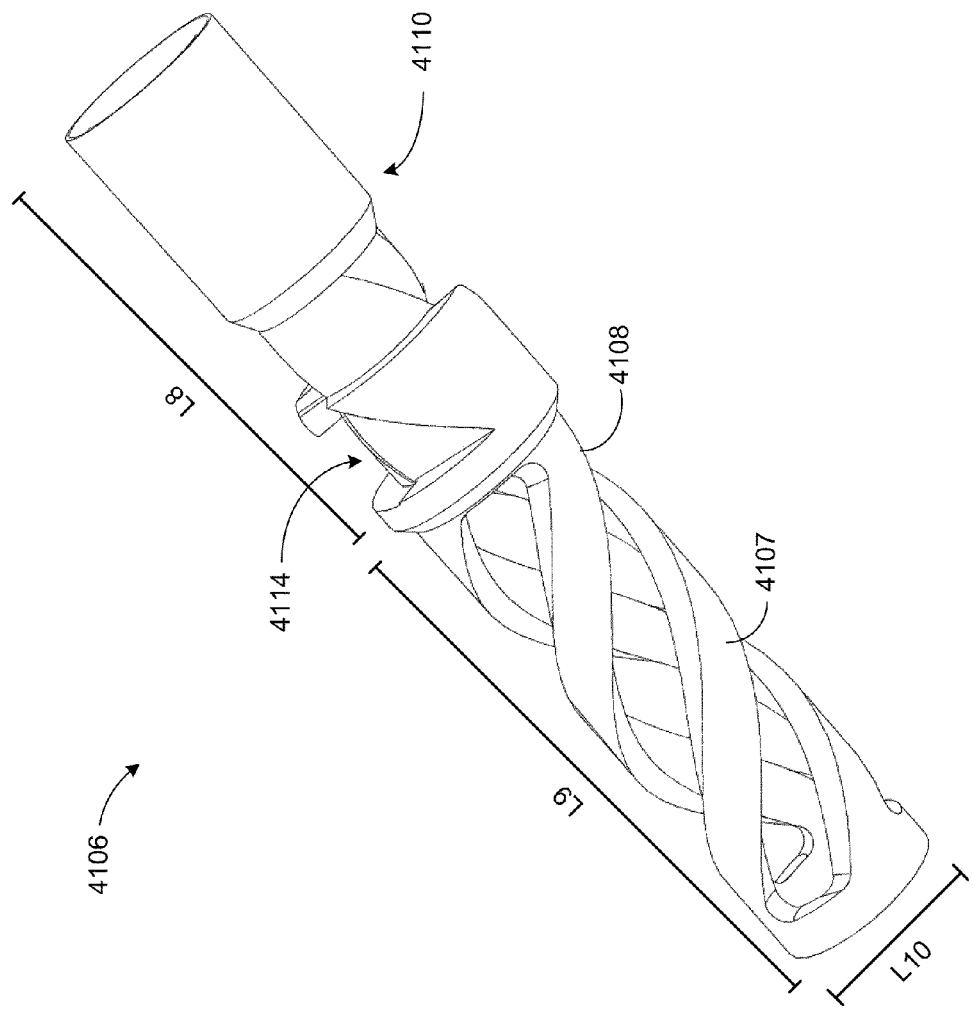

MINIMALLY INVASIVE DISCECTOMY

CROSS-REFERENCE TO RELATED APPLICATIONS

This application claims benefit under 35 U.S.C. §119(e) to U.S. Provisional Application Ser. No. 61/165,968, filed on Apr. 2, 2009, and is also a continuation-in-part of U.S. application Ser. No. 12/509,356, filed on Jul. 24, 2009, which claims benefit under 35 U.S.C. §119(e) to U.S. Provisional Application Ser. No. 61/223,343, filed on Jul. 6, 2009, all of which are hereby incorporated by reference in their entirety.

BACKGROUND

Vertebral disc herniation is a common disorder where a portion of a vertebral disc, a cushion-like structure located between the vertebral bodies of the spine, bulges out or extrudes beyond the usual margins of the disc and the spine. Disc herniation is believed to be the result of a excessive loading on the disc in combination with weakening of the annulus due to such factors as aging and genetics. Disc herniation and other degenerative disc disease are also associated with spinal stenosis, a narrowing of the bony and ligamentous structures of the spine. Although disc herniation can occur anywhere along the perimeter of the disc, it occurs more frequently in the posterior and posterior-lateral regions of the disc, where the spinal cord and spinal nerve roots reside. Compression of these neural structures can lead to pain, parasthesias, weakness, urine and fecal incontinence and other neurological symptoms that can substantially impact basic daily activities and quality of life.

Temporary relief of the pain associated with disc herniation is often sought through conservative therapy, which includes positional therapy (e.g. sitting or bending forward to reduce pressure on spine), physical therapy, and drug therapy to reduce pain and inflammation. When conservative therapy fails to resolve a patient's symptoms, surgery may be considered to treat the structural source of the symptoms. Surgical treatments for disc herniation traditionally involve open procedures that require extensive dissection of muscle, connective tissue and bone along a patient's back as well as nerve manipulations to achieve adequate surgical exposure. These surgeries also expose the patient to a significant risk of complications, due to the presence of critical neurovascular structures near the surgical site as well as prolonged anesthesia. For example, a discectomy procedure may be used to decompress the herniation by accessing the affected disc and removing a portion of the disc and any loose disc fragments. To achieve sufficient access to the affected disc, a portion of the lamina or bony arch of the vertebrae may be removed, thereby increasing the invasiveness of the procedure and can destabilize the spine post-surgery. When discectomy fails to resolve a patient's symptoms, more drastic measures may include disc replacement surgery or vertebral fusion.

Fractures of the vertebrae bodies are another common disorder of the spinal column. When a vertebra fractures, the usual shape of the bone becomes compressed and distorted, which results in pain. These vertebral compression fractures (VCF), which may involve the collapse of one or more vertebrae in the spine, are a common finding and result of osteoporosis. Osteoporosis is a disorder that often becomes more severe with age and results in a loss of normal bone density, mass and strength. Osteoporosis often leads to a condition in which bones are increasingly porous or full of small holes and vulnerable to breaking. In addition to osteoporosis, vertebrae can also become weakened by cancer or infection.

In some instances, fractures of the vertebral bodies may be treated with surgical removal of the vertebral body and the implantation of a vertebral body replacement device. Other treatments may include vertebroplasty and kyphoplasty, which are minimally invasive procedures for treating vertebral compression fractures (VCF). In vertebroplasty, physicians use image guidance to inject a cement mixture through a hollow needle into the fractured bone. In kyphoplasty, a balloon is first inserted through the needle into the fractured vertebral body to restore at least some of the height and shape of the vertebral body, followed by removal of the balloon cement injection into the cavity formed by the balloon.

BRIEF SUMMARY

A cannula system may comprise a cannula that has a curved configuration and a straightened configuration, and a straight stylet that is configured to strain the cannula from the curved configuration to the straightend configuration when inserted into the cannula. In some variations, the straight stylet comprises a piercing tip that may be suitable for piercing tissue. Additionally, the straight stylet may comprise a distal section connected by a bend section to a proximal section. The distal section may have a piercing tip. The bend section may be between the distal and proximal sections, and may have a reduced axial cross-sectional area relative to the proximal section and/or the distal section. The bend section and the proximal section may comprise a tapered transition or an abrupt transition.

Another variation of a cannula system may comprise a first cannula with a first configuration and a second configuration, and a first stylet configured to bend the first cannula from the first configuration to the second configuration when inserted into the first cannula. The cannula system may further comprise a second cannula, a second stylet, and an exchange wire. The second cannula may have a straight configuration. The first stylet may have a configuration that corresponds to the second configuration of the first cannula, and the second stylet may have a configuration that corresponds to the first configuration of the first cannula. The first configuration of the first cannula may be a curved configuration, and the second configuration of the first cannula may be a less-curved configuration. The less-curved configuration may be a substantially straightened configuration. In some variations of a cannula system, the first stylet is a straight stylet and the second stylet is a curved stylet.

One variation of a spinal treatment kit may comprise a cannula comprising a proximal connector, and a tissue removal device that is configured to reside in the cannula. The tissue removal device may comprise a handle, a shaft, and a travel limiter configured to be coupled to the proximal connector, and to provide the tissue removal device with a range of axial movement relative to the cannula when attached to the cannula. The travel limiter may comprise a releasable lock configured to reduce the range of axial movement of the tissue removal device relative to the cannula. In some variations, the range of axial movement may be from about 0 mm to about 10 mm, or from about 0 mm to about 5 mm. Additionally or alternatively, the travel limiter may be configured to provide a first selectable range of movement, and a selectable lock position that provides substantially no range of movement. Optionally, the travel limiter may be configured to provide a second selectable range of movement. The first and second selectable ranges of movement may both be preset ranges of movement. The cannula may comprise a first configuration and a second configuration, where the second configuration is more straightened than the first configuration.

Methods of accessing a target site in a patient are also described here. One variation of a method for accessing a target site in a patient may comprise inserting a straight stylet into a cannula comprising a non-linear configuration to at least partially straighten the non-linear configuration. The at least partially straightened cannula may be inserted into a patient, and the straight stylet may be removed from the cannula while substantially maintaining the cannula in the patient. The method may additionally comprise inserting an instrument into the cannula. In some variations, the method may comprise manipulating axial displacement of the instrument relative to the cannula.

Methods of accessing a target site in the spine region of a patient are also described here. One variation of a method for accessing a target site in the spine region of a patient may comprise inserting a straight stylet into a curved cannula with a curved distal portion to form a first cannula-stylet assembly with a straight distal portion. The first cannula-stylet assembly may access the spine region, and the straight stylet may be proximally withdrawn from the first cannula-stylet assembly. A curved stylet with a curved distal portion may be inserted into the curved cannula to form a second cannula-stylet assembly with a curved distal portion. The second cannula-stylet assembly may be advanced to the target site in the spine region.

Methods for treating a herniated disc are also described here. One variation of a method for treating a herniated disc may comprise inserting a straight stylet into a curved cannula with a curved distal portion to form a first cannula-stylet assembly with a straight distal portion. The first cannula-stylet assembly may penetrate the disc annulus of the herniated disc. The straight stylet may be proximally withdrawn from the first cannula-stylet assembly, and a curved stylet with a curved distal portion may be inserted into the curved cannula to form a second cannula-stylet assembly with a curved distal portion. The second cannula-stylet assembly may be advanced to a herniated area. The curved stylet may be proximally withdrawn from the second cannula-stylet assembly, and a tissue removal device may be inserted into the curved cannula. A portion of the nucleus pulposus may be removed using the tissue removal device. The tissue removal device may be proximally withdrawn from the curved cannula, and a straight stylet may be inserted into the curved cannula. The straight stylet and the curved cannula may be proximally withdrawn.

Methods for treating a vertebral body are described here. One variation of a method for treating a vertebral body may comprise inserting a straight stylet into a curved cannula with a curved distal portion to form a first cannula-stylet assembly with a straight distal portion. The first cannula-stylet assembly may penetrate the surface of the vertebral body, and the straight stylet may be proximally withdrawn from the first cannula-stylet assembly. A curved stylet with a curved distal portion may be inserted into the curved cannula to form a second cannula-stylet assembly with a curved distal portion. The second cannula-stylet assembly may be advanced into a target site within the vertebral body, and the curved stylet may be proximally withdrawn from the second cannula-stylet assembly. A tissue removal device may be inserted into the curved cannula, and may remove a portion of cancellous bone. The tissue removal device may be withdrawn proximally from the curved cannula. A straight stylet may be inserted into the curved cannula, and the straight stylet and the curved cannula may be proximally withdrawn.

In some variations, a tissue removal system may be provided, comprising a rotatable shaft, a tissue removal element attached to the rotatable shaft and configured to displace and retract from the rotatable shaft, and a tissue transport structure comprising at least one helical element with a serrated edge. The tissue transport structure may comprise a plurality of helical elements. At least one helical element may comprise a distal serrated edge and a proximal non-serrated edge. The tissue transport structure may comprise a tubular structure with a plurality of helical slots arranged with the plurality of helical elements. The rotatable shaft may be located in a lumen of the tubular structure. The tubular structure may further comprise a recess configured to receive the tissue removal element. The tissue removal element may comprise a helical configuration. The tissue removal element and the at least one helical element may have the same helical winding direction, which may be a right-handed helical winding or a left-handed helical winding. In other embodiments, the tissue removal element and the at least one helical element may be opposite helical winding directions. The tissue removal system may further comprise an outer tube in which the tissue transport structure at least partially resides. The outer tube may comprise a beveled distal opening.

In another variation, the tissue removal system comprises a rotatable shaft, a tissue removal element attached to the rotatable shaft and configured to displace and retract from the rotatable shaft, and a tubular impeller comprising a lumen, wherein the rotatable shaft is located in the lumen. The tubular impeller may comprise at least one strut and at least one slot. The tubular impeller may comprise a plurality of struts and a plurality of slots. The at least one strut may comprise a leading edge and a trailing edge. The leading edge may comprise a serrated section. The leading edge may comprise proximal non-serrated section and a distal serrated section. The trailing edge is non-serrated. The tubular impeller may further comprise a recess in which a portion of the tissue removal element resides. The tissue removal system may further comprise an outer tube in which the tubular impeller at least partially resides. The outer tube may comprise a beveled distal opening.

BRIEF DESCRIPTION OF THE DRAWINGS

FIG. 5A is a side elevational view of an embodiment of a tissue removal device; FIG. 5B is a detailed cutaway view of the device in FIG. 5A.

FIGS. 18A and 18B are perspective and side elevational views of another embodiment of a tissue removal device.

FIG. 19A schematically depicts one embodiment of a flexible tissue removal device; FIG. 19B is a schematic side elevational view of the proximal end of the flexible tissue removal device of FIG. 19A with a portion of the housing removed.

FIGS. 20A and 20B are schematic side and superior cross-sectional views of a steerable tissue removal device inserted into a vertebral disc, respectively.

FIG. 21A depicts the distal end of another embodiment of a tissue removal device with a blunt tip and in an extended configuration; FIGS. 21B to 21D depict various views of the tissue removal device in FIG. 21A in the retracted configuration.

FIGS. 38B and 38C depict how a portion of the travel limiter may be assembled together. FIG. 38D to 38G depict a latch mechanism that may be used with the travel limiter.

FIGS. 39D to 39F schematically illustrate examples of cable configurations that may be used with the tissue removal assembly depicted in FIG. 39A.

FIGS. 41A to 41H depict examples of a tissue transport assembly that may be used to transport tissue between the tissue removal assembly and a collector of the tissue removal device. FIG. 41A depicts one variation of a drive member. FIGS. 41B to 41H depict variations of impellers that may be used with the drive member of FIG. 41A.

DETAILED DESCRIPTION

Figure 1:
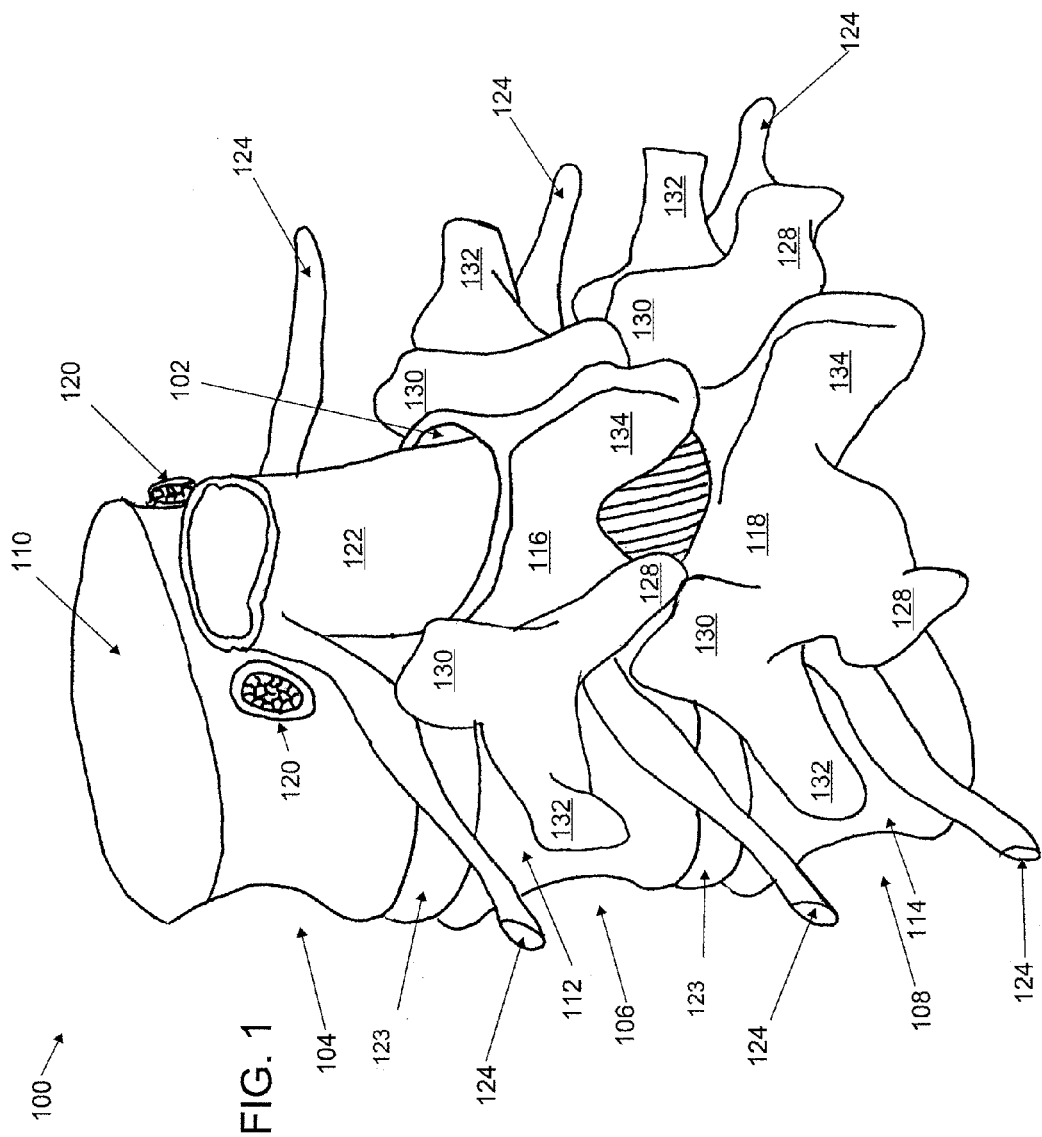
FIG. 1 is a schematic perspective view of a portion of a lumbar spine.
Figure 2:
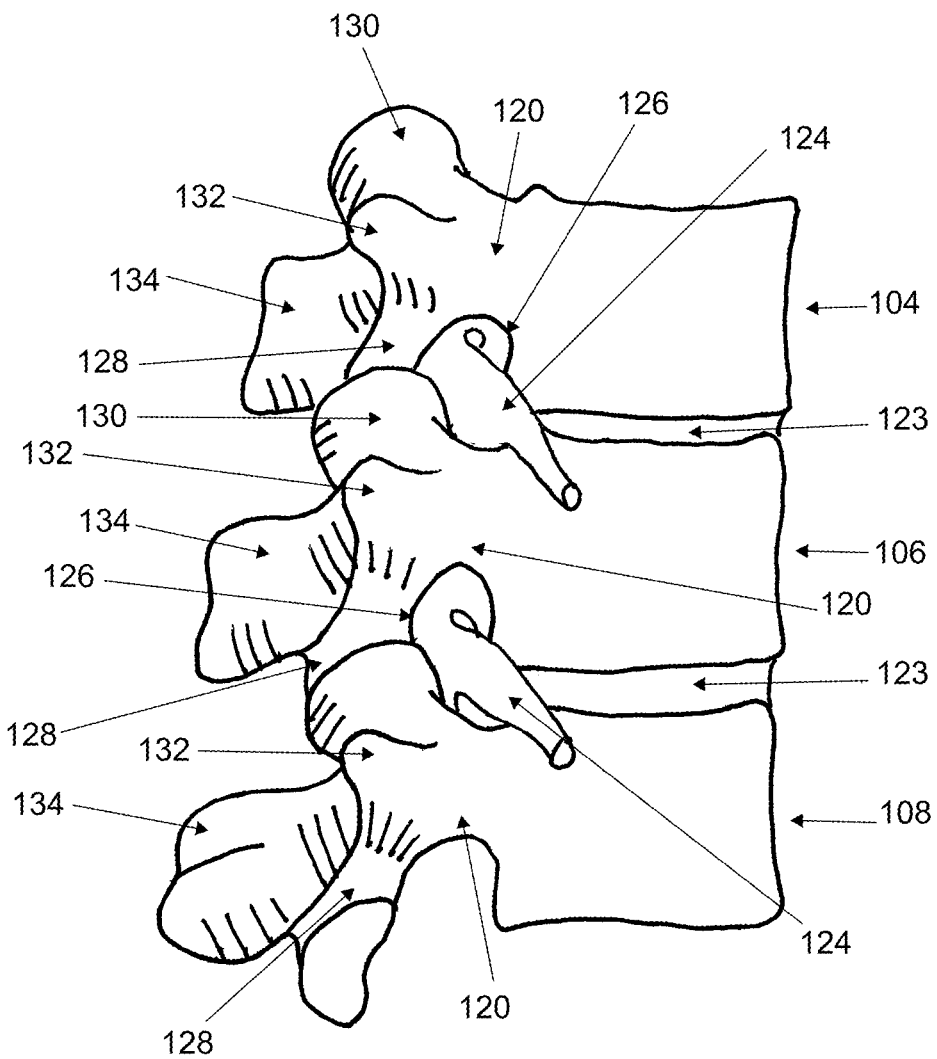
FIG. 2 is a schematic side elevational view of a portion of the lumbar spine.

FIGS. 1 and 2 are schematic views of a lumbar region of a spine 100. The vertebral canal 102 is formed by a plurality of vertebrae 104, 106, and 108, which comprise vertebral bodies 110, 112 and 114 anteriorly and vertebral arches 116 and 118 posteriorly. The vertebral arch and adjacent connective tissue of the superior vertebra 104 has been omitted in FIG. 1 to better illustrate the spinal cord 122 within the vertebral canal 102. Spinal nerves 124 branch from the spinal cord 122 bilaterally and exit the vertebral canal 102 through intervertebral foramina 126 (seen best in FIGS. 2 and 3) that are formed by the adjacent vertebra 104, 106 and 108. The intervertebral foramina 126 are typically bordered by the inferior surface of the pedicles 120, a portion of the vertebral bodies 104, 106 and 108, the inferior articular processes 128, and the superior articular processes 130 of the adjacent vertebrae. Also projecting from the vertebral arches 116 and 118 are the transverse processes 132 and the posterior spinous processes 134 of the vertebrae 106 and 108. Located between the vertebral bodies 110, 112 and 114 are the vertebral discs 123.

Figure 3:
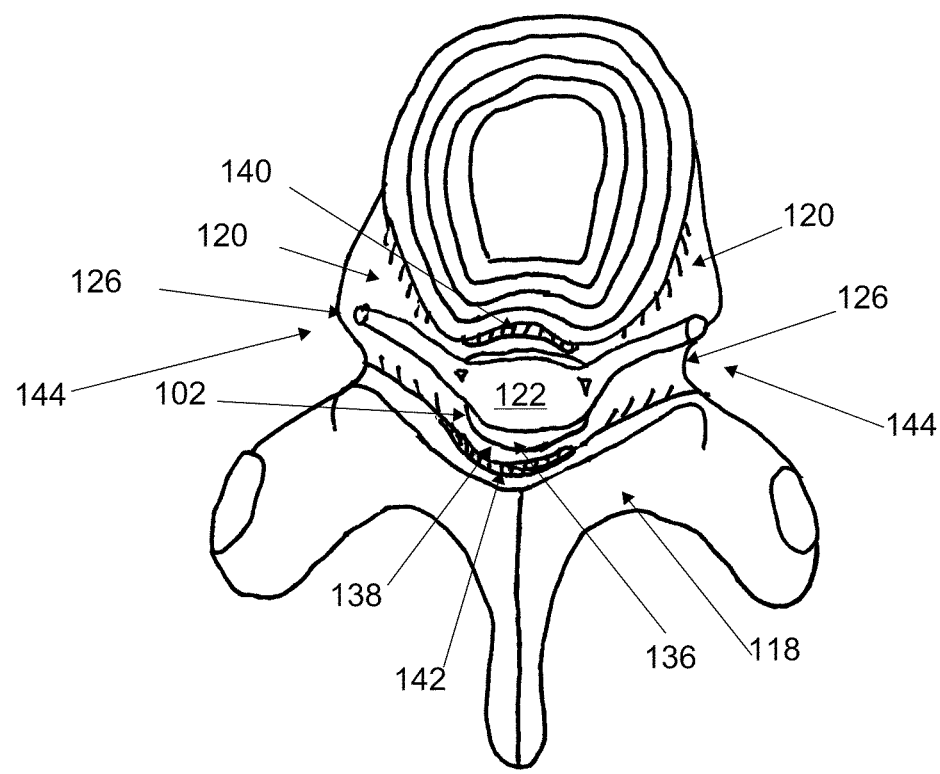
FIG. 3 is a schematic superior view of a portion of a lumbar vertebra and disc.

Referring to FIG. 3, the spinal cord 122 is covered by a thecal sac 136. The space between the thecal sac 136 and the borders of the vertebral canal 102 is known as the epidural space 138. The epidural space 138 is bound anteriorly and posteriorly by the longitudinal ligament 140 and the ligamentum flavum 142 of the vertebral canal 102, respectively, and laterally by the pedicles 120 of the vertebral arches 116 and 118 and the intervertebral foramina 126. The epidural space 138 is contiguous with the paravertebral space 144 via the intervertebral foramina 126.

Figure 4A:
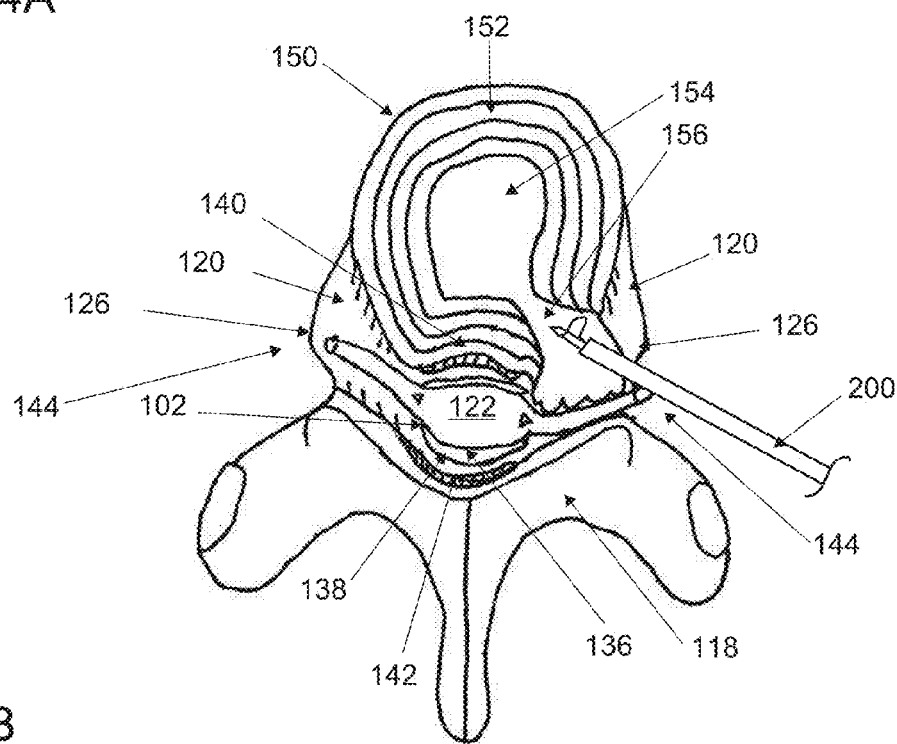
FIGS. 4A and 4B are schematic superior views of a herniated disc during and after treatment, respectively.

Referring to FIG. 4A, a vertebral disc 150 typically comprises an outer, multi-layer, annular band of connective tissue, known as the annulus fibrosus 152, which encases a gel-like resilient material known as the nucleus pulposus 154. The nucleus pulposus 154 acts as a shock-absorbing structure for the forces acting on the spine. Both the annulus fibrosus 152 and the nucleus pulposus 154 are elastic collagenous structures which, over time, may decrease in elasticity and cause the nucleus pulposus to bulge out at a weakened region of the annulus fibrosus 152, and even extrude through the annulus fibrosus 152. FIG. 4A schematically depicts an extrusion 156 of the nucleus pulposus 154, which has penetrated through the wall of the annulus fibrosus 152 within an intervertebral foramen 126 and compressed a nerve 124 exiting the spine. Although the extrusion 156 remains in continuity with the remaining nucleus pulposus 154, the extrusion 156 may sometimes pinch off or separate, resulting in the sequestration of a portion of the nucleus.

Figure 4B:
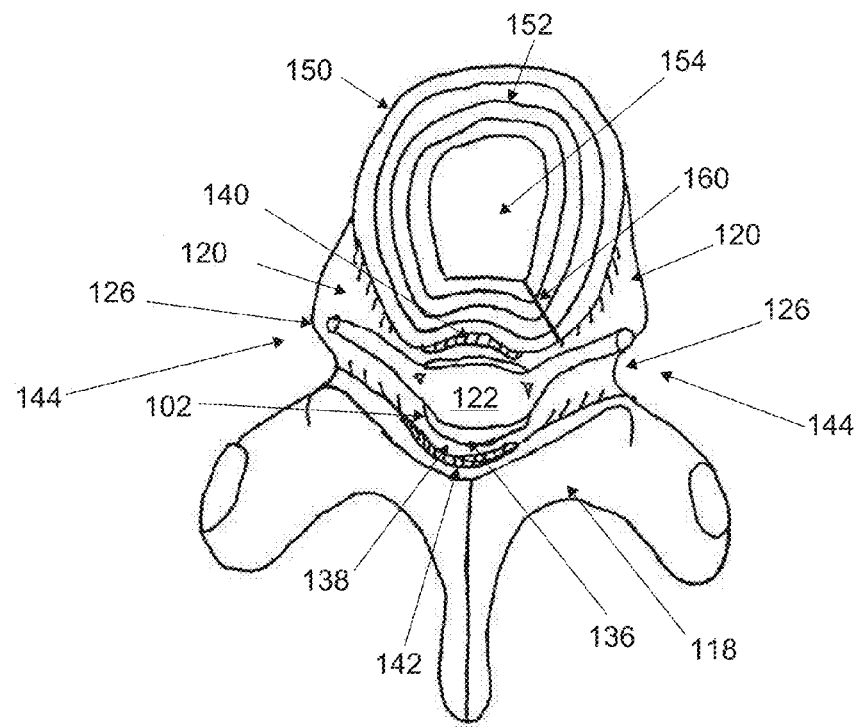

As mentioned previously, treatments of disc herniation may involve internal access to the affected disc with removal or volume reduction of the disc material. This may relieve the pressure causing the bulging or extrusion to at least partially restore the profile of the disc. In FIG. 4A, for example, a tissue removal device 200 has been inserted into the extrusion 156 extending out of the herniated disc 150. The tissue removal device 200 is then actuated to break up and remove the extruded material. In some embodiments, the tissue removal device 200 may be further inserted distally into the disc 150. Additional tissue with the disc 150 may then be removed. As shown in FIG. 4B, after removing a volume of the nucleus pulposus 154 and relieving some of the pressure causing the extrusion 156, the extrusion 156 was able to retract back into the disc 150, thereby reducing the extrusion pathway 160 and relieving compression of the spinal nerve 124. Although contralateral access of the herniated disc is depicted in FIG. 4A, ipsilateral access may also be used. Furthermore, direct tissue removal of the extruded herniated disc may also be performed.

Devices used to remove disc tissue for discectomy or nucleotomy may include lasers, discectomes, trephines, burrs, rongeurs, rasps, curettes and cutting forceps. Many of these devices have a substantial cross-sectional size, and when inserted into a disc, create an insertion channel which substantially compromises the integrity of the annulus fibrosus at the insertion site. Thus, any remaining nucleus pulposus material may extrude or herniate through the insertion site without taking measures to suture or otherwise close the insertion site, thereby adding complexity to the discectomy or nucleotomy procedure.

In contrast, a tissue removal device may be configured for minimally invasive insertion toward or into a vertebral disc without requiring suturing, gluing or other procedures to seal or close the access pathway into the disc. The tissue removal device may be used for any of a variety of procedures, including but not limited to discectomy, nucleotomy, lysis of adhesions, and other tissue removal procedures in the spine and throughout other regions of the body. FIG. 5A depicts one embodiment of a tissue removal device 2, comprising an outer tube 4 coupled to a housing 6. The static outer tube 4 covers a rotating drive shaft (not shown) that is attached to a tissue removal assembly 8. In other embodiments, the tissue removal device 2 may lack an outer tube and the drive shaft of the tissue removal device may be inserted into a lumen of a cannula or other access device. The housing 6 contains one or more components configured to control the tissue removal assembly 8 and other optional features of the tissue removal device 2. The tissue removal assembly 8, examples of which are described in greater detail below, may be configured to cut, chop, grind, burr, pulverize, debride, debulk, emulsify, disrupt or otherwise remove tissue when rotated at various speeds. Emulsification includes, for example, forming a suspension of tissue particles in a medium, which may be the existing liquid at the target site, liquid added through the tissue removal device, and/or liquid generated by the debulking of the tissue. Optional components may include, but are not limited to, a motor configured to rotate or move the tissue removal assembly, a power source or power interface, a motor controller, a tissue transport assembly, an energy delivery or cryotherapy assembly, a therapeutic agent delivery assembly, a light source, and one or more fluid seals. The optional tissue transport assembly may comprise a suction assembly and/or a mechanical aspiration assembly. One or more of these components may act through the outer tube 4 to manipulate the tissue removal assembly and/or other components located distal to the housing 6, or from the housing 6 directly. For example, the tissue removal device 2 further comprises an optional port 20 that may be attached to an aspiration or suction source to facilitate transport of tissue or fluid out of the target site or patient. The suction source may be a powered vacuum pump, a wall suction outlet, or a syringe, for example.

The housing 6 may further comprise a control interface 10 that may be used to control the power state of the tissue removal device 2, including but not limited to on and off states. In this particular embodiment, the control interface 10 comprises a lever or pivot member, but in other embodiments, control interface 10 may comprise a push button, a slide, a dial or knob. In some embodiments, the control interface 10 may also change the motor speed and/or movement direction of the tissue removal assembly 8. A bi-directional tissue removal device may be provided, for example, as a potential safety feature should the tissue removal assembly 8 get lodged in a body tissue or structure. The web-like connective tissue that may be found in the epidural space may get wound onto or caught up on the burr device or other tissue removal device. This connective tissue may be dislodged with a bi-directional tissue removal device by reversing the direction of rotation to unwind the tissue. The control interface 10 may be analog or digital, and may comprise one or more detent positions to facilitate selection of one or more pre-selected settings. In other embodiments, a separate motor control interface may be provided for one or more features of the motor. In still other embodiments, control interfaces for other features of the tissue removal device may be provided.

Figure 6A:
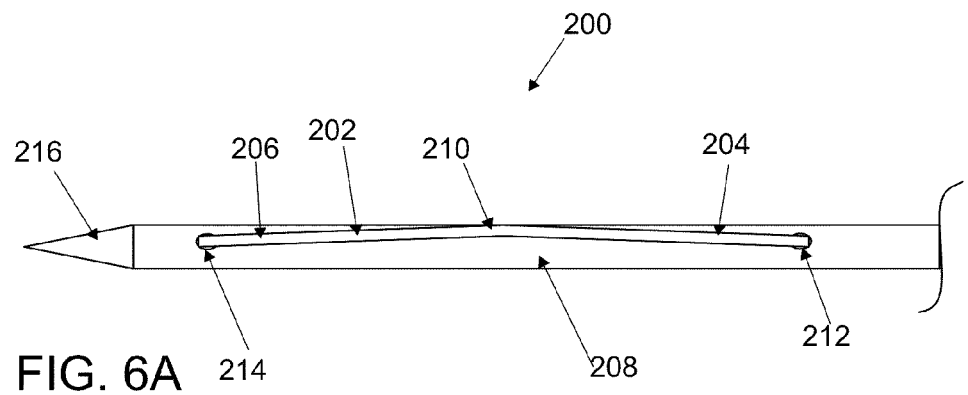
FIGS. 6A and 6B are side elevational views of an embodiment of tissue removal device with a rotatable elongate member in its retracted and extended configurations, respectively.
Figure 6B:
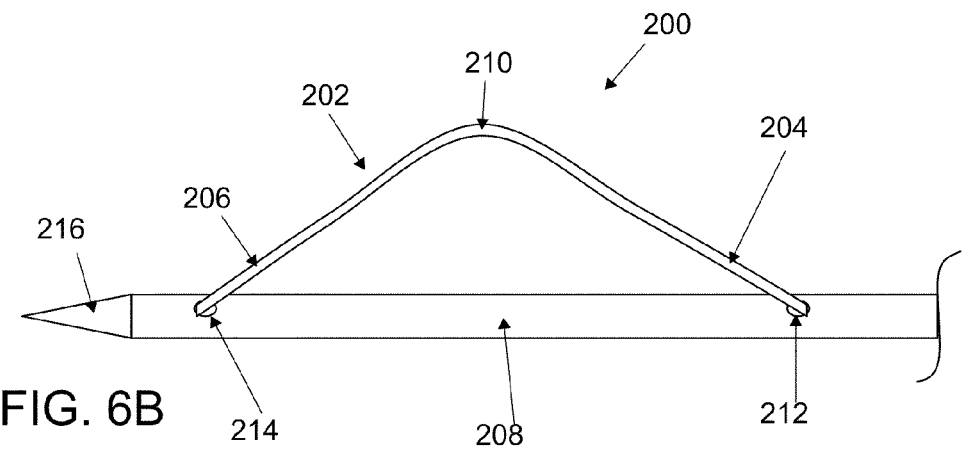

Referring to FIGS. 6A and 6B, the tissue removal assembly 200 may comprise at least one elongate member 202 having a proximal section 204 and distal section 206, with each section coupled to a rotatable shaft 208. The elongate member 202 has a retracted configuration, shown in FIG. 5A, and an extended configuration, shown in FIG. 5B. In the extended configuration, at least a portion 210 of the elongate member 202 is displaced farther away from the rotatable shaft 208 than the same portion 210 in the retracted configuration. To adjust the configuration of the elongate member 202, the proximal section 204 of the elongate member 202 may be slid in or out of a proximal opening 212 of the rotatable shaft 208 to alter the exposed length of the elongate member 208 between the proximal opening 212 and a distal opening 214 (or distal attachment of the distal section 206) of the elongate member 202. The percentage change in the length of the elongate member 202 from its retracted configuration to its extended configuration may be in the range of about 10% to about 60% or more, sometimes about 20% to about 40%, and other times about 15% to about 20%. In some embodiments, transformation of the elongate member 202 between configurations may include sliding its distal section 206 in or out of the distal opening 214, in addition to or in lieu of movement between the proximal section 204 and the proximal opening 212.

The tissue removal device 200 may further comprise a distal head 216 with a conical configuration, as depicted in FIGS. 6A and 6B. Other head configurations are also contemplated, including but not limited to an ovoid configuration, a dome configuration, a concave configuration, a cube configuration, etc. The head 216 may be configured to penetrate or dissect body tissue, such as the annular wall of a vertebral disc, and may be used while the rotatable shaft 208 is being rotated, or when the rotatable shaft 208 is not rotated. In other embodiments, the head may comprise multiple points or edges that may be used to cut, chop, grind, burr, pulverize, debride, debulk, emulsify, disrupt or otherwise remove tissue or body structures. In still other embodiments, the head may comprise surfaces with a grit that may be used as a burr mechanism. The grit number may range from about 60 to about 1200 or more, sometimes about 100 to about 600, and other times about 200 to about 500.

The head may optionally comprise a port or aperture which may be used to perform suction or aspiration at the target site and/or to perfuse saline or other biocompatible fluids or materials to the target site. Use of saline or other cooling materials or liquids, for example, may be used to limit any thermal effect that may occur from frictional or other forces applied to the target site during removal procedures. The saline or other materials may or may not be chilled. In other embodiments, one or more therapeutic agents may be provided in the saline or fluid for any of a variety of therapeutic effects. These effects may include anti-inflammatory effects, anti-infective effects, anti-neoplastic effects, anti-proliferative effects, hemostatic effects, etc.

Figure 7:
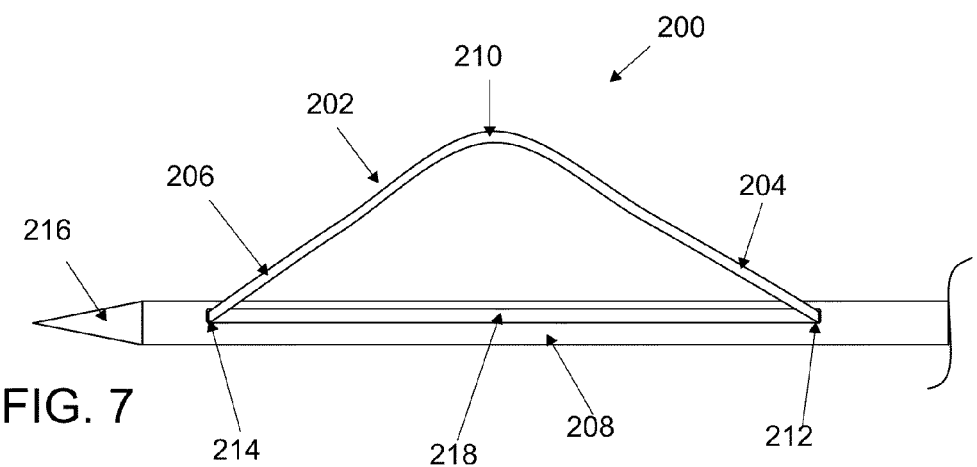
FIG. 7 depicts another embodiment of a tissue removal device with a recessed groove.

In some embodiments, the rotatable shaft may optionally comprise one or more recesses or grooves on its outer surface to receive the elongate member 202. For example, FIG. 7 depicts a single groove 218 between the proximal and distal openings 212 and 214 of the rotatable shaft 208. The depth and cross-sectional shape of the groove 218 may be configured to partially or fully receive the elongate member 202.

Figure 8:
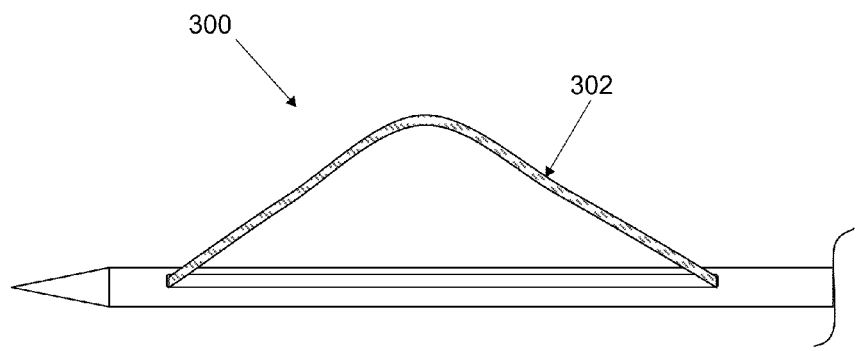
FIG. 8 depicts another embodiment of a tissue removal device with a multi-filament elongate member.

The elongate member 202 may comprise any of a variety of materials and structures. For example, the elongate member 202 may comprise titanium, a nickel-titanium alloy, stainless steel, a cobalt-chromium alloy, a polymer (e.g. nylon, polyester and polypropylene) or a combination thereof. The elongate member 202 may also have a monofilament or multi-filament structure. FIG. 8, for example depicts a tissue removal device 300 with an elongate member comprising a multi-filament cable 302. In some embodiments, a multi-filament elongate member may provide greater flexibility and/or stress tolerance than a monofilament elongate member. A multi-filament elongate member may comprise any number of filaments, from about 2 filaments to about 50 filaments or more, sometimes about 3 filaments to about 10 filaments, and other times about 5 filaments to about 7 filaments. In some embodiments, the elongate member has a flexural modulus that is less than the flexural modulus of bony tissue, such as the endplates of the vertebral bodies adjacent to a vertebral disc. In some instances, by providing a flexural modulus that is lower than certain body structures, damage to those body structures may be reduced or substantially eliminated. Thus, in some discectomy or nucleotomy procedures, a tissue removal device with an elongate member that has a flexural modulus that is less than the flexural modulus of both the bony tissue of the vertebral endplates and the flexural modulus of the annular fibrosus walls of the disc may be able to pulverize the inner tissue of a disc without damaging the adjacent walls of the disc or the vertebral bone. In some examples, the flexural modulus of the elongate member may be less than about half of the flexural modulus of intact bone or the annular fibrosis tissue, while in other embodiments, the flexural modulus of the elongate member is at least about 5 times lower, or even at least about 10 times or 20 times lower. In some embodiments, the flexural modulus of the elongate member is generally uniform along its exposed length or between its coupling sites on the rotatable shaft. For example, in some embodiments, the flexural modulus may not vary by more than about a 10× range along the length of the elongate member, while in other embodiments, the variation may be no greater than a range of about 5× or about 2×.

In some variations, the elongate member (e.g., multifilament or monofilament) of any of the variations described herein may be coated or sheathed with one or more materials. For example, the elongate member may be coated with polyimide, parylene, silicone, or urethane, or other polymer, or with an adhesive. The material may or may not penetrate into or between the filaments of a multi-filament elongate member. The coating may be applied by spray coating or dip coating, or other coating method, for example. In other examples, the material may be provided between the filaments but not on the exposed outer surfaces of the filaments, e.g. the material may be at least partially wiped or removed by air blowing from the outer surface of elongate member after spraying or dipping. In other variations, the coating material may comprise a sheath or tube that is glued or heat shrunk to the elongate member 202. In some variations, the sleeve or coating has an average thickness in the range of about 0.001 to about 0.01 inches, about 0.002 to about 0.008 inches, or about 0.003 to about 0.005 inches. The coating, sheath or tube may further comprise one or more support structures, such as a helical L304 stainless steel wire that is partially or completely embedded into the coating, sheath or tube, or adhered to the inner and/or outer surface of the coating, sheath or tube. The coating or sleeve may or may not cover the entire length of exposed or exposable elongate member or cable, and may also cover the unexposed portions of the elongate member or cable. In some variations, the coating or sleeve may be cover a portion of the proximal, middle, or distal portion of the elongate member and may be characterized as a percentage of coverage relative to the overall exposed or exposable length of the elongate member or cable, e.g. about 10%, about 20%, about 30%, about 40%, about 50%, about 60%, about 70%, about 80%, about 90%, or about 100%.

Although the elongate member 202 may have a retracted configuration and an extended configuration, the elongate member 202 may also have a native or base configuration in which the stress acting on the elongate member 202 is reduced compared to other configurations. This native configuration, if any, may be the retracted configuration, the extended configuration, or a configuration between the retracted configuration and the extended configuration. Thus, the stress exerted on the elongate member 202 in the native configuration may be lower in either the retracted configuration or the extended configuration, or a third configuration that is different from the retracted configuration or the extended configuration. In some embodiments, a native configuration that is similar to the extended configuration may be beneficial because a lower baseline stress acting on the elongate member 202 while in its extended configuration may provide greater stress tolerance from impacting tissues or bone before stressing the elongate member 202 beyond its fracture point. Although adjusting the elongate member 202 to its retracted configuration may result in greater stress acting on the elongate member 202, the stress may occur only during insertion and removal of tissue removal device 2, and without the impact stressed that act on the elongate member 202 during use. To produce the elongate member 202 with a particular native configuration, the manufacturing steps may vary depending upon the particular material or composition used. In embodiments where the elongate member 202 comprises stainless steel (e.g. 304L or 316L stainless steel) or nickel-titanium alloys, for example, a series of deformation steps and heat annealing steps may be used to form the elongate member 202 in a native, expanded configuration.

The elongate member 202 may have any of a variety of cross-sectional shapes, including but not limited to square, rectangular, trapezoidal, circular, elliptical, polygonal, and triangular shapes, for example. The cross-sectional shape and/or size may be uniform along its length, or may vary along one or more sections. In one example, the elongate member may have a tapered configuration, with a cross-sectional area that decreases from its proximal section to its distal section, or from its distal section to its proximal section. In some embodiments, the elongate member 202 may comprise a metallic wire or other elongate structure with a diameter or maximum cross-sectional dimension in the range of about 0.2 mm to about 1.5 mm or more, sometimes about 0.3 mm to about 1 mm, and other times about 0.3 mm to about 0.5 mm.

In some embodiments, the elongate member may be micropolished. Micropolishing may or may not reduce the risk of chipping or fragment formation when used to debride harder or denser body structures or tissues. In other embodiments, the elongate member may comprise a grit surface or a cutting edge along one or more portions of its length. For example, the elongate member may comprise a cutting edge with an edge angle in the range of about 90 degrees to about 10 degrees, sometimes about 75 degrees to about 15 degrees, and other times about 60 degrees to about 30 degrees, and still other times about 45 degrees to about 40 degrees. The configuration of the elongate member surface may be the same or different on opposing sides of the elongate member. For example, having different configuration on the leading surface compared to the trailing surface of the elongate member, may permit changes in the cutting, chopping, debriding, or emulsifying characteristics of the elongate member 202, depending upon its direction of rotation. In other embodiments, the leading and trailing surfaces may generally have the same features and may have similar performance in either rotation direction, but may also permit users to switch from one surface to the other if one surface has worn out. In still other embodiments, the rotation direction may be user-selected, depending upon the relative location of the tissue to be removed and any critical anatomical structures. For example, the rotation direction may be selected such that if the cutting edge 58 or 60 catches on the tissue or structure, tissue disrupting element 8 will be rotated away from the critical anatomical structure(s), if any.

Figure 9:
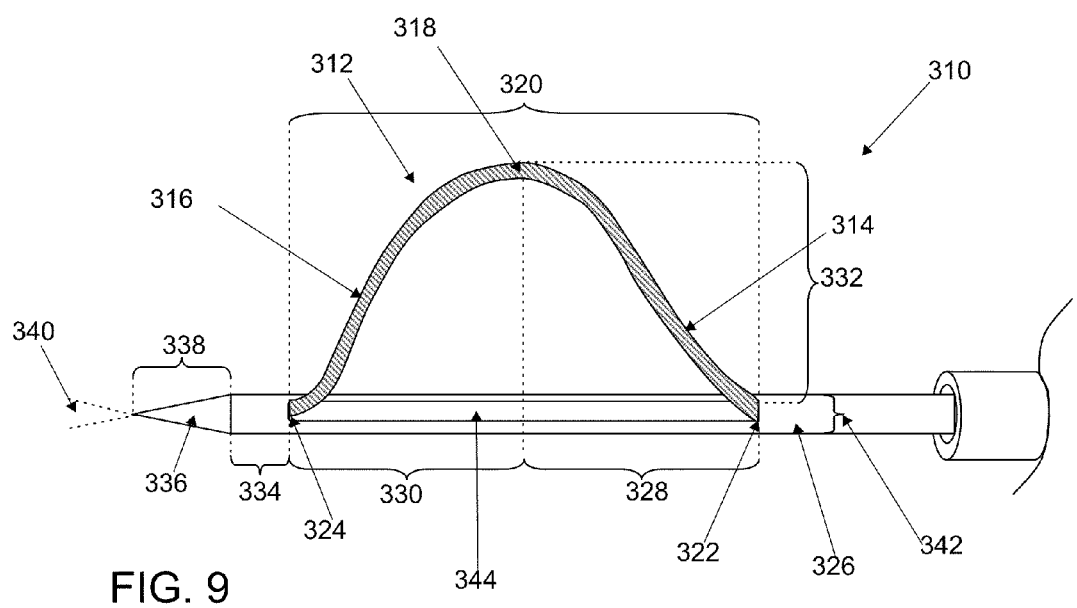
FIG. 9 depicts another embodiment of a tissue removal device.

As depicted in FIG. 6B, the elongate members 202 may have proximal and distal sections 204 and 206 with generally similar lengths and generally straight configurations, and a curved or angled middle portion 210 between them. FIG. 9, however, depicts another embodiment of a tissue removal device 310, comprising an elongate member 312 with proximal and distal sections 314 and 316 with concave configurations and a middle section 318 with a convex configuration. Other configurations are also contemplated, comprising any of a variety of linear, curved, or angled sections, and comprising symmetrical or asymmetrical configurations. In the embodiment depicted in FIG. 9, the longitudinal distance 320 between the proximal and distal openings 322 and 324 of the rotatable shaft 326 may be in the range of about 4 mm to about 30 mm or more, sometimes about 6 mm to about 15 mm, and other times about 9 mm to about 12 mm. The longitudinal distances 328 and 330 from the proximal and distal openings 322 and 324 to the peak displacement distance 332 of the elongate member 302, respectively, may be similar or different. In some embodiments, the distances 328 and 330 may be in the range of about 2 mm to about 20 mm or more, sometimes about 3 mm to about 10 mm, and other times about 4 mm to about 6 mm. The peak displacement distance 332 between the middle section 318 and the rotatable shaft 326 can vary, depending upon the particular configuration of the elongate member. The minimum displacement distance (not shown) of the middle section need not be zero, as in embodiments where the elongate member does not fully retract along its entire length against the rotatable shaft. In some embodiments, the displacement distance 318 may be in the range of about 2 mm to about 10 mm or more, sometimes about 3 mm to about 8 mm, and other times about 4 mm to about 6 mm. In some embodiments, the peak displacement distance 322 may be characterized relative to the longitudinal distance 320 or the proximal or distal distances 328 and 330 to the peak distance. For example, the ratio of the peak displacement distance to the longitudinal distance may be in the range of about 0.2 to about 1 or more, sometimes about 0.3 to about 0.8, and other times about 0.4 to about 0.5. The distance 334 between the distal opening 324 of the rotatable shaft and the distal head 336 may be in the range of about 0.5 mm to about 5 mm or more, sometimes about 1 mm to about 4 mm, and other times about 2 mm to about 3 mm. The length 338 of the head 336 may be in the range of about 2 mm to about 15 mm or more, sometimes about 3 mm to about 10 mm, and other times about 4 mm to about 5 mm. In embodiments comprising a conical or tapered head, the angle 340 of the head configuration may be in the range of about 10 degrees to about 90 degrees or more, sometimes about 20 degrees to about 60 degrees, and other times about 30 degrees to about 45 degrees.

The diameter 342 (or maximum transverse axial dimension) of the rotatable shaft 326 and/or head 336 may be in the range of about 0.5 mm to about 5 mm or more, sometimes about 1 mm to about 3 mm, and other times about 1 mm to about 2 mm. The diameter of the shaft 326 and the head 336 may be similar or different. The maximum cross-sectional dimension of the proximal and distal openings may be the same or different, and may be in the range of about 0.1 mm to about 1.5 mm or more, sometimes about 0.2 mm to about 1 mm, and other times about 0.4 mm to about 0.8 mm.

The width of the groove 344 of the rotatable shaft 326, if any, may be in the range of about 0.2 mm to about 1.5 mm or more, sometimes about 0.3 mm to about 1 mm, and other times about 0.4 mm to about 0.7 mm. The width of the groove 344 may also be characterized as a percentage of the diameter or width of the elongate member, which may be in the range of about 80% to about 400% or more, sometimes about 105% to about 300%, and other times about 150% to about 200%. As mentioned previously the depth of the groove 344 may be less than, similar to, or greater than the maximum transverse dimension of the elongate member 312. In some embodiments, the groove depth or average groove depth may be in the range of about 0.2 mm to about 2 mm or more, sometimes about 0.4 mm to about 1 mm, and other times about 0.6 mm to about 0.8 mm. In other embodiments, the depth of the groove may be a percentage of the depth of the elongate member, in the range of about 20% to about 200% or more, sometimes about 50% to about 125%, and other times about 40% to about 100%.

Although a single elongate member 202 is provided in the tissue removal device 200 depicted in FIG. 6A, other embodiments may comprise two or more elongate members. In some embodiments, however, a single elongate member may permit higher rotational speeds, due the reduced surface drag compared to tissue removal devices with multiple elongate members. In embodiments with multiple elongate members, the elongate members may be distributed uniformly or non-uniformly around the perimeter of the rotatable shaft. In some embodiments, each elongate member may have its own proximal and distal openings, but in other embodiments, two or more elongate members may share a proximal and/or distal opening. The proximal and/or distal openings may be located at the same or different longitudinal position on rotatable shaft, and each elongate member may have the same or different length or configuration. The elongate members may be independently adjustable or adjustable in groups.

Figure 10:
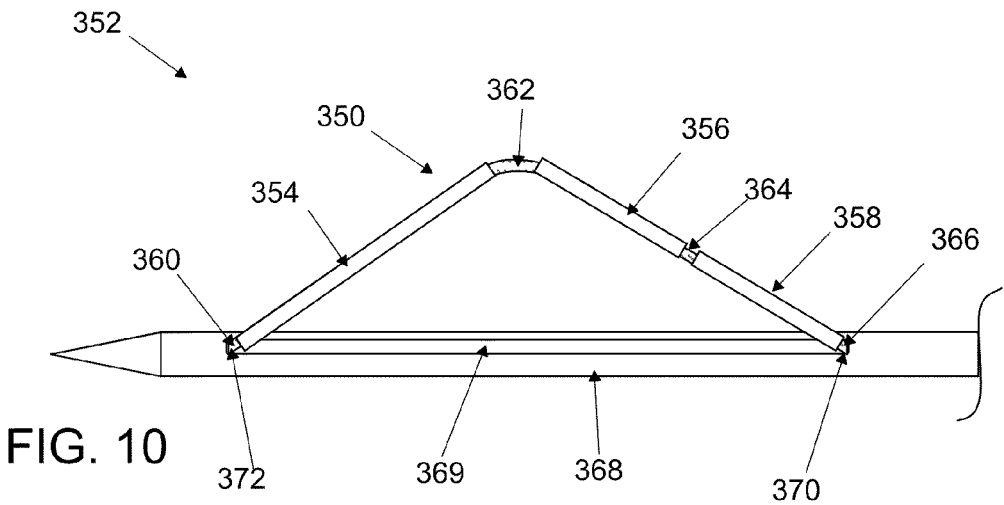
FIG. 10 depicts one embodiment of a tissue removal device with a plurality of rigid supports.

Referring to FIG. 10, in some embodiments, the elongate member 350 of the tissue removal device 352 may comprise other structures 354, 356 and 358 attached or coupled to the flexible elongate member 350. These structures may comprise any of a variety of structures, including tubes, rods, bars, cutting discs or other cutting members, beads or other structures. In the specific example depicted in FIG. 10, the elongate member 352 comprises rigid sections 354, 356 and 358 alternating between flexible segments 360, 362, 364 and 366. One or more flexible segments may also be substituted with a mechanical joint, such as a pin joint or a hinge joint. In some embodiments, the flexible elongate segments 360, 362, 364 and 366 are part of a single contiguous flexible elongate member that passes through a lumen of each rigid section 354, 356 and 358 or are otherwise coupled to each rigid section 354, 356 and 358. In other embodiments, one or more of the flexible segments 360, 362, 364 and 366 are separate and interconnect only two rigid sections 354, 356 and 358 or a rigid section and the rotatable shaft 368 or a structure therein. The particular number, shape, flexibility/rigidity, lengths and locations of the rigid segments and flexible segments may vary and need not be uniform or symmetrical. In some embodiments, the percentage of rigid section to flexible section along the length of the fully extended elongate member may in the range of about 0 to about 99%, sometimes about 50% to about 95%, and other times about 75 to about 90%. In some embodiments, the length of the flexible segment may be less than about 75% of the length of the adjacent rigid segments, sometimes less than about 50%, and other times less than about 20% or about 10%.

In the example shown in FIG. 10, the tissue removal device 352 comprises one rigid section 354 that is larger than the other rigid sections 356 and 358. The section located at the peak displacement distance of the elongate member 350 may be a flexible segment 362 as shown in FIG. 10, or a rigid section in other embodiments. The rigid sections 354, 356 and 358 are generally linear in shape, but may also be curved or angled or any combinations thereof. The elongate member 350 in FIG. 10 is also generally configured to lie in a single plane in both the retracted and extended configurations, but in other embodiments, one or more rigid or flexible sections may be oriented out of plane in the retracted and/or extended configurations. As further illustrated in FIG. 10, the shaft 368 may comprise a groove 369, or a region of the shaft with a narrow diameter or axial transverse dimension, which may reduce the overall cross-sectional area of the tissue removal device 352 by permitting the elongate member 352 to protrude less when in the retracted configuration.

Figure 11:
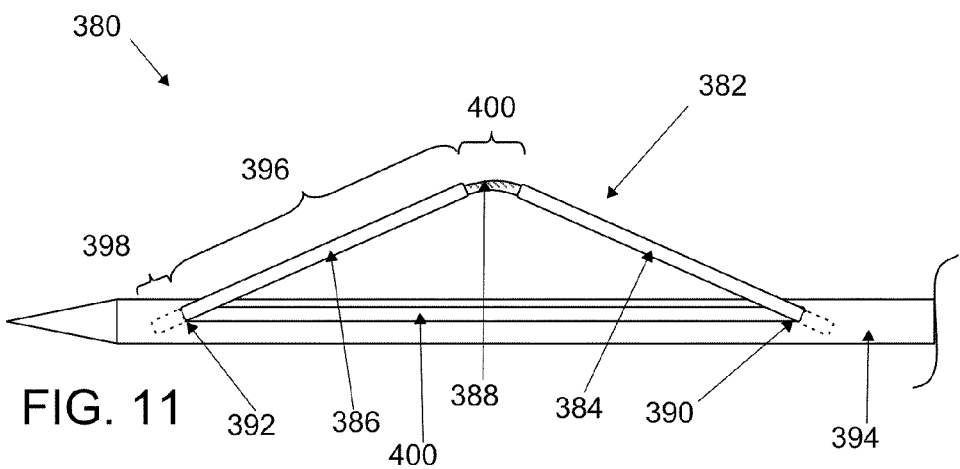
FIG. 11 depicts another embodiment of a tissue removal device with rigid supports.

As shown in FIG. 10, the elongate member 350 in the extended state may have flexible sections 366 and 360 located about its proximal and distal openings 370 and 372. In other embodiments, however, the elongate member may have a rigid section or other structure about the proximal or distal openings in the extended state. In FIG. 11, for example, the tissue removal device 380 comprises a generally symmetrical elongate member 382 with proximal and distal rigid members 384 and 386 interconnected by a flexible cable 388. In the extended configuration, the rigid members 384 and 386 are partially located or recessed within the proximal and distal openings 390 and 392 of the rotatable shaft 394. In some further embodiments, having rigid members 384 and 386 at the proximal and distal openings 390 and 392 may reduce the tilting or bending of the elongate member 382 with respect to the shaft 394. The degree with which the elongate member 382 is restricted may depend, for example, on the widths of the openings 390 and 392 and the rigid member 384 and 386, the lengths 396 and 398 of the rigid member 384 and 386 outside and inside the shaft 394, the lengths 400 of the flexible segment(s), and the overall diameter of the shaft 394, and the degree of rigidity of the rigid members 384 and 386. As further shown in FIG. 11, the shaft 394 may further comprise a groove 400 or other configuration with a reduced diameter or transverse axial dimension. At least a portion of the groove 400 or configuration is located between the proximal and distal openings 390 and 392, but the groove 400 or configuration may also be located proximal or distal to the openings 390 and 392, respectively.

Figure 12A:
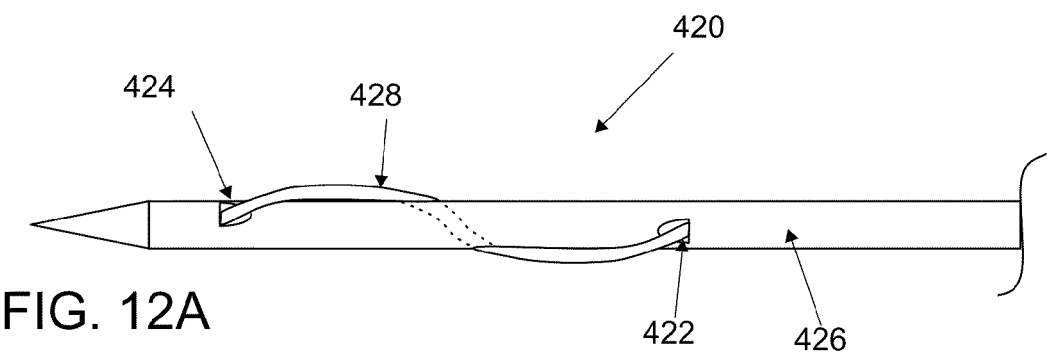
FIGS. 12A and 12B illustrate another embodiment of a tissue removal device with a helically-oriented elongate member in the retracted and extended states, respectively.
Figure 12B:
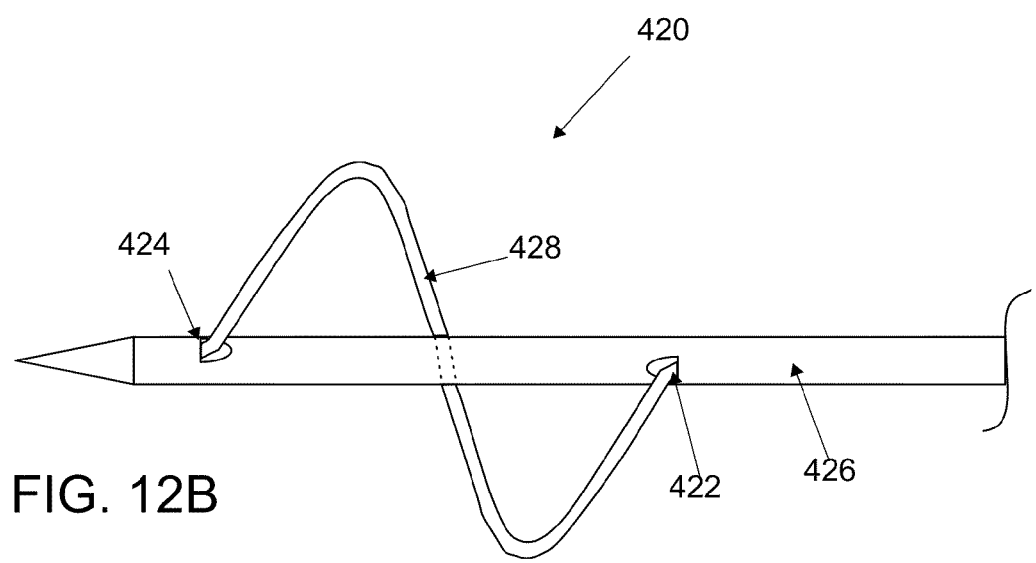

As shown in FIGS. 12A and 12B, in some embodiments, the tissue removal device 420 may have proximal and distal openings 422 and 424 which are located at different circumferential locations along the longitudinal length of the rotatable shaft 426, and/or where the elongate member 428 comprises at least one section having a helical, twisted or skewed configuration with respect to the rotatable shaft 426. FIG. 12A depicts the tissue removal device 420 in a retracted or collapsed configuration, while FIG. 12B depicts the tissue removal device 400 in an extended or expanded configurations. By extending the elongate member 408 through the proximal opening 422 of the shaft 426, the elongate member 426 may become axially compressed and expand radially outward from the shaft 426.

The configuration of the elongate member may vary in the direction of turning. For example, the elongate member may have a right or left-handed spiral orientation (i.e. a clockwise or counter-clockwise orientation). In FIGS. 12A and 12B, for example, the elongate member 428 has a left-handed or counter-clockwise spiral orientation (as viewed from the proximal end of the tissue removal device 420). The spiral orientation of the elongate member 428 may be in the same as the rotation direction of the shaft 426, or be the opposite of the rotation direction. The spiral configuration of the elongate member 428 may be characterized in any of a variety of ways. For example, the absolute number of turns may be the elongate member may be anywhere in the range from about zero (e.g. a linear elongate member) to about 4 turns or more, sometimes about a ¼ turn to about 1½ turns, and other times about ½ turn to about one turn. In other embodiments, the spiral configuration may be characterized by its rate of turning, which may be calculated as the number of turns per millimeter or centimeter. In some embodiments, the rate of turning may be in the range of about 0.3 turns/cm to about 2 turns/cm or more, sometimes about 0.7 turn/cm to about 1.5 turns/cm, and other times about 0.9 turns/cm to about 1 turn/ cm. The elongate member 428 may also be characterized by its pitch angle, which may be in the range of about 0 degrees to about 90 degrees, sometimes about 5 degrees to about 90 degrees, and other times about 45 degrees to about 85 degrees. The spiral configuration of the elongate member may be generally curved along its length, but may also comprise multiple linear segments with angled or curved bends in between. The configuration of the spiral elongate member in the retracted and extended configuration may vary, depending upon the flexibility of the elongate member, the manner and angle with which one or more ends of the elongate member are attached or fixed to the rotatable shaft, and the native configuration of the elongate member.

Figure 13A:
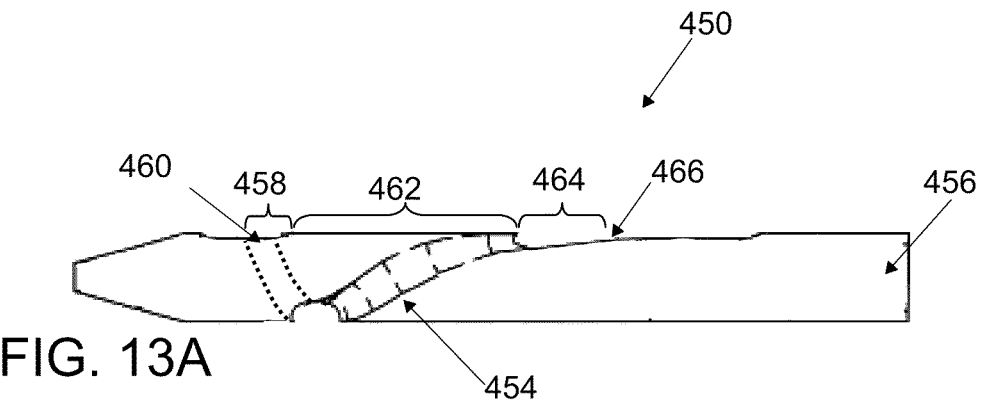
FIGS. 13A and 13B are side elevational and longitudinal cross-sectional views of another embodiment of a tissue removal device.
Figure 13B:
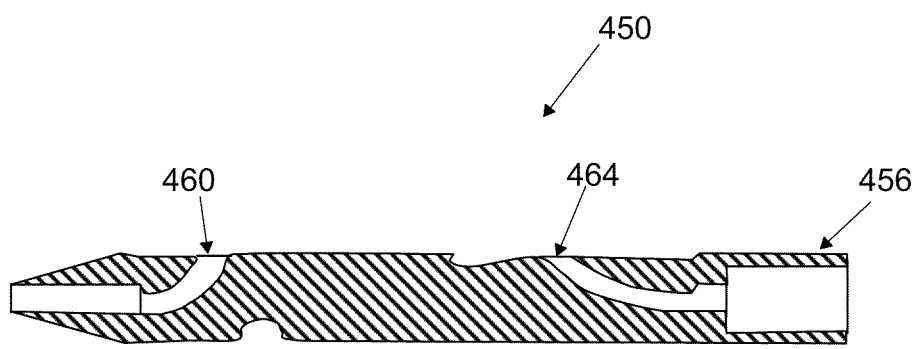
Figure 13C:
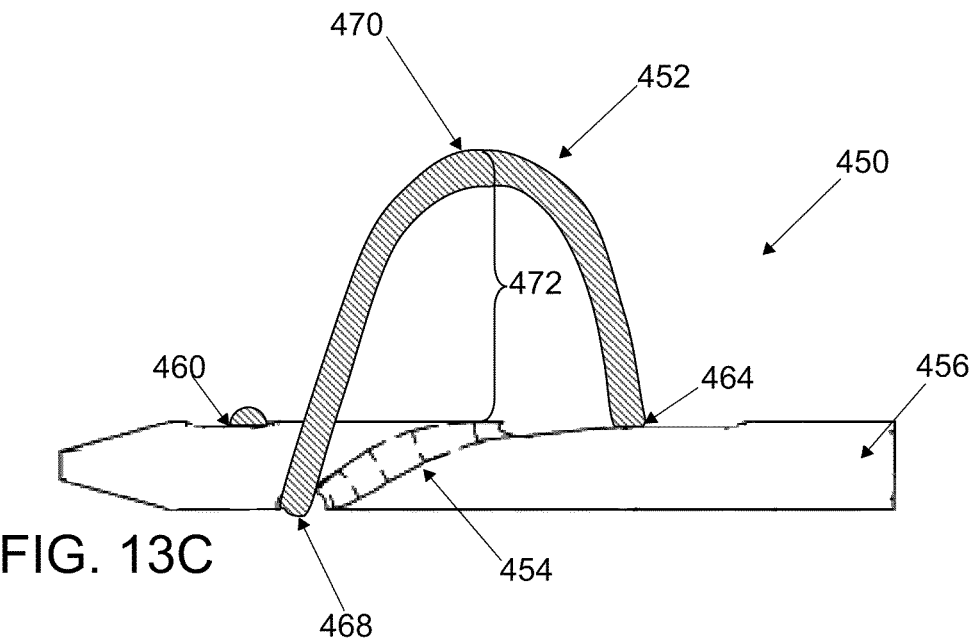
FIG. 13C is a side elevational view of the tissue removal device of FIG. 13A with a tissue-removing cable in an extended state.

As shown in FIGS. 13A to 13C, a tissue removal device 450 with a spiral elongate member 452 may also comprise one or more grooves 454 on the rotatable shaft 456. The groove 454 may facilitate seating and/or securing of the elongate member 452 in its retracted configuration. As can be seen in FIG. 13C, the spiral configuration of the elongate member 452 and the groove 454 may not be uniform along the length of the rotatable shaft 456. The distal groove 458 adjacent to the distal opening 460 comprises approximately a ½ turn along a longitudinal distance that is about 50% shorter than the ½ turn of the middle groove 462, while the proximal groove 464 between the middle groove 462 and the proximal opening 466 is generally linear. In some embodiments, the change in turn rate may be in the range of about zero to about 4 turns/cm or more, other times about zero to about 1 turn/cm, and other times about zero to about 0.5 turns/cm. In the particular embodiment depicted in FIGS. 13A to 13C, the distal portion 468 of the elongate member 452 remains generally wrapped around the shaft 456 in the distal groove 458 in the extended configuration, while the proximal portion 470 of the elongate member 452 bows radially outward. As can be seen in FIG. 13C, in this particular configuration, the peak displacement distance 472 of the elongate member 452 is located closer to the proximal opening 466 of the shaft 456 than the distal opening 460. The proximal and distal openings 466 and 460 may be oriented perpendicular to the outer surface of the shaft 456, or may be oriented at an angle or tangent with respect to the outer surface of the shaft 456, which may reduce stresses exerted onto the elongate member 452 at the openings 460 and 466. The edges of the groove 454 may also rounded along its length or at least about the openings 460 and 466. The elongate member, however, may be configured with a peak displacement distance located anywhere between the proximal and distal openings, or even extending distal to the distal opening and/or proximal to the proximal opening. In other embodiments, the elongate member may even comprise multiple peak displacement distances (e.g. a multi-angle, undulating or sinusoidal elongate member in the extended configuration). In some embodiments, the peak displacement distance 472 is in the range of about 0.5 to about 10 times greater than the diameter or transverse axial dimension of the shaft 456, sometimes about 1 to about 5 times greater, and other times about 2 times to about 3 times greater. The longitudinal location of the peak distance may be characterized as a relative position from the proximal to distal openings, which may be about −20% or less, about −10%, about 0%, +10%, about +20%, about +30%, about +40%, about +50%, about +60%, about +70%, about +80%, about +90%, about +100%, about +110% or about +120% or more.

Figure 14A:
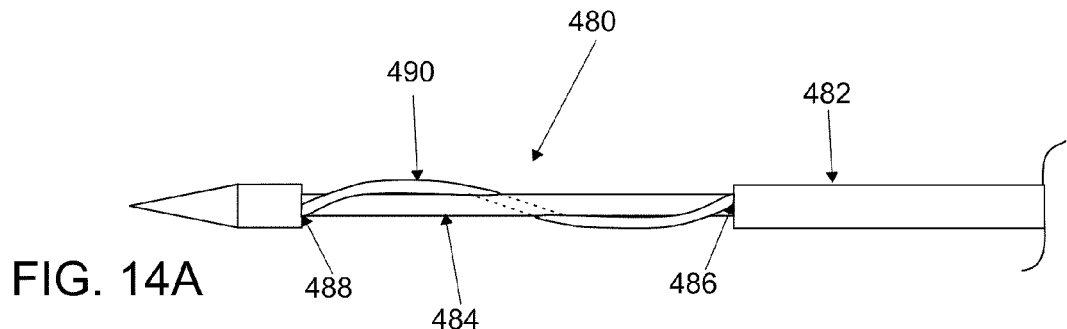
FIGS. 14A and 14B are side elevational views of another embodiment of tissue removal device in the retracted and extended configurations, respectively.
Figure 14B:
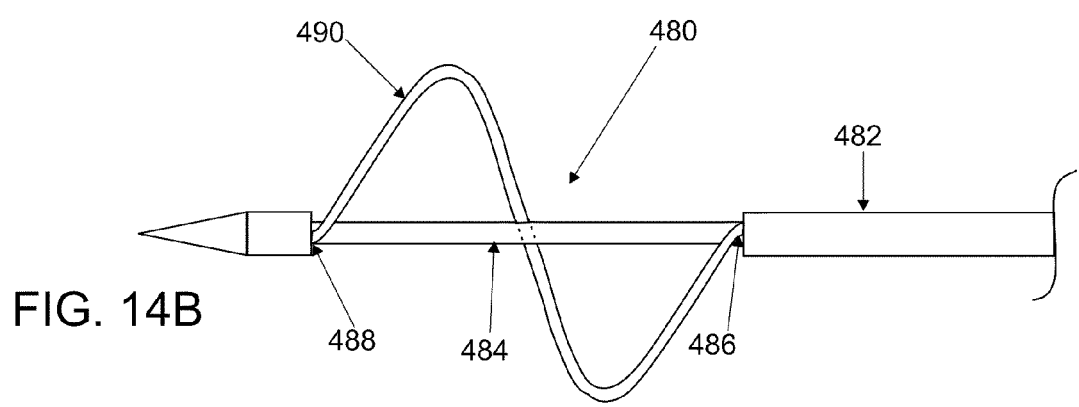

Referring now to FIGS. 14A and 14B, in some embodiments, the tissue removal device 480 may comprise a shaft 482 with a narrowed region 484. At least a portion of the narrowed portion 484 may be located between the proximal and distal attachments or openings 486 and 488 from which the elongate member 490 protrude, but in other embodiments, at least a portion of the narrowed portion 484 may be proximal or distal to the openings 486 and 488, respectively. As depicted in FIG. 14A, the narrowed portion 484 of the shaft 482 may facilitate a low profile retracted configuration, but may also provide additional space for snagged tissue or adhered biological material to occupy. This may occur, for example, when the elongate member 490 in FIG. 14B is retracted into its retracted configuration in FIG. 14A, or during a prolonged procedure. This additional space may be beneficial when withdrawing tissue removal device from an endoscopy instrument or cannula. As further illustrated in FIGS. 14A and 14B, the attachments or openings 486 and 488 may have a transverse axial orientation, rather than the surface orientation of the openings 422 and 424 of the tissue removal device 420 depicted in FIGS. 12A and 12B.

Figure 15:
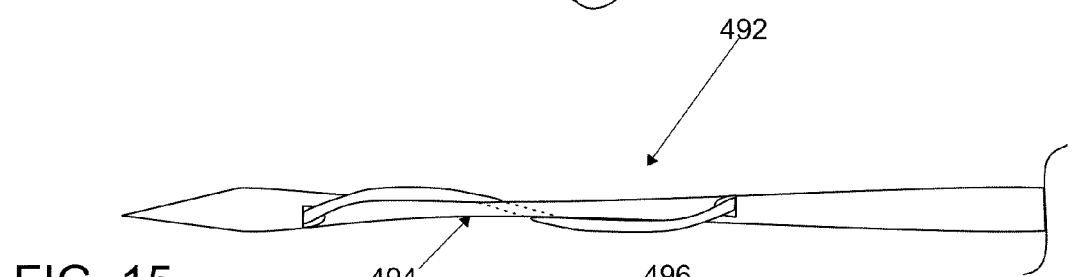
FIG. 15 is an embodiment of a tissue removal device with tapered central region.
Figure 16:
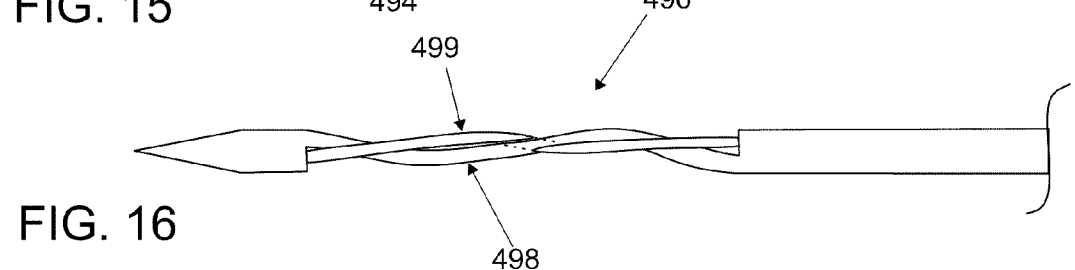
FIG. 16 is an embodiment of a tissue removal device with a narrow corkscrew region.

Although the narrowed portion 484 in FIGS. 14A and 14B has a uniform diameter and configuration, in other embodiments, such as the tissue removal device 492 in FIG. 15, the narrowed portion 494 may have a tapered configuration with a variable diameter or configuration. Referring back to FIGS. 14A and 14B, the longitudinal axis of the narrowed portion 494 may be co-axial with the axis of the rest of the shaft 482, but in some embodiments, the longitudinal axis may be different, e.g. eccentric or variable. In FIG. 16, for example, the tissue removal device 496 comprises a narrowed portion 498 with a non-linear longitudinal axis comprising a helical or corkscrew configuration. Also, although this example of the tissue removal device 496 has narrowed portion 498 and an elongate member 399 with the same helical orientation, in other example, the helical orientations may be different or opposite.

Referring now to FIG. 5B, the tissue removal device 2 in FIG. 5A is illustrated with a portion of the housing 6 removed to show various internal components. In this embodiment, the tissue removal device 2 further comprises a battery 12 to provide power to the motor 14 which drives the tissue removal assembly 8. In other embodiments, a connector to an external power source may be provided in addition to, or in lieu of, the battery 12. The type of battery and power provided may differ depending upon the particular power needs of the motor and/or other components of the tissue removal device 2.

In some embodiments, the motor 14 of the tissue removal device 2 is a DC motor, but in other embodiments, the motor 14 may have any of a variety of configurations, including but not limited to an AC or a universal motor. The motor 14 may be a torque, brushed, brushless or coreless type of motor. In some embodiments, the motor 14 may be configured to provide a rotational speed of about 500 rpm to about 200,000 rpm or more, sometimes about 1,000 rpm to about 40,000 rpm, and at other times about 5,000 rpm to about 20,000 rpm. The motor 14 may act on the tissue removal assembly 8 via the outer tube 4, or a by drive member located within the outer tube 4. In some further embodiments, a fluid seal 16 may be used to protect the motor 14 and/or other components of the housing 6 from any fluids or other materials that may be transported through the outer tube 4, or through the housing aperture 18. In some embodiments, a connector or seal may be provided about the housing aperture 18 to permit coupling of the housing 6 to a trocar, an introducer, a cannula or other tubular member into which the tissue removal assembly 8 and the outer tube 4 are inserted. In some embodiments, the tissue removal device may be used with an introducer or cannula having an outer diameter of about 0.01 cm to about 1.5 cm or more, sometimes about 0.1 cm to about 1 cm, and other times about 2 mm to about 6 mm.

As shown in FIGS. 5A and 5B, the tissue removal device 2 may further comprise a conduit 24 which may be used to connect the tissue removal device 2 and an aspiration or suction source. An aspiration or suction source may be used, for example, to transport fluid or material through a lumen or conduit of the outer tube 4 or through a tubular member in which the outer tube 4 is inserted. In one particular embodiment, the conduit 24 comprises a port 20 which communicates with the fluid seal 16 via a length of tubing 22. The fluid seal 16 is configured to permit flow of fluid or material between the outer tube 4 and the tubing 22, while permitting movement of the outer tube 4 or a drive member therein coupled to the motor 14. In other embodiments, the conduit 24 may further comprise additional components, including but not limited to a fluid or material trap, which may be located within or attached to the housing 6, or attached to the port 20 or the tubing 22, or located anywhere else along the pathway from the tissue removal assembly 8 to the suction source. In some embodiments, a separate port may be provided for infusing or injecting substances into target site using the tissue removal device 2. In other embodiments, the conduit 24 may be used for both withdrawal and infusion of materials and/or fluids, or for infusion only. Depending upon the configuration of the tissue removal device, withdrawal and/or infusion may occur at the distal end of the outer tube 4, and/or through one or more openings of the tissue removal assembly 8. In other embodiments, a port may be used to insert a coagulation catheter, an ablation catheter or other energy delivery device to the target site.

In some embodiments, the outer tube comprises an outer tubular member with at least one lumen, and an elongate drive member configured to mechanically couple the motor to the tissue removal assembly. In other embodiments, the outer tube may contain additional members, for example, to adjust or control the configuration of the tissue removal assembly. In some embodiments, the outer tube 4 may comprise one or more lumens containing control wires, which may be used to manipulate the deflections of the distal end of the outer tube. The outer tube and optional drive members may be rigid or flexible. The outer tube may be pre-shaped with a linear or a non-linear configuration. In some embodiments, the outer tube and the components is configured to be user-deformable, which may facilitate access to particular target sites, or may be user-steerable using a steering mechanism comprising one or more pull wires or tension elements. In some embodiments, a stiffening wire or element may be inserted into the outer tube to provide additional stiffness to the tissue removal device. The length of the outer tube between the tissue removal element and the motor or housing may vary from about 0 cm to about 30 cm or more in some embodiments, sometimes about 4 cm to about 20 cm, and other times about 10 cm to about 14 cm.

In other embodiments, the tissue removal device may comprise a tissue removal assembly that may be detachably attachable to the shaft of a motor or coupled to a motor. In still other embodiments, the tissue removal device may comprise a tissue removal assembly coupled to a shaft, wherein the shaft may be detachably attachable to a motor or a shaft coupled to a motor.

In some embodiments, the housing 6 is configured with a size and/or shape that permits handheld use of the tissue removal device 2. In other embodiments, the tissue removal device 2 may comprise a grip or structure located about the outer tube 4 to facilitate handling by the user, while the proximal end of the outer tube 4 is attached to a benchtop or cart-based machine, for example, or a mounted or fixed machine. In these embodiments, the grip may or may not contain any other components of the tissue removal device, such as a motor, while the machinery at the proximal end of the outer tube 4 may contain one or more other components, such as a suction system or various radiofrequency ablation components, for example. In some embodiments, the housing 6 may have a length of about 1 cm to about 12 cm or more, sometimes about 2 cm to about 8 cm, and other times about 3 cm to about 5 cm. The average diameter of the housing (or other transverse dimension to the longitudinal axis of the housing) may be about 1 cm to about 6 cm or more, sometimes about 2 cm to about 3 cm, and other times about 1.5 cm to about 2.5 cm. The housing 6 may further comprise one or more ridges, recesses or sections of textured or frictional surfaces, including but not limited to styrenic block copolymers or other polymer surfaces.

Figure 17:
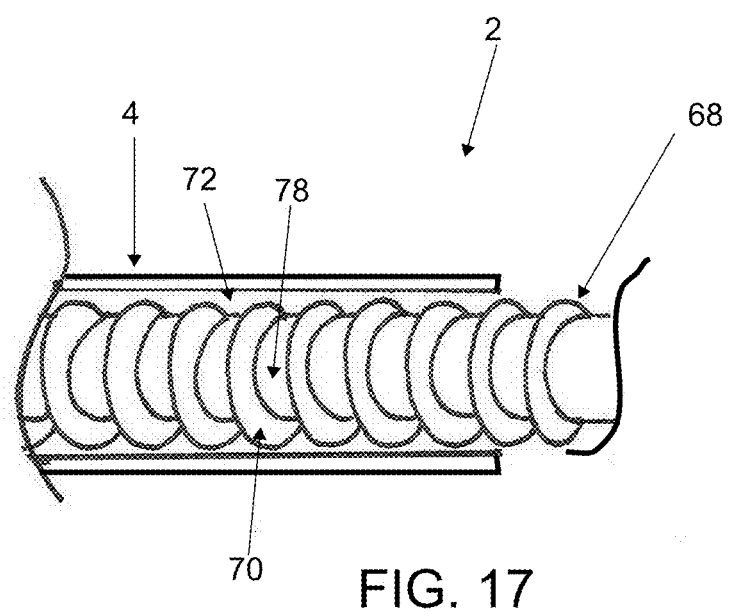
FIG. 17 is a detailed view of one embodiment of an optional tissue transport mechanism.

As illustrated in FIG. 17, a tissue removal device may optionally comprise a tissue transport assembly 68, which may be used to facilitate transport or removal of tissue within or along the outer tube 4. In the particular embodiment depicted, the tissue transport assembly 68 comprises a helical member 70 mounted on a drive member 78 that may be rotated. Actuation of the drive member 78 may mechanically facilitate proximal movement of tissue or other materials within the channel or the lumen 72 of the outer tube 4 by rotating the helical member 70. The actuated drive member 78 will also rotate the distal burr element or other tissue removal assembly 8. In some embodiments, use of the tissue transport assembly 68 may be performed at lower rotational speeds when tissue debulking is not concomitantly performed. When rotated in the opposite direction, the helical member 70 may be used expel or distally transport tissue, fluid or other materials or agents from the outer tube 4 or supplied to an infusion port of the housing 6.

In some embodiments, the helical member 70 may have a longitudinal dimension of about 2 mm to about 10 cm or more, sometimes about 3 mm to about 6 cm, and other times about 4 mm to about 1 cm. In other embodiments, the longitudinal dimension of the helical member 70 may be characterized as a percentage of the longitudinal dimension of the outer tube 4, and may range from about 5% to about 100% of the longitudinal dimension of outer tube 4, sometimes about 10% to about 50%, and other times about 15% to about 25%, and still other times is about 5% to about 15%. Although the helical member 70 depicted in FIG. 17 rotates at the same rate as the tissue removal assembly, due to their mounting or coupling onto common structure, drive member 78, in other embodiments, the helical member may also be configured to rotate separately from drive member. For example, a helical member may comprise a helical coil located along at least a proximal portion of the lumen of the outer tube but is not mounted on the drive member. In this particular example, the helical member may rotate independently of the drive member. In still other embodiments, the helical member 70 may be mounted on the surface of the lumen 72 and can be used to transport tissue or substances along the lumen 72 by rotation of the outer tube 4, independent of the drive member 78 or a tissue removal assembly.

Although the helical member 70 is depicted as a continuous structure, in some embodiments, the helical member 70 may be interrupted at one or more locations. Also, the degree or angle of tightness of the helical member 70 may vary, from about 0.5 turns/mm to about 2 turns/mm, sometimes about 0.75 turns/mm to about 1.5 turns/mm, and other times about 1 turn/mm to about 1.3 turns/mm. The cross-sectional shape of the helical member 70 may be generally rounded as depicted in FIG. 17, but in other embodiments, may have one or more edges. The general cross-sectional shape of the helical member 70 may be circular, elliptical, triangular, trapezoidal, squared, rectangular or any other shape. The turn tightness and cross-sectional shape or area of the helical member 70 may be uniform or may vary along its length. In some embodiments, multiple the helical members 70 may be provided in parallel or serially within the outer tube.

In some embodiments, the drive member 78 may be configured to extend distally and retract from the outer tube 4 by a length of about 0.004 inch to about 0.8 inch or more, sometimes about 0.008 inch to about 0.6 inch and other times about 0.01 inch to about 0.4 inch. In some embodiments, the helical member 70 is located proximal to the tissue removal assembly at a distance of about 0.004 inch to about 0.8 inch or more, sometimes about 0.008 inch to about 0.6 inch and other times about 0.01 inch to about 0.4 inch. In some embodiments, when drive member 78 is maximally extended from outer tube 4, helical member 70 may protrude from outer tube 4 by a longitudinal dimension of about 0.004 inch to about 0.8 inch or more, sometimes about 0.004 inch to about 0.4 inch, and other times about 0.1 inch to about 0.2 inch. In some embodiments, the degree of extension of the drive member 78 and/or the helical member 70 may affect the degree of tissue transport by the tissue transport assembly.

Referring to FIGS. 18A and 18B, in another embodiment, a tissue removal device 500 comprises a housing 502 and an outer shaft 504. The housing 502 may include an adjustment mechanism with a thumbwheel 506 configured to adjust the retraction and extension of extendable tissue removal assembly (not shown). The thumbwheel 506 may provide a continuous range of change to extendable tissue removal assembly, but in other embodiments, the turning of thumbwheel 506 may be configured with clicks or detents that provide one or more preset positions. As mentioned previously, any of a variety of other control mechanisms and interfaces may be used. The adjustment mechanism may comprise one or more blocking elements or other adjustment limiting configurations to resist or prevent overextension of extendable tissue removal assembly. For example, limit structures may be provided in housing 502 to resist overextension of extendable tissue removal assembly (not shown). In this particular embodiment, tissue removal device 500 is configured to rotate the tissue removal assembly at a fixed rotational speed, controllable by a rocker-type power switch 508. As mentioned previously, however, any of a variety of power and/or speed control mechanisms may be used.

Figure 18C:
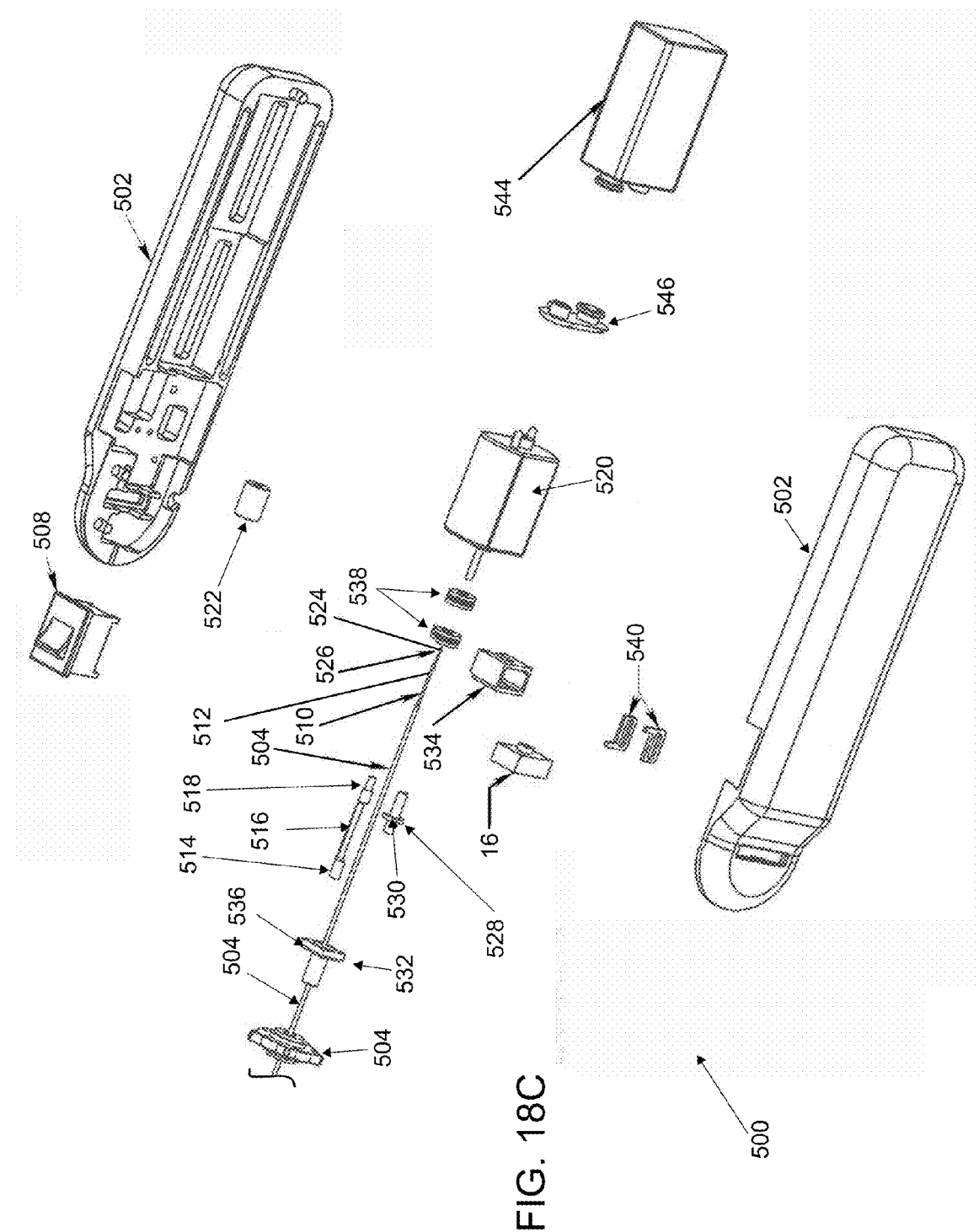
FIG. 18C is a component view of the tissue removal device in FIGS. 18A and 18B.
Figure 18D:
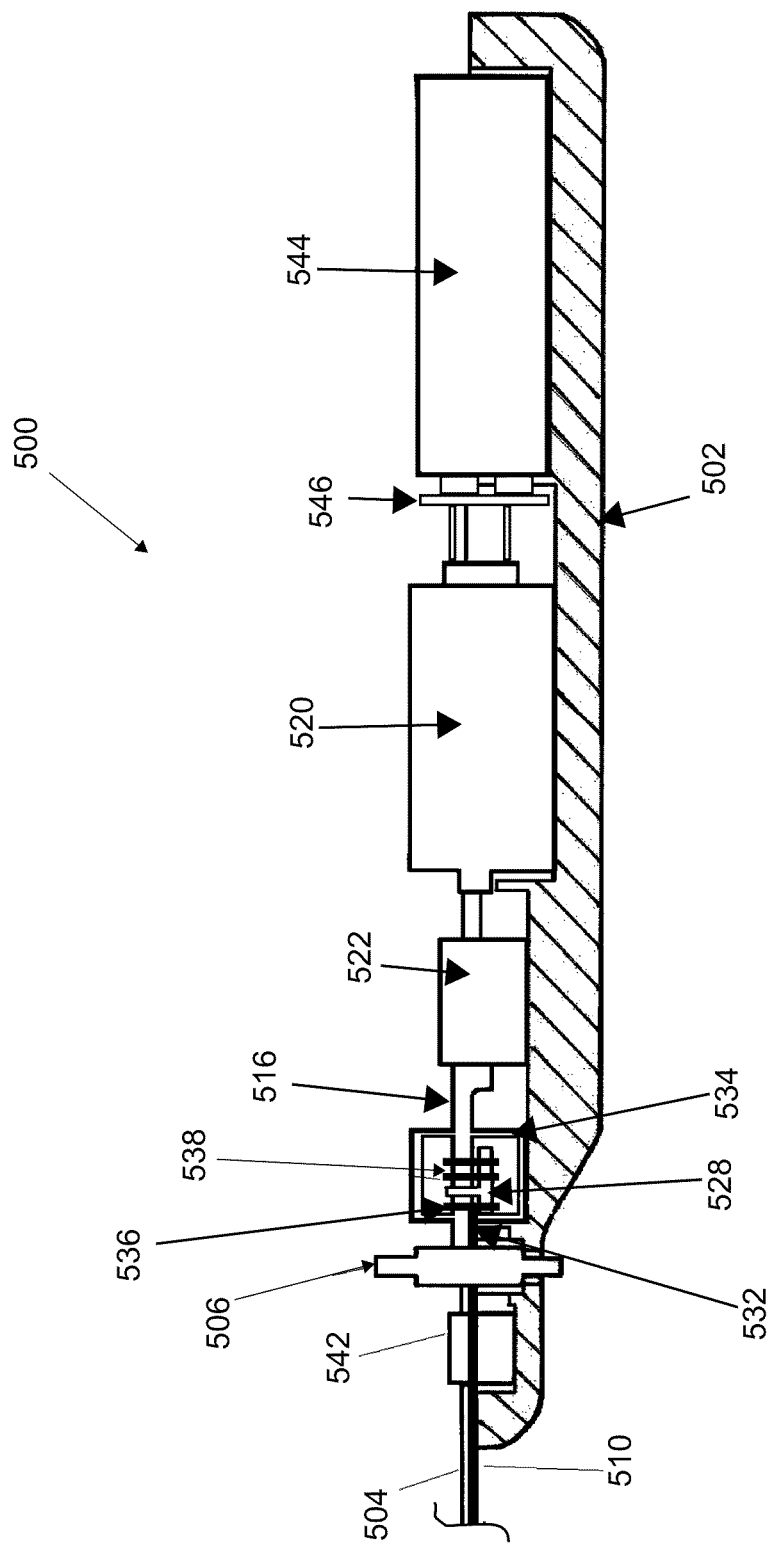
FIG. 18D is a cross-sectional view of the tissue removal device in 18A and 18B with a portion of the housing removed.

FIG. 18C is a component view of the internal components within housing 502, while FIG. 18D is a schematic cross-sectional view of the internal components with a portion of housing 502 removed. As shown in FIG. 18C, a drive member 510 rotatably resides within the outer shaft 504 of the tissue removal device 500. The distal end (not shown) of the drive member 510 is coupled to the tissue removal assembly (not shown), while the proximal end 512 of the drive member 510 is coupled to the distal end 514 of a driveshaft 516. The proximal end 518 of the driveshaft 516 may be coupled to a motor 520, either directly or through a coupler 522. The coupler 522 may be configured to permit some axial movement of driveshaft 526. The proximal end 524 of an adjustment member 526 protrudes from the proximal end 510 of drive member 512 and is attached to a drive key 528. The drive key 528 may comprise a flange 530 that is slidably located between the proximal and distal ends 518 and 514 of the driveshaft 516. The thumbwheel 506 may be movably coupled to a thrust member 532 so that the rotation of the thumbwheel 506 results in the axial movement of thrust member 532. In some embodiments, the thrust member 532 may be configured with helical threads that are complementary to a threaded lumen of the thumbwheel 506. In other embodiments, however, the thrust member may comprise a slide member, a pivot member or other coupling structure. The thrust member 532 may be configured to axially slide the drive key 528 through a retaining structure 534 which movably couples the thrust member 532 to the drive key 528. The retaining structure 534 permits the rotation of the driveshaft 516 by the motor 520 while also coupling the axial movements of the thrust member 532 to the drive key 528, thereby permitting adjustment of the tissue removal assembly located at the distal end of the shaft 504 while maintaining the ability of the drive member 510 to rotate. The thrust member 532 may comprise a flange 536 to facilitate retention of the thrust member 532 within the retaining structure 534. The flange 536 may comprise one or more bearings to facilitate rotational movement of the drive key 528 against the non-rotating flange 536. The retaining structure 534 may also contain one or more retaining bearings 538 to facilitate the rotation of the driveshaft 516 against the drive key 528 while transmitting any axial forces to the drive key 528. The retaining structure 534 is optionally provided with one or more limiters 540, which may be used to restrict overextension or retraction of the tissue removal assembly. A seal 542 may be provided around the outer shaft 504 to protect the contents of the housing 502.

As illustrated in FIG. 18D, the tissue removal device 500 may be powered using a battery 544 that is coupled to the motor 520 using a battery connector 546. As depicted in FIG. 18C, battery 544 may be a standardized battery, such as a 9-volt battery, but may also be a customized battery. Other examples of drive shafts couplings and adjustment mechanisms that may be used are disclosed in U.S. Pat. No. 5,030,201, which is hereby incorporated by reference in its entirety.

In the various examples described herein, the outer tube and the driveshaft of the tissue removal device may comprise a rigid structure and material, but may also optionally comprise at least one flexible region which may bend while still permitting rotation of the driveshaft. Examples of flexible driveshafts that may be used are disclosed in U.S. Pat. Nos. 5,669,926 and 6,053,907, which are hereby incorporated by reference in their entirety. In some examples, the flexible region(s) may comprise a substantial portion or all of the length of the driveshaft and outer tube. A tissue removal device with a flexible region may facilitate access to certain regions of the body, such as the central spinal canal through an intervertebral foramen. In some examples, the flexible tissue removal device may comprise a steering assembly that uses one or more steering wires that are attached distal to the flexible region and manipulated by a steering member in the proximal housing. Other steering mechanisms used with catheters and other elongate instruments may also be used. In other examples, an active steering mechanism is not provided on the flexible tissue removal device, but the flexible tissue removal device may be steered by an endoscopic instrument into which the tissue removal device has been inserted. Some examples of steerable endoscopic instruments are disclosed in application Ser. No. 12/199,706, which is hereby incorporated by reference in its entirety.

Figure 19C:
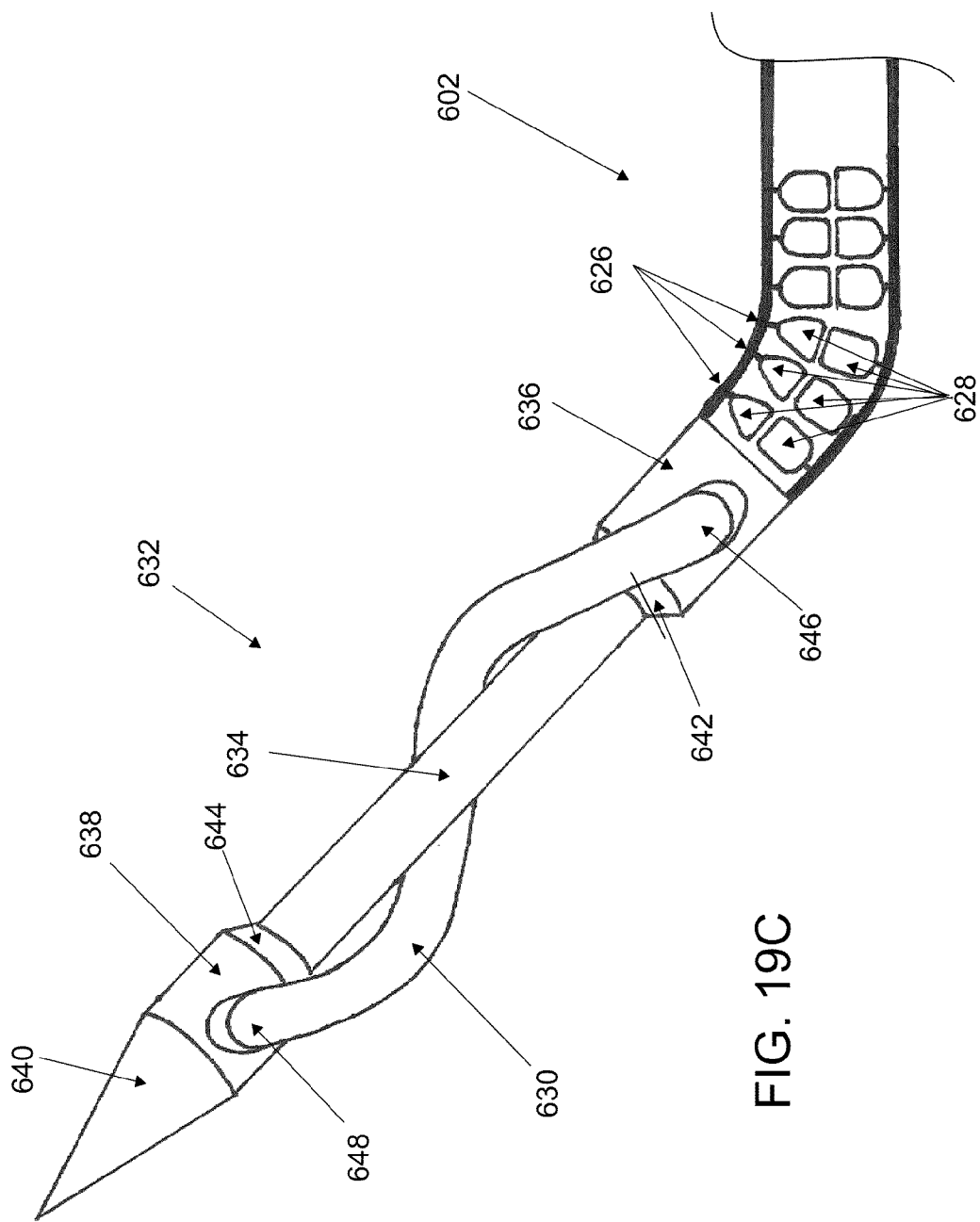
FIG. 19C is a detailed view of the distal end of the flexible tissue removal device of FIG. 19A in a bent configuration.

FIGS. 19A to 19C depict one embodiment of a tissue removal device 600 with a flexible region 602 and a steering assembly 604 located in the housing 606 of the tissue removal device 600. In addition, the housing 606 includes a power switch 608 which actuates the motor 610 that rotates the driveshaft (not shown) located in the outer tube 612, and an irrigation tube 614 which may be used infuse fluid or provide suction about the distal end of the device 600. As shown in FIG. 19B, the steering assembly 604 comprises a pivoting lever 616 with two arms 618 and 620 protruding from the housing 606. In other embodiments, the steering assembly 604 may comprise a single arm lever, a slider, knob or other type of actuator. The steering assembly 604 may optionally comprise one or more springs or bias structures, which may facilitate springback of the lever 616 once released. The steering assembly 604 may also optionally comprise a releasable locking mechanism to maintain the steering assembly in a particular configuration. The locking mechanism may be a frictional interfit or an interlocking mechanism, for example.

Coupled to the lever 616 are two steering elements or wires 622 and 624, which are slidably movable within the outer tube 614 and are distally coupled to a distal site of the flexible region 602. The steering wires 622 and 624 may be separate wires, or two segments of the same wire looped through the lever 616. When a steering wire 622 or 624 is tensioned by actuating one of the lever arms 618 and 620, the flexible region 602 will curve or bend. The flexible region may comprise any of a variety of flexible materials and/or flexible structures, including any of a variety of polymeric or metallic structures. In the depicted embodiment, the flexible region 602 comprise a plurality of optional slots 626, which may augment the bending characteristics, but in other embodiments, an accordion-like configuration or other type of bending configuration may be provided. The ends 628 of the slots 626 depicted in FIG. 19C have optional enlarged arcuate configurations, which may redistribute at least some of the bending forces that may act of the flexible region 602 and may resist tearing or reduce any resulting damage to the flexible region. The length of the flexible region may be in the range of about 0.04 inch to about 8 inches or more, sometimes about 0.2 inch to about 2 inch, and other times about 0.3 inch to about 0.8 inch. The width of the ends 628 of the slots 626, as measured in the unbent configuration along the longitudinal axis of the tissue removal device, may be in the range of about 0.02 inch to about 0.15 inch or more, sometimes about 0.04 inch to about 0.1 inch, and other times about 0.04 inch to about 0.07 inch. In still other embodiments, the flexible region may lack a particular configuration but comprises a flexible material that has a lower durometer than the other portions of the outer tube. The maximum degree of bending may vary from about 5 degrees up to about 10 degrees or more, sometimes about 15 degrees up to 25 degrees or more, and other times about 45 degrees to about 75 degrees or more, and even about 90 degrees to about 105 degrees or more in certain embodiments. In embodiments of the tissue removal device having bi-direction steering from its neutral axis, the maximum degree of bending in each direction may be the same or may be different.

As depicted in FIG. 19C, the exposed proximal and distal ends 646 and 648 of the flexible elongate member 630 may be coupled to the rotatable shaft assembly 632 through either openings or attachment sites located on the circumferential surfaces of the proximal and distal ends 646 and 648. Other sites where one or both ends of the flexible elongate member 630 may be coupled include but are not limited to the taper regions 642 and 644, if any, or any other transversely surface have at least some degree of transverse orientation with respect to the longitudinal axis of the rotatable shaft assembly 632. Still other coupling sites may include the reduce diameter core 634 and the piercing element 640.

A steerable tissue removal device may be used during some procedures to increase the region or amount of tissue removed, compared to a rigid tissue removal device, for example. In some instances, anatomical restrictions or increased risks of injury may limit the range with which a rigid tissue removal device may be manipulated. FIGS. 20A and 20B, for example, schematically depict some of the movement axes and the potential tissue removal zones that may be achieved with a steerable tissue removal device 650. Here, a steerable tissue removal device 650 with an extendable cable 652 may be inserted into a vertebral disc 653. While the steerable tissue removal device 650 and a rigid linear tissue removal device may translate and rotate with respect to its longitudinal axis 654, the pivoting range 656 of the rigid portion of the outer tube 658 of the tissue removal device 650 (and the corresponding structure on a rigid tissue removal device) may be substantially limited because even small angular movements of the outer tube 658 may be require substantial absolute displacement of the more proximal portions of the outer tube 658. This displacement, however, will be limited by the amount, the location and/or the compliance of the body tissues and structures between the proximal end (not shown) and the distal end 660 of the rigid portion of the outer tube 658. In contrast, a tissue removal device 650 with a flexible segment 662 located distally permits a range of angulation or bending 664 from the longitudinal axis 654 of the tissue removal device 650 without requiring substantial displacement or leveraging of the rigid portion of the outer tube 658. Thus, the flexible segment 662 may be able to reach tissue that is spaced apart from the longitudinal axis 654 with less physical effort, and may be even be able to reach tissue that cannot be reached by pivoting a rigid portion of the outer tube 658.

In addition to the bending of the flexible segment 662, the steerable tissue removal device 650 may also access tissues located away from the longitudinal axis 654 by increasing the extension of the extendable cable 652 along its extension range 665. The extension range 665 may be characterized as a dimension that is perpendicular to the longitudinal orientation of the core section 668 to which the extendable cable 652 is coupled. For example, a tissue removal device with about a 0.04 inch diameter core and configured with an extendable cable that may be adjusted to a perpendicular distance of about 0.1 inch away from the core can remove tissue in a zone that is about 0.27 inch in at its maximum diameter (i.e. 0.04 inch shaft plus 2 times 0.1 inch of the rotated elongate member). In embodiments where the extendable cable is extended to a greater degree, even greater volumes or zones of tissue removal may be achieved. Thus, by manipulating the degree of cable extension, the volume or range of tissue removal that may be performed may be adjusted without requiring repositioning the tissue removal device, either by torqueing its shaft or using its steering mechanism (if any).

Because the particular tissue removal device 650 in FIGS. 20A and 20B permits the actuation of the extendable cable 652 while the flexible segment 662 is bent by providing a flexible or bendable driveshaft (not shown), the tissue removal zone 670 may be displaced away from the longitudinal axis 654. Furthermore, because each of the movement described above may be synergistically combined with one or more other movements, even greater larger tissue removal zones may be achieved. For example, rotation 672 of the bent tissue removal device 650 around the longitudinal axis 654 by torqueing the rigid portion of the outer tube 658, may achieve an even larger tissue removal zone 674. The rotation 672 of the bent tissue removal device 650 may occur while the extendable cable 652 is being rotated, or when the cable 652 is not rotating. The amount of rotation 672 may be anywhere in the range of about 1 degree to about 360 degrees or more. Any of a variety of combinations of cable extension, flexible zone bending, and outer tube rotation and translation may be used to achieve the desired tissue removal.

While various flexible, steerable and rigid embodiments of the tissue removal device may be used to remove larger volumes of tissue as described above, in other embodiments, a tissue removal device may be used to perform focal debulking of tissue. For example, by utilizing the small profile and/or the steerable features of certain embodiments of the tissue removal device, the tissue removal device may be more accurately positioned or navigated to a specific target site in a body structure. In some instances, the removal of lower volumes of tissue at a specific target location may be used to achieve a desired result, in comparison to the removal of a larger volume of tissue from a general target location. Furthermore, by adjusting the cable or tissue removal element relative the shaft of the tissue removal device, the volume of mechanical tissue removal may be adjusted relative to the shaft without requiring repositioning of the shaft. By removing less disc tissue to reduce a herniation, for example, a larger amount of non-pathologic disc tissue and structural integrity of the disc may be preserved. In some instances, relatively greater preservation of the disc tissue which may slow the rate of further disc degeneration and reherniation compared to lesser degrees of tissue preservation.

In one example, a herniated disc may be accessed and visualized endoscopically. A steerable tissue removal device may be inserted into the disc and steered toward the region of herniation, rather than to the center of the disc, for example. The extendable cable or other adjustable tissue removal element is actuated to pulverize an initial amount of tissue at the region of herniation and removed by the auger. In some embodiments, to facilitate controlled volume tissue pulverization, the distance between the couplings of the extendable cable to its rotatable shaft may be less than about 0.4 inch, sometimes less than about 0.3 inch, and other times less than about 0.2 inch. To facilitate precise removal of the pulverized tissue, the distal suction opening of the tissue removal device may be located less than about 0.4 inch from the proximal coupling of the extendable cable, sometimes less than about 0.3 inch, and other times less than about 0.2 inch or about 0.1 inch. After the initial actuation of the extendable cable, the herniation is reevaluated endoscopically and the degree of cable extension may be adjusted higher in a stepwise manner and reevaluated until the desired reduction in the herniation is achieved.

In some uses of the tissue removal device, in both steerable and non-steerable configurations, the tissue removal zones may positioned whereby structures such as the annulus fibrosus and the vertebral body endplates may be unintentionally damaged or contacted. In embodiments where the tissue removal device has been configured as described previously to limit or avoid significant damage to these structures, greater tissue removal may be safely achieved even when the distal tip of the tissue removal device cannot be directly visualized, e.g. when the endoscope is located in the epidural space while the tissue removal device is located inside the vertebral disc.

In some instances, embodiments of the tissue removal device may be characterized by the ratio of the maximum diameter or cross-sectional area of tissue removal of a rotating extended elongate member, and the diameter or cross-sectional area of the outer tube of the tissue removal device or the tissue pathway formed by the tissue removal device. In the example described above, the diameter of the elongate member in its rotating deployed configuration to the diameter of the outer tube is a ratio of about 7:1. In some embodiments, this ratio is at least about 3:1 or higher, but in other embodiments, the ratio is at least about 5:1 or higher, or even about 10:1 or about 20:1 or higher in certain embodiments. In other examples, the tissue removal device may be characterized by the maximum perpendicular distance that the elongate member may be extended, or by the ratio of this distance to the diameter (or an axial transverse dimension) of the outer tube. In some examples, this ratio is at least about 3:1 or more, sometimes about 5:1 or more, or even about 7:1 or about 10:1 or more.

Examples of procedures that may be used to access the spine are disclosed in U.S. Pat. No. 7,108,705, U.S. Pat. No. 4,573,448, U.S. Pat. No. 6,217,5009, and U.S. Pat. No. 7,273,468, which are hereby incorporated by reference in their entirety. The various embodiments of the tissue removal device disclosed herein may be used to perform a discectomy or nucleotomy, but may also be used to perform any of a variety of tissue removal procedures in the spine and outside of the spine. The tissue removal device may be used in minimally invasive procedures as well as open surgical procedures or limited access procedures. These procedures may include but are not limited to interlaminar, translaminar and intralaminar access procedures. In one particular embodiment, a patient may be placed into a prone position with a pillow or other structure below the abdomen to limit lumbar lordosis. The patient is prepped and draped in the usual sterile fashion and anesthesia is achieved using general, regional or local anesthesia. Under fluoroscopic guidance, a sharp tipped guidewire, or a needle with a guidewire may be inserted into the paravertebral space or epidural space from a posterior or postero-lateral location of the patient's back at a location in the range of about 2 inch to about 6 inches lateral to the midline. In some instances, guidewire insertion may be facilitated by inserting a needle into the tissue first. In alternate embodiments, an anterior procedure through the abdominal cavity or anterior neck region may be performed. Once access to the target location is confirmed, a dilator may be used with the guidewire to enlarge the insertion pathway. Then, an introducer or cannula may be inserted over the guidewire, followed by subsequent guidewire removal and insertion of an endoscope into the introducer or cannula. Alternatively, an endoscope may be inserted over the guidewire. The endoscope may be manipulated or steered to directly visualize and identify the relevant structures such as the disc, the nerve or other adjacent structures and site(s) of tissue removal. In some embodiments where the patient is under local or regional anesthesia, the suspected nerve impingement may be confirmed by contacting or manipulating the suspected nerve with the endoscope, or other device inserted through the endoscope, and assessing the patient's response or symptoms. One embodiment of an endoscope that may be used is described in U.S. application Ser. No. 12/199,706, which has been hereby incorporated by reference in its entirety. Once the target region has been evaluated, a tissue removal device may be inserted through the spinal access device or endoscope and to pierce through the annular wall of a herniated disc. Once inserted, the tissue removal device is manipulated the elongate member to its extended or deployed configuration and actuated to emulsify or pulverize the tissue of the nucleus fibrosus. In some embodiments, the tissue removal device may be actuated for a duration in the range of about 5 seconds to about 90 seconds or more, sometimes about 15 seconds to about 60 seconds, and other times about 30 seconds to about 60 seconds. The pulverized material may then be suctioned through the device and then the effect of the tissue removal may be reevaluated by the endoscope or other visualization mechanisms. In some embodiments, a liquid or lubricant may be injected or infused into the treatment site. In some examples, the liquid or lubricant may be useful to facilitate removal of the pulverized material, including but not limited to vertebral discs that may be desiccated. In other examples, the liquid or lubricant may be injected or infused before or during the actuation of the tissue removal device. In some examples, the liquid or lubricant may comprise a contrast agent that may facilitate viewing of the tissue site on fluoroscopy, x-ray, CT, MRI, ultrasound or other imaging modalities. The contrast agent may be used at any time or at multiple times during the procedure, including but not limited to confirmation of guidewire or tissue removal device placement, and also to verify the volume and/or location of tissue removal. In some specific embodiments, actuation of the tissue removal device may be stopped to verify that annulus of the vertebral disc or the cortical bone of the vertebral body has not been compromised. Also, in some examples, the contrast agent may be injected and imaged after device to assess proper operation of the device, including but not limited to tissue pulverization and aspiration mechanisms.

During actuation, the tissue removal device may be held in place or may be moved around the treatment site. The movement may include moving the device back and forth along its insertion access, side to side, up and down, or with an orbital motion (clockwise or counterclockwise), or any combination thereof. The range of cable displacement from the rotatable shaft may also be cyclically varied during device actuation. The cycling movements may be performed based upon tactile feedback or rotational resistance of the device, or may be done in repeating motion with an average frequency in the range of about one complete motion about every 0.5 sec to about 4 seconds, about 1 second to about 2 seconds, or about 0.5 seconds to about 1.5 seconds, for example. The duration of each cycling period may be in the range of about 1 second to about 30 seconds or more, about 3 seconds to about 20 seconds, about 5 seconds to about 10 seconds, for example. Suction or aspiration may be applied during these motions to assess the amount of tissue pulverized and removed.

The actuation of the tissue removal device may be repeated as desired to remove disc material. In some embodiments, the tissue removal device may be withdrawn from the disc and reinserted directly into or against the extruded disc material and actuated. Once the tissue removal is completed, the tissue removal device may be withdrawn. The puncture site in the annular wall may have a cross-sectional area of less than about 0.003 inch$^2$ or less, sometimes about 0.0016 inch$^2$ or less, and other times about 0.001 inch$^2$ or less, and thus may self-seal without requiring treatment of the puncture location with an adhesive, a suture or coagulation probe. The body location may be rechecked with the endoscope or spinal access device to verify that no bleeding or comprise of the integrity of the disc or spinal nerves has occurred, and then the endoscope or spinal access device is removed from the body and the skin access site is bandaged.

While the embodiments described above may be used to remove soft tissue without substantially removing calcified or bony tissue, in other embodiments, the tissue removal device may be configured to remove bone. In some examples, this may include configuring the tissue removal device various bone-removing coatings and/or a higher rotational speed. The coatings may comprise coarser grit structures made from materials including, but not limited to titanium nitride, chrome alloy coating, tungsten carbide, diamond grits, silicon carbide grits, ceramics, or other suitable materials. The spiral cable may be spun at high speed (e.g. about 10,000 rpm to about 30,000 rpm or more) to grind the bone to smaller pieces that can be aspirated by the auger. Saline irrigation may be used to clean and/or cool the spiral cable and/or the surround tissue. In some further configurations, the tissue removal device may be further configured to differentially removing cancellous bone while generally preserving compact bone. Such a tissue removal device may be used, for example, to form a passageway or cavity within a vertebral body or a long bone without disrupting the integrity of the outer surface of the bony structure.

In one example, a hollow needle or trocar may be passed through the spinal muscles until its tip is precisely positioned within the fractured vertebra. This may be performed under external imaging guidance (e.g. fluoroscopy, CT or ultrasound) or using an endoscopy system. In other examples, intraosseous venography may be performed in conjunction with other visualization modalities. In some instances, intraosseous venography may be used to visualize the basivertebral venous plexus or a paravertebral vein and to possibly avoid inadvertent entry into these structures.

Upon reaching the outer surface of the vertebral body, the distal tip of the tissue removal device (e.g. the distal head 336 of the tissue removal device 300 in FIG. 8) may be used to penetrate the compact bone of the vertebral body to provide access to its interior. In other embodiments, a bone penetration device, such as a trephine or a burr, may be used to form a channel or passageway into the vertebral body. The bone penetration device is then removed and the cable-based tissue removal device may be inserted into the passageway and into the vertebral body. In other embodiments, the tissue removal device may be provided with a distal burr or drill head rather than a conical head. In some examples, the spiral cable is displaced radially outward before the rotating is initiated, while in other examples, rotation is initiated first before the spiral cable it let out. In some examples of vertebroplasty, the spiral cable may have a maximum radial displacement of about 0.15 inch, about 0.2 inch, about 0.25 inch, about 0.28 inch, or about 0.4 inch or more. In some examples, the volume of space formed by the tissue removal device may be further augmented similar to the range of tissue removal disclosed for removal of annular tissue depicted in FIGS. 20A and 20B. As mentioned previously, the spiral cable may be rotated in the directional sense as the spiral configuration, but may also be rotated in the opposite direction.

The spiral cable may be as a single filament or a multi-filament cable. Each filament may comprise the same or a different material or configuration. In some examples, each filament comprises stainless steel (e.g. 304, 316 or 17-4 stainless steel) which is wound into a cable. The stiffness of the cable may be altered by the changing the tightness of the winding, the number of filaments, and/or the thickness of the filaments. One or more of these characteristics, in combination with an optional grit surface may be used to adjust the preferential grinding features of the tissue removal device. In some procedures, by preferentially cutting the cancellous bone while preserving the compact bone, the compact bone shell or structure of the vertebrae or other bone may protect the soft tissue structures located outside the shell or surface. The compact bone shell or structure may also restrict flow of any bone cement injected into the target site. In some examples, contrast dye or other visualization agents may be injected into the target site to assess the integrity of the target site prior to cement injection or other treatments.

In another example, depicted in FIGS. 21A to 21D and FIG. 22, the tissue removal system 700 may comprise an extendable spiral cable 702 with a blunt distal tip 704. In some instances, a blunt distal tip 704 may be used when a passageway or channel has been previously formed, or when blunt dissection is sufficient. For example, during a discectomy or a vertebroplasty procedure, a cannula 706 containing a removable obturator with sharp distal end 708, as shown in FIG. 23, may be used to form a passageway or channel through the tissue surrounding the spine and/or through the surface of a vertebra. The obturator may be removed from the cannula 706 to insert the tissue removal system 700. In other examples, a trocar with a sharp distal end may be used to form a passageway and then removed to permit insertion of the tissue removal system 700. Alternatively, a trephine or bone burr, which may be either motorized or manually activated, may be used with the cannula 706, in addition to or in lieu of the obturator. The cannula 706 may comprise an optional proximal connector 709, such as Luer lock, to releasably couple the obturator and/or the tissue removal system 700. Additional variations of cannulas and stylets that may be used to create a passageway through the tissue to the spine and/or through the surface of a vertebra will be described later.

Referring to FIG. 21A, which depicts the spiral cable 702 in an extended position, and to FIGS. 21B to 21D, which depicts the spiral cable 702 in a retracted position, the cable 702 is attached distally to the blunt distal tip 704 and proximally to a base 710. The cable 702 may be partially recessed in channels 712 and 714 of the tip 704 and base 710. Between the tip 704 and base 710 is a cable shaft 716 with a cross-sectional size that is smaller than the tip 704 and/or base 710. In other embodiments, the cable shaft may have a cross-sectional size that is similar to or greater then the tip 704 or base 710. The cable shaft may also comprise an optional groove or recess to at least partially retain the cable 704 when in a retracted position.

FIGS. 21A to 21D further depict an optional feature of the tissue removal system 700 comprising an outer tubular shaft 718 with a cutting edge 720. In this particular example, the cutting edge 720 is a beveled edge, which may or may not be at least partially sharpened. In other examples, the cutting edge may be sharpened but not beveled. As further depicted in FIGS. 21A to 21D, the inner shaft 722 located in the outer tubular shaft 718 may comprise at least one optional thread structure 724 which is configured to draw fluids and/or other materials into the outer tubular shaft 718 for removal from the target site. A beveled or sharpened edge may further shear or break-up materials pulled into the outer tubular shaft 718 by the thread structure 724. In some examples, the rotational sense of the thread structure 724 may be the same as the spiral cable 702, but in other examples, the thread structure 724 and the spiral cable 702 may be opposite rotational senses.

The thread structure 724 may be made from the same or a different material as the inner shaft 722 and/or the outer tubular shaft 718. In some examples, use of a different material between the thread structure 724 and the outer tubular shaft 718 may reduce or eliminate galling effects from the relative rotation between the two structures. In some instances, galling may generate dark or black materials that may pigment the pulverized material. This pigmentation may interfere with various analyses of the pulverized material, and/or the ability of the user to assess heat-related effects of the tissue removal device on the pulverized tissue. In one specific example, the outer tubular shaft 718 may comprise 304 stainless steel while the thread structure 724 may comprise 17-4 stainless steel. The thread structure 724 may be integrally formed with the inner shaft 722, e.g. grounded or formed from a base hypotube structure, but in other examples the thread structure 724 may be attached to the inner shaft 722 by welding, adhesives or other attachment processes. For example, the thread structure 724 may comprise a coiled stainless steel or Parylene wire that may be attached using epoxy along its entire length to the inner shaft 722 or may be attached at certain locations, e.g. the proximal end and the distal end of the thread structure 724. In some instances, partial attachment of the thread structure 724 to the shaft 722 may permit greater flexion or other deformation of that section of the tissue removal system 700 by permitting greater tensile or compressive strain in the thread structure 724 compared to the inner shaft 722. This greater flexion may also reduce heat generation between the thread structure 724 and inner shaft 722.

Figure 21E:
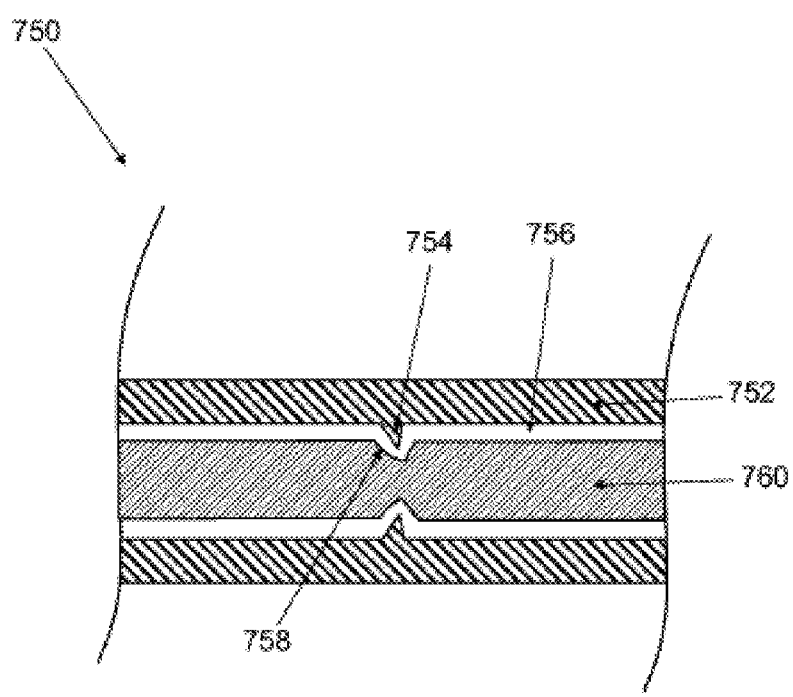
FIG. 21E depicts one example of a cutting mechanism that may be used with the tissue removal device in FIG. 21A.

FIG. 21E schematically depicts another example of a cutting mechanism where instead of a cutting edge 720 located at the distal opening of the outer tubular shaft 718 as depicted in FIGS. 21A to 21D, the tissue removal system may comprise an internal cutting or grinding mechanism 750. This mechanism comprises an outer tubular shaft 752 with an inner cutting or grinding structure 754 that protrudes into the inner lumen 756 of the outer tubular shaft 752 and cooperates with a circumferential groove or recess 758 on the inner tubular shaft 760 to morcellize, cut or otherwise breakdown any larger tissue fragments that may enter the outer tubular shaft 752. The inner cutting structure 754 may have any of a variety of configurations, including different rake angles and/or surface configurations. The configuration of the recess 758 on the inner tubular shaft 760 may vary in width and cross-sectional shape. Although only a single internal mechanism 750 is depicted, in other examples, multiple mechanisms may be provided along the shafts 752 and 760. In some further examples, an internal mechanism 750 may be used with the tip-based mechanism illustrated in FIGS. 21A to 21D.

Figure 22:
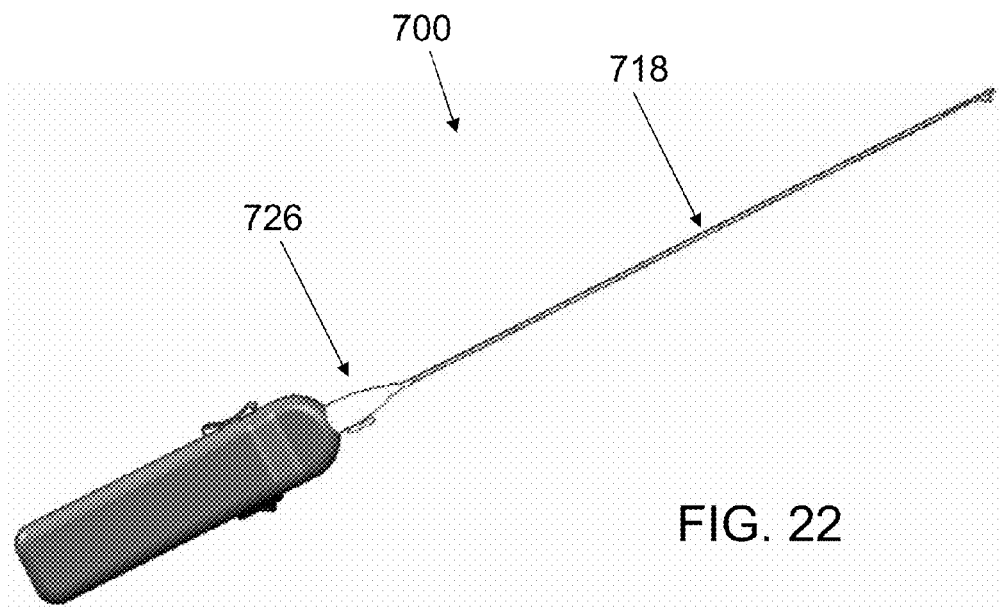
FIG. 22 illustrates the tissue removal device of FIG. 21A with an optional viewing chamber.
Figure 23:
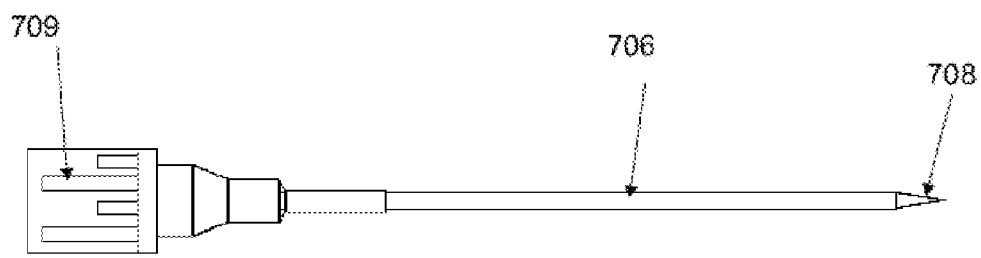
FIG. 23 illustrates an embodiment of a cannula and obturator device usable with various access systems.

FIG. 22 further depicts another optional feature of a tissue removal system 700, comprising an optically transparent chamber 726. Although the optically transparent chamber section 726 in FIG. 22 is located distally at the attachment of the outer tubular shaft 718, in other examples, the optically transparent housing chamber 726 may be located at a more proximal location. The optically transparent housing section 726 comprises an optically clear passageway or cavity in communication with the lumen of the outer tubular shaft 718 so that any fluid and/or materials either injected distally or removed proximally may be viewed by the user. In some instances, the passageway or cavity may have a volume of at least about 0.5 cubic centimeters, sometimes about 1 cubic centimeter, and other times about 2 cubic centimeters or 15 cubic centimeters or more. The quantity of fluid or tissue that may be contained within the optically transparent chamber may be less than or equal to the total volume of the chamber. For example, the total volume of an optically transparent chamber may be about 15.0 cubic centimeters, but may be configured to collect up to 10.0, 12.0, or 14.0 cubic centimeters of material. The optically transparent housing chamber 726 may also comprise markings to identify the volume of material that has aspirated or prepared for infusion or irrigation, for example. The optically transparent chamber 726 may also feature a port with a removable cap to empty the contents of the chamber 726, to reduce clogging or to collect a diagnostic tissue sample. In some examples, the tissue removal system may have one or more infusion lumens with one or more openings at the base, cable shaft, and/or distal tip of the tissue removal system, which may be used in addition to or in lieu distal end of the outer tubular shaft 718. In other examples, the tissue removal system may be removed from the vertebral body and a separate infusion instrument may be used to deliver therapeutic agents or materials.

Figure 35A:
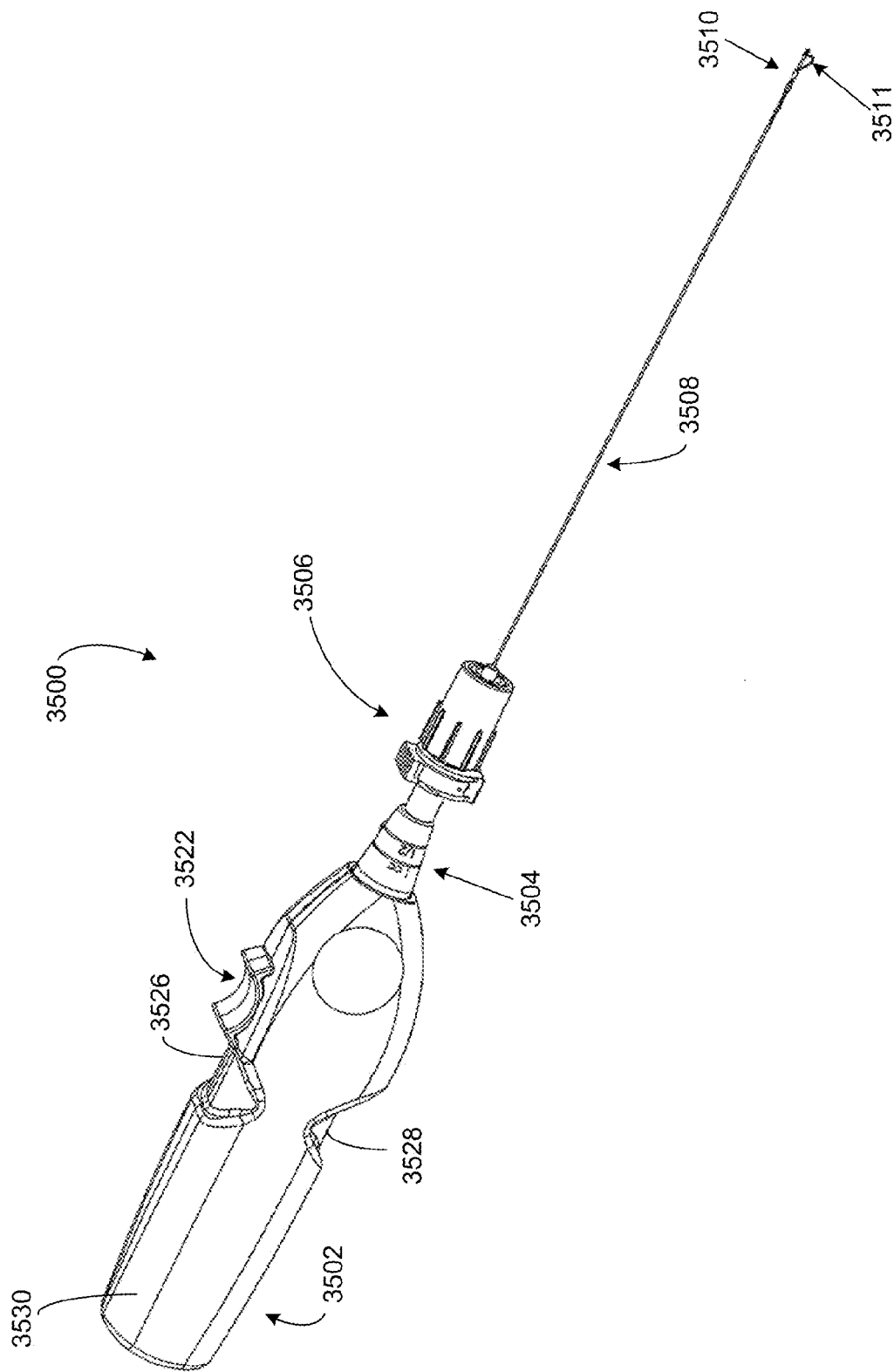
FIGS. 35A and 35B depict another variation of a tissue removal device that may be used in a discectomy procedure.

Another variation of a tissue removal device is shown in FIG. 35A. This tissue removal device 3500 comprises a handle 3502, a collection chamber 3504 which is located at a distal portion of the handle 3502, an outer tube 3508 extending from the handle through the collector 3504, a travel limiter 3506 slidable over the outer tube 3508, and a tissue removal assembly 3510 attached to a distal portion of the outer tube 3508. The tissue removal assembly 3510 further comprises an elongate member 3511, as described previously. In other embodiments, the collection chamber may be located elsewhere with respect to the handle, or may be separately attachable to a port or conduit of the handle. Additional variations of tissue removal assemblies and configurations are described below.

The outer tube 3508 may be used to provide a conduit between the distal tissue removal assembly 3510 and the collection chamber 3504 and/or handle 3502 via a longitudinal lumen therethrough. As described previously, the outer tube may be flexible, steerable, deformable, and/or bendable, as appropriate for directing the distal tissue removal assembly to the target tissue. Different flexibilities and curvatures of the outer tube may help the tissue removal device to access spinal and/or vertebral tissue, or another particular region of the body. For example, the outer tube 3508 may have one or more malleable or flexible regions along its length, which may provide additional maneuvering capability to a practitioner. In some variations, there may be one or more slotted regions along the outer tube that facilitate bending or flexing of the tube. The orientation of the slots, e.g., transverse slots, angled slots, axial slots, etc. may provide the outer tube to preferentially bend in certain directions. While the outer tube 3508 is depicted to be substantially straight, in other variations, an outer tube may have one or more pre-shaped curves, where the curves may be substantially rigid or substantially flexible. For example, a straight or curved access pathway to the target tissue may be additionally adjusted and/or shaped by the curvature of the outer tube. In some variations, access to the target tissue may be provided through a straight or curved cannula. An outer tube with one or more flexible curved regions may be straightened by sliding it into a straight cannula, or flexed by sliding it into a curved cannula. Alternatively, an outer tube with rigid curved regions may be inserted into a bendable flexible cannula and cause it to curve along the curved regions. In other variations, the outer tube may be flexed or otherwise manipulated using a steering mechanism as previously described.

The outer tube 3508 may have a tensile modulus of about 2500 MPa to about 4500 MPa, and a tensile strength greater than about 60 MPa. The outer tube may have an inner diameter of about 1 mm to about 1.5 mm, for example, 1.25 inch, and an outer diameter of about 1.3 mm to about 1.6 mm, e.g., 1.4 mm. The thickness of the outer tube wall may be from about 0.05 mm to about 1 mm, e.g., 0.075 mm. The outer tube may have a length from the tissue removal assembly to the handle housing of about 100 mm to about 500 mm, for example, at least length of about 300 mm or about 400 mm, etc.

The location of the travel limiter 3506 on the outer tube 3508 and the length of the outer tube may determine the working length of the tissue removal device 3500. For example, the travel limiter 3506 may be located at a position along the outer tube 3508 such that the tissue removal device has a working length between 4 inches and 20 inches, e.g., 6.5 inches or 7 inches. Some variations of an outer tube may have a diameter that is suitable for the insertion of an endoscope therethrough, so that the procedure, e.g., discectomy, may be directly visualized. For example, an outer tube may have a lumen through which an endoscope may be inserted. The one or more visualization lumens may be located alongside the outer tube, or may be an internal lumen of the outer tube. Some outer tube variations may be a hypotube or a multifilament braided or coiled cable. The filaments of the coil or braid in the outer tube may be about 0.001 inch to about 0.007 inch wide, and about 0.01 mm to about 0.1 mm thick. The outer tube 3508 may be made of a metal such as 304 stainless steel, a metal alloy such as nickel titanium alloy, or a polymer, such as polyimide, or a combination thereof, and may comprise any of a variety of structural configurations. For example, the outer tube may comprise a braided or extruded polyimide. Certain variations of an outer tube may be coated with an additional material to help prevent galling effects, and/or to provide thermal insulation, which may help prevent thermal damage to any tissue structures.

Figure 35B:
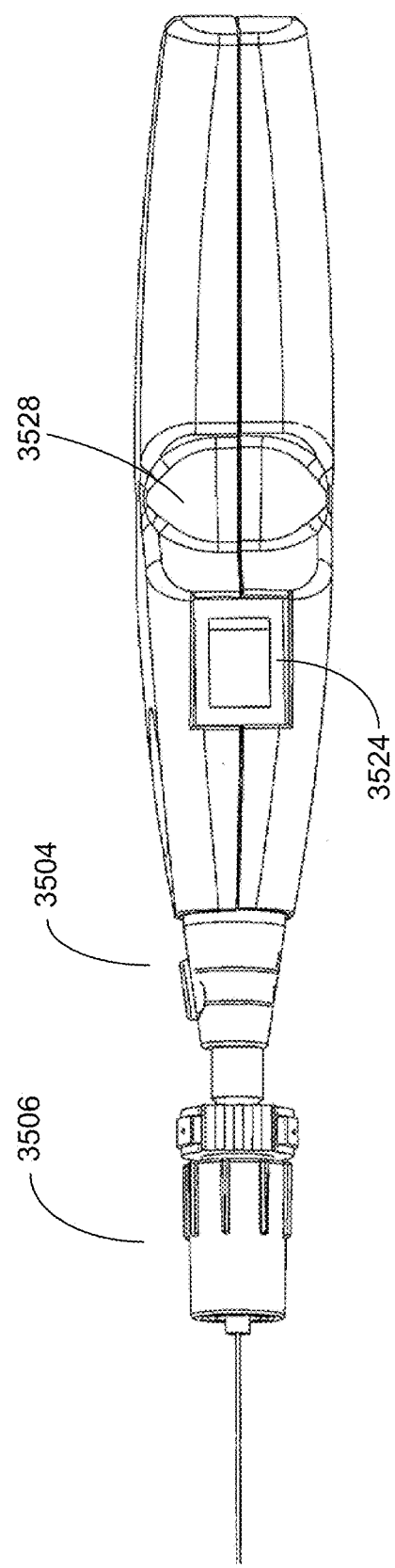

The handle 3502 may comprise a control interface that may be used to control the power state and the use of the tissue removal device 3500. The control interface may comprise a slider 3522 and a rocker-type power switch 3524, as illustrated in FIGS. 35A and 35B. The slider 3522 may regulate the configuration and use of the tissue removal assembly 3510. Other handle variations may comprise one or more push buttons, sliders, dials, or knobs. The handle housing 3530 may be ergonomically sized and shaped, such that the various components of the control interface may be readily accessed and actuated by a user. For example, the handle housing 3530 has a first recessed region 3526 and a second recessed region 3528, where the first and second recessed region are located to be suitable for a hand-hold such that the slider 3522 and the power switch 3524 may be actuated by the fingers of the same hand. The handle housing 3530 may also comprise one or more ridges, recesses or sections of textured or frictional surfaces, and may have components and dimensions similar to the variations of handles previously described.

Figure 36A:
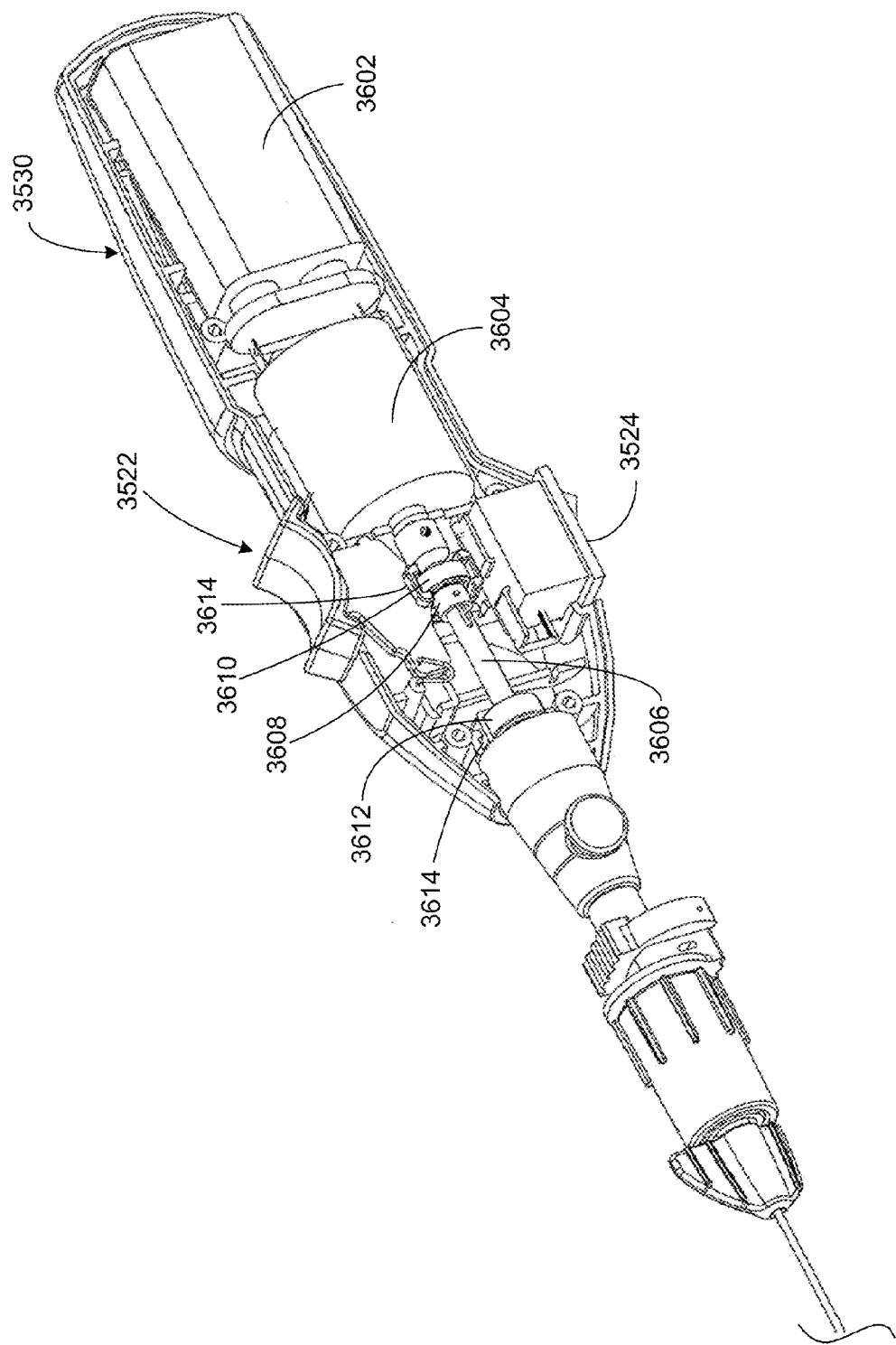
FIG. 36A depicts a partial cutaway view of the handle of a tissue removal device.

FIGS. 36A to 36E depict a perspective view of the handle 3500 with a portion of the handle housing 3530 removed and various component views of the internal mechanisms of the handle 3500. The mechanisms may serve any of a variety of function. For example, some mechanisms may control the navigation of the tissue removal assembly 3510, as well as control the configuration of the elongate member between a retracted state and an extended state. One mechanism that may be used to transition the elongate member from a retracted state and an extended state while being rotated by a motor has been previously described in FIGS. 18C and 18D. Another variation of such a mechanism is depicted in FIGS. 36A to 36E and described below. FIG. 36A illustrates a rotatable shaft 3606 that is coupled to a motor 3604 that is configured to rotate the tissue removal assembly at rotational speeds previously described. The motor 3604 may be powered by a battery 3602, e.g., a 9 volt battery, or may be coupled to an external power source. The operating range of the motor 3604 may be between 1.5 to 4.5 volts, nominally with a 3 volt constant.

The tissue removal device may be configured to provide a rotatable shaft with an axially extendable and retractable mechanism to alter the configuration of the elongate member 3511 located distally. For example, a rotatable shaft 3606 may be rotatably maintained in the handle with a first ball bearing 3610 and a second ball bearing 3612. The ball bearings may be configured to facilitate rotation of the rotatable shaft 3606. The second ball bearing 3612 is retained within a retaining structure 3613 that is affixed to the handle housing 3530, while, the first ball bearing 3610 may be movably retained in a retaining structure 3614 that is affixed to the slide actuator 3522. A coupler 3608 may be provided along the rotatable shaft 3606, where the coupler 3608 is configured to slide along the length of the rotatable shaft 3606 and interfaces with the movable first ball bearing 2610. The displacement of the coupler 3608 along the shaft 3504 by the first ball bearing 3610 provides movement of structures within the rotatable shaft while also permitting rotation of the coupler 3608 and the shaft 3606 within the first ball bearing 3610. Together, this configuration permits axial translation of the elongate member within the rotatable shaft 3606 to during rotation. In some variations, the coupler 3608 may be attached to the proximal section of the elongate member 3511 of the tissue removal assembly 3510, whereby manipulation of the slide actuator 3522 results in reconfiguration of the elongate member 3511 between a retracted state and an extended state while rotating.

Figure 36B:
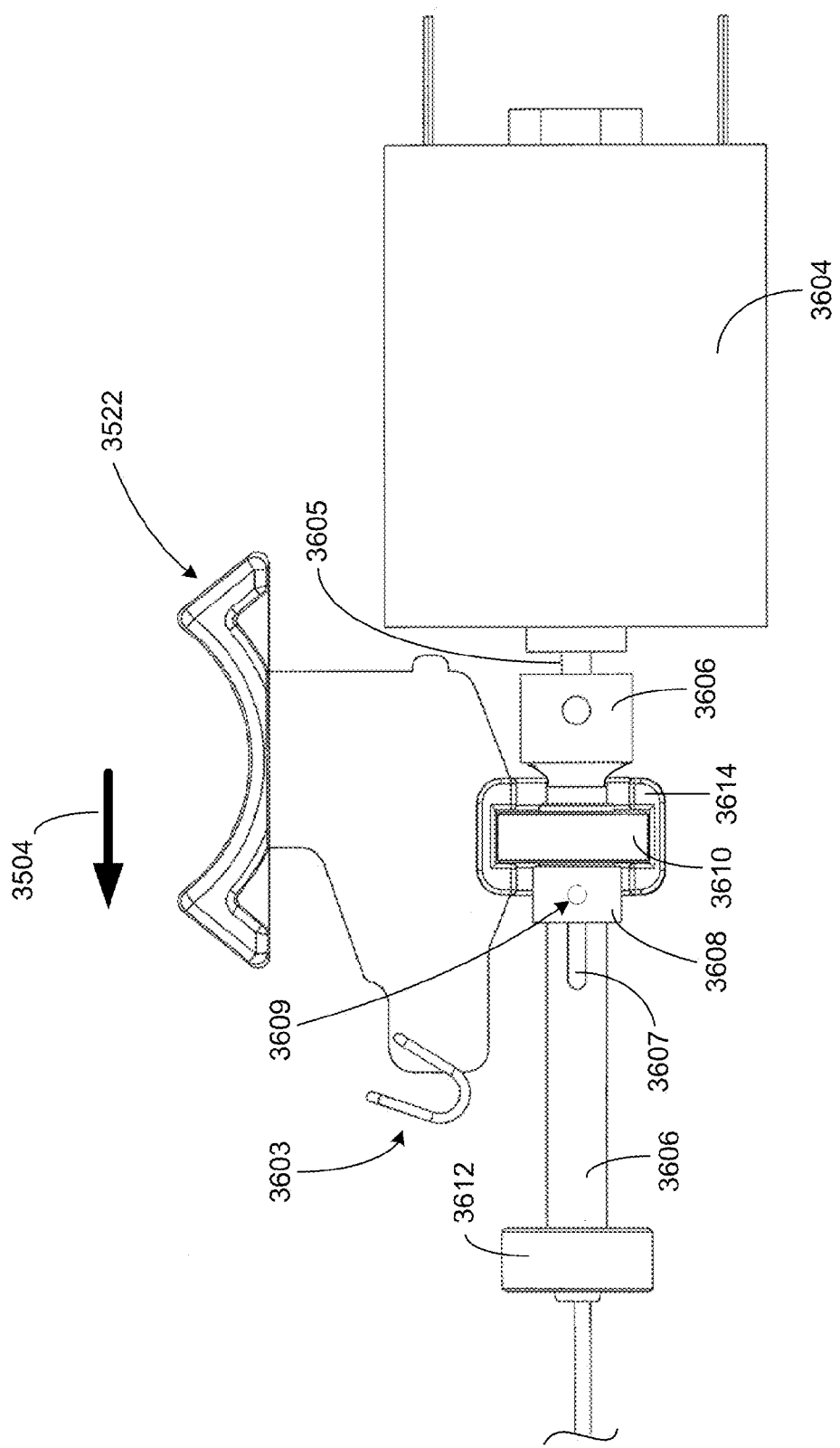
FIGS. 36B to 36E illustrate one example of a mechanism that enables a cable of a tissue removal assembly to be rotated by a motor and simultaneously axially translated by a slider.
Figure 36C:
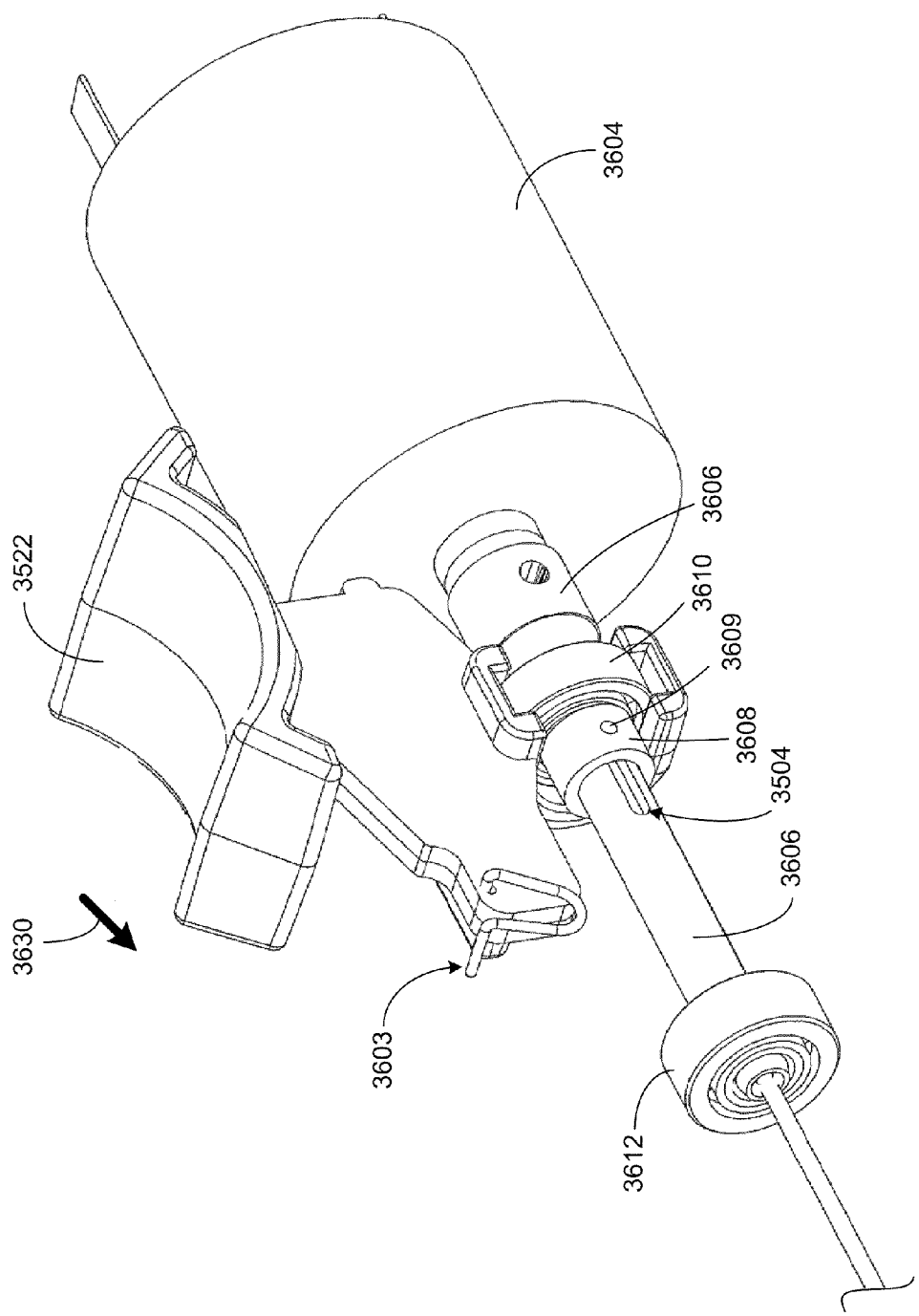
Figure 36D:
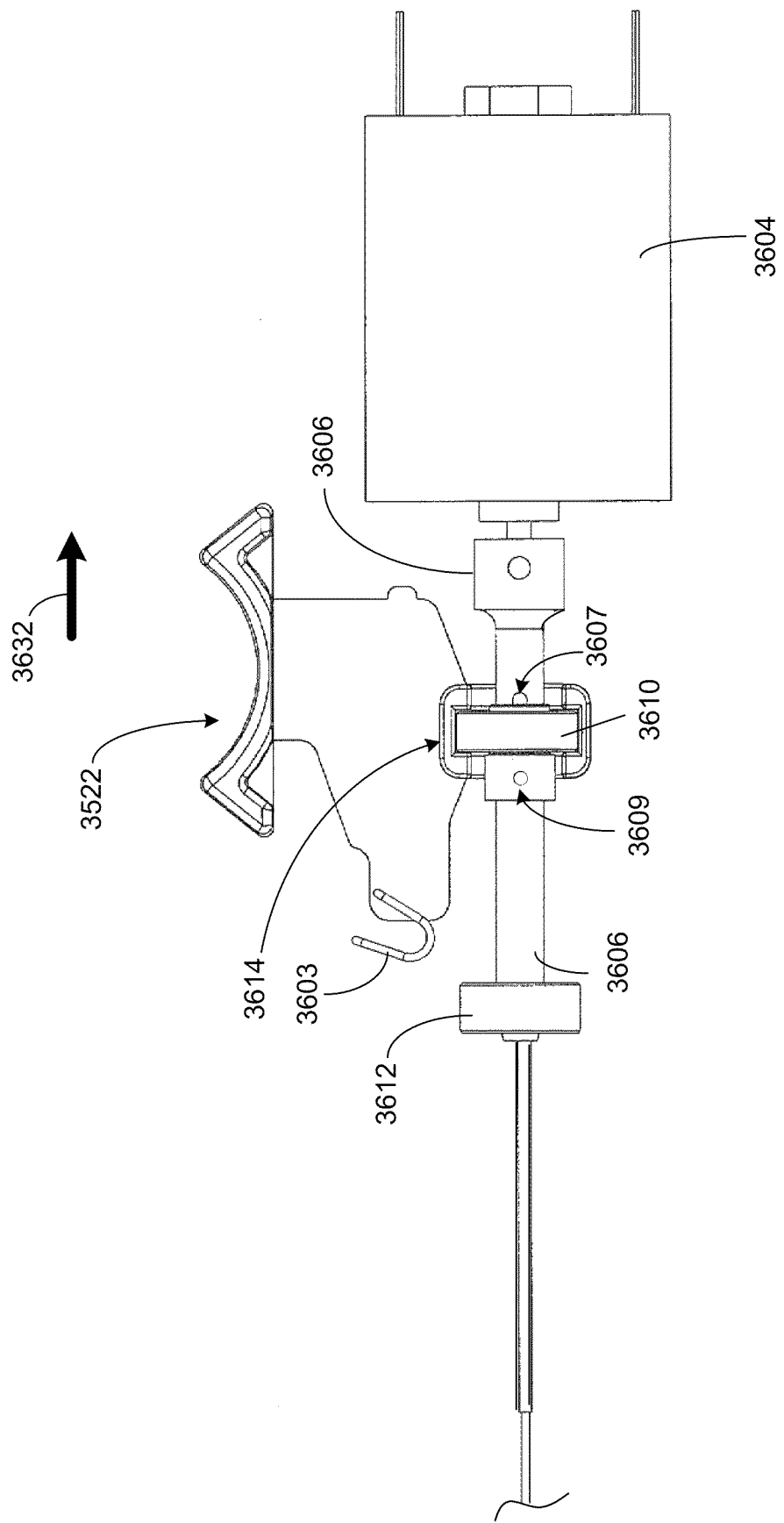
Figure 36E:
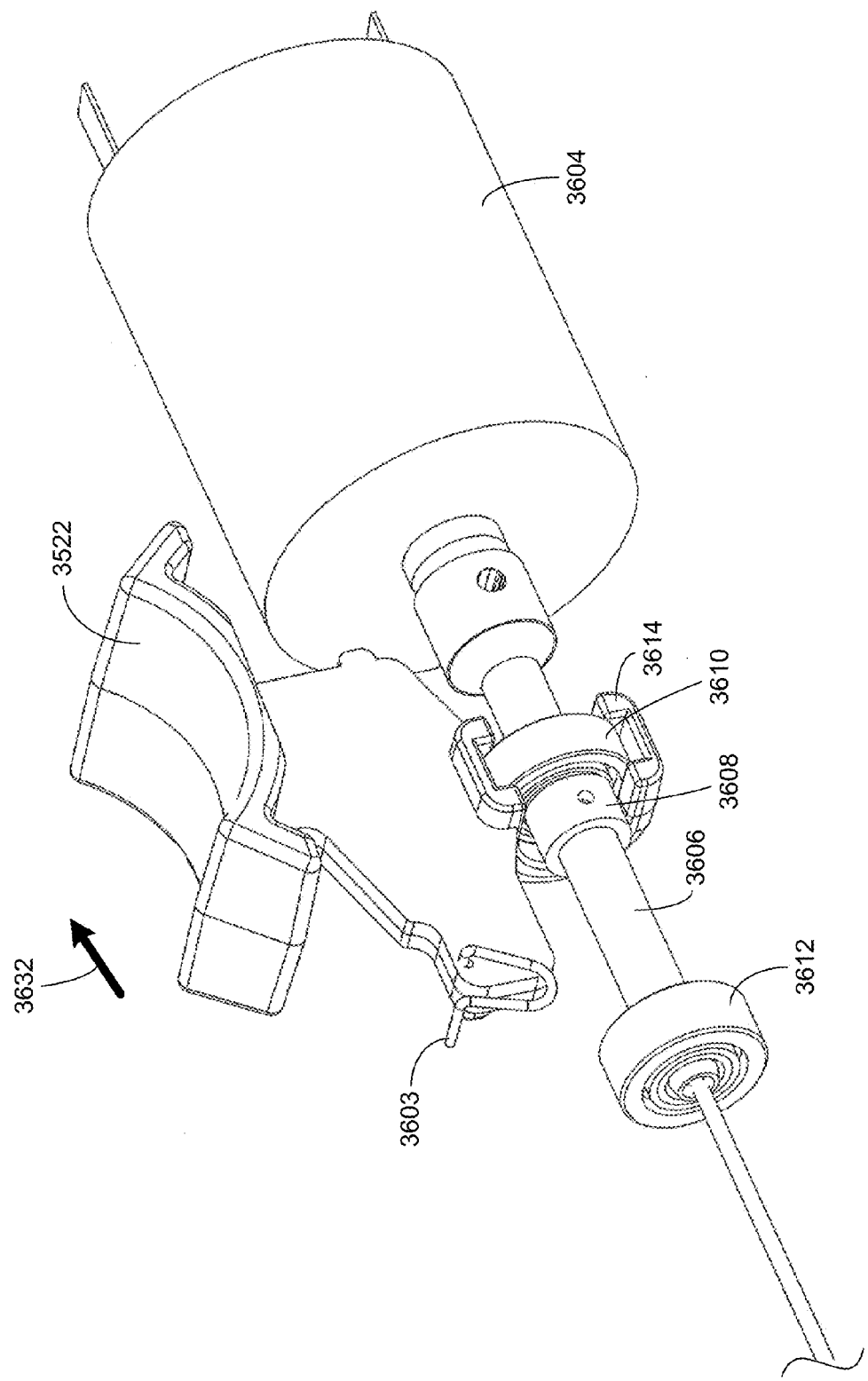

FIGS. 36B-36E provide additional details of the mechanism by which an elongate member that is housed within the rotatable shaft 3606 may be transitioned between an extended and retracted configuration during rotation. FIGS. 36B and 36C depict a side view and a side perspective view of the mechanism when the elongate member is in a retracted configuration. The rotatable shaft 3606 extends from the second ball bearing 3612 through the first ball bearing 3610 and is connected proximally to the motor 3604 via a motor connector 3605. The rotatable shaft 3606 may be soldered, welded, brazed, heat bonded, chemically bonded, snap fit, mechanically attached (e.g. set screw, press fit, swaged, crimped, etc.) or otherwise securely and fixedly attached to the motor connector 3605. As described previously, the coupler 3608 may be slidable along the rotatable shaft 3607, and may couple an elongate member within the shaft (not shown) to the shaft with a pin 3609 such that the elongate member may rotate as the rotatable shaft is rotated by the motor. For example, an elongate member within the shaft may be coupled to the pin 3609 via a metal lug that is slidably disposed within the rotatable shaft 3606. The rotatable shaft 3606 may comprise a longitudinal slot 3607 that extends along a length of the shaft. The length of the slot 3607 provides a range of movement for the coupler 3608, and may be from about 0.25 inch to about 2 inches, for example, 0.6 inch. Sliding the slider 3522 in the direction of arrow 3630 pushes the first ball bearing 3610 retained by the retaining structure 3614 in the same direction. The first ball bearing 3610 then pushes against the slidable coupler 3608, which is also urged in the direction of the arrow 3630 along the slot 3607. Displacement of the slidable coupler 3608 distally (as illustrated by arrow 3630), results in the distal displacement of the elongate member within the rotatable shaft 3600. FIGS. 36D and 36E depicts the coupler 3608 in a distalmost position of the slot 3607 after maximum distal actuation of the slider 3522. The slider 3522 may also be moved proximally (as illustrated by arrow 3632) to transition the elongate member back to the retracted configuration. An optional spring member 3603 that may be attached to the handle housing 3530 may bias the slider 3522 to a distal or proximal location, and/or may help the slider 3522 snap into position as the slider is urged according to the arrow 3630.

Figure 37:
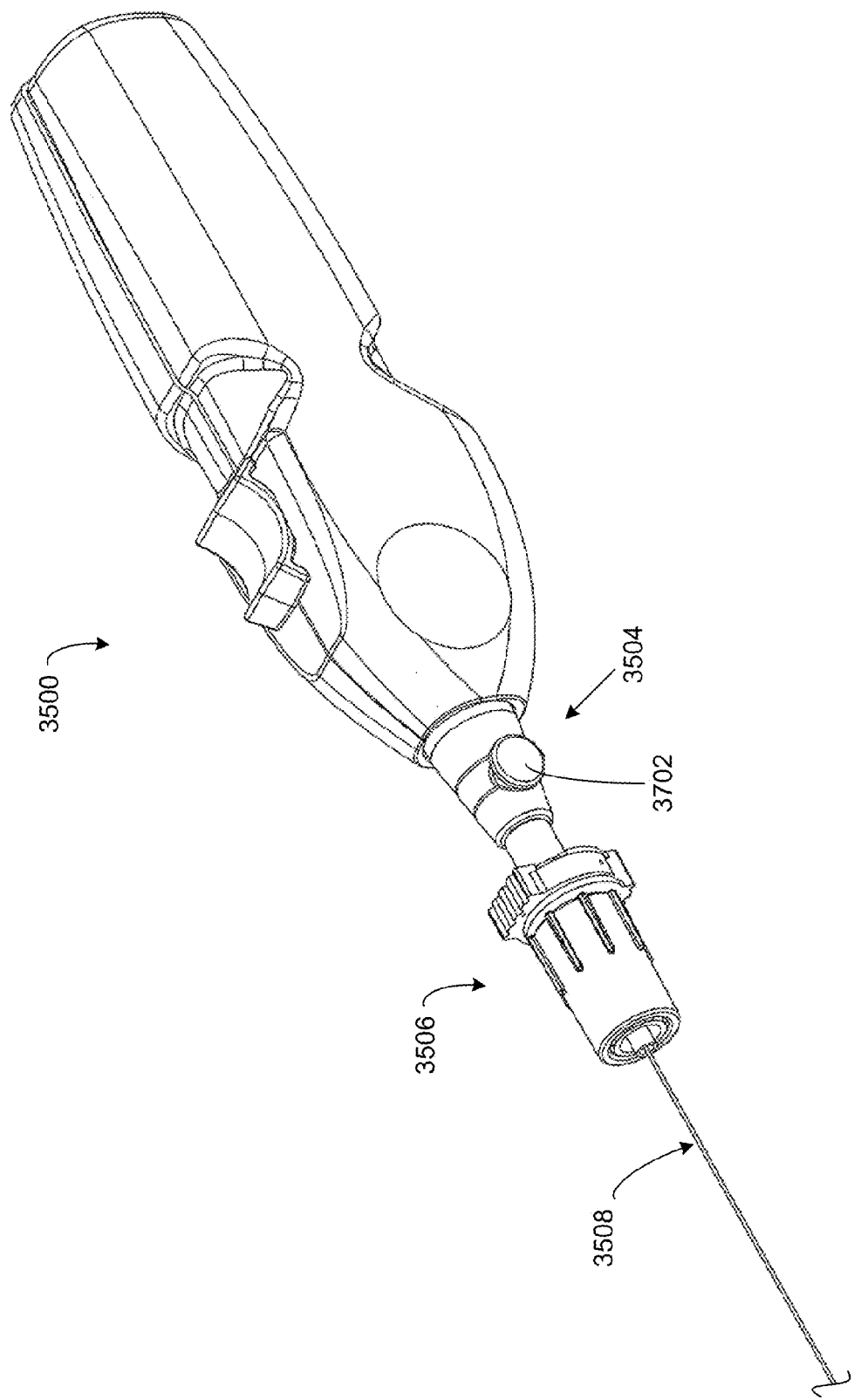
FIG. 37 illustrates a perspective view of the tissue removal device from FIG. 35A.

The tissue removal device 3500 may also comprise an optically transparent chamber, as described above. For example, as depicted in FIG. 37, the tissue removal device 3500 comprises a collection chamber 3504. The collection chamber 3504 may comprise one or more collection ports 3702 with a removable cap or plug. The collection port 3702 is shown to be circular, but may be rectangular, triangular, hexagonal, etc., as appropriate. The collection port 3702 may have a diameter from about 0.06 inch to about 0.28 inch, e.g., about 0.07 inch to about 0.25 inch. Tissue and/or fluid may be delivered from the target tissue site to the collector 3504 via a tissue transport assembly, one variation of which has been described above, and additional variations will be described below. Alternatively or additionally, a vacuum source may be used to draw tissue and/or fluid from the target tissue site to the collector. Optionally, a portion of the collection chamber 3504 may be a configured as a magnifying lens which may be used to visually inspect any collected samples. In some variations, the collection port plug or cap itself may be a magnifying lens.

Figure 38A:
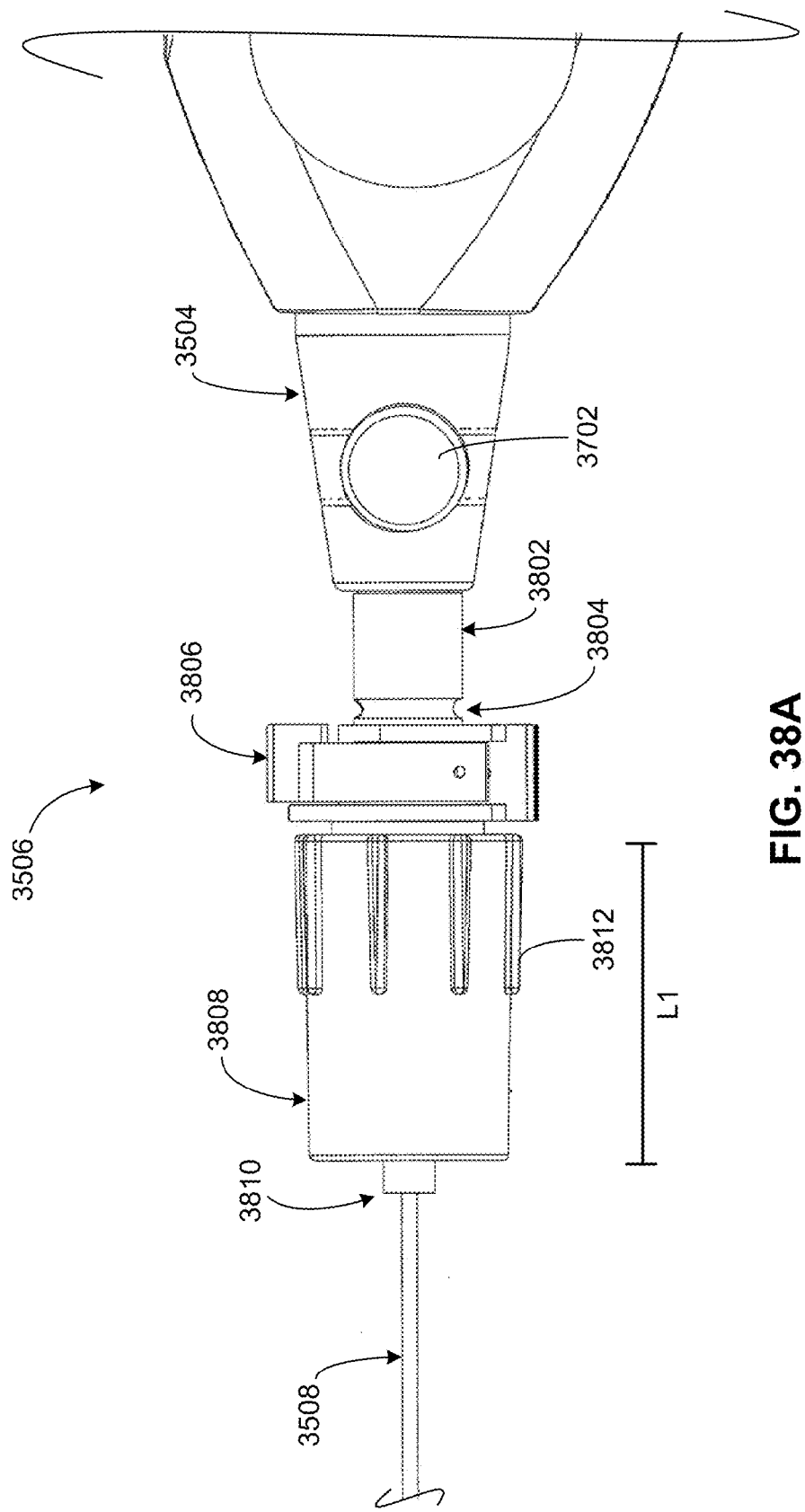
FIGS. 38A to 38G illustrate one variation of a travel limiter that may be used with a tissue removal device.

A tissue removal device 3500 may also comprise a travel limiter 3506, as shown in FIG. 37, and enlarged in FIG. 38A. A travel limiter may be used to constrain and/or define the range of axial and rotational movement of a tissue removal device after it has been inserted into a patient. For example, a travel limiter may be configured to regulate and/or restrict the position and orientation of the tissue removal assembly located distal to the outer tube. Some variations of a travel limiter may be configured to be fixedly connected to an access cannula, which may act as a reference point around which the tissue removal assembly may be positioned. Travel limiters may have a number of configurations that allow varying degrees of motion to the tissue removal device. For example, in a first configuration, the distal portion of a tissue removal device may be constrained to axial movement of up to 13.5 mm, and a second configuration where the tissue removal device may be constrained to axial movement of up to 18.5 mm. In a third configuration, the tissue removal device may be restrained from any axial movement. In certain configurations, the travel limiter may allow the position and/or orientation of the tissue removal assembly to be adjusted along two or more degrees of freedom, e.g., adjusted axially and/or perpendicularly to the longitudinal axis of the device, and/or rotated around the longitudinal axis of the device. In other configurations, the travel limiter may immobilize the device so that it cannot be repositioned, or may constrain the movement of the device such that it may only be repositioned along one degree of freedom, e.g., perpendicular to the longitudinal axis of the device. Immobilizing or constraining the movement of the tissue removal device after insertion into a patient may help prevent accidental withdrawal of the device, or unintentional shifts in location or orientation, which may damage peripheral tissue and neural structures. For example, restricting the movement of the tissue removal device during a vertebral disc procedure may be a desirable safeguard against damage of nearby nerves by unintentionally twisting, rotating, pulling, or pushing the tissue removal assembly.

Figure 38B:
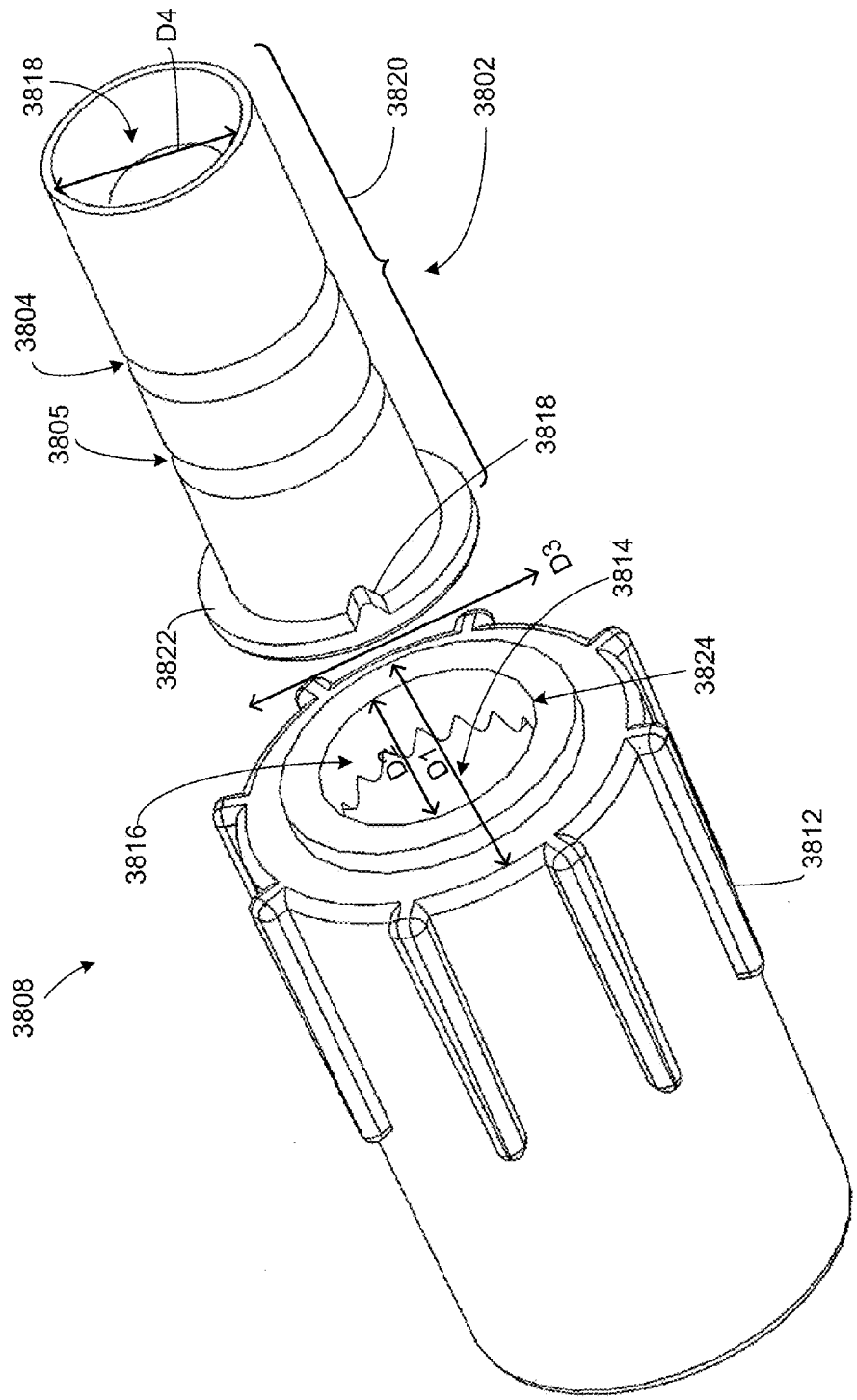

One variation of a travel limiter 3506 comprises a grooved tube 3802, a latch 3806 that is slidable over the grooved tube 3802, and a slide tube 3808 that is slidable over the body of the grooved tube 3802 as permitted by the latch 3806. The slide tube 3808 may also rotate around the grooved tube 3802. The slide tube 3808 may also comprise a connector 3810 that is configured for the attachment of cannula, stylets, tubes, etc. as desired. A cannula that is attached to the slide tube 3808 via the connector 3810 may move in conjunction with the slide tube 3808, e.g., sliding and/or rotating the slide tube 3808 may also slide and/or rotate the cannula. In other variations, the cannula may be in a fixed position, and engaging the travel limiter fixedly with the cannula may allow the tissue removal device to slide and rotate with respect to the cannula position. The connector 3810 may be a friction-fit, snap-fit, screw-fit, or Luer-Lok™ type connector. The slide tube 3808 comprises one or more grips 3812 around the perimeter to enable a user to translate the slide tube 3808 over the grooved tube 3802. The connecter 3810 may have an aperture and/or channel configured to pass the outer tube 3508 through the slide tube 3808. The connector channel may extend partially or entirely across the length of the slide tube 3808, within the slide tube lumen 3814. A component perspective view of the slide tube 3808 is illustrated in FIG. 38B, which shows the slide tube lumen 3814, with inwardly pointing serrated locking features 3816 arranged around the circumference of the lumen 3814. There may be any suitable number of serrated locking features 3816, for example, 2, 3, 4, 5, 6, 8, 9, 10, 12, 15, 16, 20, etc., serrations that may be used to restrain relative motion between the slide tube 3808 and the grooved tube 3802.

The grooved tube 3802 comprises a tube body 3820 with a tube stop 3822 attached at the distal portion of the tube body 3820. The proximal portion of the grooved tube 3802 may be fixedly attached to the distal portion of the collector 3504. In some variations, the grooved tube and the collector may be integrally formed. The grooved tube body 3820 may have one or more grooves, for example, a first groove 3804 and a second groove 3805, and a grooved tube lumen 3818 through the tube body. The tube lumen 3818 may be located and shaped to receive the outer tube 3508 that may be inserted through the slide tube 3808. The grooves may extend around the perimeter of the tube body, e.g., along the outer surface of the tube body 3820. The axial movement of the slide tube 3808 over the grooved tube 3802 may be determined in part by the spacing between the first and second grooves, as will be described in detail below. The spacing between the first groove 3804 and the second groove 3805 may be from about 1 mm to about 10 mm, for example, 5 mm. The tube stop 3822 may have one or more locking feature mates 3818 that are configured to engage the locking features 3816 of the slide tube 3808. While the tube stop 3822 has two locking feature mates 3818 (the first is shown in FIG. 38B, and the second is located directly opposite the first locking feature mate), other variations may have 1, 3, 5, 6, 8, 9, 10, 12, 15, 16, 20, etc., locking features mates. When the locking features 3816 are engaged with the locking feature mates 3818, the slide tube 3808 is restrained from rotating around the grooved tube 3802. For example, when the locking feature 3818 is engaged between the serrations of the locking feature 3816, the slide tube 3808 is rotatably locked with the grooved tube 3802, i.e., the slide tube is no longer rotatable around the grooved tube.

Figure 38C:
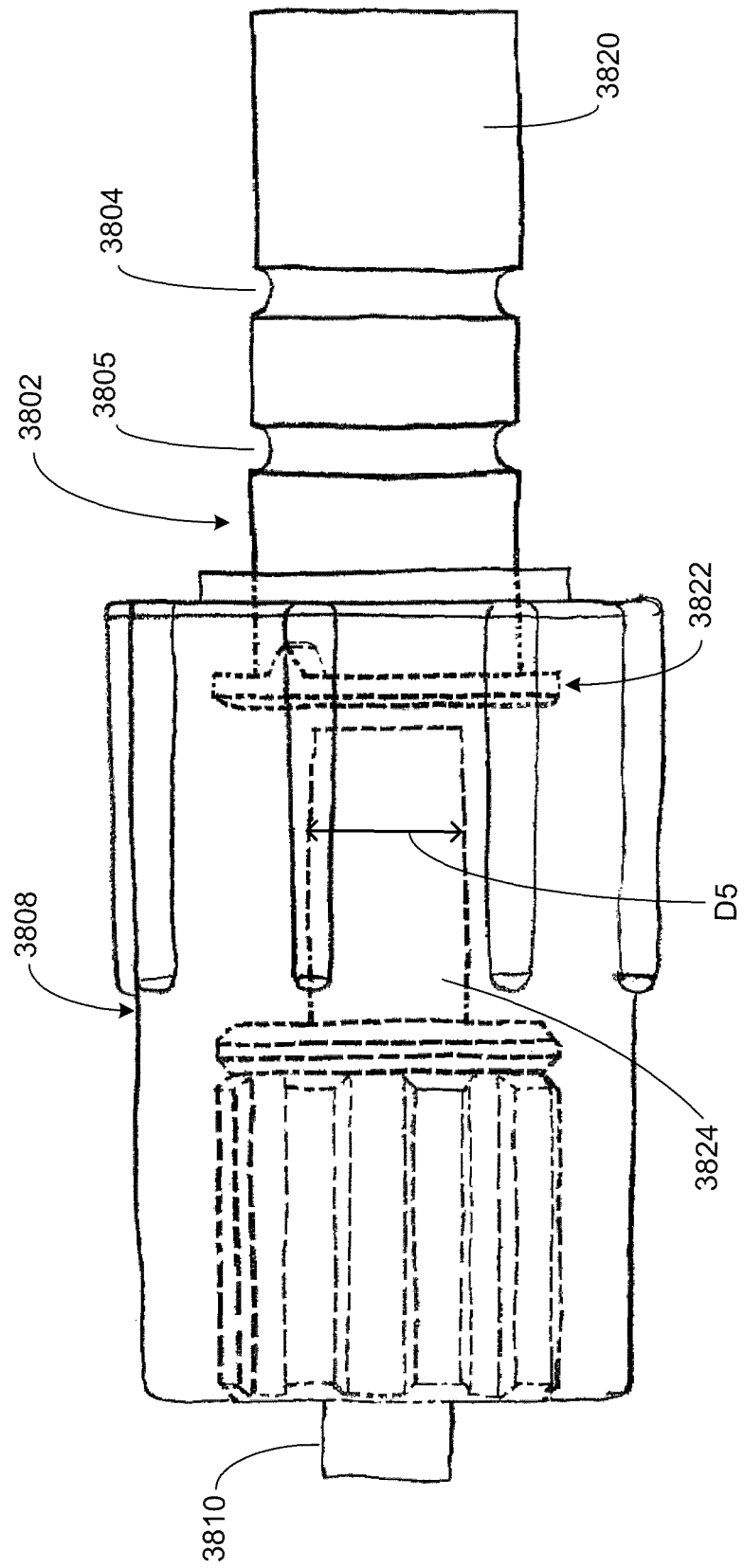

The slide tube 3808 and grooved tube 3802 may be sized and shaped such that the slide tube may slide along and/or rotate over the grooved tube. For example, the slide tube 3808 may have a length L1, where L1 is about 0.5 inch to about 2 inches, a first diameter D1, where D1 is about 0.35 inch to about 1.5 inches. The lumen 3814 may have a diameter that is the same as, or less than, D1. The opening 3824 to the lumen may have a second diameter D2, where D2 is less than D1, for example, about 0.2 inch to about 1 inch. The tube stop 3822 has a diameter D3, where D3 may be less than or equal to the diameter D1 of the slide tube 3808, but greater than the diameter D2 of the opening 3824. The diameter D3 may be from about 0.3 inch to about 1.25 inch, for example, 0.44 inch. The tube body 3820 has a diameter D4, where D4 may be less than or equal to the diameter D2 of the opening 3824. The diameter D4 may be from about 0.1 inch to about 1 inch, for example, 0.34 inch. In the variation of the travel limiter 3506 depicted in FIG. 38A, the connector 3810, slide tube 3808, and the grooved tube 3802 may be configured as shown in FIG. 38C. The connector 3810 and collector channel 3824 may be affixed within the slide tube 3808. In this variation, the grooved tube body diameter D4 is less than the slide tube opening diameter D2, which may allow the slide tube 3808 to slide over the grooved tube 3802. The connector channel 3824 may have a diameter D5 that is smaller than grooved tube body diameter D4, so that it may be inserted into the grooved tube lumen 3818. However, the tube stop diameter D3 may be greater than the opening diameter D2, so that the grooved tube 3802 is retained within the lumen of the slide tube. Other arrangements may also be used where the slide tube may be moved with respect to the grooved tube, and limited by the tube stop.

While the slide tube 3808 and the grooved tube 3802 may comprise a rounded and cylindrical configuration, other variations of slide tubes and grooved tubes may have other suitable geometries, such as triangular, rectangular, hexagonal, octagonal, etc. In some variations, the slide tube 3808 may be made of an optically transparent material, such as polyethlyene terepthalate (PET), nylon, polycarbonate, polyethylene, acrylonitrile butadiene styrene (ABS), polypropylene, and the like, while in other variations, the slide tube may be optically opaque. Optionally, the surfaces of the slide tube and the grooved tube may be coated with a friction-modification agent, which may either increase or decrease the friction between the surfaces. It may be desirable in some variations to increase the frictional forces between the sliding surfaces to help prevent slippage, while in other variations, the frictional forces may be reduced to facilitate adjustment of the slide tube.

Figure 38D:
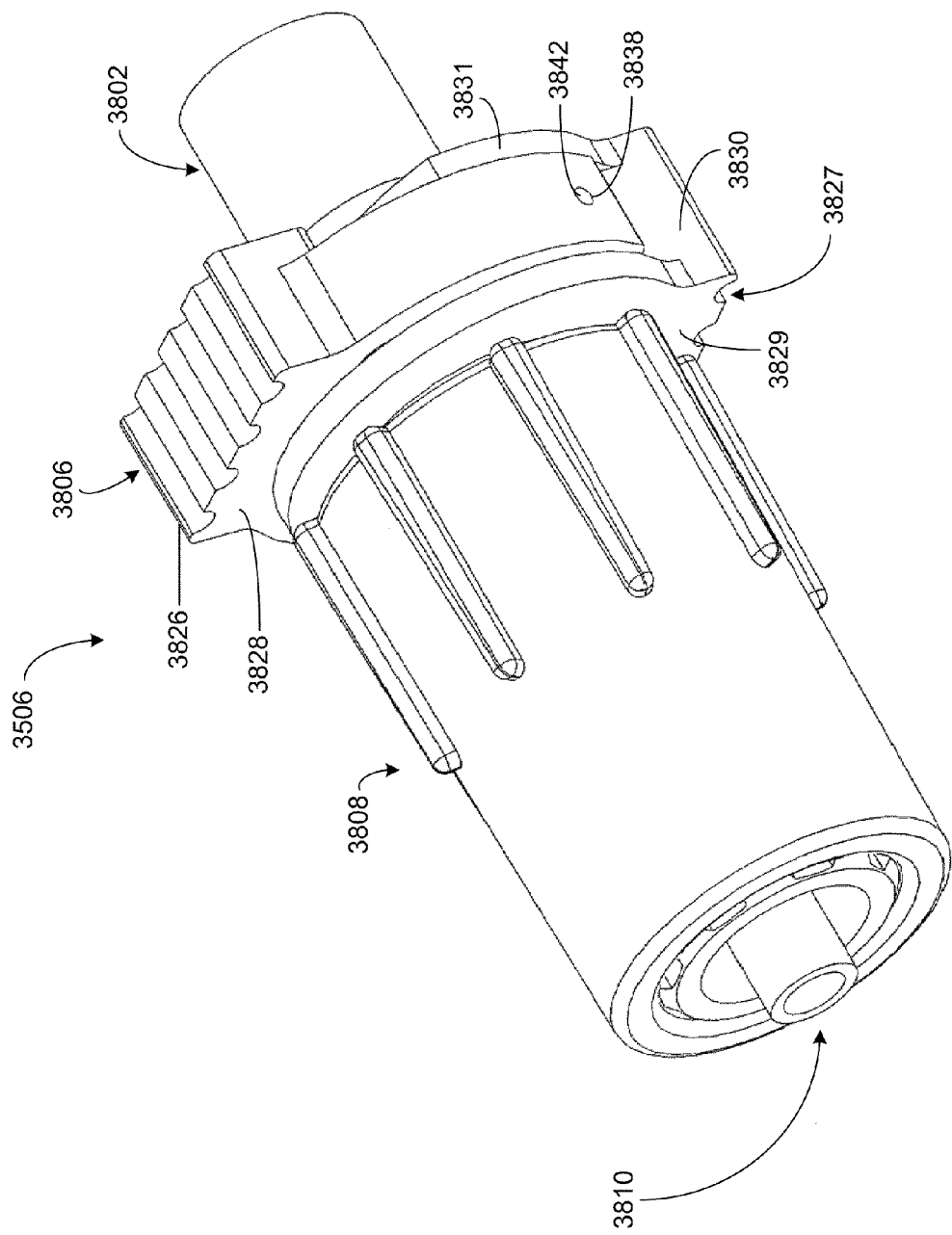
Figure 38E:
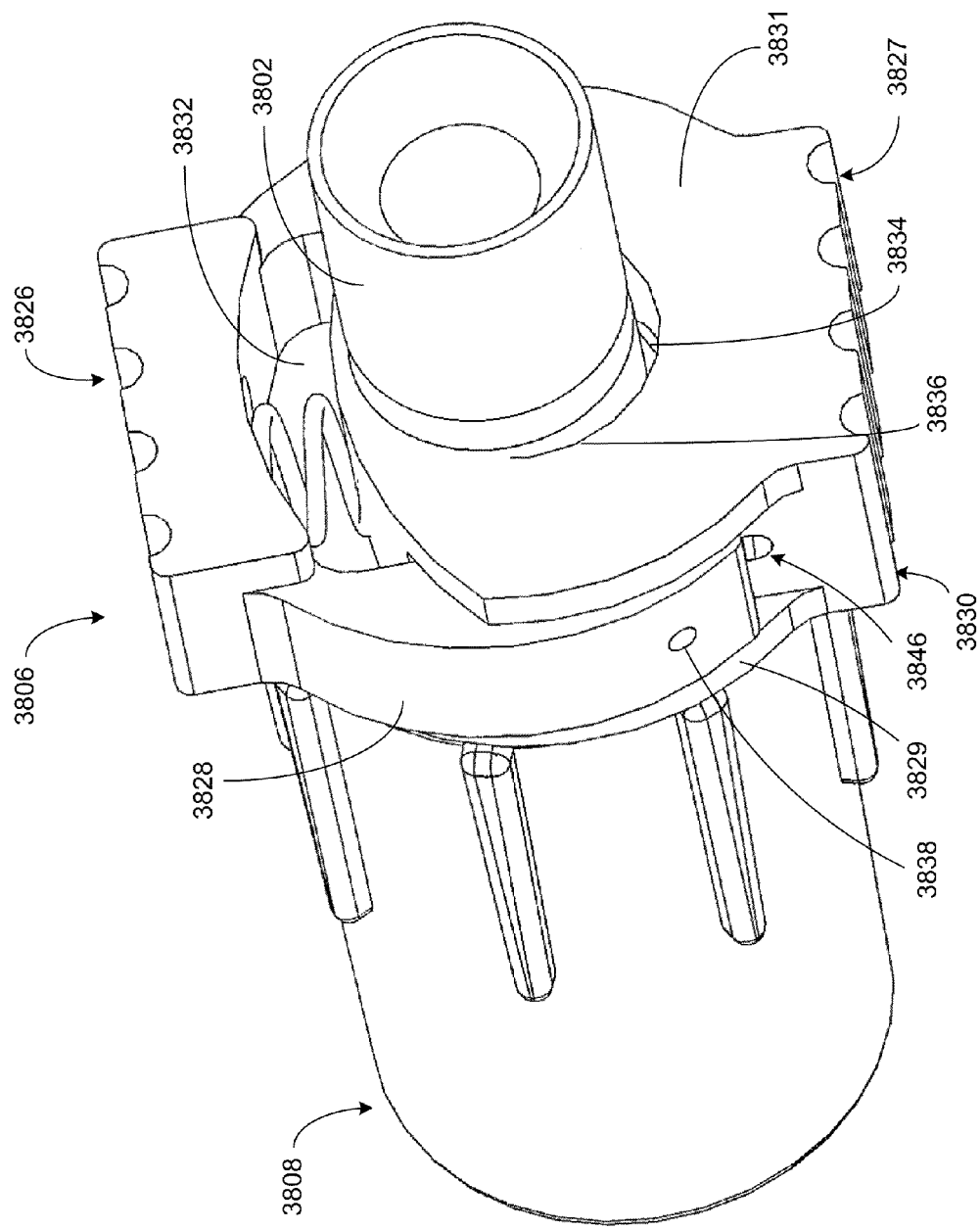

A perspective view of the travel limiter 3506 is shown in FIG. 38D, where the slide tube 3808 is slidably coupled over the grooved tube 3802 as previously described. Additionally, the latch 3806 is slidably coupled over the grooved tube 3802. The position of the latch 3806 along the length of the grooved tube 3802 may define the range of relative movement between the slide tube and the grooved tube. For example, the slide tube 3808 of the tissue removal device 3500 may be fixedly attached to an access cannula that is inserted within a patient. The location of the latch 3806 along the grooved tube 3802 which may be fixedly attached to the handle defines the movement range of the tissue removal device with respect to the access cannula. The latch 3806 may comprise a circular bracket 3828 that is fitted between the two plates of a latch base 3830. The latch base 3830 may also comprise a latch base lumen 3836 that is sized and shaped to fit over the grooved tube 3802, as illustrated in FIG. 38E. The circular bracket 3828 and the latch base 3830 may be coupled by a pin 3842 that is inserted through a first aperture 3838 in the circular bracket, through a first pin-shift aperture in the latch base, through a pin channel, out a second aperture in the circular bracket. A portion of the first pin-shift aperture 3846 is depicted in the back perspective view of the travel limiter 3506 shown in FIG. 38E. The latch 3806 may have a first ridged region 3826 on the circular bracket 3828, and a second ridged region 3827 on the latch base 3830. Pressing the first ridged region 3826 and the second ridged region 3827 towards each other may adjust the position of the circular bracket 3828 and the pin 3842 within the pin-shift apertures and pin channel.

Some variations of a latch may comprise a mechanism that biases the latch to a locked configuration or an unlocked configuration. Such a bias mechanism enables the travel limiter to constrain the motion and/or position of the tissue removal device without the practitioner constantly applying pressure to the latch. One example of a bias mechanism may comprise a spring 3832 that may be located between the first ridged region 3826 of the circular bracket 3828 and the top portion of the latch base 3830. The spring 3832 may bias the position of the circular bracket 3828 and the pin 3842 with respect to the latch base 3830. For example, the spring 3832 bias the travel limiter to a locked configuration by pressing against the circular bracket 3828 and the latch base 3830 such that the pin 3842 is urged to the top of the pin channel. Various latch configurations are described below.

Figure 38F:
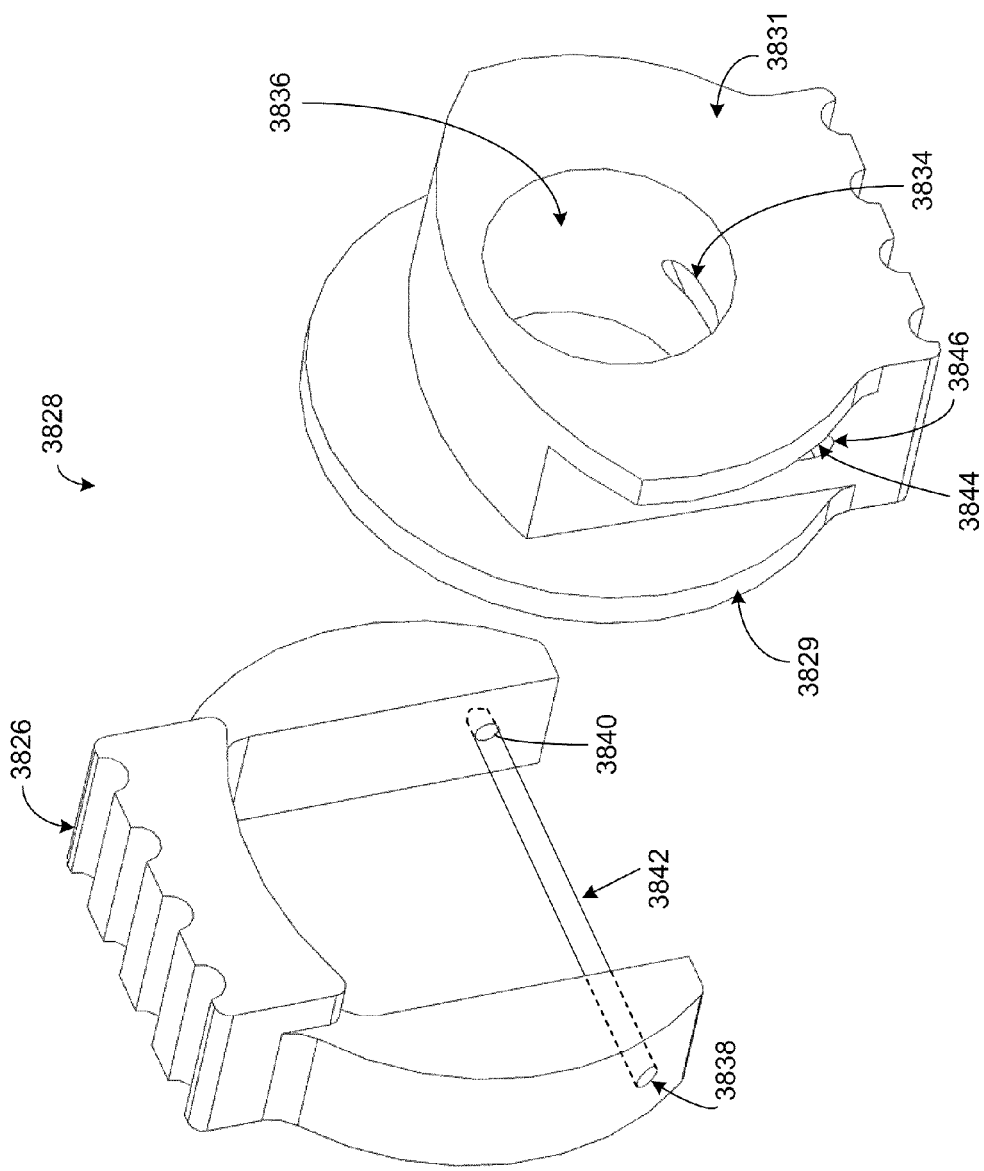
Figure 38G:
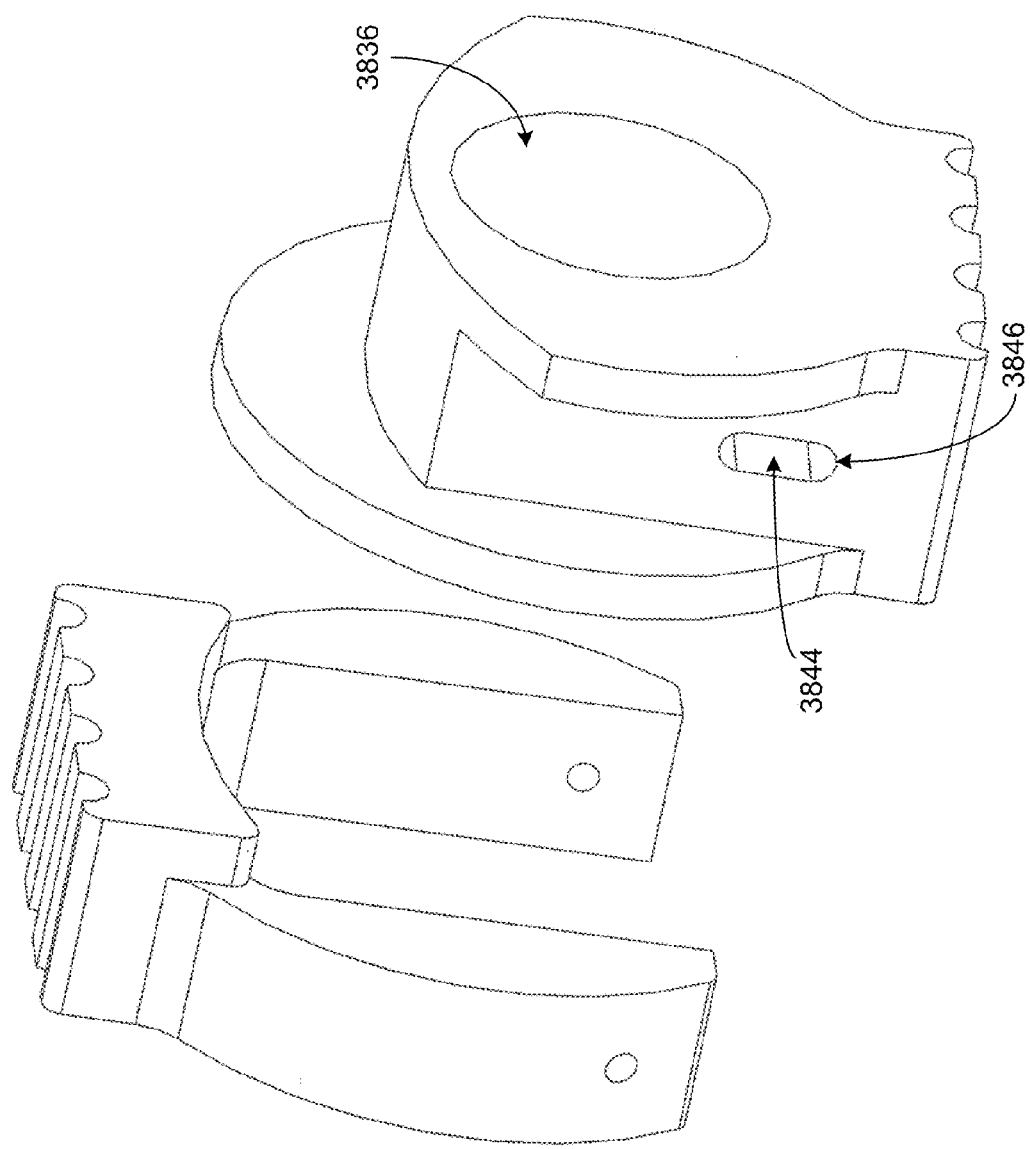

FIGS. 38F and 38G are perspective component views that illustrate one variation of a latch that has a locked configuration and an unlocked configuration. When the latch is fully assembled, the pin 3842 may be inserted from the first aperture 3838, through a first pin-shift aperture 3846 and pin channel 2844 in the latch base 3830, to the second aperture 3840. The circular bracket 3828 is coupled to the latch base 3830 via the pin 3842, and is also held in place by the distal base plate 3829 and the proximal base plate 3831. The latch base lumen 3836 may have a diameter that is equal to, or somewhat larger than, the diameter D4 of the grooved tube body 3820. There may be a pin channel cutout 3834 that allows a segment of a pin that is inserted through the pin channel 3844 to enter the latch base lumen 3836. FIG. 38G depicts a perspective side view of the circular bracket 3828 and the latch base 3830. The pin-shift aperture 3826 and the cross-section of the pin channel 3844 may have an elongated rounded shape. The pin-shift aperture and the pin channel cross-section may be any suitable shape such that the bottom portion of the shape is below the bottom of the latch base lumen 3836, and the top portion of the shape is above the bottom of the latch base lumen. For example, when the latch is in an unlocked configuration, a pin that is inserted through the pin channel 3844 is positioned at the bottom of the pin channel 3844, and may be entirely outside the latch base lumen 3836. In the unlocked configuration, the latch may slide freely over the grooved tube. In the locked position, the pin is positioned at the top of the pin channel, and a segment of the pin enters the latch base lumen 3836 via the pin channel cutout 3834, which may impede the sliding of the latch 3806 over a grooved tube. In the variation of the latch 3806 described here, when in the locked configuration, the pin may engage within one of the grooves of the grooved tube in the locked configuration, which may immobilize the position of the latch along the tube. In some variations, the latch may be biased to either the locked configuration or the unlocked configuration. For example, as shown in FIG. 38E, the spring 3832 biases the latch to the locked position by pushing upwardly on the circular bracket 3828. When the spring 3832 is compressed, the pin 3842 may be disengaged from the groove, and urged to the bottom of the pin channel 3844. This may unlock the latch 3806 and allow it to slide over the grooved tube.

The position of the latch 3806 along the grooved tube 3802 may limit the movement range of the slide tube 3808. Where a cannula, stylet, or other tool is attached to the connector 3810 over the outer tube 3508, the movement of the slide tube determines the movement of the attached tool. Referring back to FIG. 38A, the latch 3806 is shown to be locked over the second groove 3805. In the configuration shown there, the serrated locking features 3816 on the slide tube are engaged with the locking feature mate 3818 on the grooved tube, which prevents the slide tube and the attached tube from rotating, and also restricts axial movement. When the latch 3806 is locked into the first groove 3804, the serrated locking features 3816 may be disengaged from the locking feature mate 3818, which allows the slide tube and the attached tool to rotate, as well as to move axially.

The components and configurations of one variation of a travel limiter have been described above. While the travel limiter 3506 has two evenly spaced grooves, other variations may have more than two grooves, where the spacing between the grooves may be varied. For example, grooves may be more closely spaced towards the distal portion of the travel limiter than at the proximal portion of the travel limiter. The travel limiter 3506 as shown has one latch 3806, however, other travel limiters may have two or more latches. For example, a first latch may be positioned proximal to the slide tube, while a second latch may be positioned distal to the slide tube. These optional features may allow the travel limiter to limit either or both the axial and rotational movement of the tissue removal device with respect to slide tube. For example, when the slide tube is fixedly attached to an access cannula, the movement of the tissue removal device with respect to the slide tube may be constrained by the latch position on the grooved tube. Any combination of the above described travel limiter components may be used to control and regulate the position and/or orientation of the distal portion of the tissue removal device.

Figure 39A:
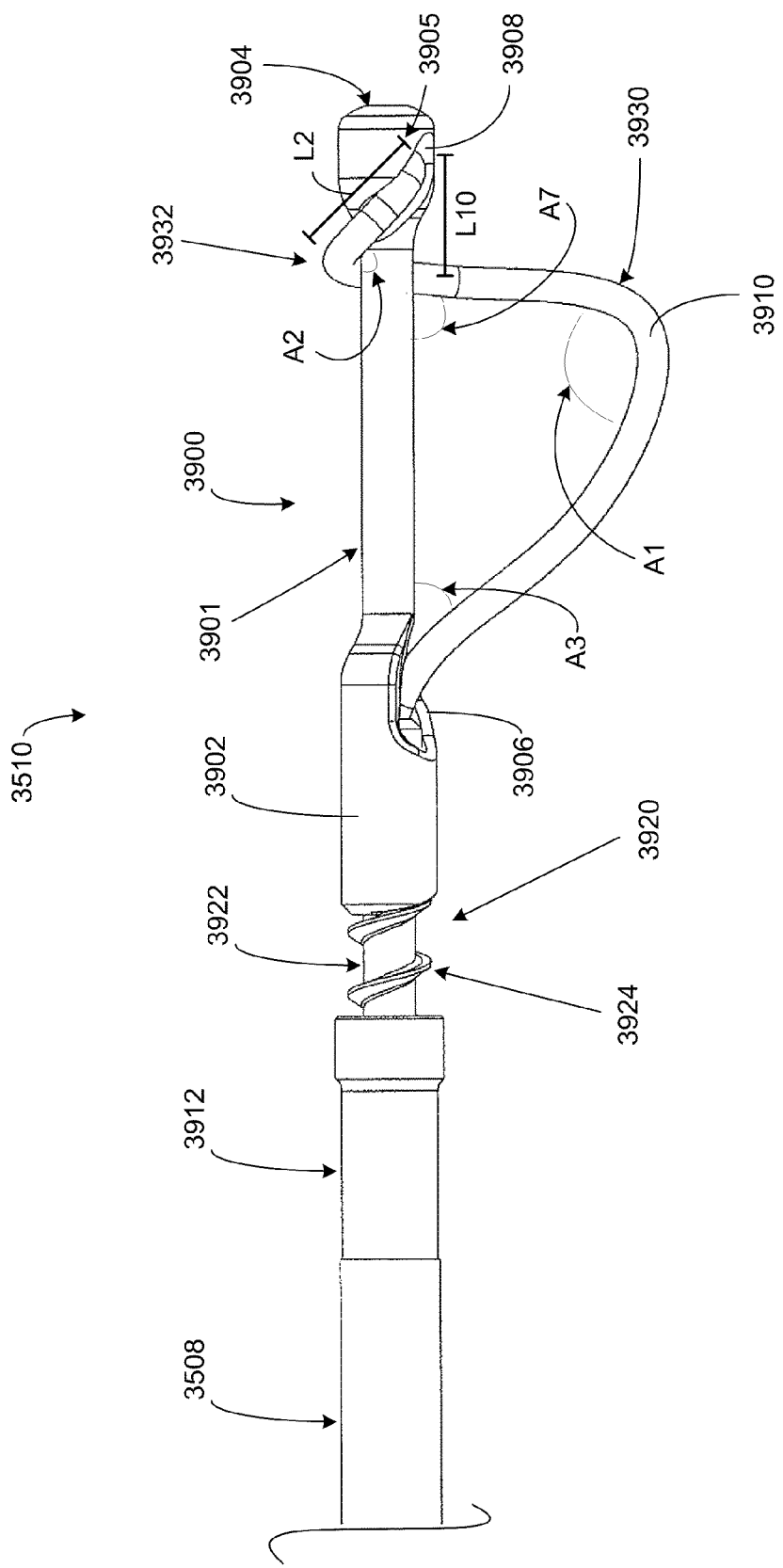
FIGS. 39A to 39G illustrate different configurations and variations of tissue removal assemblies that may be used with the tissue removal devices described herein.
Figure 39B:
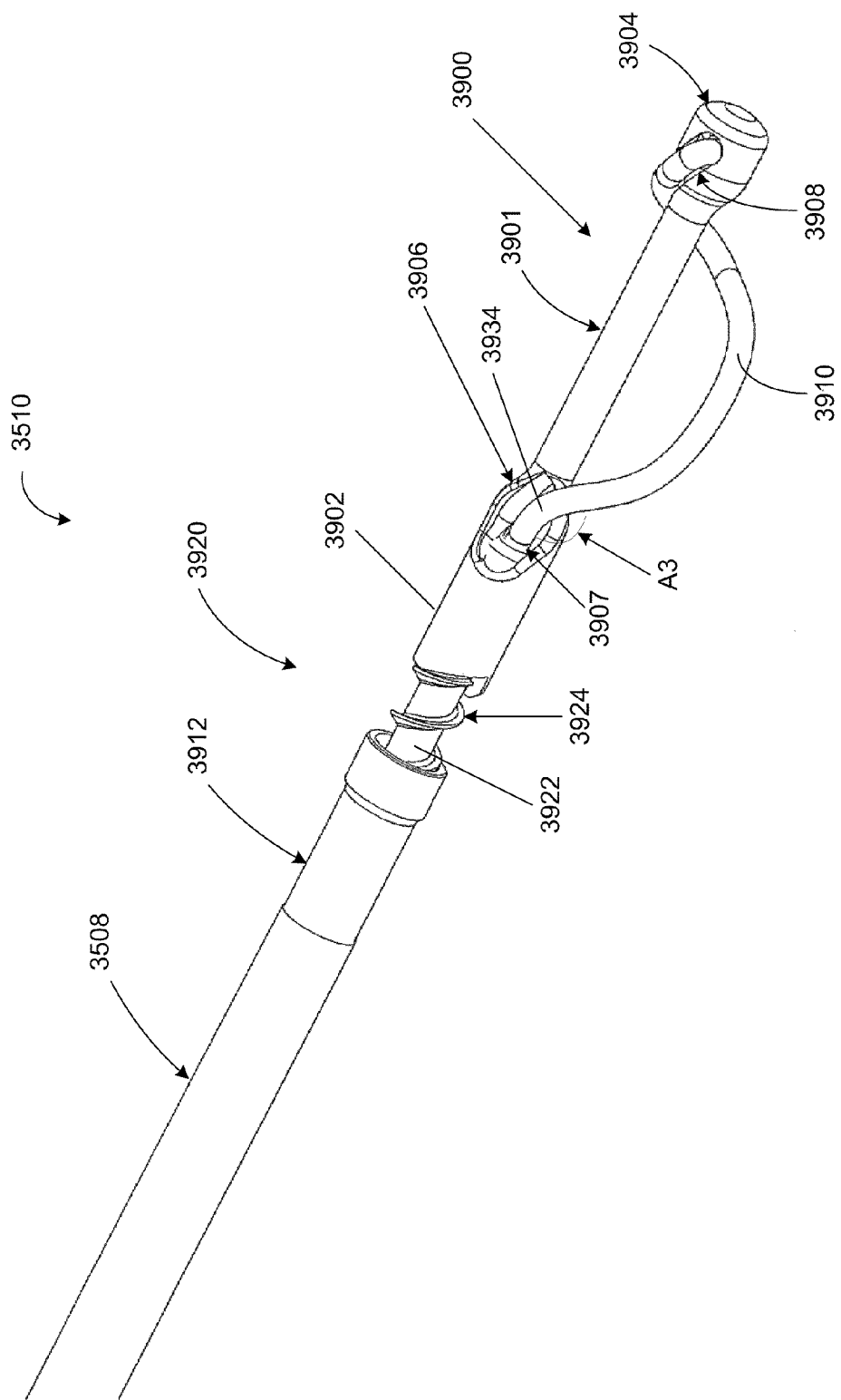
Figure 39C:
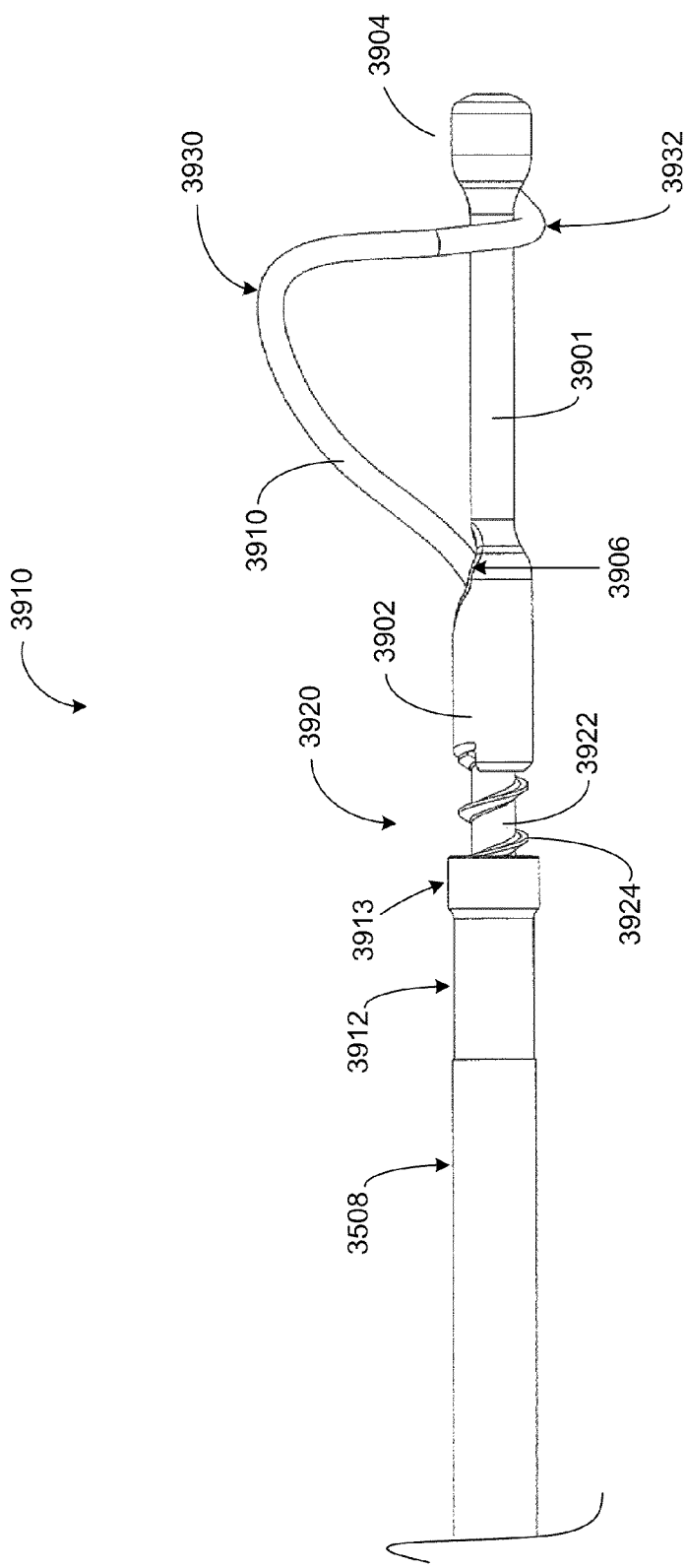

Tissue removal assemblies, such as the variations described above, may vary according to the geometry, consistency, location, and size of the target tissue. Another variation of a tissue removal assembly is illustrated in FIGS. 39A to 39C. The tissue removal assembly 3510 comprises a tube stop 3912 attached distally to the outer tube 3508, a rotatable drive member 3922 extending through the tube stop 3912, and a cable 3910 extending from the rotatable drive member 3922 that is threaded through a rotatable cable shaft 3900. The rotatable cable shaft 3900 may comprise a distal tip 3904 with a distal channel 3908, a shaft base 3902 with a proximal channel 3906, and a shaft body 3901 connecting the shaft base and distal tip. The rotatable cable shaft base, body, and distal tip may be integrally formed, or may be separately formed and assembled. The cable 3910 may be threaded from the handle 3502 through the rotatable drive member 3922, through the proximal channel 3906, around the rotatable cable shaft 3900, into the distal tip 3904, and attached within the distal tip 3904. The cable 3910 may have an extended configuration, as shown in FIG. 39A, where at least a portion of the cable 3910 is displaced further away from the rotatable cable shaft 3900 than the same portion in a retracted configuration. The cable 3910 configuration may be adjusted by sliding the cable 3910 in or out of the proximal channel 3906. One or more components of the tissue removal assembly 3510 may be made of a radiopaque material. Other details regarding the movement of the cable between the retracted and extended configurations have been described previously.

The tube stop 3912 comprises a tubular body that has a diameter that is similar to the diameter of the outer tube 3508, and a rim 3913 that has a diameter that may be larger than the outer tube diameter. The larger diameter rim 3913 may help to prevent any devices that may be threaded over the outer tube 3508 near the proximal portion of the tissue removal device from unintentionally sliding down towards the tissue removal assembly, where it may disrupt the function of the rotating components. Optionally, portions of the tube stop 3912, such as the rim 3913, may comprise one or more cutting edges, which may help to break up tissue as it is transported proximally by the tissue transport assembly 3920. The tube stop 3912 tubular body may have a diameter of about 0.02 inch to about 0.5 inch, for example, 0.05 inch, and may be made of any suitable metallic or polymeric materials as previously described. For example, the tube stop 3912 may be made of stainless steel or a titanium alloy, and may be soldered, welded, or brazed onto the outer tube 3508.

In the variation of a tissue removal assembly described here, the rotatable cable shaft 3900 is attached distal to the tube stop 3912, e.g., to the tissue transport assembly 3920. In other variations, the rotatable cable shaft 3900 may be directly affixed to the tube stop 3912. As seen in FIGS. 39A and 39B, the rotatable cable shaft base 3902 may be attached to the rotatable drive member 3922. The shaft base 3902 may be attached to the drive member 3922 by soldering, welding, brazing, heat bonding, chemical bonding, other forms of adhesive bonding, snap fitting, and the like, as described previously. While FIG. 39A depicts that the rotatable shaft 3900 is attached to the drive member 3922 distal to the tube stop 3912 and the outer tube 3508, in other variations, the rotatable shaft may be attached to the drive member at a more proximal location, e.g., within the tube stop, within the outer tube. In some variations, the rotatable cable shaft 3900 may be integrally formed with the rotatable drive member 3922.

A rotatable cable shaft may be sized and shaped to retain the cable such that the cable is able to be extended, retracted, and/or rotated. Various features may be provided on a rotatable cable shaft to provide adequate attachment of the cable while dissipating and/or stabilizing forces and heat that may result from rotating the cable. These heat dissipating and force stabilization features may help prevent trauma to surrounding tissue structures. The rotatable cable shaft 3900 may comprise a shaft body 3901 that connects the proximal shaft base 3902 and the distal tip 3904. The shaft body 3901 may have a diameter of about 0.010 inch to about 0.030 inch, or 0.025 inch, and a length of about 0.1 inch to about 0.2 inch, e.g., 0.3 inch. The shaft body 3901 may be made of metallic and/or polymeric materials which may help to reduce abrasion of the cable 3910 during use, for example, materials such as stainless steel (17-4, 303, 304, 316, 400 series), cobalt chromium, titanium alloy, PEEK, Pebax, nylon, polyethylene, polyimide, etc. In some variations, a shaft body may comprise protrusions, tortuous grooves, recesses, or other surface features that may help position and stabilize a cable that is in the retracted configuration. Optionally, a shaft body may have one or more ports, channels, slots, apertures, openings, etc. for aspiration and collection of tissue and/or fluids, as well as for the infusion of fluids or therapeutic agents. For example, there may be one or more aspiration windows on the shaft body 3901 near the distal tip portion 3904.

The distal tip 3904 may have an atraumatic shape, such as a blunt or rounded configuration as shown. Other atraumatic configurations have been described and depicted above. An atraumatic geometry may help to prevent or reduce tissue damage as the tissue removal assembly is advanced to the target tissue region. In some variations, the distal tip may have an angled, pointed, or tapered configuration. These configurations may help the distal tip to gain entry to tighter tissue regions, for example, between tissue folds, tubular structures, and the like. Optionally, the distal tip may comprise multiple points or edges that may be used to disrupt or otherwise remove tissue or body structures. For example, the surface of the distal tip may comprise surfaces with a grit that may be used as a burr mechanism. The distal tip 3904 may have a larger diameter from the shaft body 3901, for example, the distal tip may have a diameter of about 0.025 inch to about 0.040 inch, or 0.033 inch. In some variations, the distal tip may have one or more apertures that may be used to draw tissue and/or fluids to the tissue transport assembly, where the tissue and/or fluids may be transported proximally by the helical member 3924 mounted on the rotatable drive member 3922. The distal tip 3904 may be made of metallic and/or polymeric materials that may help to reduce abrasion of the cable 3910 during use, for example, materials such as PEEK, Pebax, nylon, polyethylene, polyimide, etc.

The rotatable cable shaft 3900 may have one or more pre-formed recesses or grooves on along the cable shaft body 3901, the distal tip 3904, and/or the shaft base 3902 to receive the cable 3910, and stabilize the cable in either its extended or retracted configurations. In some variations, pre-formed recesses or grooves along the shaft body 3901 may be angled and positioned to reduce focal forces or stresses on the cable shaft 3900. For example, the distal channel 3908 and/or the proximal channel 3906 may be formed at an angle with respect to the cable shaft body 3901 to better accommodate the curvature of the cable 3910. The angle of the distal channel 3908 and the proximal channel 3906 with respect to the longitudinal axis of the cable shaft body may be the similar or different, and may be from about 5° to about 170°, e.g., about 45° or about 135°. The distal channel 3908 and the proximal channel 3906 may be substantially aligned along the outer surface of the cable shaft 3900, or may be in rotated positions with respect to each other, e.g., the proximal channel 3906 may be located from about 10° to about 359° around the cable shaft body from the location of distal channel 3908. As depicted in FIGS. 39A-C, the distal channel 3908 may at least partially wrap along an outer surface of the distal tip 3904 before attaching at the distalmost portion of the distal tip 3904. There may be any number and configuration of tapered regions, tortuous grooves, recesses, protrusions, and cable shaft surface features that accommodate the curvature and motion of the cable 3910. Surface contours as described above may also help prevent the cable from slipping under dynamic tension during use. The rotatable cable shaft 3900 may be made of polymeric and/or metallic materials, including metal alloys, such as stainless steel, titanium alloys, etc.

The cable 3910 may be made of any materials similar to the materials used for the elongate member. For example, the cable 3910 may be made of one or more of the following metallic and/or polymeric materials: polyimide, stainless steel, titanium alloy, cobalt chromium, tungsten, polyethylene, nylon, carbon fiber, urethane, polyaramide, PEEK, and/or polyester. The cable 3910 may also have any diameter that may be appropriate for removing tissue. For example, the cable 3910 may have a diameter of about 0.1 mm to about 0.5 mm, for example, about 0.25 mm to about 0.35 mm, about 0.2 mm to about 0.35 mm, or may be 0.25 mm or about 0.3 mm. The cable 3910 may be a multifilament cable, e.g. a metal cable such as a 304 stainless steel cable, or 316LVM stainless steel wherein the cable 3910 may have a diameter that is about 2 to 12 times, e.g., 2 to 4 times, or 3 times, the diameter of one filament. The filaments may be assembled in a left hand lay orientation to form the cable. Where the cable is made of multiple polymeric filaments, the cable diameter may be about 25 times, 50 times, or 100 times, the diameter of one polymeric filament. The filaments may be twisted around a core filament at a pitch of about 0.25 mm to about 6 mm, e.g., about 0.75 mm to about 3 mm, about 0.75 mm to about 1 mm, and may be braided or woven. In some variations, the cable 3910 may be encased by a sheath that may have a tensile modulus of about 2000 MPa to about 5000 MPa, e.g., about 2500 MPa to about 4500 MPa, and a tensile strength greater than about 60 MPa. The sheath may be made of polyimide and may have a thickness of about 0.075 mm. The sheath may have a steel braid or coil therein, where the braid or coil filaments may be about 0.025 mm to about 0.18 mm wide, or about 0.012 mm to about 0.12 mm thick, e.g., 0.1 mm thick. A cable sheath along at least a part of the cable (and optionally, along the entire length of the cable) may help to prevent the cable 3910 from slipping along the rotatable cable shaft 3900, which may unintentionally change orientation of the tissue removal assembly 3510. The cable 3910 may have sheath configurations, surface modifications and coatings, cross-sectional shapes, and material characteristics, e.g., flexural modulus, that are similar to the elongate members as described above.

The proximal end and the distal end of the cable 3910 may be attached to the motor and the tissue removal assembly using any method appropriate for the material composition of the cable and the structure to which it is attached. For example, the distal portion of a metal cable may be soldered, welded, or brazed to the distal tip 3904 of the rotatable cable shaft 3900, where the attachment may be optionally reinforced by a ring, where the ring may be made of metals, e.g. stainless steel, and/or polymers, e.g. PEEK, polyimide. The proximal portion of a metal cable may also be similarly attached to a distal portion of the rotatable drive member 3922, at the shaft base 3902, and/or to components in the handle 3502, e.g., the coupler 3608, the rotatable shaft 3606, the pin 3609, a slidable metal lug coupled to the pin 3609 disposed within the rotatable shaft, etc. A polymeric cable may be adhesive bonded, e.g., using epoxy, to the components described above, and may be optionally reinforced by a metallic and/or polymeric ring.

The cable 3910 may have one or more pre-shaped curves as it wraps the rotatable cable shaft 3900 from where it extends from the proximal channel 3906 and inserts along the distal channel 3908. In some variations, the cable may be attached in or around the distal channel at an attachment point 3905. The geometry, size, and location of the pre-shaped curves may help to define the cutting volume and geometry of the tissue removal assembly. Pre-shaped curves that may be used with a cable in a tissue removal assembly may be flexible, where the pre-shaped curves may be straightened when tension is applied. For example, in a retracted configuration, tension applied to the cable from a proximal location may act to straighten the cable, so that the cable tracks along the surface of the rotatable cable shaft. When the tension is released, the cable may turn along the pre-shaped curve, and as the cable is further urged into the expanded configuration, the angle of the pre-shaped curve may become sharper. Cable materials with varying degrees of compliance may be used to enhance or limit the curvature of the cable. For example, a stiffer material may impose an upper bound on cable curvature, while a flexible material may permit the cable to flex to angles beyond the curvature of the pre-shaped curve. Examples of pre-shaped curves are depicted in FIGS. 39A to 39C, and FIGS. 40D to 40F. A first pre-shaped curve 3930 may be formed along a portion of the cable 3910, and may have a curve angle A1, where A1 may be from about 30° to about 75°, and may form a peak along any desired length of the cable 3910. The cable 3910 may extend away from the cable shaft 3900 towards the first pre-shaped curve 3930 at an angle A7 with respect to the longitudinal axis of the cable shaft 3900. The cable 3910 may extend back towards the cable shaft 3900 from the first pre-shaped curve 3930 at an angle A3, where the angle A3 may be different from the angle A7. The angle A7 may be substantially perpendicular to the cable shaft 3900, and/or may be from about 20° to about 110°, e.g., 85°, 90°. The angle A3 may be from about 2° to about 100°, e.g., 30°, 45°. The curve 3930 may be located centrally along the length of the cable 3910, with the angles A7 and A3 substantially equal to each other, such that the cable may be symmetric in the expanded configuration, e.g., similar to a normal curve. Alternatively, the curved cable 3910 may not be symmetric, e.g., the curve 3930 may be biased towards, or located at a distal portion of the cable 3910, as shown in FIG. 39A. In other variations, an asymmetric cable may have curves that are biased toward, or located at a proximal portion of the cable. A second pre-shaped curve 3932 may be formed along a portion of the cable 3910 that is distal to the first curve 3930, where it may form an angle with the cable shaft body 3901 as it crosses and wraps the shaft along the distal channel 3908. The cable 3910 may wrap a longitudinal length L10 of the cable shaft 3900, where L10 may be from about 10% to about 50% of the length of the cable shaft 3900, e.g., from about 0.25 mm to about 2.5 mm, e.g., 1 mm. The second curve 3932 may be from about 100° to about 170°. The portion of the cable that wraps around the shaft body 3901 and the distal tip 3904 may have a length L2 between the vertex of angle A2 and the distal attachment 3905 may be from about 0.1 inch to about 0.2 inch. The length L2 may be determined in part by the maximum pressure that can be sustained by the distal tip 3904 and distal attachment 3905 during cable rotation before the distal tip material and/or attachment fail, e.g., failure by warping, deforming, detachment, overheating, etc. For example, extending the length L2 may distribute the rotational forces over a larger region of the rotatable cable shaft 3900, which may help to reduce the failure rate of the tissue removal assembly during use. In some variations, the length of the cable 3910 that is wrapped around and/or contacting the cable shaft 3900 may be 10%, 20%, 25%, 35%, etc. of the total length of the cable 3910 in the expanded configuration. For example, in the expanded configuration, the cable 3910 may have a total length of about 10 mm to about 15 mm, and in certain variations, the length of the cable that contacts and/or wraps the cable shaft 3900 may be from about 0.1 mm to about 4 mm. The degree of turning of the cable 3910 around the cable shaft 3900 may be from about 180 degrees/turn to about 360 degrees/turn. The cable 3910 may be wrapped around the cable shaft 3900 such that it wraps from about 10° to about 540° around the circumference of the shaft body 3901, e.g., from about 200° to about 350°, or from about 340° to about 370°. Optionally, a third pre-shaped curve 3934 (FIG. 39B) may be formed along a portion of the cable 3910 that is proximal to the first curve 3930, where the third curve 3934 may be from about 100° to about 170°. Another view of the pre-shaped curves of the cable 3910 in the extended configuration is depicted in FIG. 39C. The cable 3910 extends out of the proximal channel 3906 to attain a peak displacement distal at along the first curve 3930, then angles downward to spiral around the shaft body 3901 along the second curve 3932, crossing over and along the distal tip surface into the distal channel 3908. In some variations, the cable may extend beyond the distal tip 3904 in either the extended or retracted configuration, for example, the cable may have an inflection point that is about 0.5 mm to 5 mm, e.g., 1 mm to about 5 mm, or about 2 mm away from the distal tip 3904. Extending the cable beyond the distal tip of the tissue removal assembly in the retracted configuration may allow the cable to assume a larger profile in the extended or expanded configuration. The cable 3910 may have any of the characteristics, e.g., number of turns, orientation of turns, rate of turning, inflection points, pitch angles, turning lengths, etc., of the elongate members described previously. A cable may be shaped to have the curves, turns, inflection points, etc. described above by bending the cable in a tight radius during manufacturing or using a clamping device to crimp or kink the cable. The rotatable cable shaft 3900 may have grooves, recesses, undulations, and/or curves that accommodate the turns and curves of the cable in both the retracted and extended configurations.

Figure 39D:
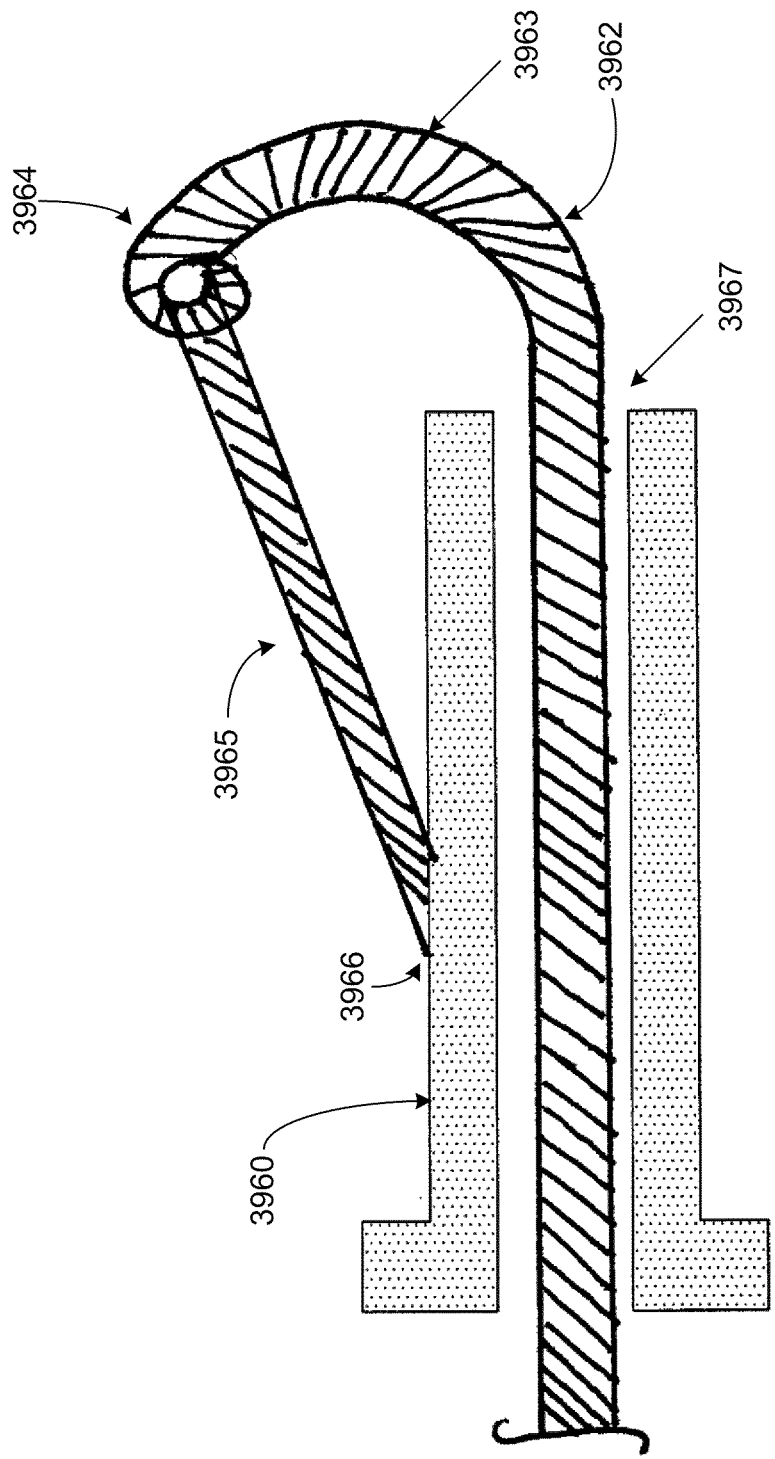
Figure 39E:
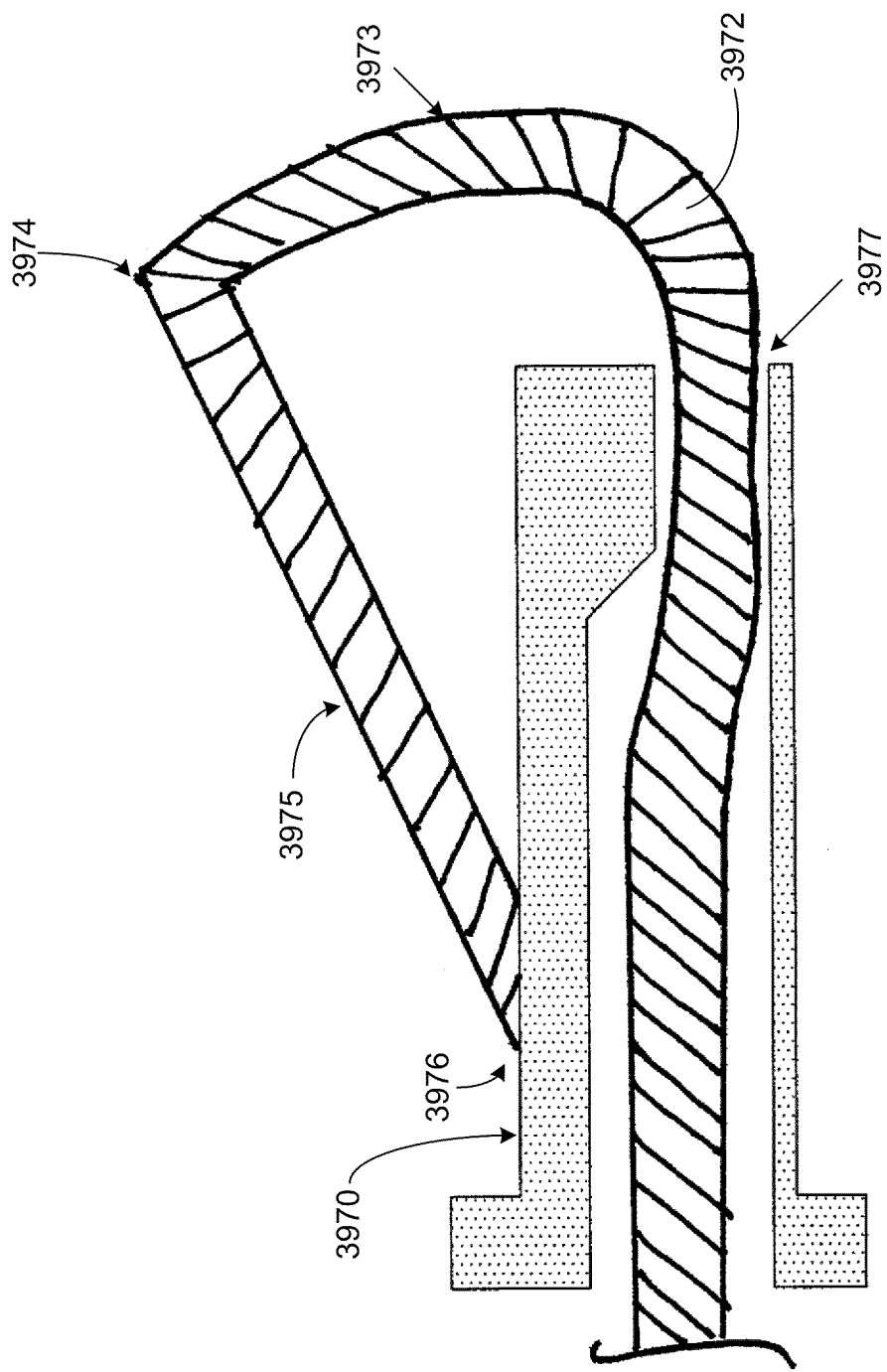
Figure 39F:
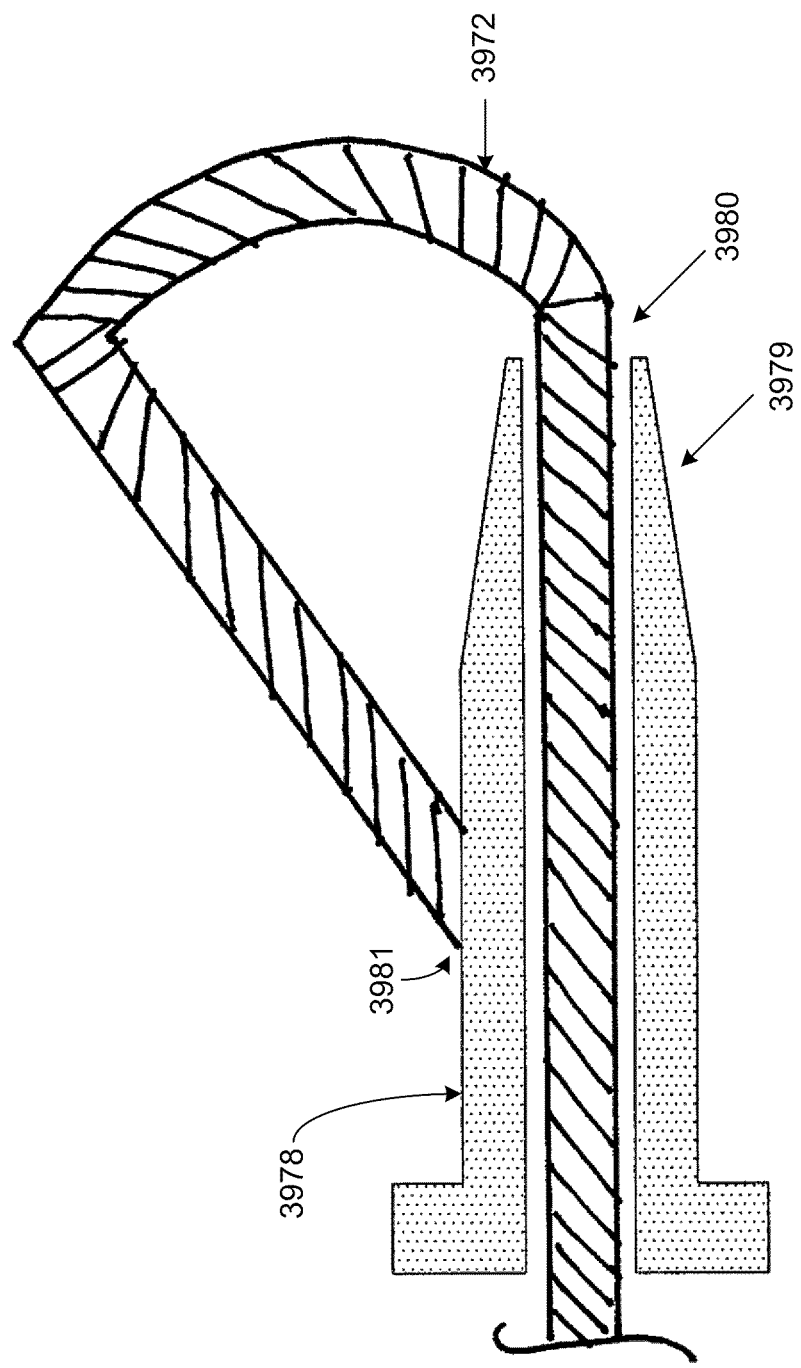

In some variations of the tissue removal assembly described above, the cable exits the rotatable cable shaft from a proximal location and is attached at a location that is distal to where it exited the rotatable cable shaft. For example, the cable 3910 exits the proximal channel 3906 and is attached at the distal attachment 3905 in the distal tip 3904, where the distal tip 3904 is distal to the proximal channel 3906. In other variations of a tissue removal assembly, the cable may be attached to the rotatable cable shaft at a location that is proximal to where it exits the shaft. This configuration may help to reduce the profile of the tissue removal assembly in the retracted configuration, which may improve the ability of the tissue removal device to access tight tissue regions, e.g., a vertebral body. Examples of the distal portion of the rotatable cable shaft and the various cable configurations are depicted in FIGS. 39D-39F. For example, in FIG. 39D, the cable 3962 extends through the rotatable cable shaft 3960, exits at the distal exit location 3967, and is attached to the proximal attachment 3966. As shown there, the cable 3962 comprises a curved portion 3963 that coils into a loop 3964, which then extends into a straightened portion 3965 that attaches to the rotatable cable shaft 3960 at the proximal attachment 3966. The loop 3964 may be continuous and/or integral with the curved portion 3963 and the straightened portion 3965, or it may be continuous with curve portion 3963, and hooked to the straightened portion 3965. The distal exit location 3967 of the cable may be centered along a cross-section of the rotatable cable shaft 3960. FIG. 39E depicts a variation of a tissue removal assembly where the distal exit location 3977 is offset with respect to a cross-section of the rotatable cable shaft 3970. As shown there, the cable 3972 exits the offset distal exit 3977, and attaches to the rotatable cable shaft 3970 at a proximal attachment 3976. The cable 3972 may have a curved portion 3972 that transitions to a straightened portion 3875 at an inflection juncture 3974. The cable 3972 may also be used with a rotatable cable shaft 3978 that has a beveled and/or tapered distal tip 3979, where the cable 3980 may exit the rotatable cable shaft 3978 at distal exit 3980, and attach to the rotatable cable shaft 3978 at the proximal attachment 3981. A tissue removal assembly that has a cable configured with a curved portion, an inflection juncture, and a straightened portion may help to remove tissue located at certain regions, while substantially preserving tissue at other regions. For example, in a discectomy to treat herniation or for nucleus replacement, this cable configuration may be used to cut and remove the nucleus, but generally preserve the cartilaginous endplate.

Figure 39G:
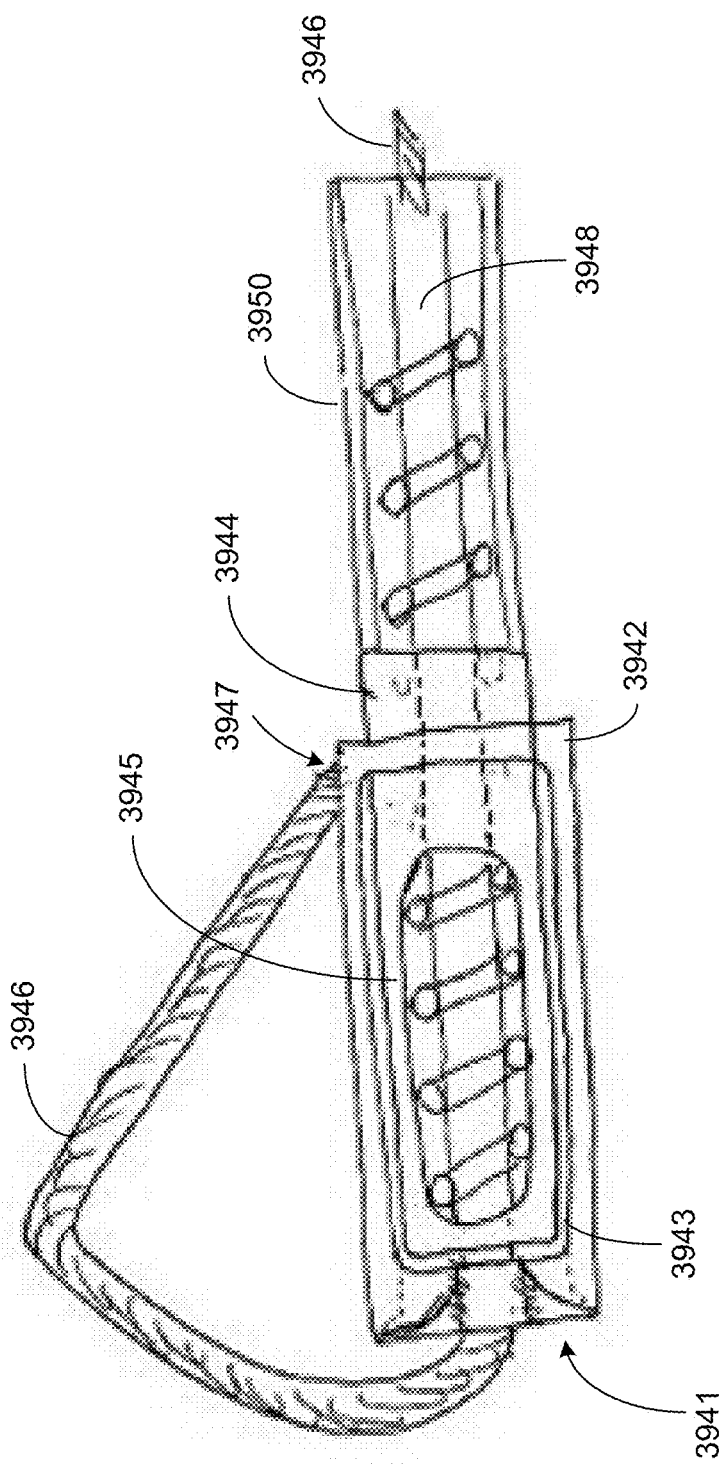

In some variations, the rotatable cable shaft may have one or more ports or windows for aspiration, infusion of therapeutic agents, and tissue and/or fluid collection. One example of a rotatable cable shaft with a distal port and at least one side window is shown in FIG. 39G. The tissue removal assembly 3940 may comprise an inner tube 3944 that is affixed to the distal portion of an outer tube 3950, a rotatable drive member 3942 in outer tube and extending through the inner tube, a rotatable cable shaft 3942 assembled over the inner tube 3944, and a cable 3946 in the rotatable drive member 3948 that extends through the inner tube 3944, exits a distal port 3941 in the rotatable cable shaft 3942, and attaches to the rotatable cable shaft at a proximal attachment 3947. The rotatable cable shaft 3942 may have a rotatable cable shaft window 3943 and the inner tube 3944 may have a corresponding inner tube window 3945, where at least a portion of both windows may be aligned. Tissue may be taken through the rotatable cable shaft window 3943, through the inner tube window 3945, and transported proximally to a collector by the rotatable drive member 3948. During use, a motor may rotate the rotatable drive member 3948, the rotatable cable shaft 3942, and the cable 3946 to cut, emulsify, and/or remove tissue. When the rotatable cable shaft window 3943 and the inner shaft window 3945 are axially aligned, e.g., in the course of rotation, the rotatable drive member 3948 may be exposed to draw in tissue, which may then be transported to a collector. Tissue and/or fluids may also be aspired, and/or otherwise drawn in through the distal port 3941. In addition to cutting, emulsifying, etc. tissue with the rotating cable 3946, the distal port 3941, rotatable cable shaft 3942, the inner tube 3944, the rotatable drive member 3948, and other features may have sharpened edges and the like to further cut or break up tissue that is being drawn proximally along the rotatable drive member, as described previously.

Other variations of tissue removal assemblies may have a plurality of aspiration apertures, as depicted in FIGS. 40A-40E. Tissue removal assembly 4000 comprises a tubular member 4004 attached distally to the outer tube 4002, a rotatable drive member 4030 extending through the tubular member 4004, a rotatable cable shaft 4010 attached distally to the rotatable drive member 4030, and an elongate member as previously described and configured. The tubular member 4004 may comprise a plurality of apertures, for example, a first aperture 4006 and a second aperture 4008 located across from the first aperture. These apertures may be sized and shaped for the passage of tissue therethrough, which may be transported by a tissue transport assembly 4034 to a collector. For example, tissue that is removed may be transported away from the target tissue site via the first and second apertures 4004 and 4008. The tubular member 4004 may be about 4 mm to about 5 mm, e.g., about 4.7 mm long, and may have an outer diameter of about 1 mm to about 1.5 mm, e.g., about 1.4 mm, and an inner diameter of about 0.5 mm to about 1 mm, e.g., about 0.9 mm. The first and second apertures 4004 and 4008 may be shaped as ellipses, with a length of about 1.25 mm to about 1.75 mm, e.g., about 1.7 mm. The rounded ends of the ellipse-shaped apertures may have a radius of curvature of about 0.45 mm. Other variations of apertures may have any suitable shapes, such as circular, rectangular, etc., and may have slotted, as appropriate for drawing tissue or fluid therethrough. The tubular member 4004 may be made of any of the metallic and/or polymeric materials as described above, for example, it may be made of passivated or electro-polished 17-4 stainless steel.

The rotatable shaft 4010 may comprise a distal tip 4018 with a distal channel 4016, and a shaft base 4020 with a proximal channel 4014. The distal tip 4018 may have a cylindrical shape, where the distalmost tip is flattened with rounded edges. As illustrated in FIG. 40B, the diameter of the shaft base 4020 and the distal tip 4018 may be similar to the diameter of the shaft body 4012, however, in other variations, the diameter of the shaft base may be larger or smaller than the diameter of the distal tip. For example, the shaft body 4012 may have a diameter of about 0.010 inch to about 0.030 inch, or about 0.025 inch, while the distal tip 4018 and/or the shaft base 4020 may have a diameter of about 0.025 inch to about 0.040 inch, or about 0.033 inch. The rotatable shaft 4010 may have a length L4 of 0.3 inch to about 0.4 inch, for example, about 0.335 inch or about 0.353 inch. The shaft base 4020 may have a length L5 of about 0.100 inch. The distal tip 4018 may have a length L7 of about 0.05 inch. The shaft base 4020 may be separated from the distal tip 4018 by a length L6 of about 0.20 inch. Optionally, the shaft base 4020 may have a rim that has a larger diameter than the shaft base, which may help the rotatable shaft 4010 attached to the drive member 4020. The rotatable shaft 4010 may be made of any of the metallic and/or polymeric materials described above, for example, it may be made of passivated or electropolished 17-4 stainless steel.

Figure 40A:
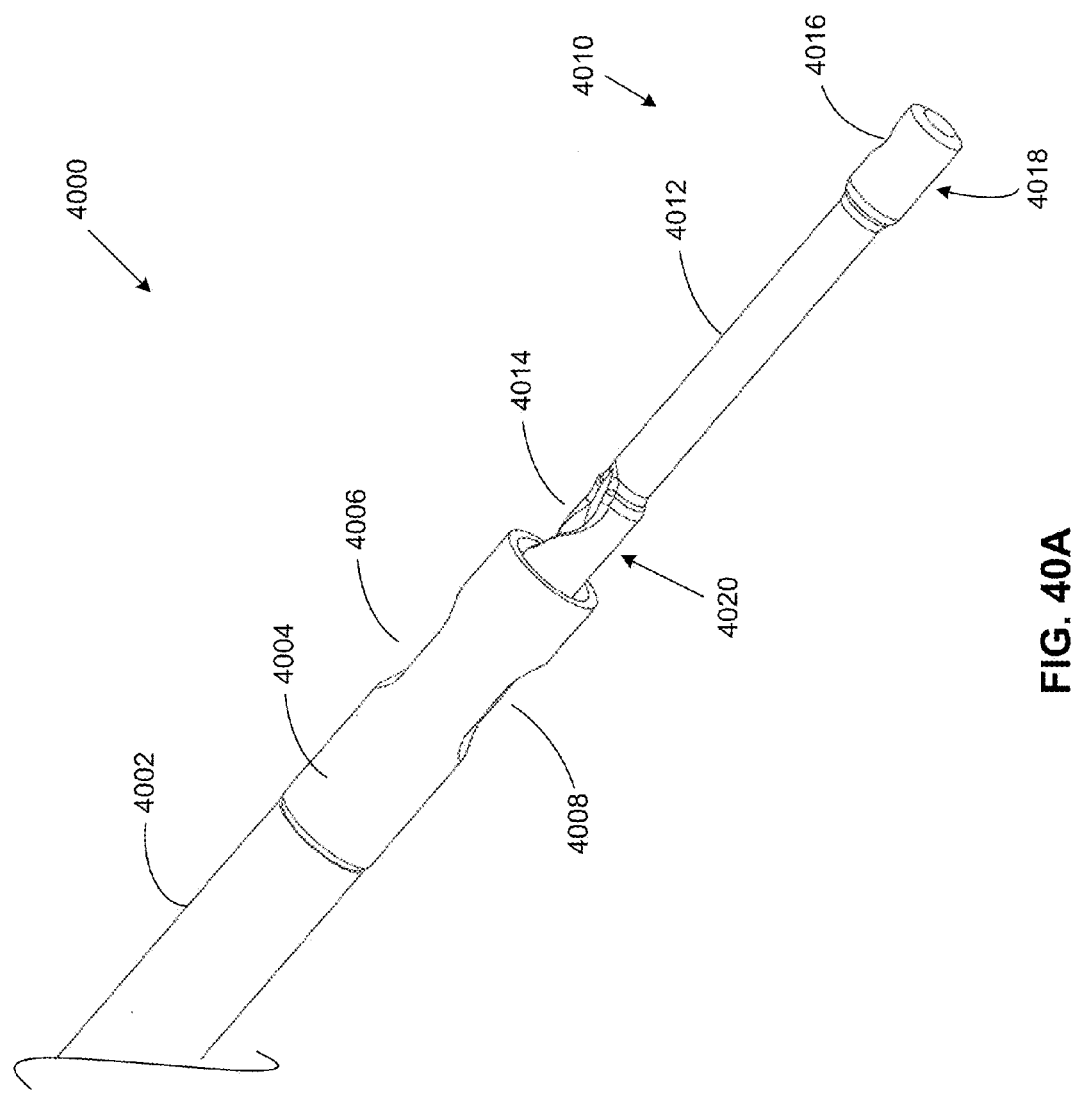
FIGS. 40A to 40F illustrate another variation of a tissue removal assembly.
Figure 40B:
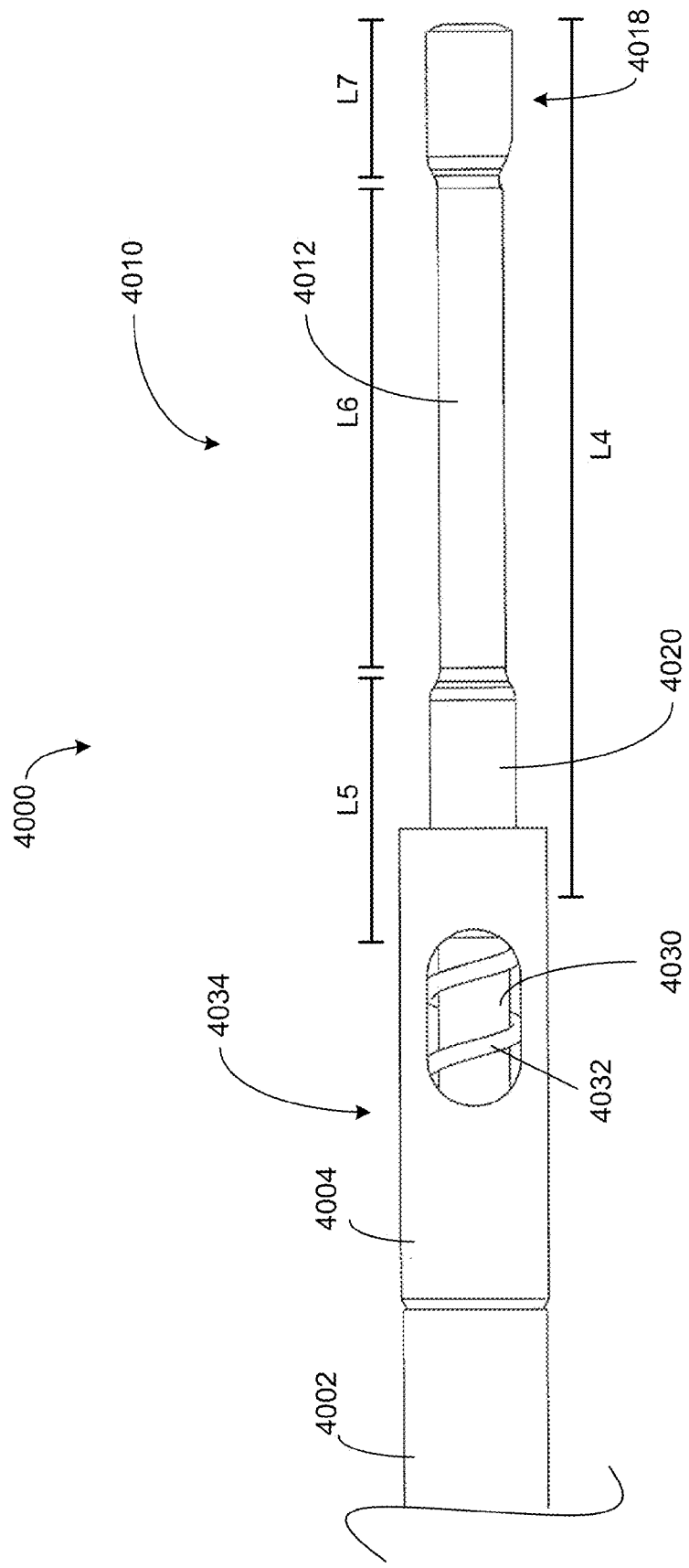
Figure 40C:
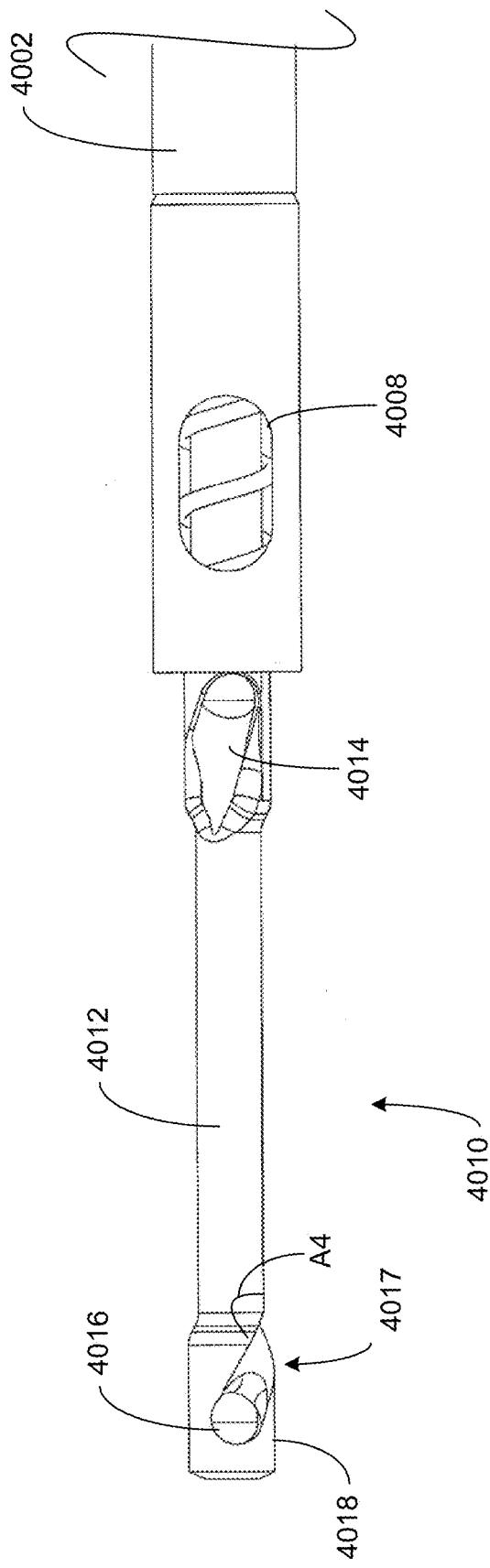
Figure 40D:
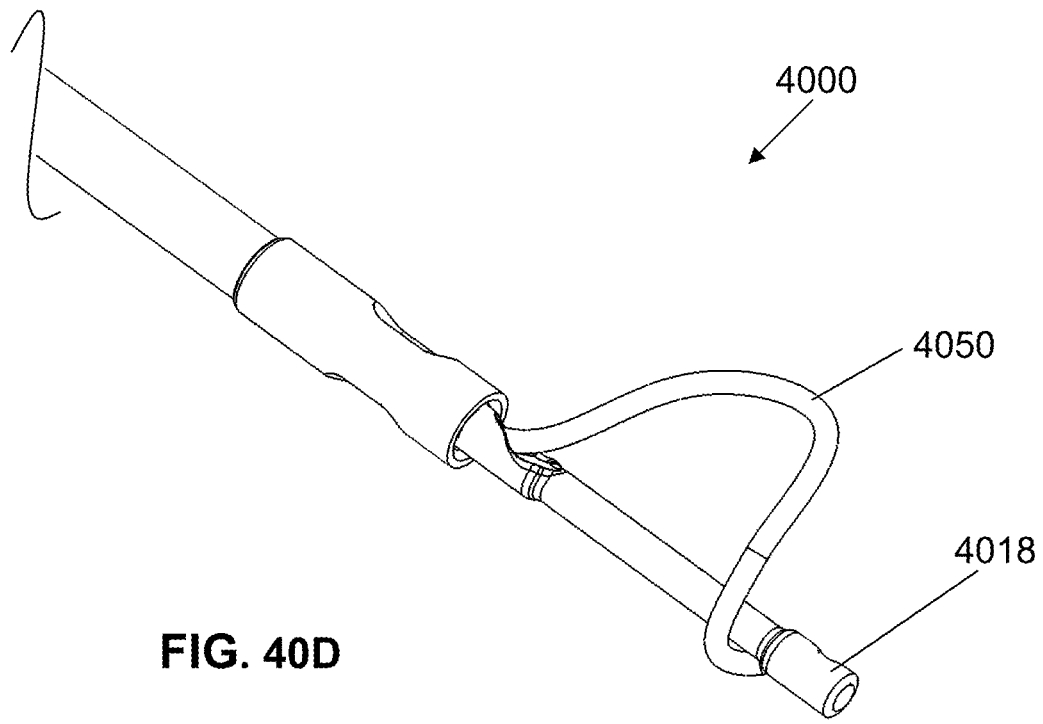
Figure 40E:
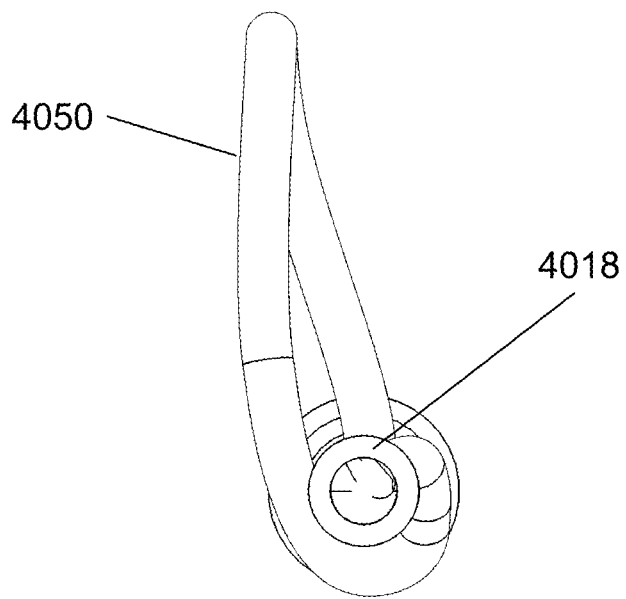
Figure 40F:
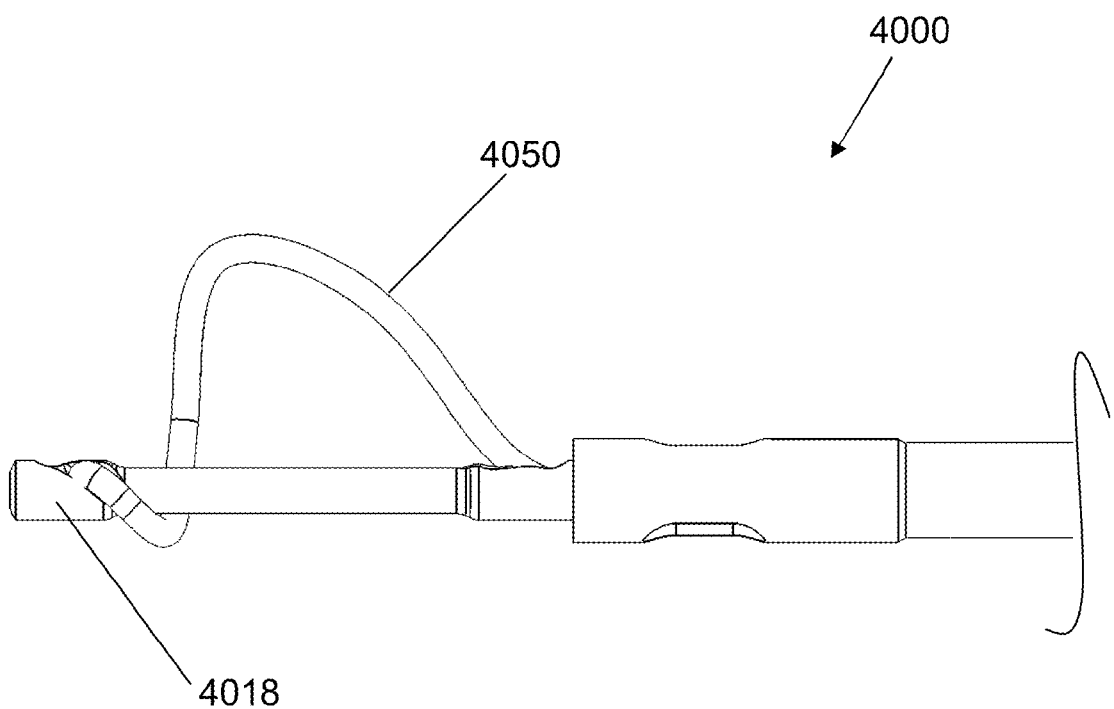

As seen in both FIGS. 40A and 40C, the distal channel 4016 and the proximal channel 4014 may be located such that they are aligned along the surface of the rotatable shaft, e.g. a line between them is substantially parallel with the longitudinal axis of the rotatable shaft 4010. In other variations, the distal channel 4016 and the proximal channel 4014 may be offset at an angle with respect to each other, e.g., the proximal channel may be located at rotated position along the surface of the rotatable shaft 4010, where the degree of rotation may be from about 10° to about 359°. The distal channel 4016 and the proximal channel 4014 may be formed at an angle with respect to the longitudinal axis of the shaft body 4012. The angles grooves and recesses associated with these channels may accommodate the curves and orientation of the cable, and may help to position the cable to reduce focal forces and/or loading on the rotatable shaft 4010. For example, a distal recess 4017 along the distal tip 4018 terminating at the distal channel 4016 may be located at an angle A4 with respect to the shaft body 4012, where the angle A4 may be from about 90° to about 170°, e.g., about 135°. The proximal channel 4014 may be formed at an angle that may be greater than, equal to, or less than the angle A4 of the distal recess 4017 associated with the distal channel 4016. The width of the recess 4017 may be determined in part by the width and/or diameter of the cable as previously described, and may have any width suitable for guiding a cable along the surface of the rotatable shaft 4010. The distal recess 4017 may curve along the surface of the rotatable shaft 4010 at any turning rate as previously described. Optionally, there may be one or more similar recesses along the shaft body 4012 or shaft base 4020, e.g., associated with the proximal channel 4014. FIGS. 40D to 40F depict perspective, anterior elevational, and side views of the tissue removal assembly 4000 with a cable 4050 in an expanded configuration. The cable 4050 may assume any of the expanded configurations previously described, for example, the cable 4050 may be configured as depicted in FIGS. 39A to 39C.

Figure 41A:
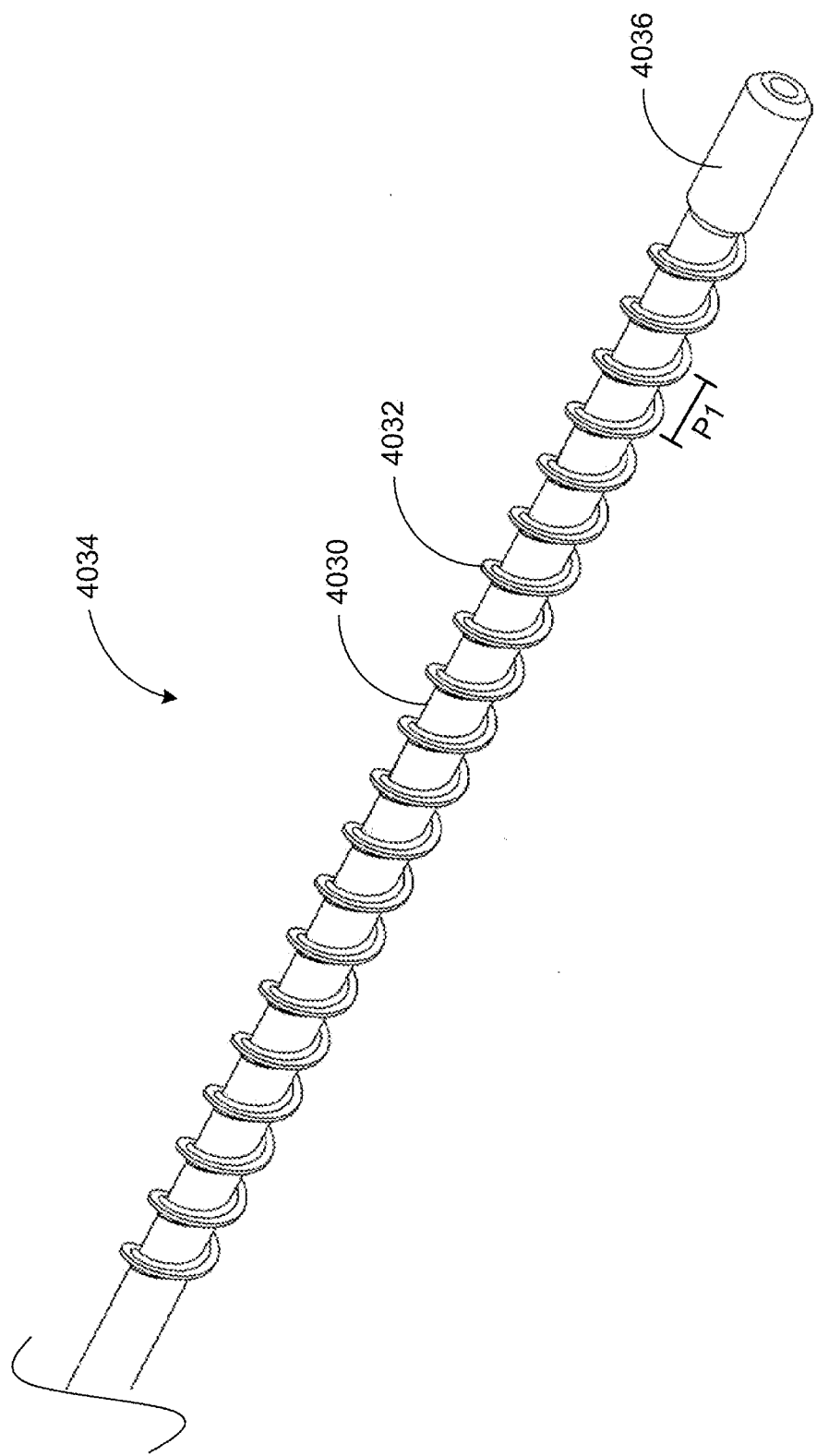

The shaft base 4020 may be attached distally to the tissue transport assembly 4034 by soldering, welding, adhesive bonding, or any material-appropriate technique for attaching the rotatable shaft 4010 to the tissue transport assembly. One variation of a tissue transport assembly that may be used with a tissue removal assembly is shown in FIG. 41A. The tissue transport assembly 4034 may comprise a rotatable drive member 4030, a helical member 4032 mounted on at least a portion of the rotatable drive member 4030, and a tubular cap 4036 attached at a distal portion of the drive member 4030. The rotatable drive member 4030 may be made of one or more polymeric and/or metallic materials that are suitable for drawing tissue up proximally from the tissue removal assembly to the collector. For example, the rotatable drive member 4030 may be made of stainless steel, nickel titanium alloy, carbon fiber, high density molecular weight polyethylene, and the like. The inner diameter of the rotatable drive member 4030 may be from about 0.010 inch to about 0.020 inch, e.g., 0.015 inch. The outer diameter of the rotatable drive member 4030 may be from about 0.0350 inch to about 0.0450 inch, e.g., 0.0407 inch. The helical member 4032 may be integrally formed with the rotatable drive member 4030, or may be separately formed and attached to the drive member. The pitch P1 of the helical member 4032 may be from about 0.010 inch to about 0.100 inch, e.g., 0.030 inch to about 0.25 inch, or about 0.060 inch to about 0.100 inch, or 0.030 inch, or 0.080 inch. The pitch P1 of the helical member may be adjusted according to the rotational speed driven by the motor, or according to the desired rate of tissue transport from the tissue removal assembly to the collector. The helical member 4032 may be made of materials similar to the rotatable drive member 4030, and may optionally include surface modifications such as friction-reducing coatings, fluid dynamic channels, etc., which may help to transport the removed tissue to the collector. The helical member 4032 may be right hand wound, or left hand wound, as appropriate for tissue transport. In some examples, the helical member 4032 may be wound in the same sense as the rotation of the drive member. The cross-section of a helical member may have any shape that is suitable for tissue transport. While the cross-section of the helical member 4032 is circular, in other variations, the cross-section may be triangular, rectangular, square, or ovoid. In certain variations, a rotatable drive shaft may be an integrally formed tube, e.g., a tube formed from a solid sheet of material that is not woven or braided, with the helical member coiled along the outer surface of the tube. In other variations, the rotatable drive shaft may be made of multiple layers of tightly wound coiled members, where the inner layers of the coiled members may have a first pitch, the outer layers of the coiled members may have a second pitch. For example, the pitch of the coiled members may vary from the innermost layer to the outermost layer, e.g., the innermost coil layer may have the tightest pitch, and the outermost layer may have the highest pitch. In this variation, polymers or other adhesives, such as epoxy, parylene, polyurethane, and the like, may be applied in between coiled layers or as an outer coat, to secure the threads of the outermost coiled member to the next inner coiled layer. These adhesives coatings and layers may help prevent the coiled layers from separating and lifting off each other. In general, the tissue transport assembly 4034 may comprise one or more recesses, grooves, channels, protrusions, and the like which may expedite tissue transport as desired. Other characteristics of drive members and helical members have been described previously, and may also be used with the tissue transport assembly 4034.

The tubular cap 4036 may be integrally formed with the rotatable drive member 4030, or may be separately formed and mounted onto the rotatable drive member 4030. The distalmost portion of the tubular cap 403 may have one or more apertures configured to pass a cable and/or tissue transport assembly therethrough. The tubular cap 4036 may be attached to the rotatable drive member 4030 by soldering, welding, adhesive bonding, friction fitting, snap fitting, and the like. In some variations, the tubular cap 4036 is made of one or more polymeric materials, such as polyethylene, nylon, carbon fiber, urethane, polyester, polyaramide, PEEK, polyimide, and other similar materials. The rotatable shaft 4010 may be attached to the tubular cap 4036 by any of the suitable methods described above.

Optionally, the tissue transport assembly may also comprise a sheath (not shown) that encases at least a portion of the rotatable drive member 4030. The sheath may be made of polymeric and/or a metal materials, for example, polyimide with a stainless steel braid. The stainless steel braid may be formed using ribbon measuring about 0.0005 inch by about 0.0025 inch and have a braid density of approximately 80 pic. The sheath may have an inner diameter for about 0.035 inch to about 0.050 inch, e.g., 0.0420 inch. The sheath may have an outer diameter of about 0.040 inch to about 0.055 inch, e.g., 0.048 inch. The wall thickness of the sheath may be about 0.0030 inch. In some variations, the sheath may have a length of about 10.00 inches to about 20.00 inches, e.g., 12.00 inches, or 12.25 inches.

Figure 41B:
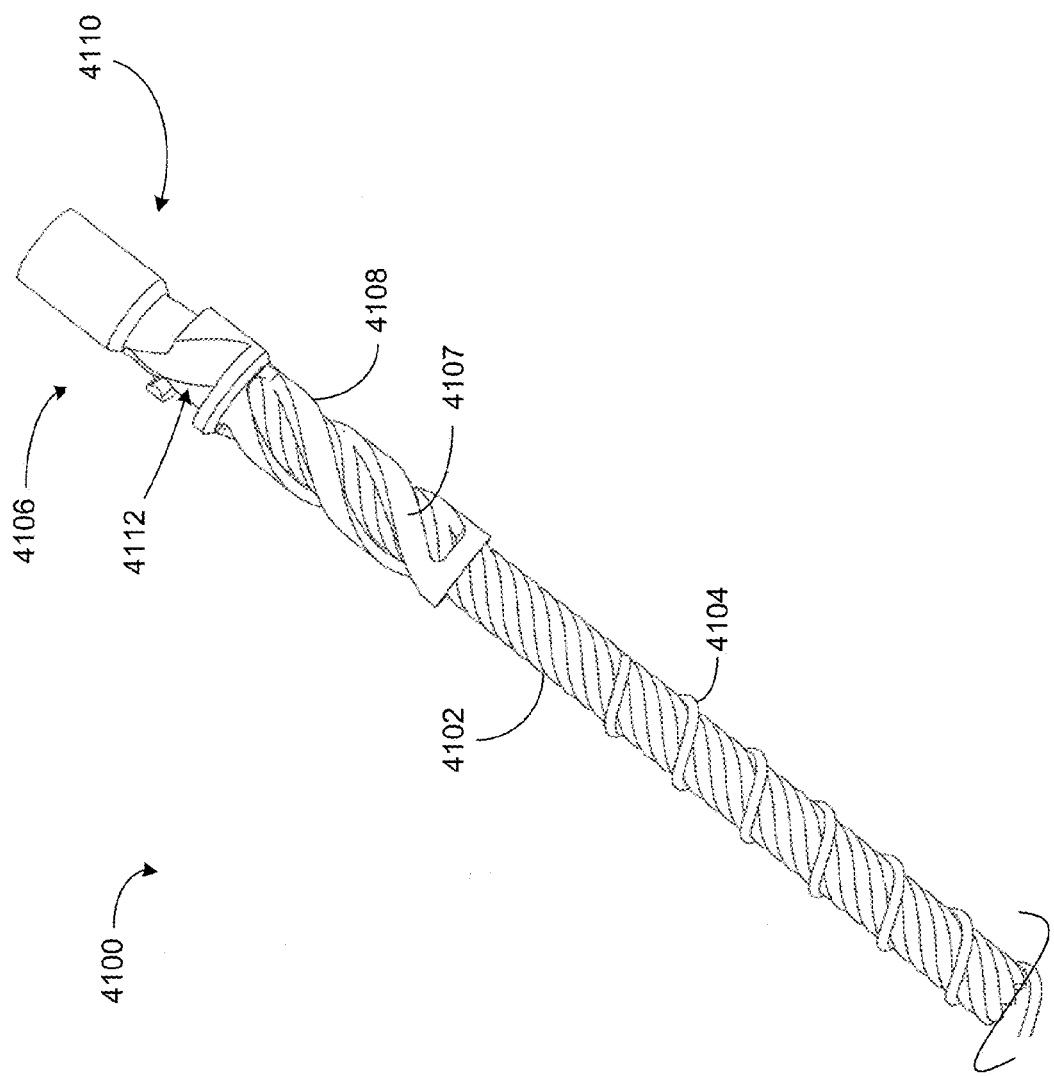

Grooves and recesses may also help to encourage any tissue or fluid to be drawn up from the target tissue site to a proximal collector. Another example of a tissue transport assembly 4100 is shown in FIG. 41B. As seen there, the tissue transport assembly 4100 comprises a drive member 4102 that is attached at its distal end to an impeller 4106, and a helical member 4104 mounted on at a least a portion of the drive member 4106. The proximal portion of the impeller 4106 may comprise a helical cage 4108, and the distal portion may comprise an impeller cap 4110. The impeller cap 4110 may be made of a polymeric material such as PEEK, Pebax, nylon, polyethylene, polyimide, and the like, and may have a length L8 of about 0.150 inch to about 0.300 inch, e.g., 0.235 inch. The impeller 4106 may also comprise one or more groves and/or cutout regions, for example, slanted groove 4112 and cutout region 4114 on the impeller cap 4110. The slanted groove 4112 and/or the cutout region 4114 may be sized and shaped for passing a cable over the surface of the impeller 4106, similar to the grooves and recesses that may be used with a rotatable shaft as previously described. In some variations, an insulating coating may be provided on a portion of the impeller to help reduce the risk of thermal nerve injury during the procedure.

Figure 41D:
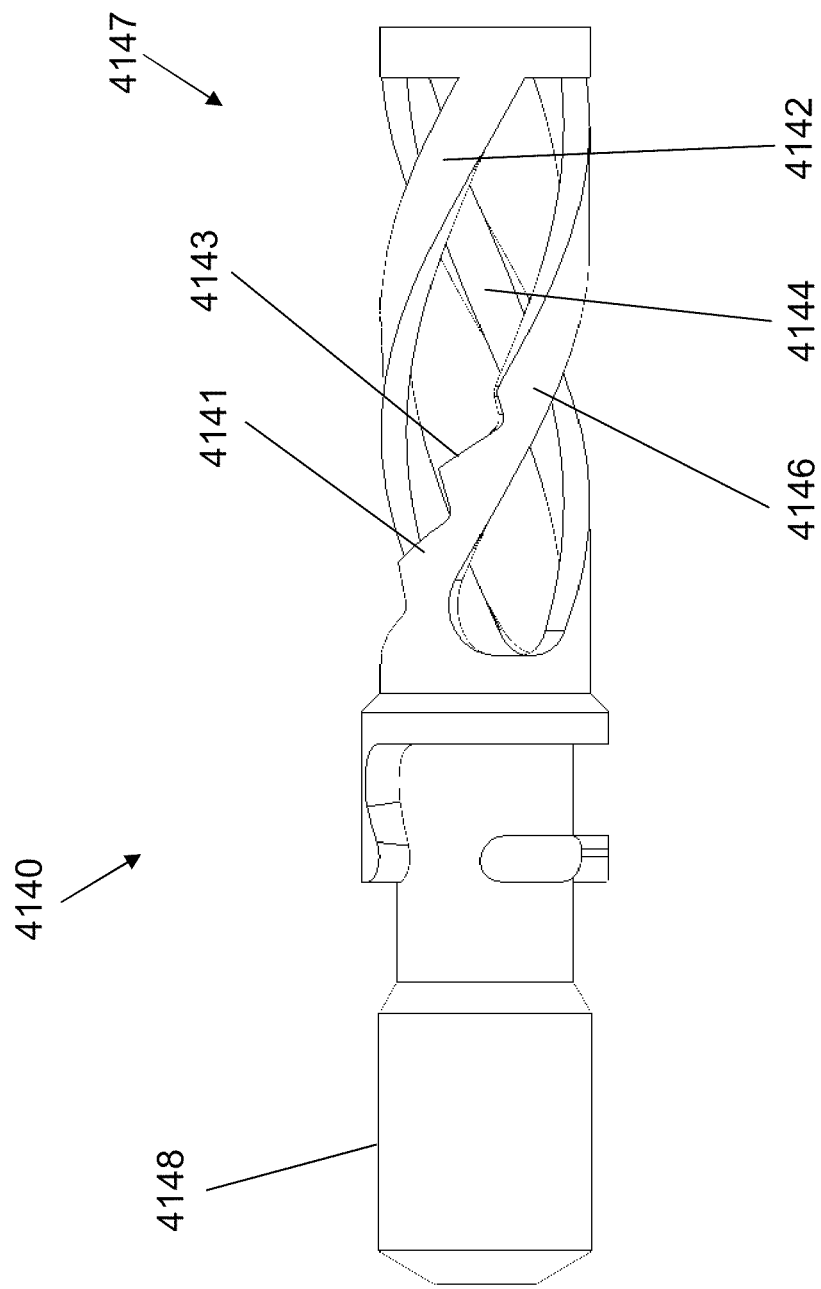
Figure 41E:
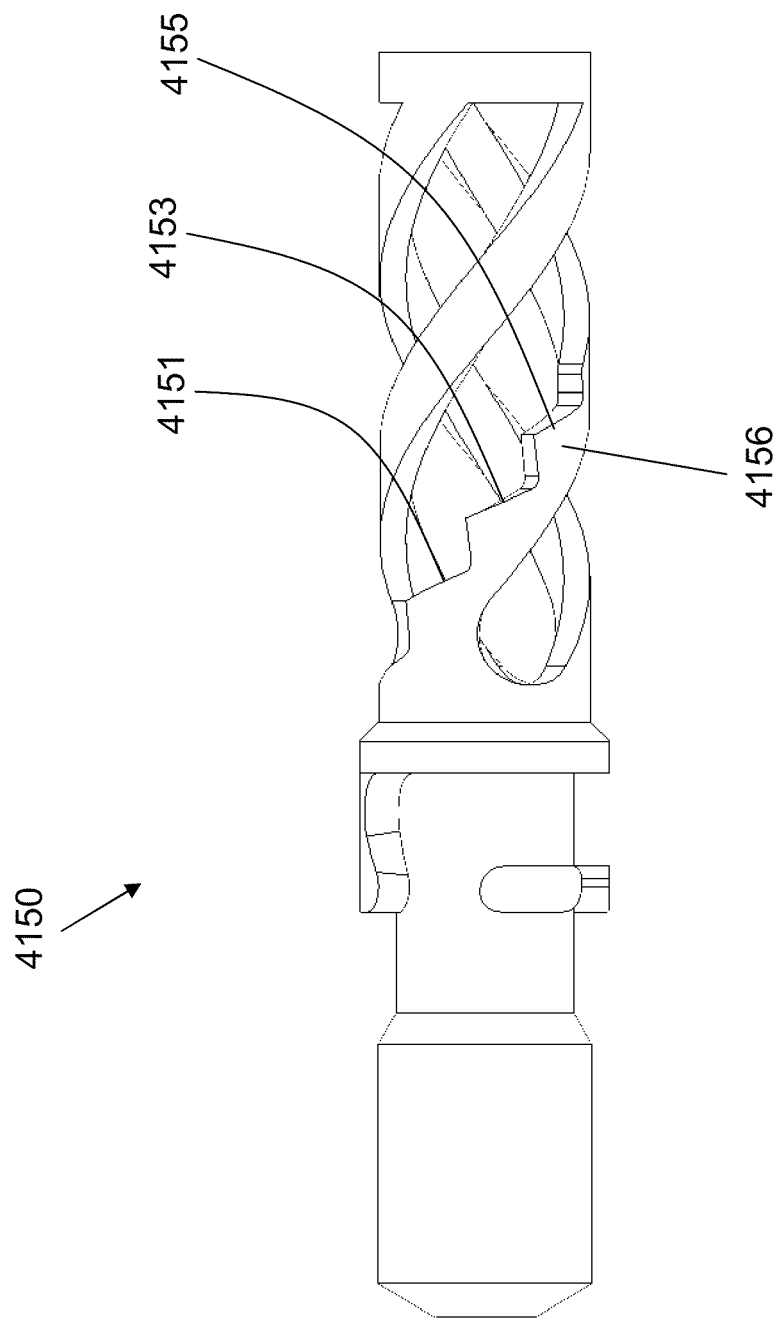
Figure 41F:
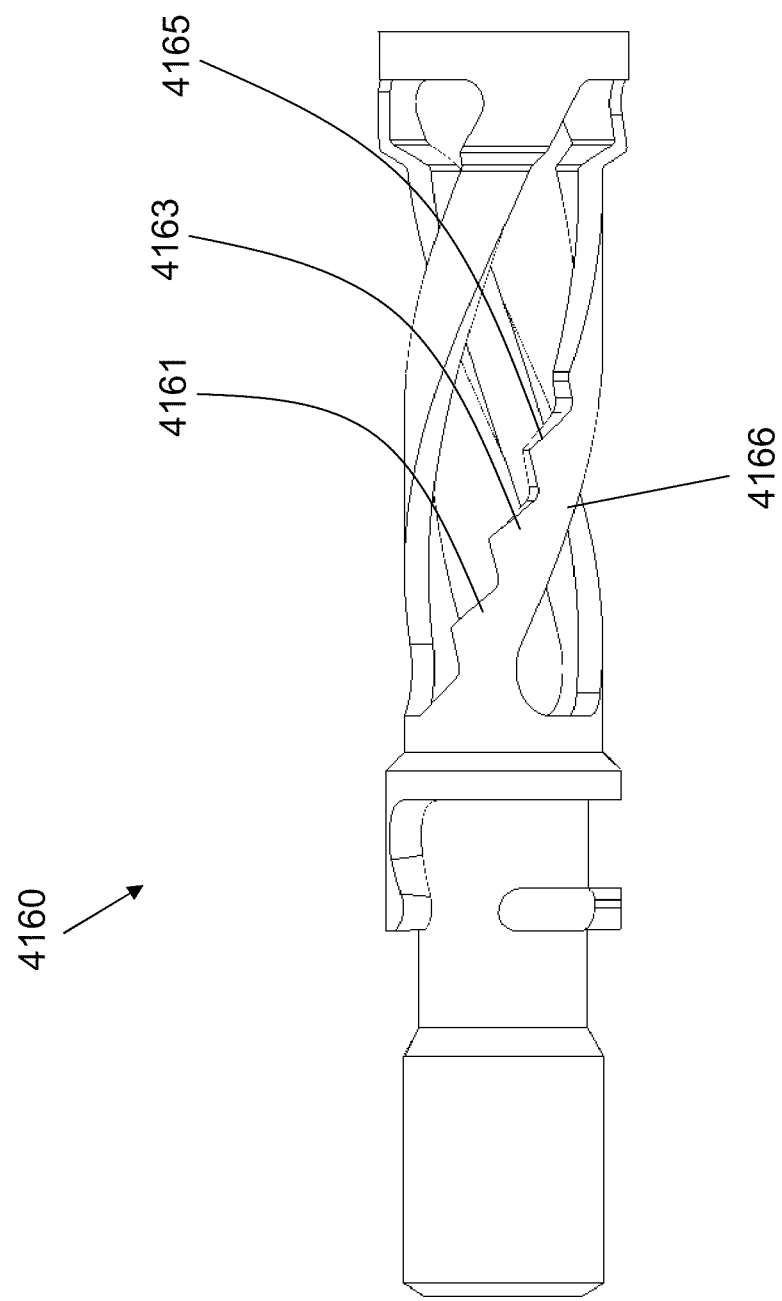
Figure 41G:
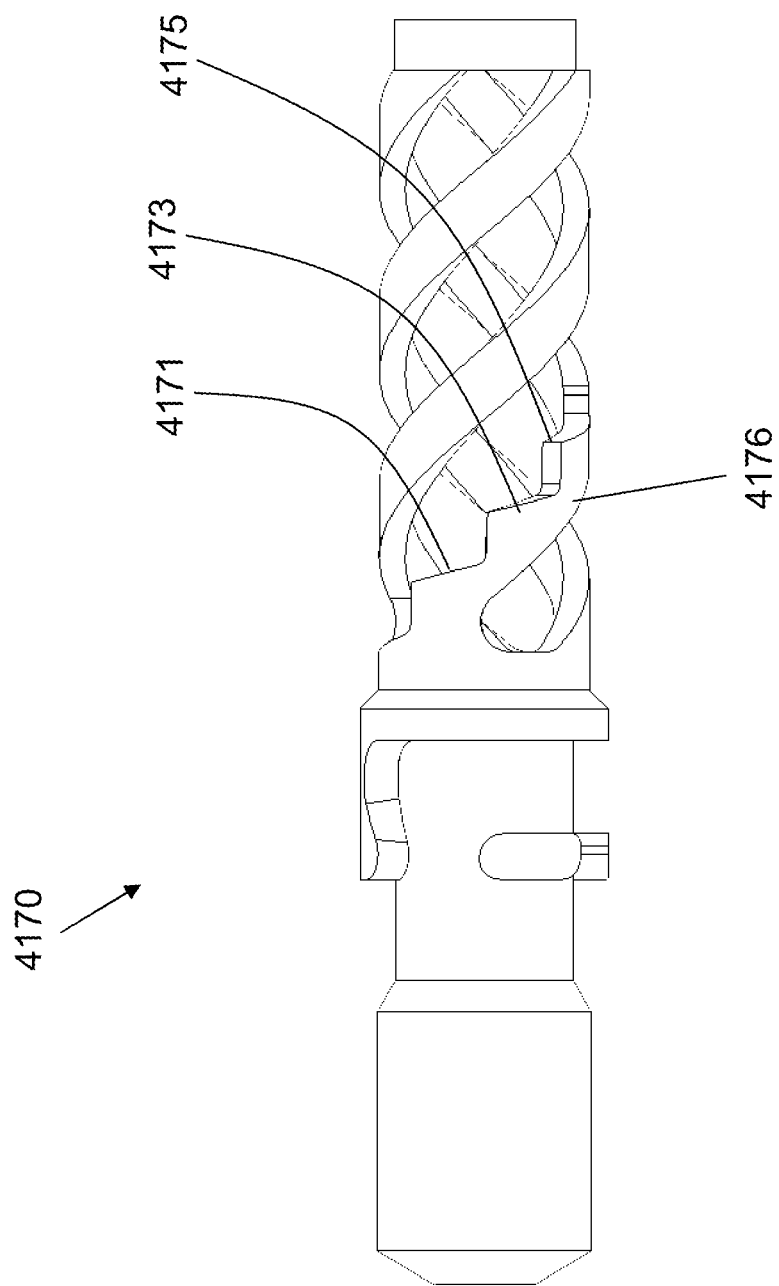
Figure 41H:
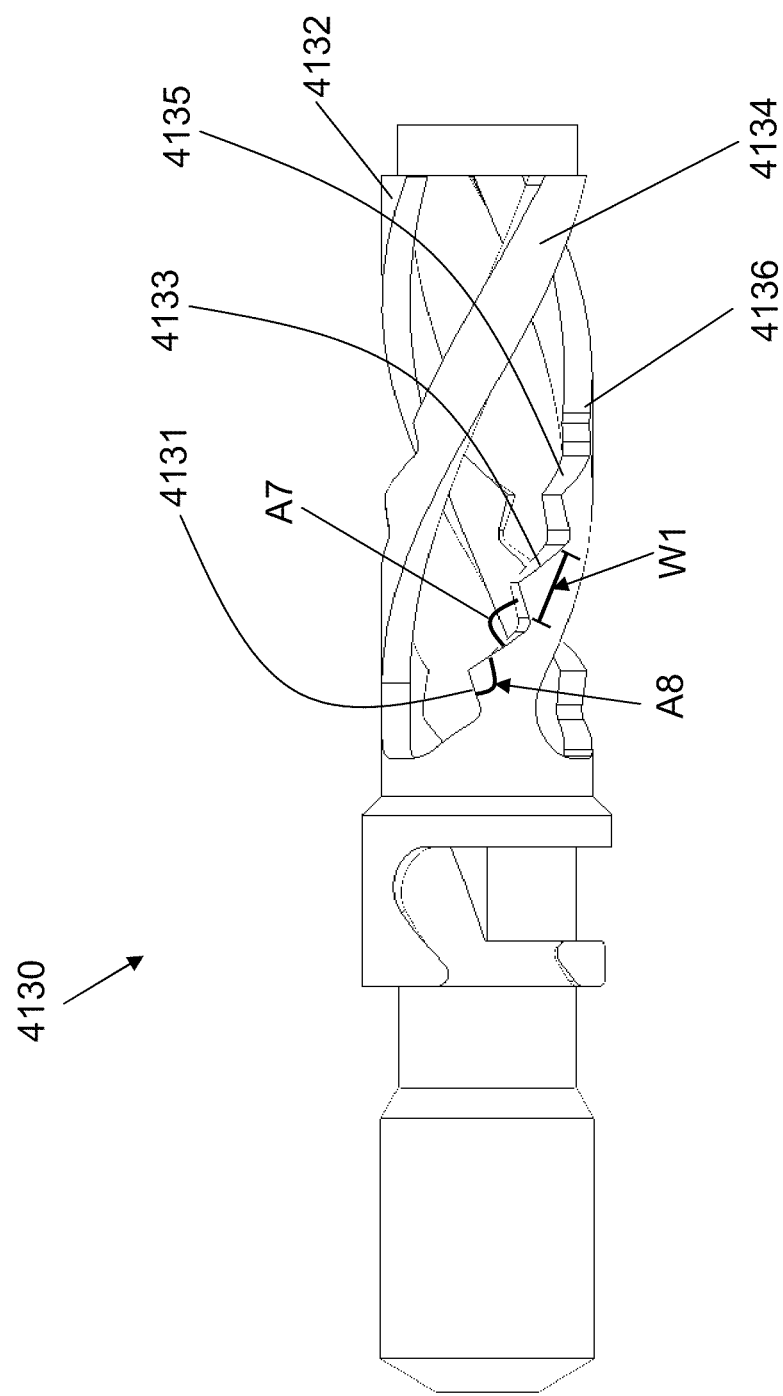

The helical cage 4108 may be made of a metallic material such as stainless steel or polymeric material such as PEEK. Certain variations of an impeller may comprise two more braids similar to braid 4107. As seen in FIG. 41C, the impeller 4106 may comprise three braids that have a clockwise pitch angle of about 30° to about 60°, e.g., 35°. The braids 4107 may have a rate of turning along the length L9 of the helical cage 4108 of about 3 turns/inch to about 5 turns/inch, e.g., 4.5 turns/inch. The length L9 of the helical cage 4108 may be from about 0.150 inch to about 0.300 inch, e.g., 0.230 inch. The braid 4107 may have a width from about 0.015 inch to about 0.030 inch, e.g., 0.028 inch. The helical cage 4108 may have any number of braids, braid twist angles, or surface structures such as serrations, ridges, etc., that may be useful for drawing tissue from the tissue removal assembly to the collector. The impeller cap 4110 may also have one or more curved, rounded, angled, tapered, etc. edges that may help to draw tissue towards the impeller. For example, the variation of an impeller 4140 shown in FIG. 41D may comprise an impeller cap 4148 with an angled distal tip and helical cage 4147. The helical cage 4147 may have a first braid 4142, a second braid 4144, and a third braid 4146. One or more of the braids may have serrations, and there may be any number of serrations on a single braid. For example, the third braid 4146 may have two serrations 4141, 4143. In another variation of an impeller 4150 depicted in FIG. 41E, a braid 4156 may have three serrations 4151, 4153, and 4155. The braids of the impeller 4150 may have a braid twist angle of about 40°. FIG. 41F depicts an impeller 4160 with three braids that have a twist angle of about 30°. The braid 4166 may have three serrations 4161, 4163, and 4165. FIG. 41G depicts an impeller 4170 with three braids that have a twist angle of about 50°. The braid 4176 may have three serrations 4171, 4173, and 4175. In other variations, such as impeller 4136 depicted in FIG. 41H, all the braids 4132, 4134, 4146 have one or more serrations, for example, three serrations 4131, 4133, 4135. The serrations may be located on a leading edge of each braid as determined by the braid angle and direction of rotation. The serrations may help to further break up the tissue as it is drawn proximally away from the target tissue site. Serrations may have a positive rake (e.g., from about 30° to 40°) or negative rake and/or may be slanted at an angle, for example, the slant angle may be between about 20° to about 40°, and/or about 60° to about 80°. The angle A7 between the serrations 4131, 4133, 4135 may be from about 80° to 150°, e.g., 105°, or 104.6°. The sharpened or pointed portion of a serration may have an angle A8, where A8 may be from about 45° to 120°. The edges of the serrations 4131, 4133, 4135 may be any length appropriate for cutting or pulverizing tissue, e.g., from about 0.001 inch to about 0.004 inch, e.g., 0.002 inch. Other variations of serrations may be larger, with edge lengths of about 0.01 inch to about 0.02 inch. The two edges of a serration may have a first short edge, and a second long edge, while in other variations, the edges may be the same length. Serrations may have a width W1 that may be from about 0.01 inch to about 0.2 inch, e.g., 0.04 inch. Some variations of serrations may be C-shaped, and/or may have other angular geometries with sharp turning edges. Other cutting features or edges may be provided along the impeller and/or drive shaft, such as sharpened helical members, enzymatic coatings, etc. that may break up tissue and expedite its transport to a collector.

Figure 24A:
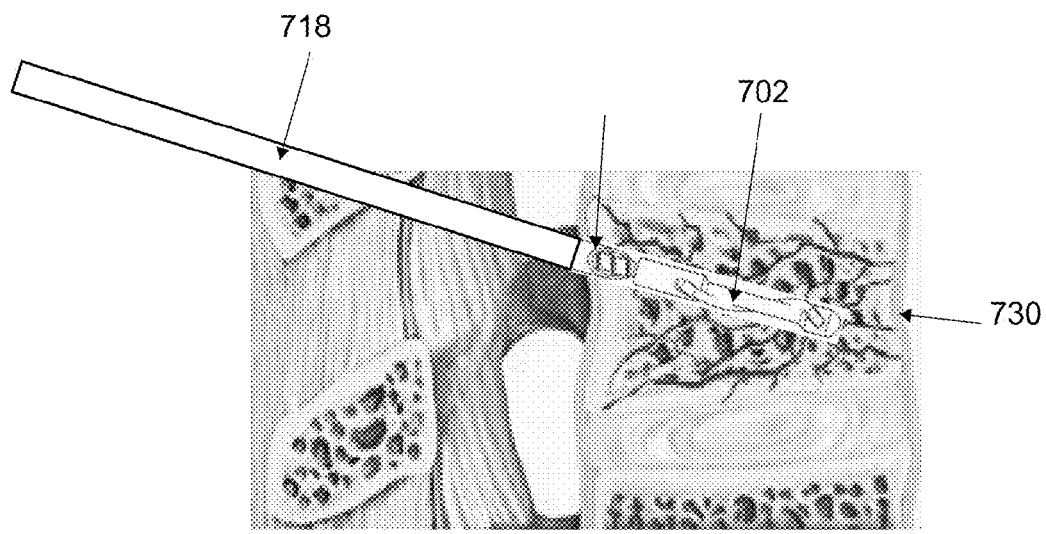
FIGS. 24A to 24C depicts one embodiment for performing vertebroplasty.
Figure 24B:
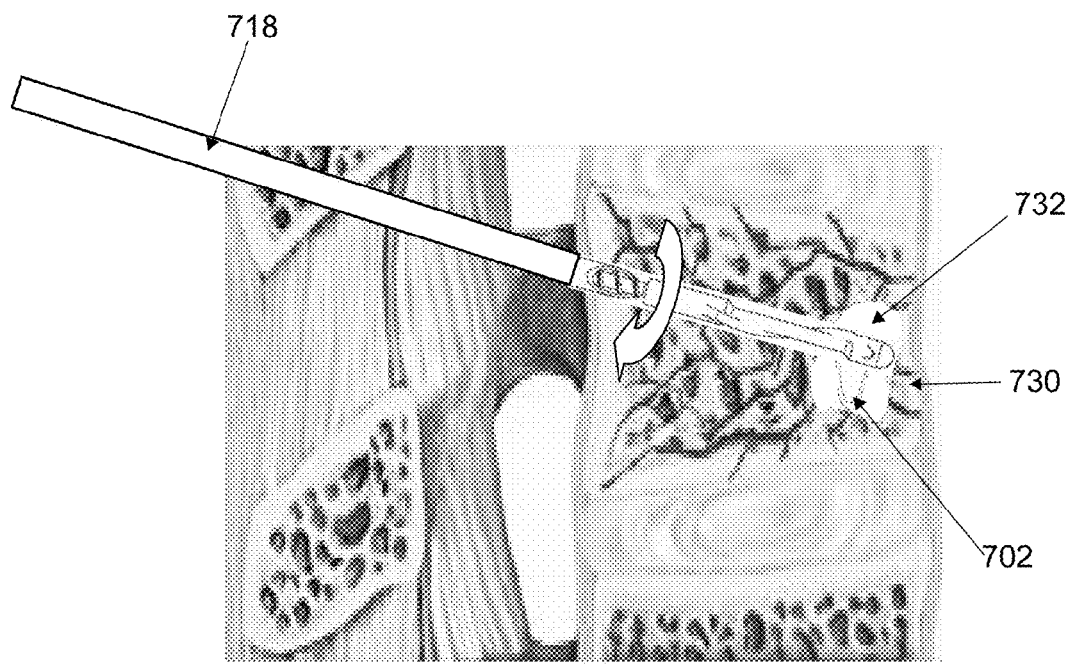
Figure 24C:
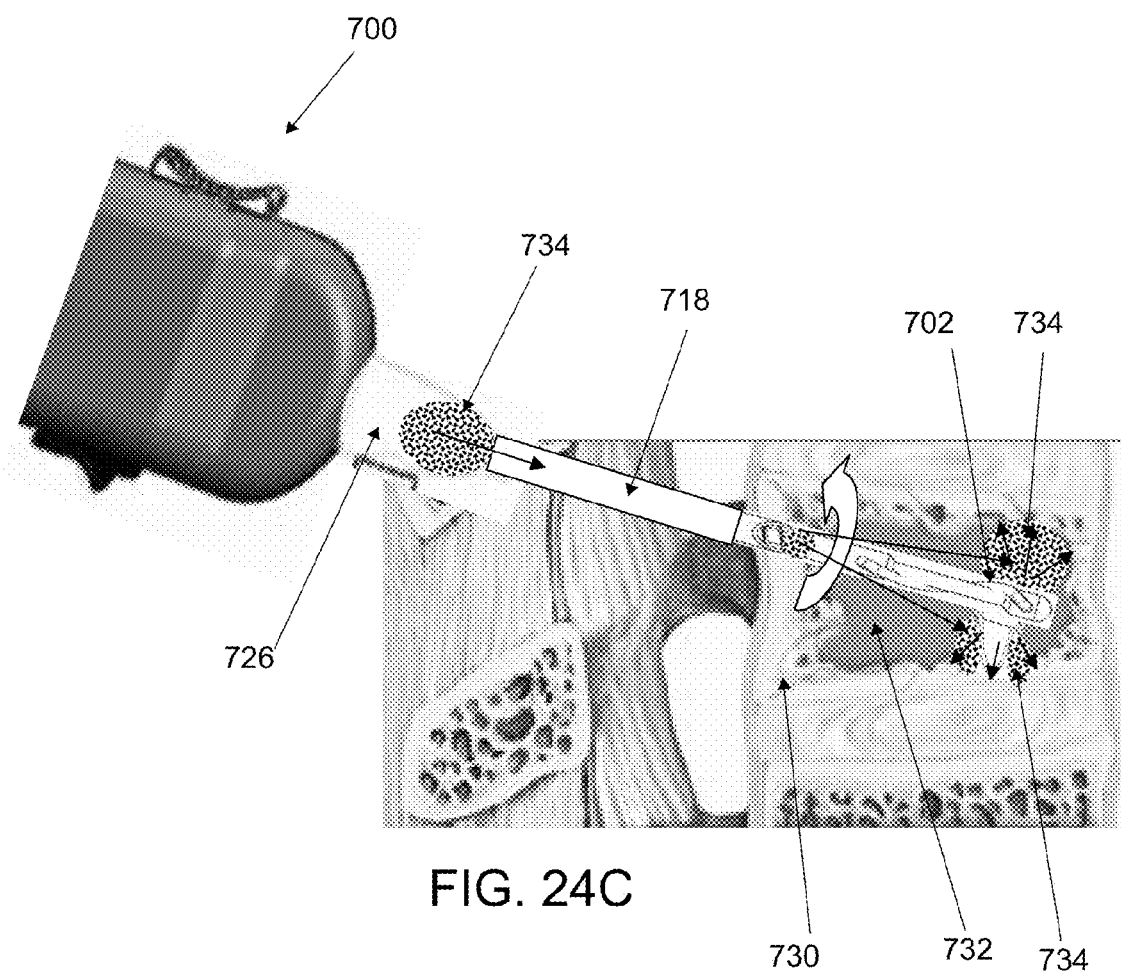

The tissue removal systems and devices depicted in FIGS. 21A to 22, and 35A to 41D may be used for any of a variety of tissue removal procedures, including discectomy and vertebroplasty. For example, referring to FIGS. 24A and to 24C, a vertebral body 730 may be accessed by any of a variety of access procedures described herein. As an example, the tissue removal system 700 may be used to remove vertebral tissue and apply bone cement to the vertebral body 730. The shaft 718 (not drawn to scale) may be inserted into the interior of the vertebral body (FIG. 24A) and then rotated with the cable 702 extended to form a cavity 732 in the vertebral body 730 (FIG. 24B). The tissue removal system 700 may be further manipulated until adequate removal of cancellous bone is achieved. As shown in FIG. 24C, the tissue removal system 700 may be loaded with a bone cement 734 which is then delivered to the cavity 732. In some examples, the bone cement 734 may comprise a material such as polymethyl methacrylate hydroxyapatite, or any of a variety of other bone cements or other hardenable or curable substances can be injected through the trocar to fill the cavity created by the by the tissue removal system 700. The cable 702 of the tissue removal system 700 may be retracted or extended during delivery of therapeutic agents. In some instances, the extended cable 702 may redistribute the therapeutic agents against the cavity walls, which may reduce the risk of leakage out of the cavity.

In some of the procedures described above, the cavity in the vertebral body is formed before the delivery of therapeutic agents, but in other procedures, the delivery of therapeutic agents may occur simultaneously. In procedure where the cavity is first formed, filling of the empty cavity may reduce initial filling pressures. In some instances, lower filling pressures may reduce the risk of leakage. In some examples, the tissue removal system may comprise a pressure sensor which may be used by the user or may be configured automatically to shut off delivery or pressurization of the therapeutic agents upon reaching a particular pressure limit.

Although some of the examples described herein are directed to treatment of vertebral disc fractures, in other examples, the tissue removal systems may be used to treat or diagnose bone lesions located in the vertebrae or other bones of the body. Diagnosis of bone lesions may include biopsy of bone. These bone lesions may include but are not limited to potentially cancerous bone lesions, including osteomas, osteosarcomas and metastatic lesions, as well as potentially infectious bone lesions, including tuberculosis. Bone cement, with or without other therapeutic agents such as anti-neoplastic and anti-infective agents, may or may not be injected into the cavity.

The procedures described herein may target vertebral tissue in different locations, and as such, access sites and pathways may vary accordingly. The tissue removal devices described above may be used with one or more access devices which may help direct the tissue removal device to the target tissue site. An access device, such as a cannula, may be positioned with different angles of entry depending on the location of the targeted vertebral tissue. The range of suitable entry angles may be at least partially constrained by the location of spinal structures with respect to the skin surface. For example, a straight cannula as described above may be positioned within the range of suitable entry angles to create a linear access pathway that extends from an access site on the skin surface to a targeted region of spinal tissue that is co-linear with access site. A curved cannula may be used to create a curved pathway to access tissue that may not be co-linear with an access site within a suitable entry angle range. While a curved pathway may provide increased accessibility to vertebral tissue, a practitioner may need to undergo additional training and practice to avoid disrupting sensitive anatomical structures along a curved pathway. Some variations of access devices may comprise a bendable flexible curvable cannula, which may have a straight configuration and a curved configuration. The cannula may be used in the straight configuration to create a substantially linear access pathway from the access site on the skin surface to the vicinity of the target vertebral tissue. Once the initial access pathway is created, the cannula may be used in the curved configuration to contact the target tissue.

In some variations, the curvature of a cannula may be determined in part by the curvature of a stylet inserted therethrough. For example, inserting a stylet with one or more curves into a bendable flexible cannula may cause the cannula to have corresponding curves. In some variations, a bendable cannula may have one or more pre-formed curves that may be straightened by inserting a straight stylet therethrough. Alternatively, a bendable cannula that is substantially straight may be curved by inserting a curved stylet therethrough. The insertion of various stylets through a bendable cannula may allow a practitioner to access spinal tissue at different locations via one access site on the skin. This may reduce the need for withdrawing the cannula from the body and re-entering the body via an additional access site to access a different tissue region. For example, the cannula and the stylet may each have one or more corresponding curves such that when the stylet is inserted through the cannula, the corresponding curves may be aligned. This may act to stiffen or reinforce the curvature of the cannula so that it may be more easily moved from a first tissue location to a second tissue location. For example, a procedure performed on one tissue location in the disc annulus may be repeated at another tissue location without removing the curved cannula from the disc annulus. While at the first tissue location, a curved or straight stylet may be reintroduced into the cannula, which may facilitate adjustment and positioning of the cannula to a second tissue location. Insertion of a straight stylet may straighten the curved portion of the cannula and allow the cannula-stylet assembly to be advanced to a target site that is relatively further away from the site that has been treated. In other embodiments where relatively insignificant cannula repositioning is involved, a curved stylet may be used to acquire access to a second target site within the disc. A straightened and/or stiffened cannula-stylet assembly may offer enhanced responsiveness and maneuverability and therefore facilitate the maneuvering of the cannula within the discal area, and may facilitate safe removal of the devices from a patient.

The length of a stylet may greater than, or substantially equal to the length of a corresponding cannula. For example, the distal portion of a stylet inserted into a cannula may extend or protrude from the distal portion of the cannula, and/or may be flush with the distal portion of the cannula, and/or may even be withdrawn into the cannula, as desirable. Similarly, the tissue removal assembly of a tissue removal device may be extended from and/or withdrawn into the distal portion of the cannula. The relative longitudinal position between a cannula and stylet, and/or cannula and a travel limiter of a tissue removal device may be adjusted and/or locked. In some variations, the orientation of one or more curves in a cannula and a stylet with respect to each other may be adjusted by rotating the stylet, and may optionally locked once the desired orientation is obtained. The cannula and stylet may each comprise complementary proximal connectors, which may be used to couple them together, such that they may be advanced and navigated together. Optionally, the proximal connectors may rotatably and/or longitudinally lock the cannula and stylet with respect to each other.

Some variations of a cannula and/or stylet may have an orientation indicator, which may help a practitioner to identify the orientation of the one or more curves of the devices, or the orientation of one or more sharpened edges of a stylet, after they have been inserted into the body of a patient. For example, the orientation of a distal curve of a cannula with respect to the longitudinal axis of the cannula shaft may be evident by observing the configuration of the orientation indicator. Orientation indicators may also help a practitioner align the curvature of a stylet to correspond with the curvature of the cannula that it is inserted through. In this way, the practitioner may proximally adjust the bend orientation of the stylet, thereby allowing the stylet to pass through the cannula bend with ease. The shape of the orientation indicator may convey the orientation of the one or more curves of the cannula and/or style to the practitioner. For example, the orientation indicator may have a shape with one or more tapered regions, where the plane of a taper is indicative of the plane of a distal curve. In some variations, orientation indicators may have multiple apices that are aligned with multiple curves in multiple planes, which may help the practitioner position and orient the distal portion of the tissue removal device as desired. The orientation indicator may be attached to the cannula and/or stylet by soldering, welding, adhesive bonding (e.g., 3311 UV adhesive that may be UV cured), snap fit, or other appropriate methods. In some variations, the orientation indicator may be attached or integrally formed with a proximal connector of the cannula and/or stylet. This may provide a mechanism for the cannula and stylet to be coupled together in a particular orientation.

Cannula and stylets may each have proximal connectors that couple them to each other. The proximal connector of a cannula may also be used to couple it with a tissue removal device, e.g., a collector port and/or travel limiter. Connectors may be any standardized connector (e.g., any luer-type connectors, screw-type connectors, taper ground joints, etc.), or may be a proprietary connector. In some variations, a cannula may have a male-type connector that is configured to connect with a stylet or tissue removal device with a female-type connector. Engagement of the proximal connectors of cannula, stylets, and/or tissue removal devices may prevent relative movement between the devices. In some variations, when a stylet is connected to a cannula, the stylet may not be able to move longitudinally within the cannula, but may be axially rotated within the cannula. This may allow a practitioner to adjust the alignment between the cannula and stylet during the insertion of the cannula and stylet into the body. Alternatively or additionally, engagement of the proximal connectors between a cannula and stylet, or a cannula and a travel limiter of a tissue removal device may prevent relative longitudinal and axial motion between the devices. Locking the orientation and position between the cannula and stylet (and/or cannula and travel limiter) may help prevent inadvertent device misalignment or movement during a procedure.

Figure 27A:
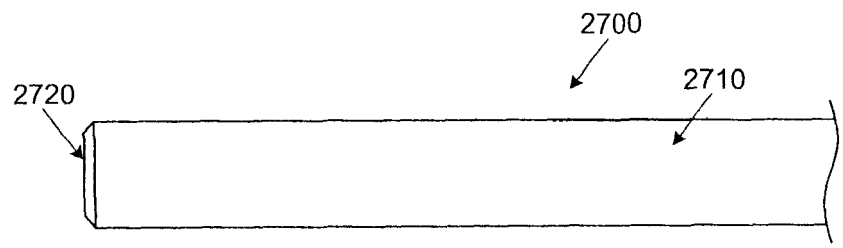
FIGS. 27A to 27E schematically illustrate various embodiments of a radiographic marker with a distal deployable wire.
Figure 27B:
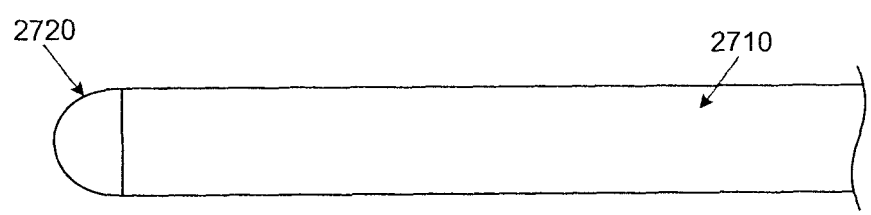
Figure 27C:
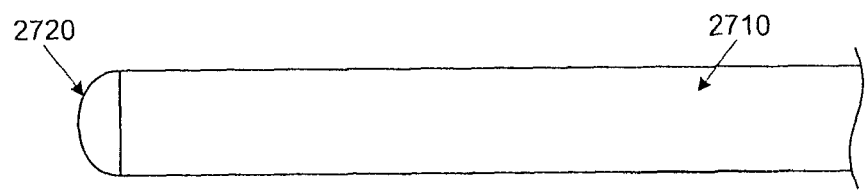
Figure 27D:
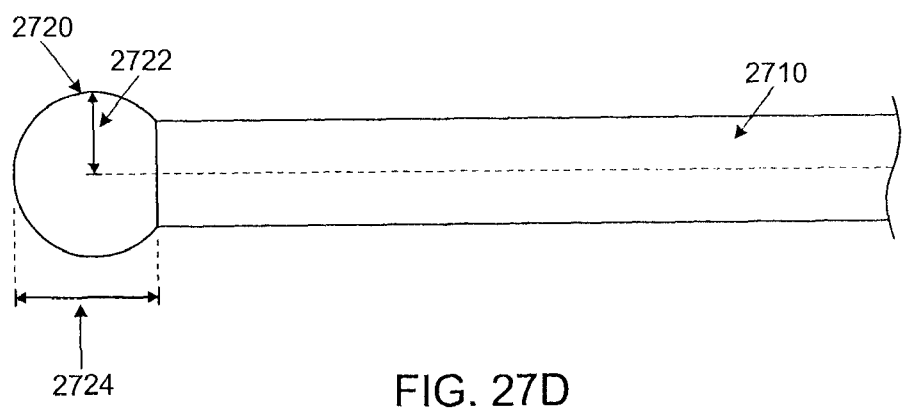
Figure 27E:
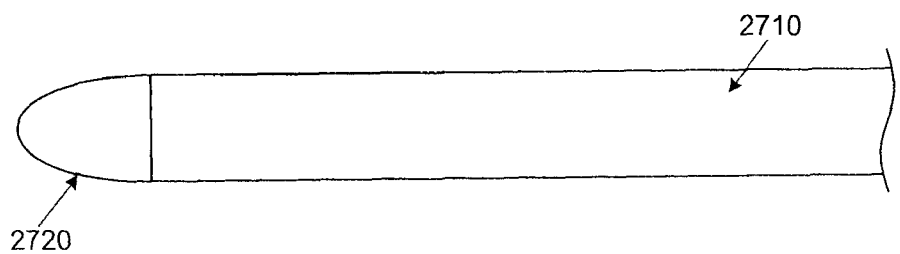

In some examples, the distal region of the cannula and/or stylet may comprise a radio-opaque structure (e.g. rings or bands) to facilitate confirmation of its position using radiographic imaging. In other examples a separate radiographic marker instrument may be used to confirm and evaluate the cannula placement. In one embodiment illustrated in FIGS. 27A to 27E, the radiographic marker 2700 comprises an elongate shaft 2710 with a piece of wire 2720 (e.g., multifilament or solid) distally attached thereto. The wire 2720 may comprise a retracted configuration and a deployed or extended configuration. As illustrated in FIG. 27A, when the wire is placed in its retracted configuration, it is disposed about the distal end of the marker shaft 2710 such that the placement and/or longitudinal movement of the marker within a cannula will not be obstructed or otherwise interfered with. As illustrated in FIG. 27B to 27E, when the wire 2720 is placed in its deployed or extended configuration, the wire 2720 may comprise a radial and a distal excursion at the distal end of the marker shaft 2710. The deployed or extended wire comprise any suitable geometric configuration, including but not limited to a semi-circle (e.g., FIG. 27B), a portion of a circle (e.g., FIGS. 27C and 27D), or an ellipse (e.g., FIG. 27E), or any other linear, non-linear or angled shape. The radial displacement 2722 of the extended wire with respect to the central axis of the marker shaft 2710 may be of about 0.07 inch to about 0.25 inch or more, sometimes about 0.1 inch to about 0.2 inch, and other times about 0.15 inch to about 0.18 inch. The distal displacement 2724 of the extended wire with respect to the distal end of the marker shaft 2710 may be of about 0.07 inch to about 0.25 inch or more, sometimes about 0.1 inch to about 0.2 inch, and other times about 0.15 inch to about 0.18 inch. In some embodiments, other types of expandable structures, such as a balloon, may be used in the radiographic marker.

In some embodiments, the distal end of the shaft 2710 may be round or otherwise blunt to reduce tissue disruption during the insertion of the marker and the deployment of the wire. Both the distal end of the marker shaft 2710 and the distal wire 2720 may be radiopaque to allow observation under fluoroscopy or other types of imaging guidance. The radiographic marker 2700 may also comprise a complimentary proximal connector that locks the marker to the cannula. The radiographic marker 2700 may also comprise an indicator that shows the orientation of the deployed wire with respect to the central axis of the marker draft 2710. The radiographic marker may be inserted into the cannula with the distal wire in its retracted configuration. Once the distal end of the shaft 2710 reaches the distal end of the cannula, the wire may be deployed to either identify relevant structures within or near the visualization zone, which is defined by the deployed wire, or to evaluate the placement of the cannula. In some embodiments, the cannula may be repositioned to facilitate better target site access.

Examples and variations of bendable cannula and stylets are described here. Variations of cannula and stylets may have any combination of the above-described features, such as connectors, orientation indicators, radio-opaque markers, etc., as appropriate.

Figure 25A:
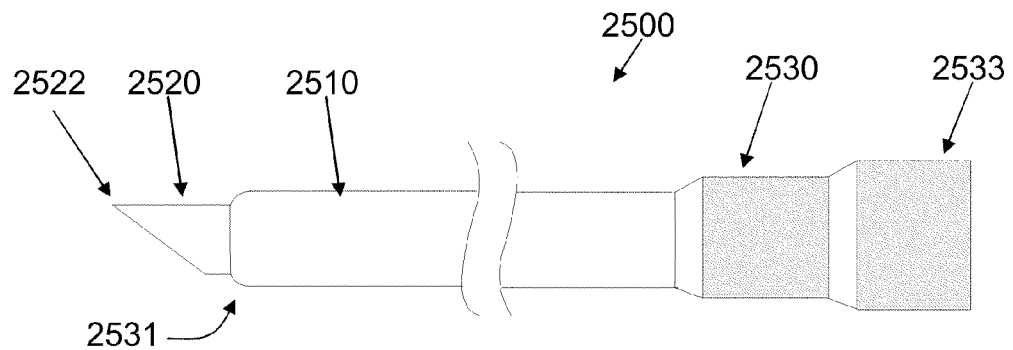
FIG. 25A schematically illustrates one embodiment of a straight cannula-stylet assembly comprising a straight cannula and a straight stylet.

As described previously, access to the spine for various spinal procedures may be achieved using a cannula containing an obturator with a sharpened end. Access to the spine may also be obtained using a cannula and stylet. FIG. 25A schematically illustrates a cannula-stylet assembly 2500 comprising a cannula 2510 and a removable stylet 2520 through a lumen of the cannula. The cannula 2510 may have one or more lumens configured to receive a stylet 2520. A proximal connector 2530 of the cannula 2510 and a proximal connector 2533 of the stylet 2520 may releasably couple the cannula 2510 to the stylet 2520. While the cannula 2510 has a straight configuration, other variations may comprise one or more curved regions. The distal end 2512 of the cannula 2510 may be round or blunt, and/or may have a rounded edge, which may reduce inadvertent damage to surrounding tissues when the assembly 2500 is advanced to a target site. The cannula 2510 may comprise an optional proximal connector 2530, where the connector may be a standardized or proprietary connector as previously described. In some embodiments, the stylet 2520 may comprise a lumen for guidewire to facilitate the placement of the stylet in a patient's body.

The straight cannula 2510 may have a length from the distal portion of the proximal connector 2530 to the distal portion of the cannula 2531 of about 4 inches to about 12 inches or more, sometimes about 5 inches to about 10 inches, and other times about 6 inches to about 9 inches. The outer diameter of the straight cannula 2510 may be about 0.05 inch to about 0.08 inch or more, sometimes about 0.06 inch to about 0.07 inch, and other times about 0.064 inch to about 0.066 inch. The inner diameter of the cannula 2510 (e.g., the diameter of the cannula lumen to receive the stylet 2520) may be about 0.04 inch to about 0.07 inch or more, sometimes about 0.05 inch to about 0.06 inch, and other times about 0.055 inch to about 0.057 inch. The straight cannula 2510 may be made from any type of rigid or semi-rigid materials, such as metals or metal alloys (e.g., stainless steel, including but not limited to cold-worked 304/416 stainless steel, full hard 17-4 stainless steel, and 400 series stainless steel, nickel titanium alloys, etc.). The proximal connector 2530 of the cannula may be made from metal or plastic materials.

Figure 25B:
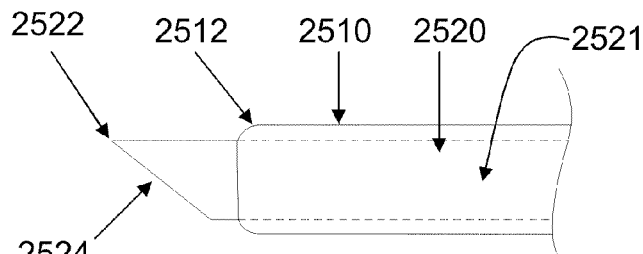
FIG. 25B to 25E depict various embodiments of the distal portion of the straight cannula-stylet assembly in FIG. 25A.

The straight stylet 2510 may comprise an elongate shaft 2521 and a distal tip 2522, which may extend distally from the cannula distal portion 2531. The straight stylet 2520 may be used to penetrate, cut, dissect, or otherwise disrupt tissues/bones, thereby forming a passageway or a working channel to a target site. The distal tip 2522 of the stylet may be sharpened, and may optionally comprise a beveled edge 2524, as illustrated in FIG. 25B. In some embodiments, the bevel may be about 10° to about 45°, sometimes about 20° to about 30°, and other times about 23° to about 26°. In some variations, the distal tip 2522 may have a plurality of beveled edges, e.g., two, three, four or more edges.

Figure 25C:
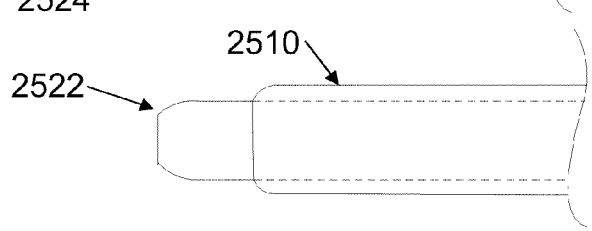
Figure 25D:
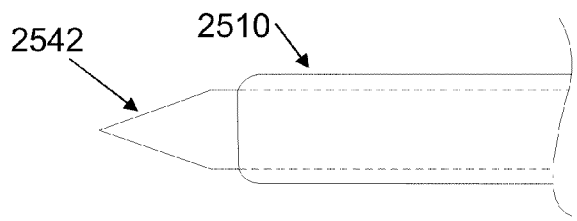
Figure 25E:
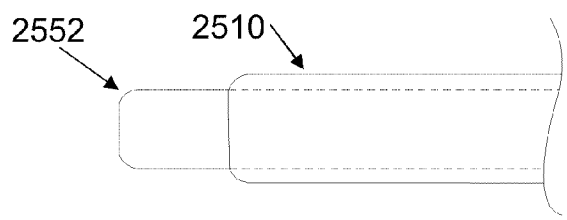

The distal tip 2522 may have a variety of shapes and geometries. For example, the distal tip may have a frusto-conical configuration 2532 (e.g., FIG. 25C) or a conical configuration 2542 (e.g., FIG. 25D). In other embodiments, the stylet tip 2552 may be round (e.g., FIG. 25E). In some examples, a round or blunt tip may reduce inadvertent damage to surrounding tissues when the stylet is extended from the cannula, or may facilitate blunt dissection along tissue planes.

The length of a straight stylet from the distal portion of a proximal connector 2533 to distal tip 2522 of the stylet may be the same as, or somewhat longer than, the length of a cannula. A stylet may have a length of about 4 inches to about 12 inches or more, for example, from about 4.01 inches to about 12.01 inches, or about 6.01 inches to about 9.01 inches. In some variations, the stylet may be substantially longer than the cannula, such that when the stylet is inserted into the cannula and coupled via the proximal connectors (2530, 2533), the distal tip 2522 of the stylet extends distally from the cannula distal portion 2531. The stylet may extend about 0.05 inch to about 0.5 inch from the distal end of the cannula, and may even extend more than 1 inch from the cannula, for example, 1.5 inches or 3 inches. In this way, the stylet and the cannula are advanced together to a target area as an assembly. In some embodiments where the stylet 2520 comprises a beveled distal tip 2524, the entire beveled edge 2524 of the stylet 2520 may be exposed distally with respect to the distal end 2512 of the cannula 2510 (as illustrated in FIG. 25B). In other embodiments, when the stylet 2520 is proximally coupled to the cannula 2510, only a portion of the beveled edge 2524 is exposed. The outer diameter of the straight stylet may be such that it can be slidably inserted through the cannula, and may be the same as, or less than, the inner diameter of the cannula. For example, the outer diameter for the straight stylet may be about 0.03 inch to about 0.067 inch, sometimes about 0.05 inch to about 0.06 inch, and other times about 0.05 inch to about 0.054 inches. The straight stylet may be made of a rigid or semi-rigid material similar to that of the straight cannula, such as stainless steel, etc. The distal tip and/or the shaft of the stylet may be radiopaque to facilitate the placement of the stylet inside the cannula.

In some embodiments, the stylet 2520 may comprise a proximal orientation indicator, where the position and orientation of the orientation indicator corresponds with the orientation of the one or more beveled edges of the distal tip with respect to the central axis of the stylet 2520. In one embodiment, the orientation indicator may be a marker on the shaft 2521 and/or proximal connector 2533 of the stylet near its proximal end. In another embodiment, the shaft 2521 and/or proximal connector 2533 of the stylet may comprise a protrusion or a groove that indicates the orientation of the bevel. The practitioner may determine the orientation of the stylet bevel by observing the position of the protrusion or groove on the shaft and/or proximal connector. In other embodiments, any other suitable indicating mechanism known to the ordinarily skilled in the art may be used to show the orientation of the stylet bevel.

In some procedures, a straight access may involve a longer insertion distance in order to achieve the desired approach angle to the target site, and/or to avoid interference from some anatomical structures. For example, as illustrated in FIG. 26B, in order to have direct access to a herniated area 2640 in a vertebral disc 2641 through disc annulus 2630, the straight cannula-stylet assembly 2600 may have to enter from an entry point that is further away from the midline 2644 of the patient's back in order to avoid the transverse spinal processes 2642. As a result, such straight access to the herniated disc 2641 may involve longer insertion path and therefore, may cause higher degree of tissue disruption. In addition, because the straight assembly 2600 only offers linear access into the discal area, if there are multiple herniated spots in the disc and the spots are not disposed along a linear path, the assembly 2600 may need to be removed and reinserted in order to treat all spots. As a result, in some procedures, a curved access may be desirable to provide a shorter insertion pathway and/or to reach certain target sites (e.g., intra-discal area) that are difficult to reach by a straight access.

In some embodiments, a bendable flexible curved cannula may be used in association with either a straight stylet or a curved stylet to obtain curved access to a spinal area. A curved access pathway not only offers a larger tissue removal zone at one target site, but it may also provide flexible access to multiple target sites in one or more herniated discs. A curved or non-linear access pathway that may be provided by a bendable flexible curved cannula may be shorter than a straight access pathway, and may be less disruptive to surround tissue structures. It may also provide better orientation towards the middle of disc, as compared with a straight access pathway.

Figure 29A:
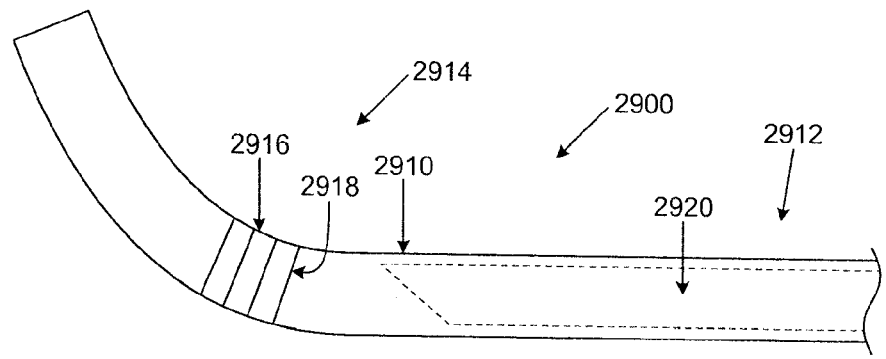
FIGS. 29A to 29C are schematic illustrations of the distal portion of a curved cannula-stylet assembly comprising a curved cannula and a straight stylet.
Figure 29B:
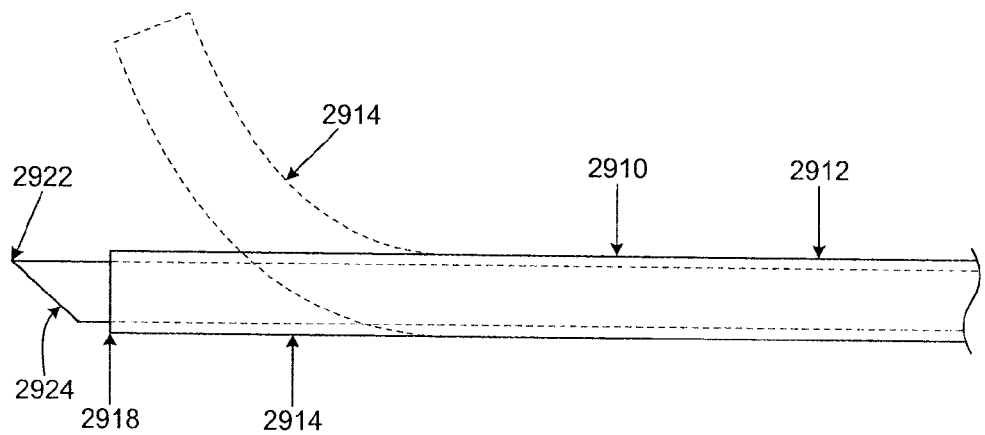
Figure 29C:
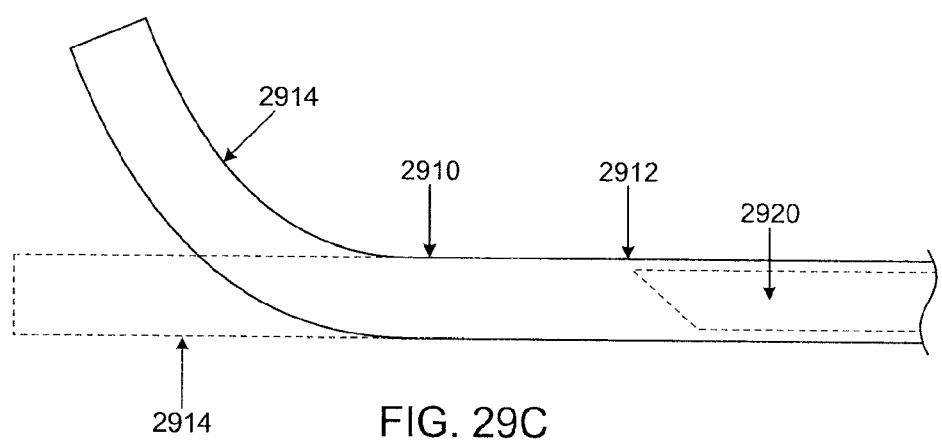

FIGS. 29A to 29C schematically illustrate an assembly 2900 of a curved cannula 2910 and a straight stylet 2920 that may be used to adjust the curvature of the cannula 2910, e.g., straighten a curved portion of the cannula. As illustrated in FIG. 29A, the curved cannula 2910 may comprise a straight proximal portion 2912 and a curved distal portion 2914. In some embodiments, the curved distal portion 2914 of the curved cannula 2910 may be pre-shaped. The cannula 2910 may be made from a flexible or semi-flexible material such that the insertion of a straight stylet 2920 into the curved cannula 2910 may straighten the curved distal portion 2914 to some degree if not completely straightened, as illustrated in FIG. 29B. In some embodiments, the curved cannula 2910 may be made from a shape memory material. The cannula 2910 may be straightened when a straight stylet 2920 is inserted but it may substantially regain its curved configuration when the stylet is removed, as illustrated in FIG. 29C. Non-limiting examples of suitable cannula materials include shape memory metal alloys (e.g., nickel-titanium alloy) and shape memory polymers. In some variations, the shape memory metal alloy may have an austenitic finish temperature that allows the curved cannula to accommodate the insertion of a straight stylet at temperatures between 65° F. and 100° F. without failing, while remaining sufficiently rigid at those temperatures to maintain the curve. Examples of appropriate austenitic finish temperature may be from about 15° F. to about 25° F. Optionally, the surfaces of either a straight or curved cannula may be modified with a coating, such as a silver finish, to reduce oxidation, and/or reduce frictional forces, as well as galling effects that may result from any rotational or axial motion from a tissue removal device inserted through the cannula. In some embodiments, the curved distal portion 2914 may comprise a plurality of slots 2916, or other types of recessed structures, either equally or unequally spaced along the longitudinal length of the cannula 2910. These structures may enhance the bending characteristics and/or facilitate redistribution of any compressing force, thereby reducing damage to the distal curved portion 2914 caused by repeated bending and straightening.

The bending range of the curved cannula may be in the range of from about 10 degrees to about 80 degrees, sometimes from about 20 degrees to about 70 degrees, and other times from about 30 degrees to about 60 degrees, and still other times from about 40 degrees to about 50 degrees. The curved distal portion 2914 may comprise a radius of curvature of about 0.5 centimeters to about 30 centimeters; sometimes about 1 centimeter to about 20 centimeters, sometimes about 5 centimeters to about 15 centimeters and other times about 8 centimeters to about 10 centimeters. When the curved distal portion is straightened, the curved cannula may comprise a length of about 4 inches to about 12 inches or more, sometimes about 5 inches to about 10 inches, and other times about 6 inches to about 9 inches. The ratio between the length of the curved distal portion (when straightened) 2914 to the length of the straight proximal portion 2912 may be about 0.1 to about 0.9; sometimes about 0.2 to about 0.8; other times about 0.4 to 0.6. The outer diameter of the curved cannula may be about 0.05 inch to about 0.08 inch or more, sometimes about 0.06 inch to about 0.07 inch, and other times about 0.063 inch to about 0.065 inch. The inner diameter of the curved cannula (e.g., the diameter of the curved cannula 2910 lumen to receive the stylet 2920) may be about 0.04 inch to about 0.07 inch or more, sometimes about 0.05 inch to about 0.06 inch, and other times about 0.055 inch to about 0.057 inch. In some embodiments, when used in conjunction with stylets of the same size, a curved cannula may comprise a slightly larger inner diameter than a straight cannula because the stylet may need more room to navigate inside the curved cannula in order to avoid damaging the inner surface of the curved cannula. In some embodiments, the stylet 2920 may comprise a non-beveled or otherwise blunt distal tip to reduce the risk of damaging the interior of the cannula 2910. In some embodiments, the curved cannula 2910 and the straight stylet 2920 may be proximally connected by complementary connectors, such as those previously described. The distance between the distalmost end 2922 of the stylet 2920 and the distalmost end 2918 of the cannula 2910 may be in the range of about 0.02 inch to about 0.4 inch, sometimes about 0.04 inch to about 0.3 inch, and other times about 0.07 inch to about 0.2 inch.

Figure 34A:
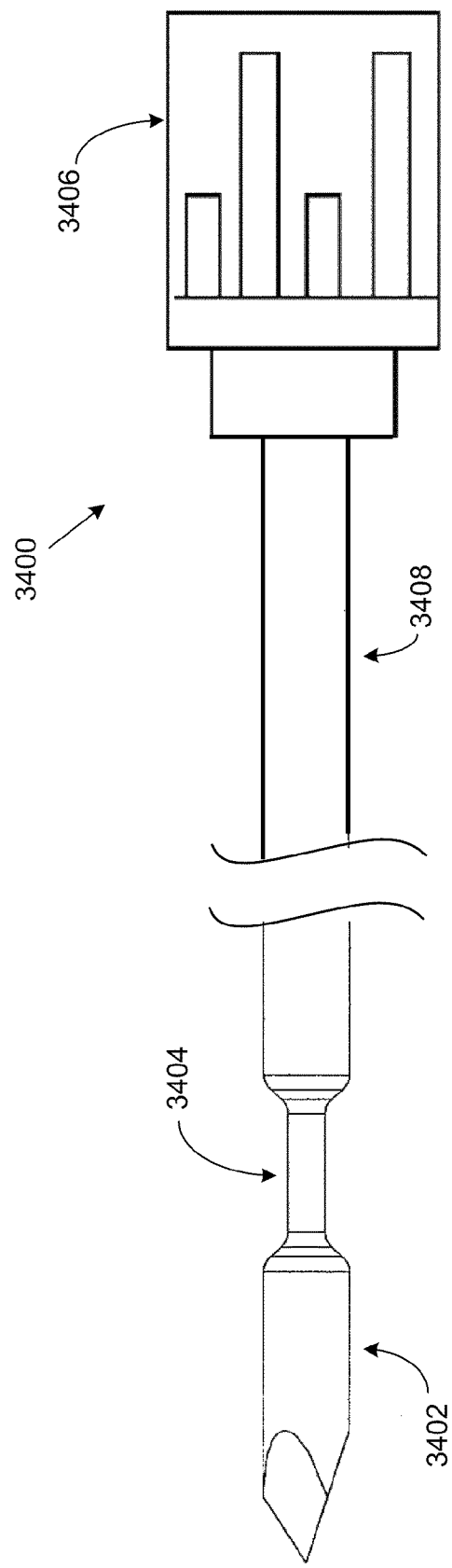
FIG. 34A depicts one variation of a stylet that may be used with a curved cannula illustrated in FIG. 34B and/or a straight cannula illustrated in FIG. 34C.

In some variations, a straight stylet that may be used with a curved cannula may have a bendable and/or deflectable region, as shown in FIG. 34A. The bendable deflectale region of the straight stylet may facilitate the movement of the style through a curved cannula without damaging it, while providing sufficient rigidity to straighten a curved cannula. Stylet 3400 has a proximal connector 3406 and an elongated body 3408 extending therefrom. The elongate body 3408 comprises a distal tip 3402 and a deflectable region 3404, where the deflectable region 3404 may be located proximal to the distal tip 3402. The deflectable region 3404 may provide some additional flexibility to a distal portion of the stylet 3400. The deflectable region 3404 is configured to bend, flex, conform, and/or deflect according to the curvature of a cannula. The distal tip 3402, the elongate body 3408, and the deformable region 3404 may be made of the same material, such as passivated 304 stainless steel (drawn hard temper) or nitinol, and may be radiopaque under fluorescence. Alternatively, the elongate body 3408 may be made of 20 Ga FEP heat shrink tubing. In some variations, the deflectable region 3404 may be made of a material with an elastic modulus that is more flexible than the elongate body material, for example, silicone, nylon, PEEK, PEBAX, or polyethylene. Alternatively or additionally, the deflectable region 3404 may be thinner than the elongate body (3408), and may be tapered or attenuated from the elongate body, i.e., the deflectable region may have a diameter that is smaller, or more narrow, than the other regions of the elongated body. The elongate body 3408 may have an diameter of about 0.030 inch to about 0.060 inch, e.g., 0.039 inch or 0.045 inch or 0.060 inch, and may have a wall thickness of about 0.004 inch to about 0.010 inch, e.g., 0.008 inch. The length of the elongate body 3408 may vary from about 6 inches to about 9 inches, e.g., 8 inches.

As described previously, the outer diameter of a stylet may be about 0.04 inch to about 0.07 inch or more, e.g., 0.054 inch, while the deflectable region 3404 may be from about 0.015 inch to about 0.035 inch, for example, 0.023 inch. In some variations, the diameter of the deflectable region may vary across its length, for example, the diameter may decrease towards the middle of the deflectable region, and increase towards the ends of the deflectable region. The deflectable region 3404 may be any suitable length that provides sufficient flexibility for tracking through a curved cannula, for example, from about 0.02 inch to about 0.15 inch, e.g., 0.085 inch. The overall length of the stylet 3400 may be from about 7 inches to about 9 inches, e.g., 8.05 inches. The deflectable region 3404 may be located a certain length away from the distalmost portion of the distal tip 3402, for example, about 0.05 inch to about 0.3 inch, such as 0.204 inch. The reduced dimension of the deflectable region can may be used as a reference marker, e.g., during fluoroscopic visualization. Accordingly, the length of the deflectable region, the diameter of the deflectable region, and distance of the deflectable region from the distal-most portion of the distal tip may be varied to provide specific dimensional measurements or references. While the deflectable region 3404 may be substantially straight, the deflectable region may have one or more pre-formed curves. In some variations, the deflectable region 3404 may be integrally formed with the distal tip 3402 and/or the portion of the elongate body 3408 that is proximal to the deflectable region. Alternatively, the deflectable region 3404 may be separately formed and attached to the distal tip 3402 and the proximal portion of the elongate body 3408. The deflectable region 3404 may be made of any of the materials previously described, for example, rigid or semi-rigid materials, such as stainless steel or nickel titanium alloy. The distal tip 3402 may be made of similar materials, and may have any geometry as described previously. Some variations of a distal tip 3402 may be blunt, while other variations may be sharpened. For example, as depicted in FIG. 34A, the distal tip 3402 has a beveled conical shape, with a sharpened distalmost tip. For example, the distal tip 3402 may be a 3-sided beveled tip. The distal tip 3402 may have a length of about 0.150 inch to about 0.300 inch, e.g., 0.204 inch. On the proximal portion of the stylet, the proximal connector 3406 may be able to interface and attach with various connectors of a tissue removal device, as described above. For example, the proximal connector 3406 may be a Luer-Lok™ type connector that may connect to a cannula with a complementary Luer-Lok™ type connector. In some variations, the proximal connector 3406 may be made of a polymeric material, such as ABS or nylon.

Figure 34B:
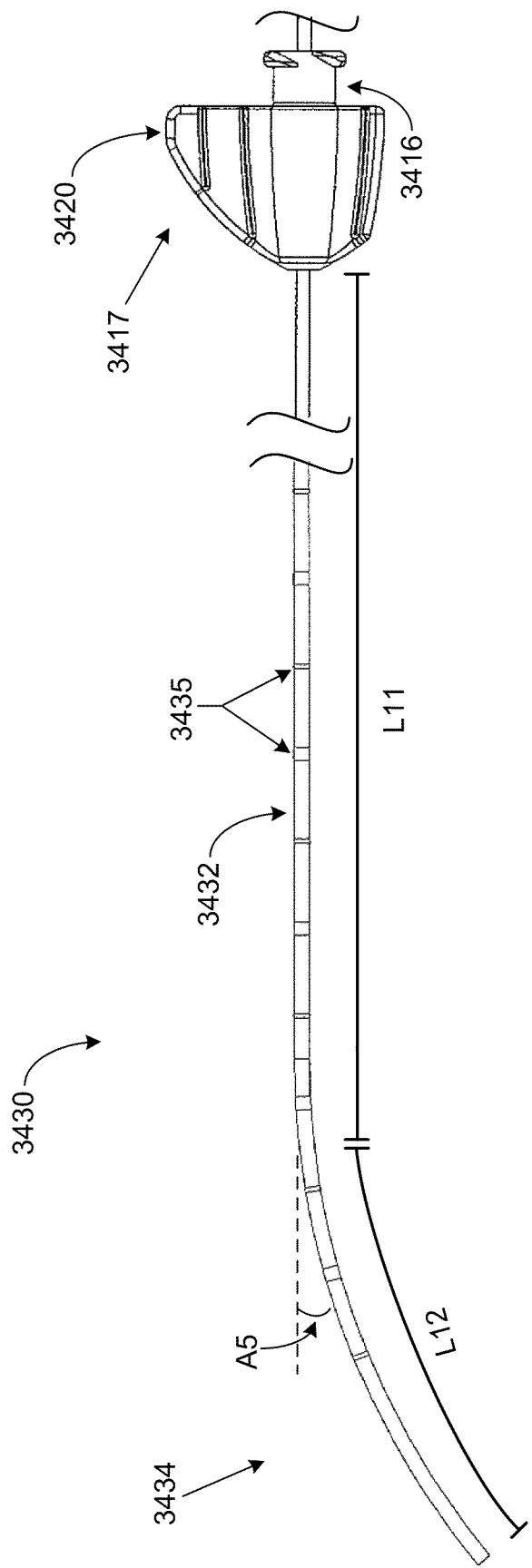

FIG. 34B depicts one variation of a curved cannula 3430 comprising a straightened portion 3432 and a curved portion 3434 distal to the straightened portion 3432. Optionally, a depth indicator, such as an adjustable flange, band, or silicone grommet, may be provided on the outer diameter of the curved cannula to reference the insertion depth of the cannula during use. The curved cannula 3430 may have a proximal hub 3420 with a connector 3416, e.g., a female Luer Lok™ connector that may be made of nylon. The proximal hub may further comprise an orientation indicator 3417 shown in FIGS. 34B and 34C. The orientation indicator 3417 may have a shape that tapers to a rounded apex 3420, where the plane of the apex 3420 is aligned and/or co-planar with the plane of the curved portion 3434. The shaft of the curved cannula may be made of 304 stainless steel or Nitinol. The straightened portion 3432 may have a length L11, where L11 may be about 3 inches to about 6 inches, e.g., 4.36 inches. The curved portion 3434 may have a length L12, where L12 may be about 2 inches to about 3 inches, e.g., 2.5 inches. The proportion of the curved portion to the total length may be from about 1:20 to about 1:2, for example, about 1:10, or 1:5, or 1:3. In some variations, the entire length of the stylet may be curved. The cannula 3430 may have any suitable diameter, e.g., 16 Gauge, or may have an outer diameter of about 0.068 inch, an inner diameter of about 0060 inch. The total length of the cannula 3430 may be from about 6 inches to about 8 inches, e.g., 7.21 inches. A similar straight cannula may have a total length of about 7 inches. The curved portion 3434 may curve at an angle A5 with respect to the straightened portion 3432, where A5 may be about 25° to about 50°, for example, about 35° to about 45°, or 40°. Alternatively or additionally, the radius of curvature of the curved portion 3434 may be from about 3 inches to about 4.5 inches, e.g., 3.5 inches. The curved cannula 3430 may have a diameter of about 0.050 inch to about 0.075 inch, e.g., 0.068 inch. Optionally, there may be one or more markings 3435 that demarcate length increments. For example, the markings 3435 may indicate 1.0 centimeter lengths. The markings 3435 may have varying thickness, e.g., alternating 0.2 inch and 0.06 inch. In the variation of a curved cannula, the length L12 of the distal curved portion 3434 is approximately 40% to 60% of the length L11 of the straightened portion 3432, but in other variations, the length proportion of the curved portion to the straightened portion may vary. A straight stylet may have one or more deformable regions as described above to accommodate the location, length, and angle of the curved portion of a curved cannula. In some variations, the curved cannula 3430 is made of 304 stainless steel, nitinol, or any suitable material which may allow the curved portion 3434 to be straightened when a straight stylet is inserted therethrough.

Figure 30A:
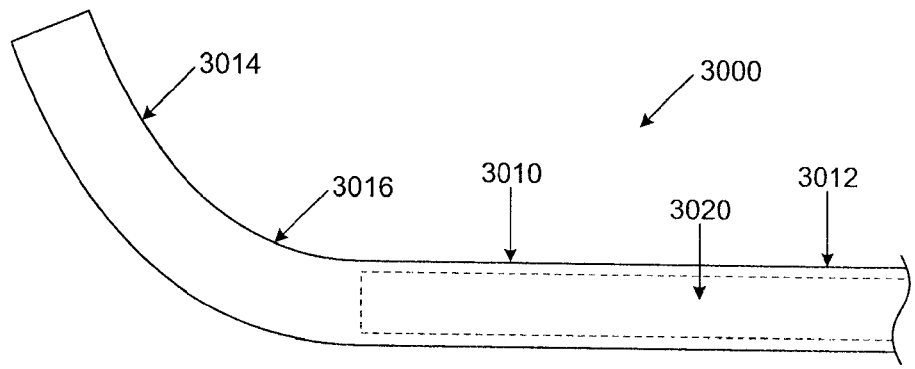
FIGS. 30A to 30C are schematic illustrations of the distal portion of a curved cannula-stylet assembly comprising a curved cannula and a curved stylet.
Figure 30B:
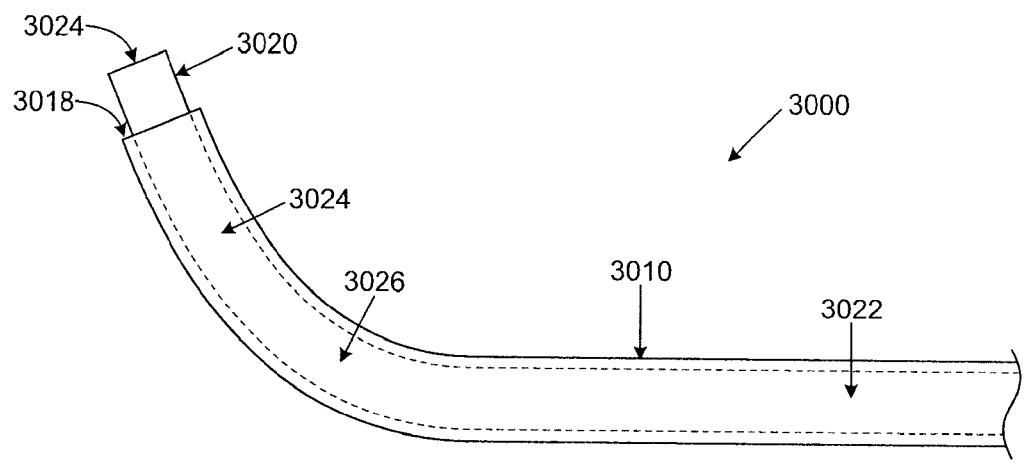
Figure 30C:
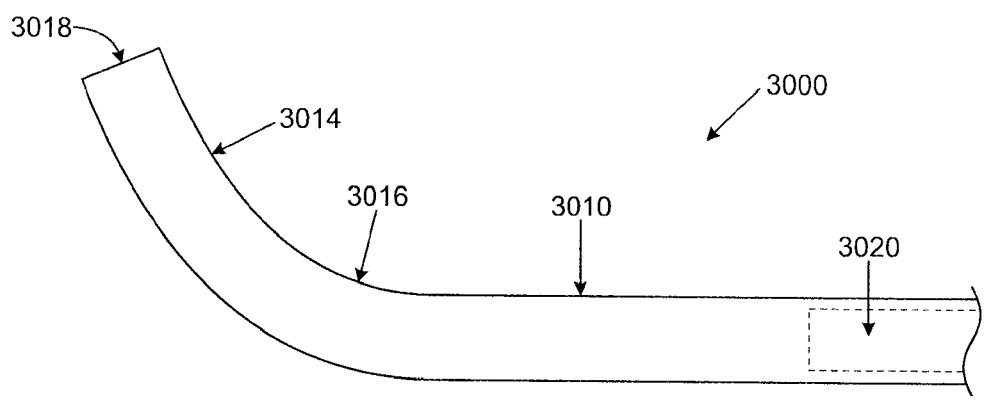

In other variations, a stylet may be sized and shaped to match the curvature of a corresponding cannula. For example, insertion of a stylet with curves corresponding to curves on a cannula may stiffen and maintain the curvature of the cannula, which may facilitate the repositioning and/or manipulation of the cannula. In some variations, the location of a deformable region along a stylet, as well as the length and flexibility of the deformable region may be determined in part by the length and/or curvature of a cannula. FIGS. 30A to 30B schematically illustrate another cannula-stylet assembly 3000 comprising a curved cannula 3010 and a curved stylet 3020. The curved stylet 3020 may comprise a straight proximal portion 3022 and a curved distal portion 3024, two of which are joined via a bend 3026. In some embodiments, the curved stylet 3020 may comprise a round or otherwise blunt distal tip 3024 such that the insertion of the stylet 3020 may not damage the interior of the cannula 3010 when the distal tip 3024 of the stylet 3020 passes through the curved cannula portion 3014. In some embodiments, a blunt distal tip may reduce the risk of tissue disruption when the cannula-stylet assembly navigates to or about a target site but still provide penetrating capability through soft tissues or bones (e.g., nucleus pulposus or cancellous bones). In some embodiments, the distal tip of the curved stylet may be sharpened to enhance its penetrating ability. The bend 3026 may be pre-shaped with a bend radius and a bending range that are substantially the same as those of the cannula bend 3016. In this fashion, a curved cannula-stylet assembly 3000 may be formed with the bend 3016 of the cannula 3010 and the bend 3026 of the stylet 3020 substantially aligned with each other, as illustrated in FIG. 30B.

The curved stylet 3020 may be made from a flexible shape memory material such that insertion of the curved distal portion 3024 into the curved cannula 3010 may straighten the stylet 3020 but the stylet 3020 may substantially regain its curved configuration as the stylet passes through the cannula bend 3016. Non-limiting examples of suitable stylet materials include shape memory metal alloys (e.g., nickel-titanium alloy) and shape memory polymers. In some embodiments, a curved stylet comprises a fixed bending range and/or bend radius such that the curved stylet may only be used with a curved cannula with substantially the same bending range and/or bend radius. In other embodiments, the curved stylet may be made from a flexible and/or malleable material such that when the stylet passes through the curved portion of a curved cannula, the stylet may deform under compressive stress and assume a bending configuration substantially the same as that of the curved cannula. In such embodiments, the curved stylet may be used in conjunction with curved cannulas with a range of bending configurations (e.g., bend radius, bending range, etc.).

Figure 34C:
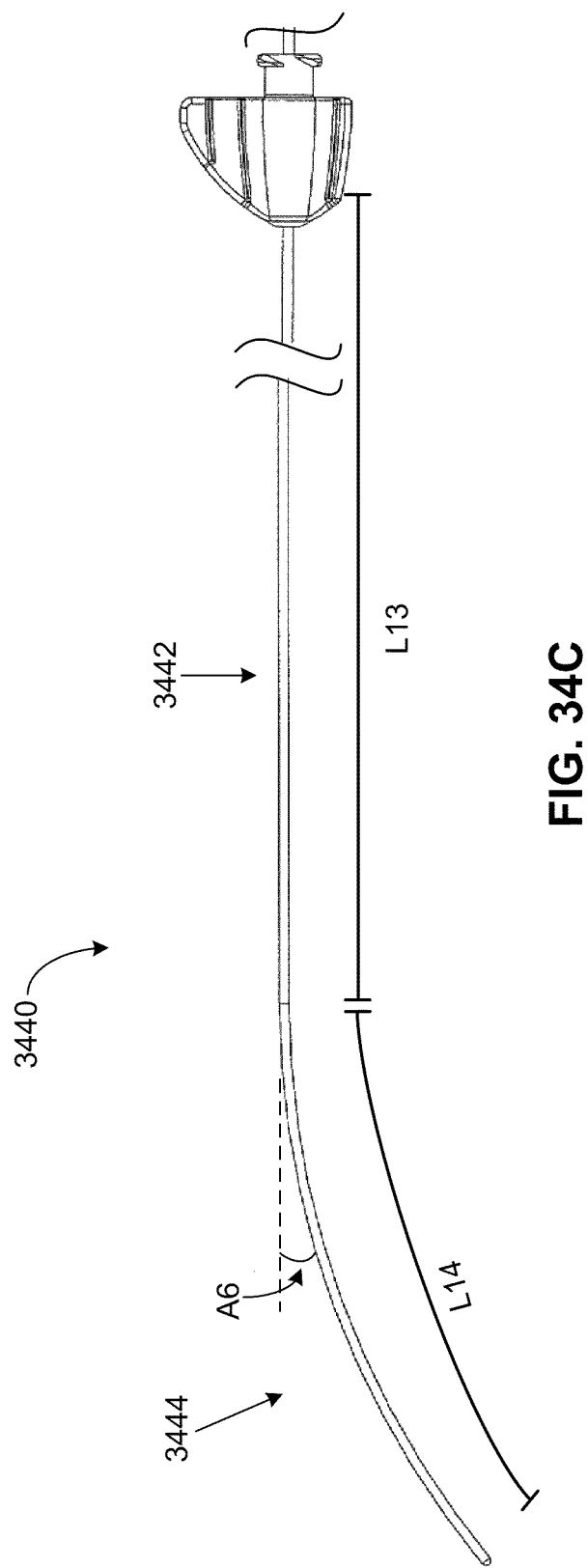

In some embodiments, the curved stylet may comprise a length (when straightened) of about 4 inches to about 12 inches or more, sometimes about 5 inches to about 10 inches, and other times about 6 inches to about 9 inches. In embodiments where the curved stylet comprises a pre-shaped bend, the ratio between the length of the curved distal portion (when straightened) to the length of the straight proximal portion may be about 0.1 to about 0.9; sometimes about 0.2 to about 0.8; other times about 0.4 to 0.6. The outer diameter of the curved stylet may be about 0.04 inch to about 0.07 inch or more, sometimes about 0.05 inch to about 0.06 inch, and other times about 0.05 inch to about 0.054 inch. The bending range and/or bend radius of a curved stylet may be selected in part based upon the configuration of the curved cannula with which the curved stylet will be used. For example, FIG. 34C depicts one variation of a curved stylet 3440 comprising a straightened portion 3442 and a curved portion 3444 distal to the straightened portion 3442. The straightened portion 3442 may have a length L13, where L13 may be about 4.5 inches to about 7 inches, e.g., 5.92 inches. The curved portion 3444 may have a length L14, where L14 may be about 2.5 inches to about 4 inches, e.g., 2.5 inches. The total length of the stylet 3440 may be from about 7 inches to about 10 inches, e.g., 8.37 inches, and when inserted into a cannula, the stylet tip may protrude from the distal end of the cannula. The curved stylet may have a diameter of about 0.030 inch to about 0.060 inch, e.g., 0.039 inch or 0.054 inch. The curved portion 3444 may curve at an angle A6 with respect to the straightened portion 3442, where A6 may be about 25° to about 50°, for example, about 35° to about 45°, or 40°. Alternatively or additionally, the radius of curvature of the curved portion 3444 may be from about 3 inches to about 4.5 inches, e.g., 3.5 inches. The shaft of the curved stylet 3440 may be made of stainless steel (304, 316, 17-4), cobalt chromium, titanium alloy, nitinol and may be covered with a fluoropolymer or coated with parylene, or materials with similar mechanical properties. Optionally, the proximal portion of the curved stylet 3440 may comprise a connector, such as a Luer Lock™ connector, and a curve orientation indicator, which will be described later on.

In some embodiments, once the curved cannula 3010 and the curved stylet 3020 are coupled proximally, the distal end 3024 of the curved stylet 3020 may be disposed at a fixed position distal to the distal end 3018 of the curved cannula 3010. The distance between the distalmost end 3024 of the curved stylet 3020 and the distalmost end 3018 of the curved cannula 3010 may be in the range of about 0.02 inch to about 0.4 inch, sometimes about 0.04 inch to about 0.30 inch, and other times about 0.07 inch to about 0.2 inch. In some embodiments, when the curved stylet 3020 is proximally connected to the curved cannula 3010, the stylet 3020 may be independently rotated inside the cannula 3010. In some embodiments, the curved cannula and the curved stylet may be coupled and/or locked by a proximal connector to prevent any relative motion. This may help to prevent any inadvertent misalignment during use of the assembly 3000.

Figure 32A:
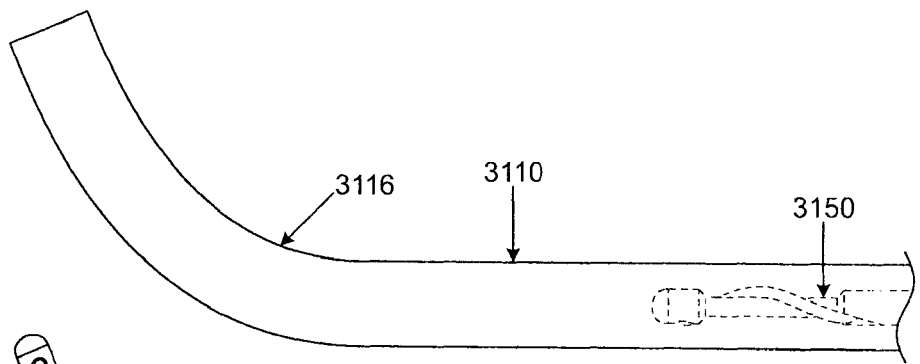
FIGS. 32A to 32C are schematic illustrations of the distal portion of a cable-based tissue removal device inserted into a curved cannula.
Figure 32B:
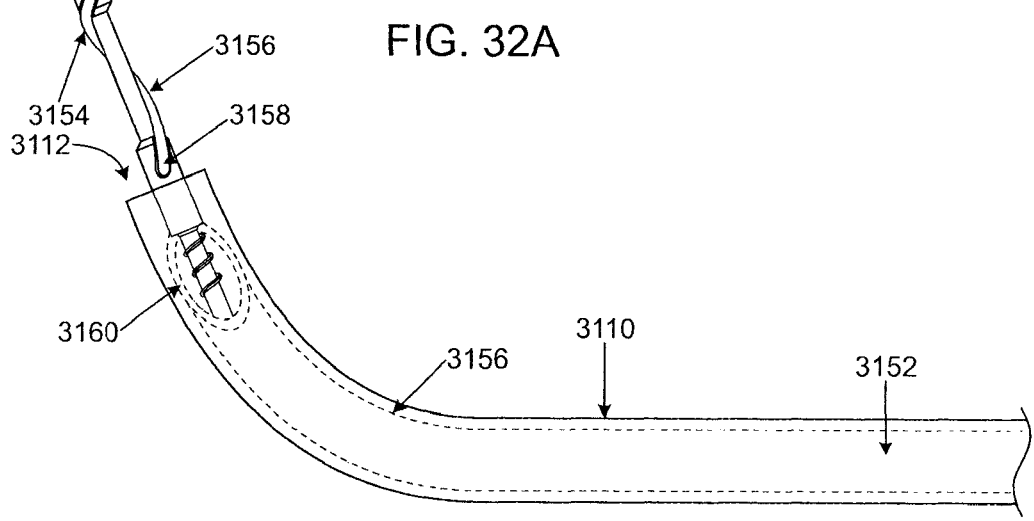
Figure 32C:
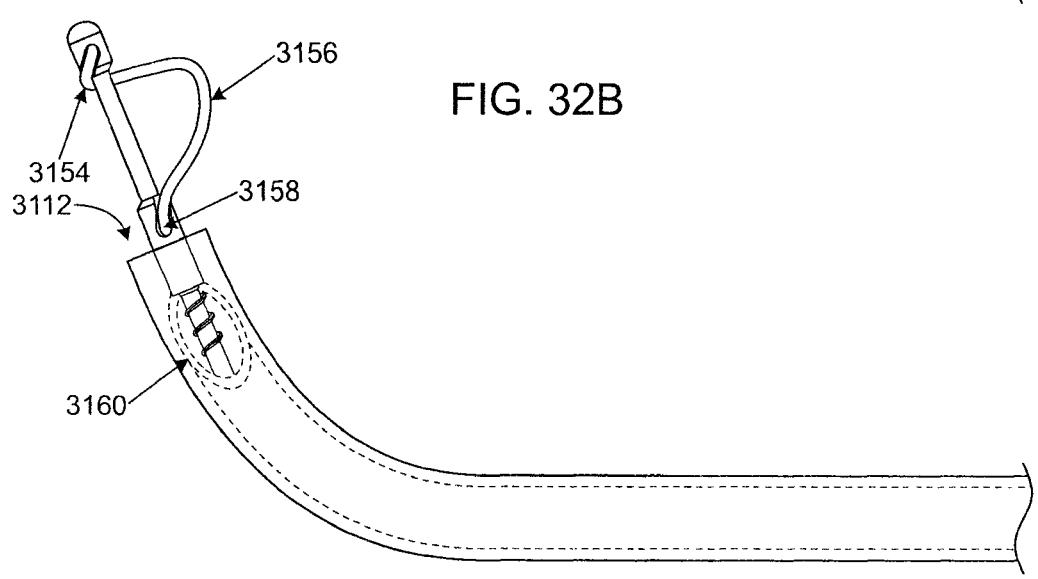

Once the cannula has been positioned at the target tissue, and optionally confirmed by imaging techniques, the stylet may be withdrawn from the cannula, and the tissue removal device may be advanced to the target tissue via the cannula. FIGS. 32A to 32C schematically illustrate the insertion of a cable-based tissue removal device 3150 into a curved cannula 3110. The cable-based tissue removal device 3150 comprises a shaft 3152 and a distal tissue removal portion 3154. In some embodiments, the shaft 3152 of the tissue removal device 3150 may comprise a pre-shaped curved configuration with a bend 3156, which may comprise substantially the same bending characteristics (e.g., bending range, bend radius, etc.) as the bend 3116 of the curved cannula 3110. In such instances, the curved tissue removal device 3150 may be used with a curved cannula with a matching bend. In other embodiments, the shaft 3152 of the tissue removal device 3150 may be made from a flexible, semi-flexible material (e.g., shape memory alloys or shape memory polymer) or otherwise malleable material such that when the tissue removal device 3150 passes through the curved cannula 3110, the shaft 3152 may assume a curved configuration, forming a bend 3156 substantially the same as the curved cannula 3110. In these embodiments, the flexible tissue removal device 3150 may be used in conjunction with curved cannula with different bending characteristics (e.g., bending range, bend radius, etc.). Additionally or alternatively, such a flexible tissue removal device may also be used with a straight cannula.

A straight cannula and a straight stylet may be used in a variety of spinal procedures and surgeries, including but not limited to discectomy and vertebroplasty, as well as diagnostic procedures. Prior to inserting the tissue removal device into a patient, the device may be turned on to confirm proper rotational and axial motion, as well as to ensure that the rotatable cable properly transitions between the retracted configuration and the extended configuration. The travel member should be locked in the distal position. Once the patient is prepared for the surgery as described above, the target disc level may be identified using fluoroscopy or another appropriate imaging modality. Access to the affected disc may be attained using either the straight cannula or the curved cannula. To access the affected disc with the straight cannula, the sharpened stylet may be inserted into to the straight cannula, and then fixedly attached together at their proximal hub, e.g. by a Luer Lok™ connector. The straight cannula-sharpened stylet assembly may be advanced into the affected disc under image guidance. For example, the cannula may be positioned parallel to disc endplates. The cannula tip may be adjusted such that it rests within the disc nucleus, at the proximal location of the desired tissue removal zone. Optionally, a silicone marker or grommet may be provided on the straight and the curved cannula to mark the cannula depth. Once the tip of the straight cannula is confirmed to be inside the disc, the sharpened stylet may be removed as the cannula is held in place. To access the affected disc with the curved cannula, the sharpened stylet may be inserted into the curved cannula, and then fixedly attached together at their proximal hub, e.g. by a Luer Lok™ connector. The curved cannula-sharpened stylet assembly may be advanced into the affected disc under image guidance. Once the tip of the curved cannula is confirmed to be inside the disc, the orientation of the curve may also be adjusted according to a wing-shaped orientation indicator at a proximal portion of the curved cannula. Optionally, a silicone marker or grommet may be provided on the straight and the curved cannula to mark the cannula depth. The sharpened stylet may be removed, leaving the curved cannula in place. Then, the curved stylet may be inserted into the curved cannula such that the stylet curve matches the cannula curve, i.e., the wing-shaped orientation indicator of the curved stylet matches the orientation of the wing-shaped orientation indicator of the curved cannula. Under image guidance, the curved cannula-curved stylet assembly may be advanced to the desired location. Once the curved cannula has been confirmed to be in the desired location, the curved stylet may be withdrawn as the cannula is held in place. As either the straight or curved cannula is advanced through the disc region, the practitioner may use any suitable imaging modality to avoid advancing the cannula (or associated stylet) into or through the distal annular wall. After cannula penetration to the vertebral disc, if the practitioner determines that an alternate cannula should be use to better access the targeted site, the exchange wire may be used to withdrawn the original cannula and to insert the alternate cannula, without creating a second access site.

Prior to inserting the tissue removal device into the cannula, approximately 0.5 cc of saline may be injected into the disc through the cannula. Under image guidance, the tissue removal device may be inserted through the cannula until the travel limiter has reached the proximal hub of the cannula. The travel limiter may be attached to the proximal hub of the cannula by rotating the handle in a clockwise direction. Releasing the locking ring and locking it in an intermediate position may allow the distal tip of the tissue removal device to be advanced up to 13.5 mm beyond the distal tip of the cannula. Securing the locking ring a distal position may allow the distal tip of the tissue removal device to be advanced up to 18.5 mm beyond the tip of the cannula. The practitioner may adjust the position of the locking ring as necessary. After each adjustment, the practitioner may confirm that within the constraints imposed by the configuration of the travel limiter, the distal end of the cannula is still in the disc nucleus. The practitioner may also confirm that the rotatable cable of the tissue removal assembly will not contact the proximal or distal annulus as the device is axially advanced and withdrawn along the axial length determined by the travel limiter. Using image guidance, the practitioner may advance the tip of the tissue removal device to the full plunge depth, and confirm that the tip is in a safe location. The tissue removal device may then be turned on, and the configuration of the rotatable cable may be adjusted by a slider actuator on the handle, e.g., the rotatable cable may be transitioned from a retracted configuration to an extended or expanded configuration. In some variations, the sweep diameter of the rotatable cable in the extended configuration is about 7 mm. While the tissue removal device is turned on, and securing the position of the cannula, the tissue removal device may be advanced and retracted to help facilitate tissue removal. The placement of the device in the course of tissue removal may be intermittently confirmed by fluoroscopy or another appropriate imaging modality. The tissue removal device may be used until sufficient tissue material has been removed, or the collector is full. In some variations, a negative pressure source may be coupled to the collector which may help expedite tissue removal. The markings on the collector indicate the quantity of tissue removed. The tissue removal device may be turned on and used continuously for about 0.5 seconds to about 6.0 minutes, e.g., 2.0 minutes.

Once a sufficient quantity of tissue material has been removed, the tissue removal device may be turned off, and the rotatable cable may be transitioned to its retracted configuration. The locking ring of the travel limiter may be secured in the distal position. The travel limiter may be disengaged from the proximal hub of the cannula, and then the tissue removal device may be withdrawn. The above steps may be repeated until the desired quantity of tissue has been removed. If additional treatment is required within the disc, the straight or curved stylet may be reinserted into the cannula, and the cannula may be repositioned. In some procedures, it may be desirable to limit the total run-time of the tissue removal device to about 6.0 minutes or less. The straight stylet may be inserted into the cannula and fixedly attached at the proximal hub. Then, the cannula-straight stylet assembly may be withdrawn from the access site. In some variations, the battery of the tissue removal device may be removed and disposed according to local regulations.

The cannula, stylet, and tissue removal devices described above may also be used to perform a discectomy. The devices may be used in a minimally invasive procedure, or an open surgery procedure. The cannula-stylet assembly may be used to form a passageway or a working channel through the tissue about a target site in the spinal region. For example, to perform a discectomy procedure, the patient is prepped and draped in the usual sterile fashion and in a lateral decubitis or prone position. General, regional or local anesthesia is achieved. A straight stylet with a sharp distal tip may be inserted into the lumen of a straight cannula. The assembly may then be percutaneously inserted through a posterior or posterolateral entry point on the back of the patient. The cannula-stylet assembly may be further inserted into the epidural space or into the paravertebral space, depending on the assembly's point of entry. Alternatively, the assembly may be used to penetrate the disc annulus directly from a point of entry further away from the midline of the patient's back. In some embodiments, the assembly may be introduced on the ipsilateral side from which the nerve impingement has been identified and at an angle of about 25 degrees to about 45 degrees to the patient's back. In other procedures, a contralateral approach and/or a different angle may be used. In alternative embodiments, an anterior procedure through the abdominal cavity of the anterior neck region may be performed.

The cannula-stylet assembly may be advanced together to a target tissue site, as described above. During the insertion of the assembly, the stylet may be independently rotatable such that the operator may adjust the orientation of the optional beveled edge of the stylet in order to form a passageway through the surrounding tissue, bones or other anatomic structures. The insertion of the cannula-stylet assembly may be performed under the guidance of external imaging and/or visualization techniques.

Figure 26A:
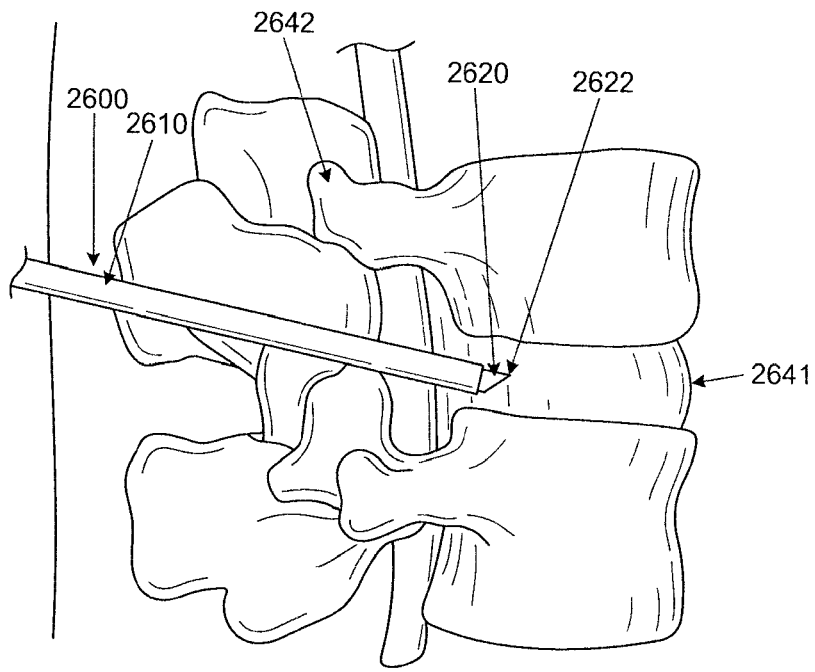
FIGS. 26A to 26D schematically illustrate one embodiment of a straight access to a target site for performing discectomy.
Figure 26B:
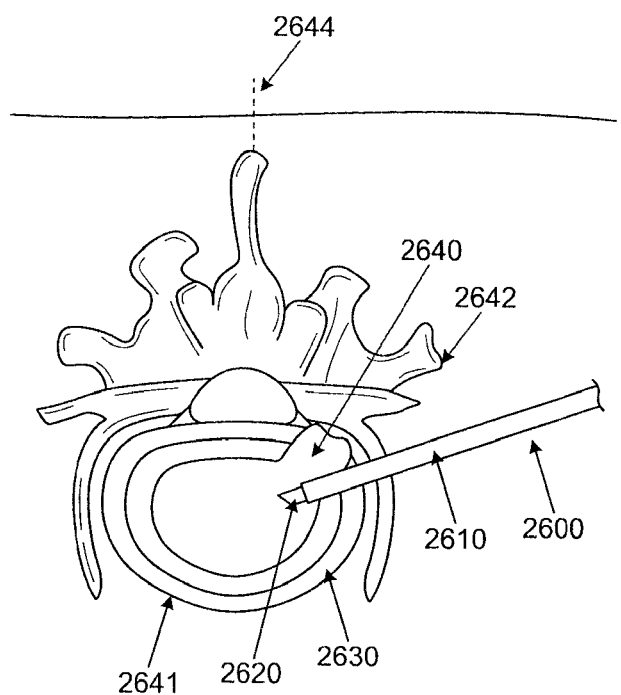

FIGS. 26A and 26B schematically illustrate one embodiment of a straight access to the spinal disc area by a straight cannula-stylet assembly 2600. FIG. 26A is a side cut-away view of the access and FIG. 26B is superior cut-away view of the access. Where the cannula 2610 and stylet 2620 comprise a relatively stiff material (e.g., stainless steel), the assembly 2600 may provide increased tactile responsiveness, torquability and/or pushability when manipulated proximally over longer insertion distances. In some embodiments, the assembly of a straight cannula 2610 and a straight stylet 2620 may be inserted directly into the disc annulus 2630. The sharp distal tip 2622 of the stylet may facilitate obtaining access to the herniated area 2640 by penetrating the disc annulus 2630.

Once access to the herniated area is confirmed by fluoroscopy or other types imaging or visualization techniques, the stylet 2620 may be removed, followed by the insertion of a tissue removal device. In some embodiments, before the tissue removal device is inserted, an endoscope may be used to evaluate the target site access. Examples of endoscopic systems that may be used with the cannula-stylet assembly are described in U.S. application Ser. No. 11/362,431, U.S. application Ser. No. 11/373,059, U.S. application Ser. No. 12/199,706, and U.S. Appl. No. 61/106,914, which are hereby incorporated by reference in their entirety. The endoscope may facilitate direct visualization and identification of the relevant structures such as the disc, the nerve or other adjacent structures and the site(s) to tissue removal. The endoscope may be inserted into the cannula subsequent to the removal of the stylet, or may be introduced through an additional lumen in the cannula. In other examples, a guidewire may be inserted into the cannula and the cannula is removed to permit positioning of the endoscope using the guidewire.

Figure 26C:
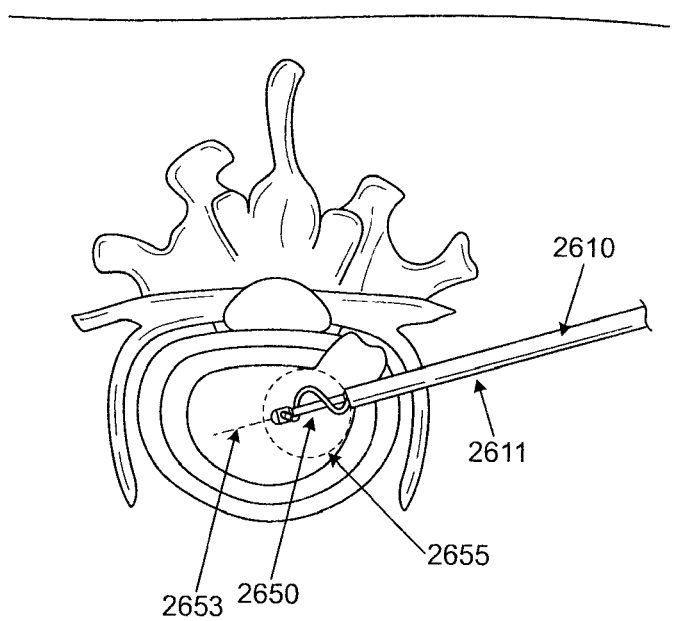
Figure 26D:
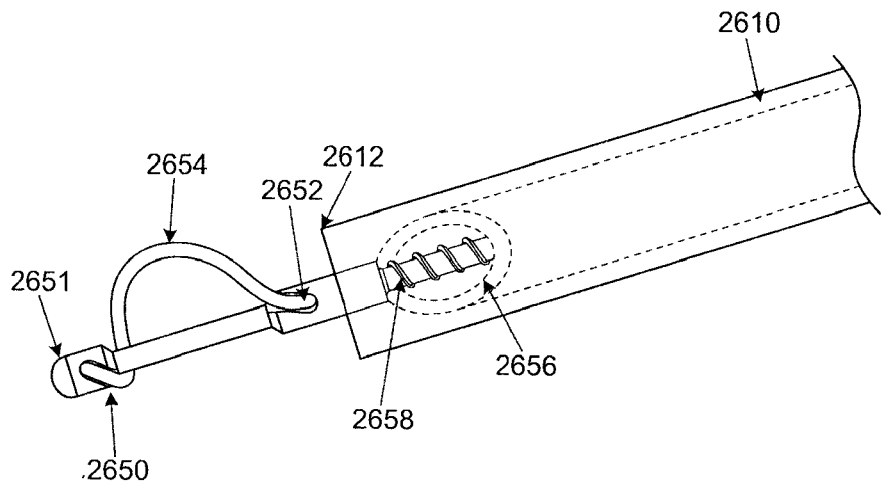

Referring back to FIG. 26C, once the cannula placement at the target site has been confirmed, a tissue removal device 2650 may be inserted into the cannula 2610 and advanced into the nucleus 2640 of the disc 2641. The tissue removal device 2650 may be a mechanical tissue removal device that may be motorized or manually activated, including but not limited to burr, trephine, or cable-based tissue removal device as described previously. In other examples, the tissue removal device may be an energy-based device (e.g. laser, RF, high-intensity focused ultrasound) or a chemical-based (e.g. injection or infusion of a sclerosant or chemical ablation agent). The tissue removal device may be used to remove disc material either by dissecting, aspirating, dissolving, or shrinking the nucleus. In one specific example, a cable-based tissue removal device 2650 may be inserted into the cannula 2610 and advanced to the herniated area 2640. The distal portion of the tissue removal device 2650 may be radiopaque to allow the device to advance under external imaging guidance. The device 2650 may comprise a proximal connector that allows releasable attachment of the device 2650 to the cannula 2610. FIG. 26D is a detailed view of the tissue removal device 2650 that is proximally attached to the cannula 2610 with the spiral cable 2654 in a deployed configuration. In some embodiments, once the device 2650 is proximally attached to the cannula 2610, the port 2652, through which the cable 2654 is proximally attached to the device 2650, is disposed distally to the distal end 2612 of the cannula 2610. This ensures that the deployment of the cable 2654 will not be interfered with by the cannula 2610. In some embodiments, the tissue removal device 2650 may comprise an aspiration port 2656, which is configured to aspirate emulsified or pulverized nucleus fibrosus broken and removed by the spiral cable 2654. In some embodiments, once the device 2650 is attached to the cannula 2610, the aspiration port 2656 may be at least partially covered by the cannula 2610 such that the port 2656 will not be clogged by larger pieces of disc material.

In some embodiments, after the tissue removal device 2650 is proximally attached to the cannula 2610, the device 2650 may be advanced further within the cannula 2610 in order to enlarge the tissue removal zone, which is defined by the motion of the deployed cable 2654. In some examples, a travel limiter may be employed to limit the distal travel of the tissue removal device 2650 with respect to the distal end of the cannula 2610, as described previously. The maximum distal travel distance of the tissue removal device may be less than about 2 centimeter, sometimes less than about 1 centimeter, and other times less than about 0.5 centimeter. The travel limiter may also be used to prevent the tissue device from traveling too far and thereby, leaving the herniated area. The advancement of the tissue removal device 2650 within the cannula may be monitored under fluoroscopy or other types of imaging guidance. The tissue removal device 2650 may be of any maximum transverse axial dimension with the spiral cable 2654 retracted that is smaller than the inner diameter of the cannula 2610. In some embodiments, with the cable 2654 extended or deployed, the maximum radial displacement of the wire 2654 may be in the range of about 0.07 inch to about 0.2 inch, sometimes in the range of about 0.09 inch to about 0.2 inch, and other times in the range of about 0.1 inch to about 0.15 inch.

Referring back to FIG. 26D, once the placement of the tissue removal device 2650 is confirmed, the cable 2654 may be deployed and actuated to emulsify or pulverize the tissue of the disc. The position of the device 2650 may be adjusted (e.g., advanced and retracted) relative to the cannula 2610 during one session of actuation in order to enlarge the tissue removal zone distally. In other embodiments, the position of the device 2650 may be adjusted during the intervals between the actuation sessions of the device.

Fluoroscopy and/or CT scan may be used before, during and/or after the procedure to assess the patient's anatomy, the position of the instruments, the structural changes after tissue removal, and/or to verify the integrity of the disc. In some embodiments, a small amount of radiopaque contrast may be injected into the disc space to enhance visualization. Such injection may be performed by the tissue removal device through an infusion or irrigation channel, or through the aspiration port. In other embodiments, the cannula may comprise an infusion or irrigation lumen to introduce the contrast agents. In some embodiments, the tissue removing procedure may be assessed by the quantity and/or color of the tissue removed through an optically transparent chamber, or collection chamber. Upon completion of the procedure, the tissue removal device 2650 may be proximally withdrawn, followed by withdrawal of the cannula 2610.

Figure 28A:
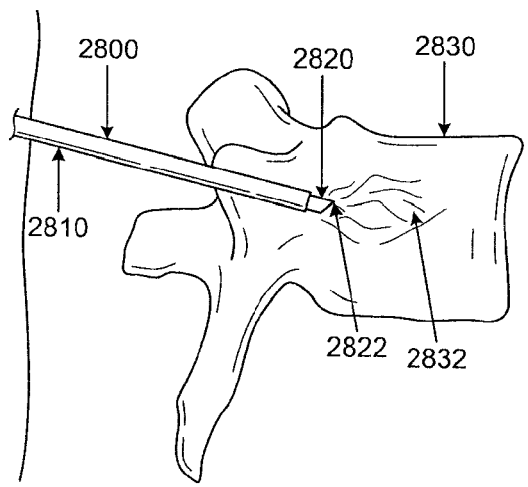
FIGS. 28A to 28C schematically illustrate one embodiment of a straight access to a target site for performing vertebroplasty.

A straight cannula and a straight stylet may also be used for vertebroplasty. In one specific example illustrated in FIGS. 28A to 28C, a straight cannula-stylet assembly 2800 may be percutaneously entered into tissue surrounding the spine until the sharp and optionally beveled stylet tip 2822 reaches the outer surface of the vertebral body 2830 of interest. The sharp stylet tip 2822 may be used to form a passageway or working channel through the compact bone of the vertebral body 2830. In some embodiments, the stylet 2820 may only be used to penetrate the outer surface of the vertebral body 2830. Another surgical instrument (e.g., a dilator or an obturator), subsequent to the removal of the stylet 2820, may be used to enlarge the penetration site to form the passageway or working channel. The placement of the assembly 2800 to acquire access to the interior of the vertebral body may be guided by fluoroscopy, CT or ultrasound. Once the access to the fractured area 2832 is confirmed, the stylet 2820 (or another tool used to form the passageway) may be removed and a tissue removal device 2840, such as the cable-based tissue removal device 2840 depicted in FIG. 28C, may be inserted into the cannula 2810 to remove diseased bone tissue (e.g., cancerous cells). In some embodiments, the cable-based tissue removal device 2840 may be used to form a cavity 2834, into which bone cement or other materials may be injected to stabilize the fracture caused by osteoporosis, tumors or severe trauma. In some embodiments, the tissue removal device 2840 may comprise an infusion or aspiration channel, which may be used to collect diseased bone tissue for diagnosis or evaluation. Such an infusion or aspiration channel may also be used to collect removed bone tissues during the tissue removing procedure. Devices and methods to use a cable-based tissue removal device in vertebroplasty have been described in detail above and will not be repeated here for the sake of brevity.

Once the tissue removing procedure is completed, a fluoroscopy or CT scan may be performed to examine the vertebral body. In some embodiments, the tissue removal device may comprise a pressure sensor, which may be used to read the internal pressure in the vertebral body. Based on the pressure reading, the operator may be informed when the fractures are adequately filled and/or integrity of the vertebral body has been regained. Upon completion of the procedure, the tissue removal device 2840 may be proximally withdrawn from the cannula 2810, followed by withdrawal of the cannula 2810.

Figure 28B:
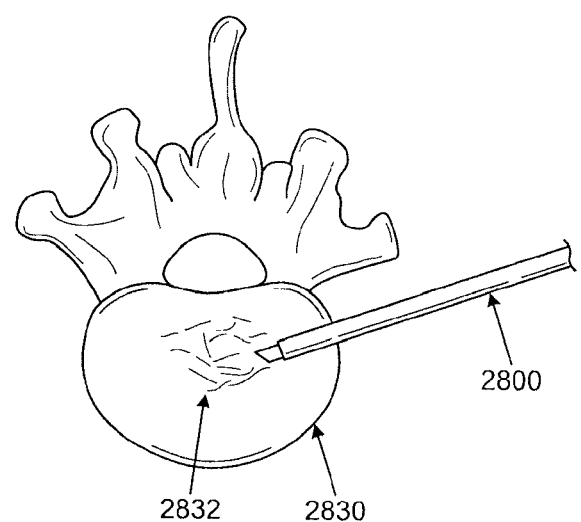
Figure 28C:
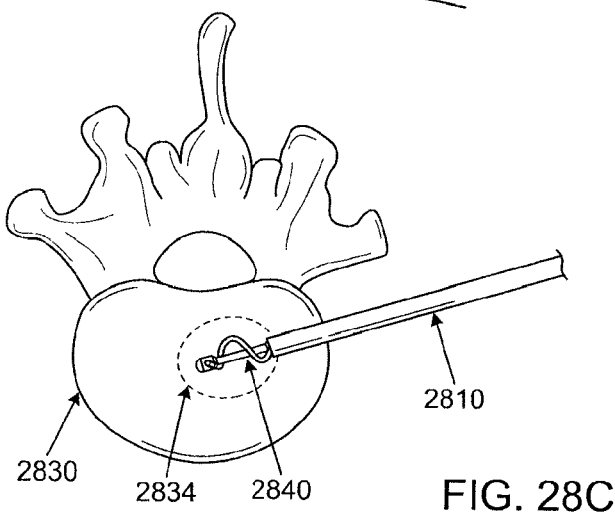

While a vertebroplasty may be performed using a straight cannula, a bendable flexible curved cannula may also be used. As described above, a straight or curved stylet may be used with a bendable flexible curved cannula to position the cannula at the targeted tissue site. As illustrated in FIGS. 33A to 33D, a straight cannula-stylet assembly 3300 comprising a curved cannula 3310 straightened by a straight stylet 3310 may first be percutaneously entered into spinal muscle to form a passageway through the outer surface of the vertebral body 3330. The initial straight assembly placement may be closer to the outer surface of the vertebral body compared to the initial placement of a straight cannula-stylet assembly in a straight access, where the distal tip of the stylet needs to reach the fractured area that is closer to the central vertebral body (as shown in FIG. 28B). As a result, the initial placement of a curved assembly in vertebroplasty may involve a shorter and more direct insertion path.

Once access to the interior of the vertebral body 3330 is confirmed, the straight stylet 3310 may be replaced with a curved stylet 3340. A curved cannula-stylet assembly 3301 is formed with the cannula 3310 and the stylet 3330 proximally coupled to each other and with their curved portions aligned.

Figure 33A:
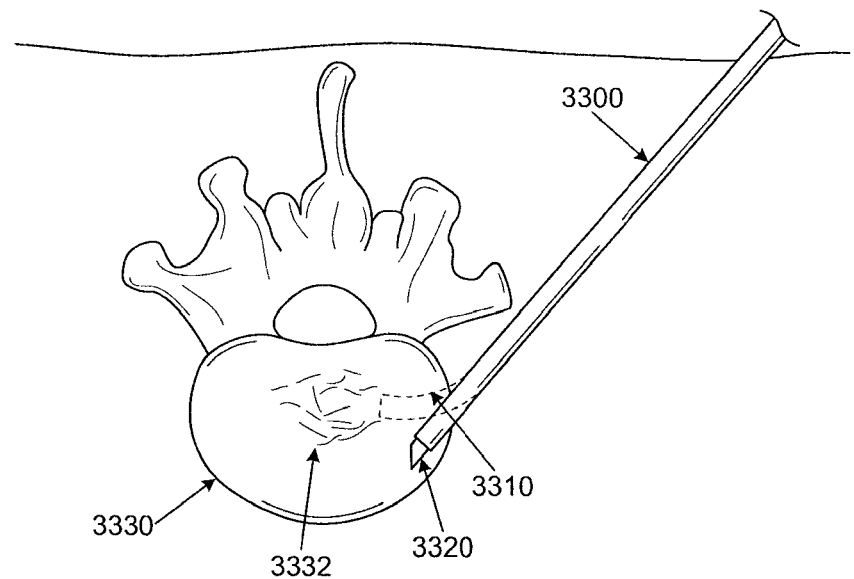
FIGS. 33A to 33D schematically illustrate one embodiment of a curved access to a target site for performing vertebroplasty.
Figure 33B:
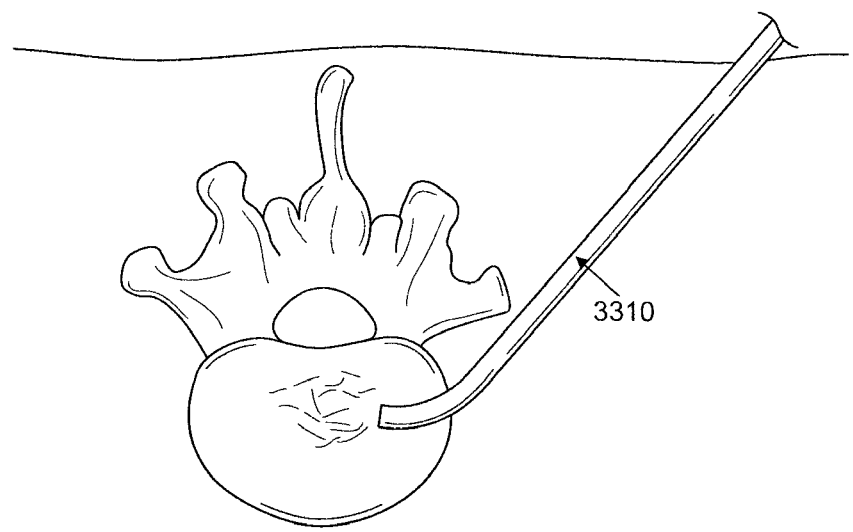
Figure 33C:
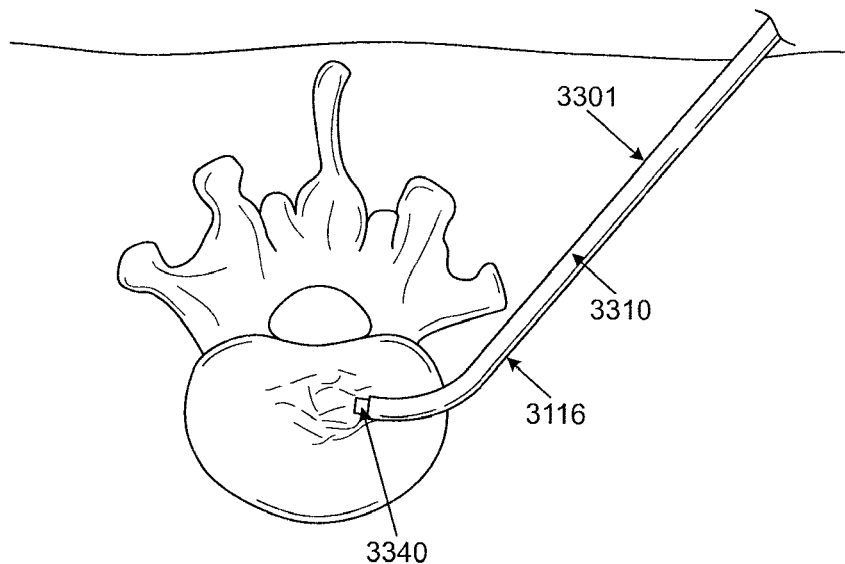
Figure 33D:
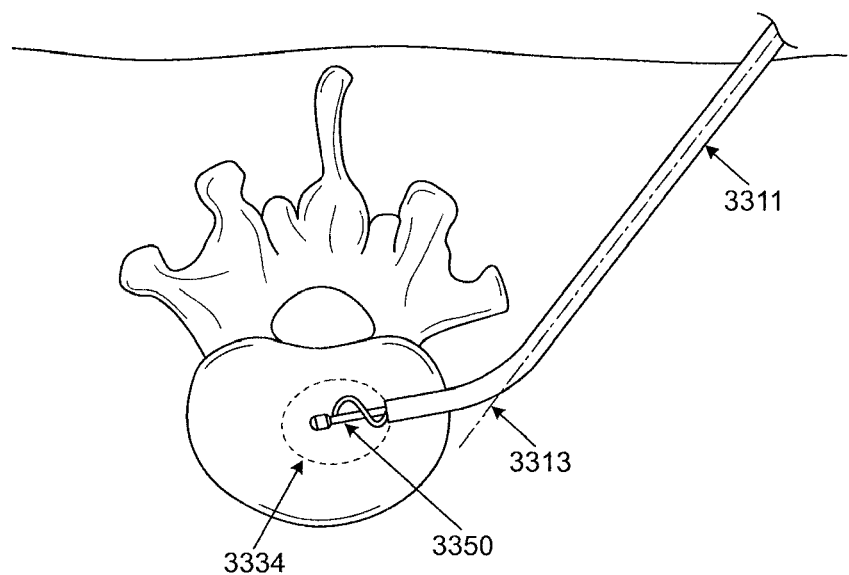

In some embodiments, the curved stylet 3340 may comprise a blunt distal tip, which may sufficiently penetrate cancellous bone, thereby facilitating the movement of the curved cannula-stylet assembly 3301 inside the vertebral body 3330. In other embodiments, the distal tip of the curved stylet 3340 may be sharpened in order to enhance its piercing ability. A curved cannula-stylet assembly 3301 may be used to access central vertebral body area that is difficult to reach by a straight cannula-stylet assembly. Once access to a target site is confirmed, a tissue removal device (e.g., a cable-based tissue removal device 3150 as depicted in FIG. 33D) may be inserted, subsequent to the proximal withdrawn of the curved stylet 3330. A tissue removal device may be used to form cavities inside the vertebral body 3330, to remove diseased tissues (e.g., cancerous cells), and/or to inject bone cement into fractured area to reinforce spine support. The tissue removal device may also be used to collect bone tissues through an aspiration and/or an infusion channel for diagnosis. A tissue removal device 3350 extended from the distal end of a curved cannula provides a greater reaching zone for tissue removal. For example, the proximal insertion of the assembly 3301 may advance the tissue removal device 3350 towards the central area of the vertebral body, thereby providing greater distal reaching distance. Further, the orientation of the cannula bend 3116 may be adjusted with respect to the longitudinal axis 3313 of the straight cannula shaft 3311, thereby providing the tissue removal device 3350 enhanced angular access, compared to a straight access. As a result, larger cavities may be formed by the tissue removal device 3350 used in conjunction with a curved cannula 3310, compared with the same device used with a straight cannula. In some embodiments, if multiple cavity formation is desired, a stylet (either straight or curved) may be reinserted into the curved cannula, subsequent to the withdrawn of the tissue removal device, in order to gain access to an adjacent target area. In some embodiments where penetration of compact bone may be involved, a straight stylet may be first reinserted and a straight cannula-stylet assembly is used to form a passage way or a working channel to another target site. The straight stylet may then be replaced with a curved stylet to obtain more accurate access to the target site. In other embodiments where the second target site may be accessible without compact bone penetration, a curved stylet may be reinserted directly following the withdrawn of the tissue removal device. Once access to the second target site is confirmed, the tissue removal device may be reinserted following the proximal removal of the curved stylet to perform bone tissue removal. Such procedures may be repeated until treatments at multiple target sites are completed. As noted above, upon the completion of bone tissue removal and/or bone cement injection, a fluoroscopy or a CT scan may be performed to examine the bone integrity. In some embodiments, the examination may be performed by examining the quantity, color and/or texture of removed bone tissue collected in the proximal collecting chamber. Upon the completion of the vertebroplasty, a straight stylet may be inserted into the curved cannula, subsequent to the removal of the tissue removal device and the cannula and stylet may then be proximally withdrawn together.

Figure 31A:
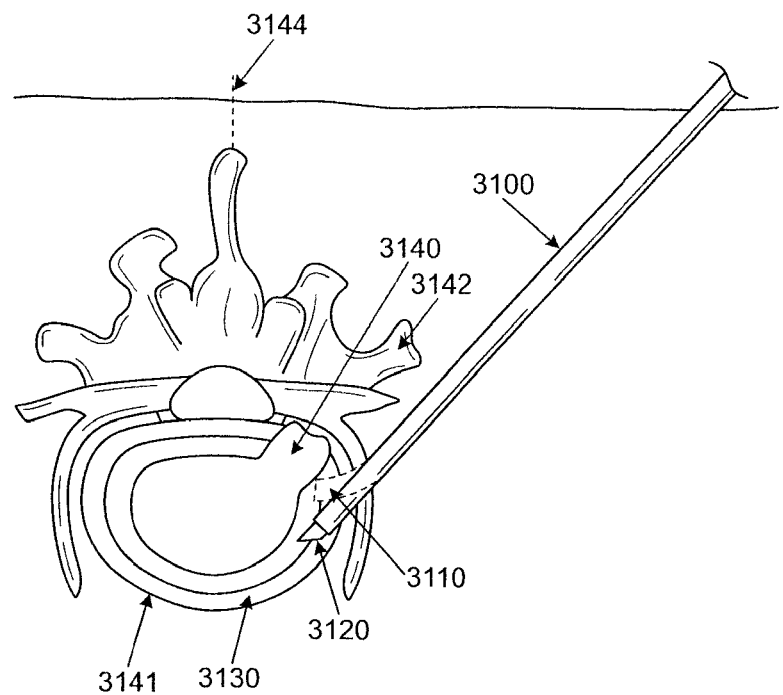
FIGS. 31A to 31D schematically illustrate one embodiment of a curved access to a target site for performing discectomy.
Figure 31B:
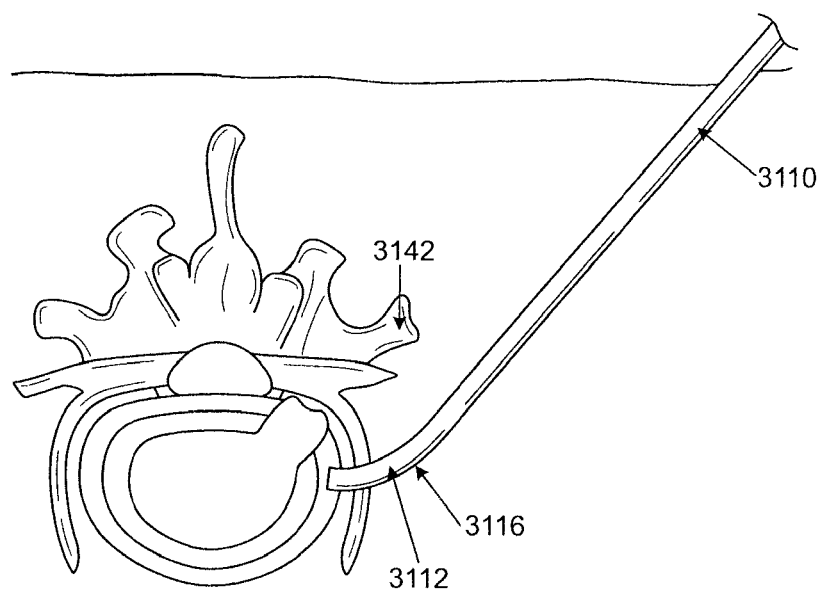
Figure 31C:
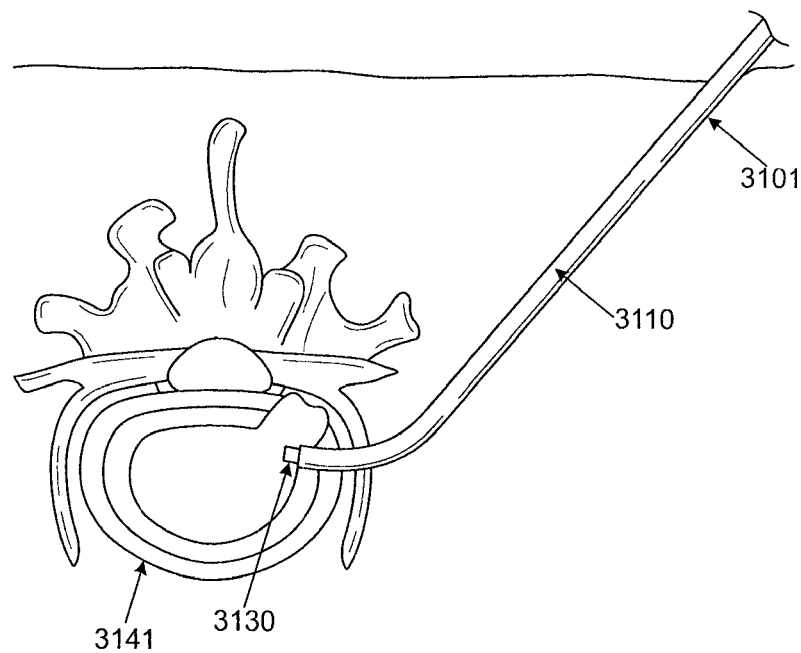

FIGS. 31A to 31C schematically illustrate a curved access to a herniated disc 3141 by a cannula-stylet assembly comprising a curved cannula 3110, a straight stylet 3120 and/or a curved stylet 3130. Once the patient is prepared for the discectomy procedure, a straight cannula-stylet assembly 3100 may be formed by inserting a straight stylet 3120 into a curved cannula 3110. The assembly 3100 may then be inserted percutaneously through a posterior or a posterolateral entry point on the back of the patient. As shown in FIG. 31A, the insertion of the straight stylet 3120 straightens the curved cannula 3110 and renders assembly 3100 in a straight configuration. Because the straight stylet 3120 is made from a relatively rigid material (e.g., stainless steel), the assembly 3100 may provide enhanced user responsiveness and maneuverability while penetrating the patient's skin, muscle, and body tissues. The straight stylet 3120 with sharpened distal tip may be used to form a passageway or a working channel through the disc annulus. As noted above, a discectomy procedure using a straight access (as shown in FIGS. 26A and 26B) may involve inserting an assembly of a straight cannula and a straight stylet over a longer path in the patient's back in order to achieve sufficient access to the herniated area for excision. By contrast, in a discectomy using a curved access, a shorter and/or more direct insertion path may be taken to the target site. For example, as illustrated in FIG. 31A, the straight cannula-stylet assembly 3100 may be inserted from an entry point closer to the midline 3144 of the patient's back until the distal tip of the stylet 3120 penetrates the disc annuals 3130 and reaches an area in close proximity to the target herniated area. As will be discussed in greater detail below, a curved cannula-stylet assembly will then be used to reach the target herniated area for treatment. Because the initial straight cannula-stylet placement is closer to the outer surface of the vertebral disc, the insertion path of the cannula-stylet assembly in a curved access may be shorter and more direct, compared to the initial placement of the assembly in a straight access.

Once the straight cannula-stylet assembly 3100 reaches the interior of the vertebral disc, the straight stylet 3020 may be proximally removed, allowing the curved cannula 3110 to substantially regain its curved configuration, as shown in FIG. 31B. In some embodiments, before proximally removing the straight stylet 3120, the operator may adjust the orientation of the bend 3116 to ensure that the distal portion 3112 cannula will bend towards the herniated area 3140 when the straight stylet 3120 is withdrawn. Following the removal of the straight stylet 3120, a curved stylet 3130 may be inserted into the cannula 3110, forming a curved cannula-stylet assembly 3101, as illustrated in FIG. 31C. The curved stylet 3130 may be radiopaque to permit the insertion under external imaging guidance. In some embodiments, a stylet with a matching pre-shaped bend with the cannula may be used. In such instances, the operator may adjust the orientation of the stylet bend during the insertion to ensure that the bend of the stylet and that of the cannula are aligned with each other. In other embodiments, a stylet made of flexible material may be used such that when the stylet passes through the curved portion of the curved cannula, it may assume a curved configuration substantially the same as the cannula.

The curved stylet 3130 may be releasably coupled with the curved cannula proximally. In some embodiments, once the stylet 3130 is attached to the cannula 3110, both the longitudinal and the axial movements of the stylet 3130 relative to the cannula 3110 are locked such that an aligned cannula-stylet assembly 3101 may be advanced together to the target site for excision. In some embodiments, the curved stylet 3130 may comprise a blunt distal tip that still may penetrate the nucleus, thereby acquiring access to the herniated area. The blunt tip may reduce the risk of tissue disruption or damage, especially in the situations where the curved assembly 3101 is misplaced during its insertion. When the curved cannula-stylet assembly 3101 is proximally inserted, its curved distal end may be advanced laterally towards the central portion of the herniated disc 3141. Such intra-discal area access may be challenging if a straight access is used. Further, during the insertion of the curved assembly 3130, the operator may adjust the orientation of the bend to steer the distal tip of the assembly 3101 in the intra-discal area, thereby acquiring access to some target site that is difficult to reach by a straight access.

Figure 31D:
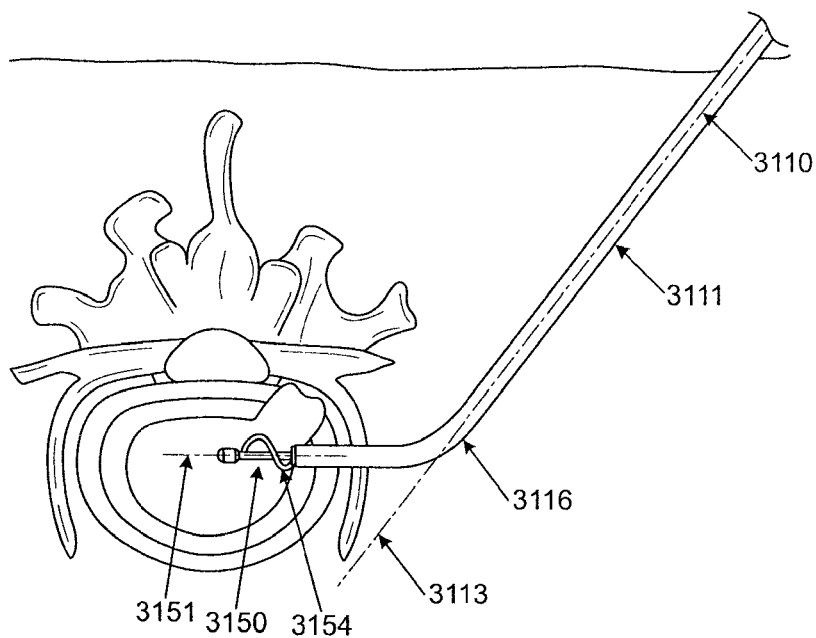

Once the access to the target site for excision by the curved cannula-stylet assembly 3101 is confirmed by fluoroscopy or other imaging or visualization techniques (e.g., endoscope or radiographic marker), the curved stylet 3130 may be proximally withdrawn, followed by the insertion of a tissue removal device. FIG. 31D schematically illustrates a cable-based tissue removal device 3150 extended distally from a curved cannula 3110.

The tissue removal device 3150 may be proximally attached to the curved cannula 3110 through complementary proximal connectors. In some embodiments, once attached, the distal tissue removal portion 3154 is exposed distally with respect to the distal end 3112 of the curved cannula 3110 such that the deployment of the spiral wire 3156 will not be blocked or otherwise interfered with by the distal end 3112 of the curved cannula 3110. In some embodiments, the tissue removal device 3150 may be further advanced distally inside the cannula 3110 after the two are proximally attached and the maximum travel distance of the tissue removal device 3150 may be limited by a travel limiter. As discussed above, the distal travel of the tissue removal device 3150 is controlled such that the aspiration port 3160 may be at least partially covered by the curved cannula 3110 during the insertion of the tissue removal device 3150 to prevent the clogging of the aspiration channel.

Where the placement of the tissue removal device 3150 is confirmed and evaluated, the device 3150 may be actuated to perform disc tissue removal. A tissue removal device used in association with a curved cannula may increase the region or amount of tissue removed, compared to the same tissue removal device used with a straight cannula. For example, as illustrated in FIG. 26C, the tissue removing range 2655 of the tissue removal device 2650 extended from a straight cannula 2610 is substantially limited by the pivoting range of the straight cannula shaft 2611. Any small annular movement of the tissue removal device 2650 may involve substantial lateral displacement of the straight proximal portion of the cannula 2610, which is limited by the body tissues along the insertion path of the cannula 2610. As a result, the tissue removal zone 2655 of a straight access is limited by the range that can be reached by the rotation of the extended cable 2654 with respect to the longitudinal axis 2653 of the tissue removal device 2650. By contrast, during a curved access as illustrated in FIG. 31D, rotating the shaft 3111 of the curved cannula 3110 and adjusting the orientation of the cannula bend 3116 allows the tissue removal device 3150 to move angularly with respect to the longitudinal axis 3113 of the cannula shaft 3111, thereby significantly increasing the range that can be reached by the extended cable 3154. Further, the tissue removal zone of the tissue removal device 3150 may be further increased by distal displacement of the tissue removal device 3150 with respect to the distal end of the curved cannula 3110. In some embodiments, the vertical displacement of the extended cable 3154 with respect to the longitudinal axis 3151 of the tissue removal device 3150 may be adjusted to further increase the tissue removal zone. If the movements described above are combined, an even greater tissue removal zone may be achieved.

After confirming a desired degree of tissue removal using imaging techniques, the tissue removal device may be removed. To treat a second tissue site, a curved or a straight stylet may be reintroduced to the cannula. In some embodiments, access to another herniated area may require removal of the curved cannula from the disc annulus (e.g., the target site is located on the other side of the disc or the target site is in another vertebral disc). In this scenario, a straight stylet may be first inserted into the cannula to replace the tissue removal device, forming a straight cannula-stylet assembly. The operator may then remove the assembly from the disc annulus and, if appropriate, re-insert the assembly into the disc annulus from another entry point, thereby acquiring access to a second target site. After the annulus is penetrated, the straight stylet may be replaced with a curved stylet and a curved cannula-stylet assembly may be formed to be placed at the second target site within the disc.

Once the placement of the cannula is confirmed at an additional tissue site, the stylet may be proximally withdrawn and a tissue removal device may be reintroduced and the tissue removal procedures as described above may be repeated. Upon completion of the treatment at the additional target sites, another fluoroscopy or CT scan may be performed to examine the outcome and/or to examine whether any other intra-discal area needs additional tissue removal. Once all herniated areas are treated, the tissue removal device may be proximally removed. In some embodiments, a straight stylet may be first inserted into the curved cannula, forming a straight cannula-stylet assembly. The assembly may then be proximally removed from the patient's back.

Use of curved cannula-stylet assemblies in conjunction with tissue removal devices may provide precise access and tissue removal at one or more target sites. Where access to a target site affected by tumors is involved, the curved access described herein may be desirable especially when the areas surrounding the target site are highly compromised by the tumor. Precise removal of diseased bone tissues while preserving healthy ones may result in fewer complications, such as bone cement leakage and/or cancerous cells spreading.

While a mechanically-operated cable-based tissue removal device used in conjunction with cannula-stylet assemblies in spinal procedures (e.g., discectomy and vertebroplasty) is described in detail herein, it should be understood that other types of mechanical tissue removal devices (e.g., burrs, trephines, etc.) or energy-based tissue removal devices may be used, and are contemplated for use in either a straight access or a curved access to a spinal area.

While certain variations of impellers have been described as being used with certain variations of rotatable cable shafts, tubular members, etc. it should be understood that the variations of impellers may be used with other variations of rotatable cable shafts, tubular members, etc. Additionally, different variations of rotatable cable shafts may also be used with different cable configurations and drive shafts. Multiple variations of the above-described components may be combined and assembled as appropriate for certain procedures. Examples of systems and kits that may be used for performing a minimally invasive discectomy that may comprise the various cannulas, stylets, tissue removal devices are described herein. Similar systems and kits may generally be used for cutting, grinding, and aspirating intervertebral disc material during procedures in the lumbar spine. One variation of a kit for minimally invasive discectomy may comprise a straight cannula, a straight stylet, and a tissue removal device. Another variation of a kit may further comprise a sharpened stylet, a curved cannula, a second straight stylet, a curved stylet, an exchange wire, and a tissue removal device. The cannula(s) may be 16 gauge, and the stylets may be appropriately sized and shaped so that they may be advanced through the cannula(s). The exchange wire may have a diameter of about 0.054 inch and be about 17 inches long, or any length that is appropriate for minimally invasively accessing a region of tissue within a vertebral disc. The exchange wire may be made of 304 stainless steel or other comparable material. The tissue removal device may comprise a handle, a collector coupled to the distal portion of the handle, a travel limiter attached distally to the collector, an outer tube that provides a conduit between the collection chamber and a distal tissue removal assembly. The tissue removal assembly may have a rotatable cable that has a retracted configuration and an extended configuration. The locking ring of a travel limiter may have a distal position, an intermediate position, and a proximal position along the axis of the outer tube, and may be configured to lock in one or more positions. The outer tube may have a length that provides a 7 inch working length. The individual devices and components of a kit for minimally invasive discectomy may be provided in a sterilized package. In some variations, the devices may not be re-sterilized after use, while in other variations, certain devices, such as the cannulas, stylets, may be re-sterilized for use in another patient.

It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

What is claimed as new and desired to be protected is:

1. A cannula system, comprising:
   a cannula comprising a distal portion including a longitudinal axis and a distal end, the distal portion being configured to deflect between a substantially curved configuration and a substantially straightened configuration, the longitudinal axis including a curved portion when the distal portion of the cannula takes on the substantially curved configuration; and
   a straight stylet configured to strain the distal portion of the cannula, such that when the stylet is inserted within the distal portion of the cannula, the distal portion of the cannula takes on the substantially straightened configuration, and when the stylet is retracted out from the distal portion of the cannula, the distal portion of the cannula takes on the substantially curved configuration.

2. The cannula system of claim 1, wherein the straight stylet comprises a piercing tip.

3. The cannula system of claim 1, wherein the straight stylet comprises a distal section, a proximal section and a bend section between the distal and proximal sections, wherein the bend section has a reduced axial cross-sectional area relative to the proximal section.

4. The cannula system of claim 3, wherein the axial cross-sectional area of the bend section is reduced relative to the distal section.

5. The cannula system of claim 3, wherein the distal section comprises a piercing tip.

6. The cannula system of claim 3, wherein the bend section and the proximal section comprises a tapered transition.

7. The cannula system of claim 1, wherein the straight stylet includes a deflectable region proximal to a distal tip of the straight stylet.

8. The cannula system of claim 7, wherein the deflectable region has a diameter that varies over a length of the deflectable region.

9. The cannula system of claim 7, wherein the deflectable region includes first and second ends, and a point positioned between the first and second ends, the deflectable region having a first diameter at the first end of the deflectable region, a second diameter at the second end of the deflectable region, and a third diameter at the point positioned between the first and second ends of the deflection region, wherein the third diameter is less than the first and second diameters.

10. The cannula system of claim 9, wherein the first and second diameters are the same.

11. The cannula system of claim 9, wherein the first diameter differs from the second diameter.

12. The cannula system of claim 7, wherein the deflectable region has first and second ends, and a diameter that remains substantially the same along a length extending from the first end of the deflectable region to the second end of the deflectable region.

\* \* \* \* \*